US009657281B2

(12) United States Patent
Vander Horn et al.

(10) Patent No.: US 9,657,281 B2
(45) Date of Patent: May 23, 2017

(54) POLYMERASE COMPOSITIONS, METHODS OF MAKING AND USING SAME

(71) Applicant: LIFE TECHNOLOGIES CORPORATION, Carlsbad, CA (US)

(72) Inventors: Peter Vander Horn, Encinitas, CA (US); Daniel Mazur, San Diego, CA (US); Theo Nikiforov, Carlsbad, CA (US); Mindy Landes, Carlsbad, CA (US); Eileen Tozer, San Diego, CA (US)

(73) Assignee: Life Technologies Corporation, Carlsbad, CA (US)

( * ) Notice: Subject to any disclaimer, the term of this patent is extended or adjusted under 35 U.S.C. 154(b) by 97 days.

(21) Appl. No.: 14/502,201

(22) Filed: Sep. 30, 2014

(65) Prior Publication Data

US 2015/0094211 A1    Apr. 2, 2015

Related U.S. Application Data

(60) Provisional application No. 61/884,921, filed on Sep. 30, 2013.

(51) Int. Cl.
  *C12N 9/12* (2006.01)
  *C12Q 1/68* (2006.01)
(52) U.S. Cl.
  CPC .......... *C12N 9/1252* (2013.01); *C12Q 1/686* (2013.01); *C12Q 1/6869* (2013.01)
(58) Field of Classification Search
  CPC .................................. C12N 9/12; C12Q 1/68
  See application file for complete search history.

(56) References Cited

U.S. PATENT DOCUMENTS

| 2011/0262903 A1* | 10/2011 | Davidson | C12N 9/1252 435/6.1 |
| 2013/0040365 A1* | 2/2013 | Vander Horn | C12Q 1/6846 435/194 |
| 2016/0130644 A1* | 5/2016 | Menchen | G01N 27/4145 435/6.1 |

FOREIGN PATENT DOCUMENTS

WO    WO-2011/106629    9/2011

OTHER PUBLICATIONS

Guo et al., Protein tolerance to random amino acid change, 2004, Proc. Natl. Acad. Sci. USA 101: 9205-9210.*

(Continued)

*Primary Examiner* — Alexander Kim

(57) ABSTRACT

The present disclosure provides compositions, methods, kits, systems and apparatus that are useful for nucleic acid polymerization. In particular, modified polymerases and biologically active fragments thereof are provided that allow for nucleic acid amplification. In some aspects, the disclosure provides modified polymerases having lower systematic error as compared to a reference polymerase. In one aspect, the disclosure relates to modified polymerases useful for nucleic acid sequencing, genotyping, copy number variation analysis, paired-end sequencing and other forms of genetic analysis. In some aspects, the disclosure relates to modified polymerases useful for the generation of nucleic acid libraries or nucleic acid templates. In some aspects, the disclosure relates to the identification of homologous amino acid mutations that can be transferred across classes or families of polymerases to provide novel polymerases with altered properties.

11 Claims, 35 Drawing Sheets

(56) References Cited

OTHER PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
PCT/US2014/058361, International Search Report and Written Opinion mailed Jan. 30, 2015, 9 pages.

* cited by examiner

FIG. 3

| Amino Acid | Number of hits at this Amino Acid Position | Protein Activity | Relative template affinity vs BST |
|---|---|---|---|
| W577Y | | 538 | 5X |
| D480R | 15 | 485 | 33X |
| D480N | | 506 | 4X |
| N485W | 3 | 613 | 3X |
| D144K | 4 | 598 | 20X |
| D144M | | 581 | 7.5X |
| N457T | | 589 | 4X |
| Q409R | 4 | 602 | 3.3X |
| A462T | | 532 | 5X |
| V418M | | 526 | 4X |
| D423K | 4 | 600 | 6X |
| I370A | | 612 | 5X |
| I331Q | | 610 | 4.5X |
| Y272R | 4 | 643 | 7 to >100X |
| F448K | | 493 | 100X2 |
| G425R | | 508 | 100X |

FIG. 4

| polymerase | run | noise 90pct | a.100 q17 | a.aq20 bases | a.ie | a.loading density | a.peak signal | a.q17 mean | a.q20 mean | a.snr | a.total reads | raw read acc |
|---|---|---|---|---|---|---|---|---|---|---|---|---|
| A5 | C23-348 | 7.05 | 5,498,096 | 1,237,214,779 | 0.46 | 0.75 | 69.5 | 234 | 224 | 19.03 | 5,748,277 | 99.24 |
| A5 | C22-361 | 7.15 | 6,456,512 | 1,445,377,961 | 0.47 | 0.84 | 74 | 234 | 223 | 19.45 | 6,713,413 | 99.22 |
| A5 | B7-111 | 6.85 | 5,830,943 | 1,193,249,000 | 0.48 | 0.84 | 63.1 | 225 | 204 | 18.36 | 6,377,273 | 98.75 |
| A5 | C21-371 | 6.85 | 6,356,248 | 1,371,262,369 | 0.48 | 0.83 | 67.5 | 230 | 216 | 18.4 | 6,675,906 | 98.99 |
|  | AVG | 6.975 | 6,035,450 | 1,311,776,027 | 0.47 | 0.82 | 69 | 231 | 217 | 18.8 | 6,378,717 | 99.05 |
| LR2 | C18-274 | 6.75 | 6,797,109 | 1,403,770,943 | 0.68 | 0.87 | 73.8 | 217 | 204 | 17.83 | 7,191,513 | 98.80 |
| LR2 | C19-285 | 6.55 | 6,472,446 | 1,309,592,605 | 0.65 | 0.85 | 71.1 | 216 | 201 | 16.47 | 6,925,906 | 98.73 |
| LR2 | C25-336 | 6.65 | 6,896,095 | 1,495,854,695 | 0.67 | 0.85 | 76.5 | 226 | 214 | 20.42 | 7,185,864 | 98.99 |
| LR2 | C18-273 | 6.75 | 6,786,338 | 1,449,857,106 | 0.7 | 0.87 | 75.7 | 224 | 211 | 19.47 | 7,107,516 | 98.88 |
| LR2 | C19-284 | 6.65 | 6,750,827 | 1,414,882,218 | 0.69 | 0.85 | 76.7 | 222 | 208 | 19.88 | 7,079,058 | 98.77 |
| LR2 | C25-335 | 6.75 | 6,038,917 | 1,281,800,488 | 0.61 | 0.74 | 76.1 | 223 | 210 | 20.45 | 6,301,424 | 98.82 |
|  | AVG | 6.68 | 6,623,622 | 1,392,626,343 | 0.67 | 0.84 | 75 | 221 | 208 | 19.1 | 6,965,214 | 98.83 |
|  | T-Test | 0% | 4% | 23% | 0% | 47% | 2% | 1% | 8% | 75% | 5% | 6% |

FIG. 5

| polymerase | noise 90pct | % above 5% error | CCTC del rate | TA_TAgGC del rate |
|---|---|---|---|---|
| A5 | 7.05 | 0.62 | 0.68 | 1.67 |
| A5 | 7.15 | 0.62 | 0.74 | 1.85 |
| A5 | 6.85 | 0.62 | 0.47 | 1.70 |
| A5 | 6.85 | 0.67 | 0.63 | 1.68 |
| AVG | 6.975 | 0.63 | 0.63 | 1.73 |
| LR2 | 6.75 | 1.03 | | 7.40 |
| LR2 | 6.55 | 1.01 | 0.62 | 7.34 |
| LR2 | 6.65 | 0.95 | 0.64 | 8.15 |
| LR2 | 6.75 | 1.08 | | 7.97 |
| LR2 | 6.65 | 1.10 | 0.59 | 9.23 |
| LR2 | 6.75 | 1.10 | 0.66 | 8.19 |
| AVG | 6.68 | 1.05 | 0.63 | 8.05 |
| T-Test LR2 v A5 | 0% | 0% | 93% | 0% |

A5 significantly decreases error at certain high deletion rate motifs

FIG.13

| run name | aq17 bases | aq20 bases | aq17 mean | a.q20 mean | library beads | aq7 alignments | 200q17/ q7alignments |
|---|---|---|---|---|---|---|---|
| C19-108--R131981-318_dh10b-sc | 1,041,928,394 | 889,692,054 | 206 | 184 | 8,094,986 | 5,326,949 | 70% |
| C18-109--R131980-318_dh10b-sc | 1,140,355,661 | 992,702,054 | 214 | 195 | 8,387,024 | 5,588,479 | 77% |
| C24-150--R131979-318_dh10b-sc | 1,070,630,267 | 919,885,938 | 212 | 190 | 7,640,200 | 5,251,708 | 75% |
| C22-149--R131978-318_dh10b-sc | 1,112,520,129 | 931,399,973 | 212 | 187 | 8,059,157 | 5,527,448 | 75% |
| AVERAGE | 1,091,358,613 | 933,420,005 | 211 | 189 | 8,045,342 | 5,423,646 | 74% |

FIG. 14

| runname | user notes | aq17 bases | aq20 bases | a.q17 mean | a.q20 mean |
|---|---|---|---|---|---|
| C25-184--R135766-318_dh10b-sc | newLR2 | 1,233,397,402 | 1,084,600,300 | 213 | 194 |
| C23-191--R135765-318_dh10b-sc | newLR2 | 1,225,652,319 | 1,061,952,597 | 207 | 186 |
| C21-204--R135764-318_dh10b-sc | newLR2 | 1,120,030,841 | 963,219,201 | 198 | 177 |
| C18-152--R135763-318_dh10b-sc | newLR2 | 1,237,744,166 | 1,061,231,242 | 212 | 192 |
|  | AVERAGE | 1,204,206,182 | 1,042,750,835 | 208 | 187 |
| C24-197--R135762-318_dh10b-sc | oldLR2 | 1,023,137,828 | 866,936,693 | 202 | 180 |
| C22-196--R135761-318_dh10b-sc | oldLR2 | 1,302,285,772 | 1,150,141,837 | 213 | 194 |
| C19-151--R135760-318_dh10b-sc | oldLR2 | 1,286,564,488 | 1,144,713,437 | 211 | 194 |
|  | AVERAGE | 1,203,996,029 | 1,053,930,656 | 209 | 189 |
|  | T-Test | 100% | 90% | 82% | 74% |

FIG. 15

| | |
|---|---|
| Filtered Q17 Coverage Percentage: | 100.00 |
| Filtered Q17 Mean Coverage Depth: | 220.8 |
| Filtered Q17 Alignments: | 2,923,863 |
| Filtered Q17 Mean Alignment Length: | 350 |
| Filtered Mapped Bases in Q17 Alignments: | 1,024,257,977 |
| Filtered Q17 Longest Alignment: | 482 base pairs |
| Filtered Q20 Coverage Percentage: | 100.00 |
| Filtered Q20 Mean Coverage Depth: | 191.9 |
| Filtered Q20 Alignments: | 2,858,185 |
| Filtered Q20 Mean Alignment Length: | 311 |
| Filtered Mapped Bases in Q20 Alignments: | 890,267,209 |
| Filtered Q20 Longest Alignment: | 471 base pairs |

FIG. 16

| | |
|---|---|
| Filtered Q17 Coverage Percentage: | 100.00 |
| Filtered Q17 Mean Coverage Depth: | 221.0 |
| Filtered Q17 Alignments: | 3,358,199 |
| Filtered Q17 Mean Alignment Length: | 305 |
| Filtered Mapped Bases in Q17 Alignments: | 1,025,247,955 |
| Filtered Q17 Longest Alignment: | 443 base pairs |
| Filtered Q20 Coverage Percentage: | 100.00 |
| Filtered Q20 Mean Coverage Depth: | 195.0 |
| Filtered Q20 Alignments: | 3,267,129 |
| Filtered Q20 Mean Alignment Length: | 277 |
| Filtered Mapped Bases in Q20 Alignments: | 904,914,922 |
| Filtered Q20 Longest Alignment: | 443 base pairs |

FIG.17

| Pol | Aq17 Bases | Aq20 Bases | Key Signal | Aq17 mean | S/N | No.of Reads |
|---|---|---|---|---|---|---|
| Taq | 367,845,128 | 296,166,931 | 41 | 152 | 9 | 3,183,990 |
| Taq | 139,445,571 | 108,093,871 | 45 | 116 | 8 | 1,873,473 |
| Taq | 388,598,232 | 321,215,885 | 45 | 190 | 9 | 2,489,655 |
| Taq | 157,478,898 | 121,085,570 | 45 | 133 | 8 | 1,837,974 |
| AVG | 263,341,957 | 211,640,564 | 44 | 148 | 9 | 2,346,273 |
| | | | | | | |
| LR1Taq | 1,147,086,198 | 1,002,173,814 | 51 | 331 | 12 | 3,585,527 |
| LR1Taq | 759,445,416 | 634,727,014 | 48 | 272 | 10 | 3,082,475 |
| LR1Taq | 688,971,544 | 590,371,449 | 50 | 255 | 10 | 3,010,189 |
| LR1Taq | 901,449,079 | 788,366,426 | 51 | 315 | 13 | 3,002,633 |
| AVG | 874,238,059 | 753,909,676 | 50 | 293 | 11 | 3,170,206 |
| T-Test | 0% | 0% | 0% | 0% | 3% | 7% |

FIG. 18

| Mutant | AQ20 total basecount | AQ20 mean | Raw read acccuracy% | Target bases with no strand bias% | systematic error% |
|---|---|---|---|---|---|
| N782A | 2,112,170 | 65 | 98.20 | 30 | 1.99 |
| N782C | 681,414 | 46 | 97.77 | 28 | 1.92 |
| N782D | 792,907 | 52 | 97.72 | 35 | 2.13 |
| N782E | 734,812 | 45 | 97.68 | 31 | 2.49 |
| N782F | 2,792,834 | 103 | 98.59 | 45 | 1.39 |
| N782G | 2,279,116 | 71 | 98.25 | 29 | 1.92 |
| N782H | 3,193,181 | 74 | 98.33 | 29 | 1.95 |
| N782I | 2,587,692 | 84 | 98.46 | 32 | 1.65 |
| N782L | 1,588,267 | 74 | 98.31 | 30 | 1.76 |
| N782M | 2,381,494 | 77 | 98.33 | 30 | 1.75 |
| N782P | 1,358,273 | 68 | 98.21 | 31 | 1.75 |
| N782Q | 1,210,902 | 65 | 98.14 | 30 | 1.86 |
| N782R | 4,112,330 | 134 | 98.92 | 71 | 0.61 |
| N782S | 1,533,024 | 67 | 98.19 | 29 | 2.05 |
| N782T | 2,248,813 | 62 | 98.11 | 26 | 2.24 |
| N782V | 1,615,579 | 74 | 98.32 | 30 | 1.82 |
| N782W | 2,319,463 | 102 | 98.54 | 50 | 1.41 |
| N782Y | 1,616,099 | 72 | 98.27 | 30 | 1.78 |

FIG. 19

| Mutant | AQ20 total basecount | AQ20 mean | Raw read acccuracy% | Target bases with no strand bias% | Systematic error% |
|---|---|---|---|---|---|
| N780A | 1,007,438 | 55 | 98.06 | 28 | 2.17 |
| N780C | 9,871 | 29 | 96.76 | 19 | NA |
| N780D | 43,796 | 24 | 96.58 | 30 | 2.58 |
| N780E | 26,687 | 23 | 97.02 | 23 | 6.56 |
| N780F | 1,115,521 | 60 | 98.11 | 29 | 2.04 |
| N780G | 539,617 | 52 | 97.88 | 31 | 2.20 |
| N780H | 12,158 | 60 | 98.08 | 41 | NA |
| N780I | 376,376 | 48 | 97.84 | 33 | 1.80 |
| N780K | 2,283,394 | 107 | 98.60 | 49 | 1.32 |
| N780L | 512,555 | 51 | 98.00 | 30 | 2.00 |
| N780M | 367,607 | 53 | 97.87 | 34 | 1.81 |
| N780P | 190,073 | 41 | 97.56 | 38 | 1.49 |
| N780Q | 430,375 | 44 | 97.77 | 30 | 2.22 |
| N780R | 242,417 | 45 | 97.42 | 41 | 1.97 |
| N780T | 267,081 | 45 | 97.69 | 34 | 2.04 |
| N780V | 453,814 | 49 | 97.93 | 30 | 1.76 |
| N780W | 1,275,906 | 68 | 98.15 | 29 | 2.20 |
| N780Y | 1,363,356 | 69 | 98.23 | 28 | 2.09 |

FIG. 20

| Mutant | AQ20 total basecount | AQ20 mean | Raw read acccuracy% | Target bases with no strand bias% | Systematic error% |
|---|---|---|---|---|---|
| E788A | 1,400,181 | 75 | 98.18 | 34 | 1.69 |
| E788C | 1,505,414 | 53 | 97.83 | 28 | 1.96 |
| E788F | 1,597,378 | 63 | 98.00 | 31 | 1.98 |
| E788G | 113,874 | 34 | 97.21 | 51 | 1.37 |
| E788H | 1,251,761 | 60 | 97.91 | 33 | 1.74 |
| E788I | 1,663,136 | 67 | 98.05 | 31 | 2.01 |
| E788L | 1,776,343 | 70 | 98.06 | 32 | 2.13 |
| E788M | 1,368,601 | 68 | 98.07 | 33 | 1.95 |
| E788N | 533,704 | 46 | 97.61 | 38 | 1.96 |
| E788P | 465,769 | 37 | 97.38 | 38 | 2.37 |
| E788Q | 2,168,590 | 85 | 98.34 | 37 | 1.76 |
| E788R | 4,232,311 | 118 | 98.66 | 71 | 1.04 |
| E788S | 132,063 | 38 | 97.24 | 51 | 1.37 |
| E788T | 5,012,021 | 88 | 98.33 | 38 | 2.05 |
| E788V | 1,923,417 | 80 | 98.22 | 33 | 2.09 |
| E788W | 396,742 | 42 | 97.50 | 38 | 1.95 |

FIG. 21

| Mutant | AQ20 total basecount | AQ20 mean | Raw read acccuracy% | Target bases with no strand bias% | Systematic error% |
|---|---|---|---|---|---|
| A558C | 4,015 | 25 | 96.23 | 12 | NA |
| A558D | 909 | 65 | 0.00 | 4 | NA |
| A558E | 1,408 | 18 | 0.00 | 8 | NA |
| A558F | 260,523 | 36 | 97.22 | 35 | 1.92 |
| A558G | 47,249 | 29 | 96.80 | 28 | 2.13 |
| A558H | 127,249 | 40 | 97.00 | 38 | 1.97 |
| A558I | 18,505 | 28 | 96.80 | 23 | NA |
| A558K | 1,798,866 | 103 | 98.58 | 48 | 0.93 |
| A558L | 18,320 | 29 | 96.91 | 23 | 1.01 |
| A558M | 69,188 | 32 | 96.89 | 31 | 1.89 |
| A558N | 243 | 16 | 0.00 | 1 | NA |
| A558P | 1,571 | 27 | 0.00 | 6 | NA |
| A558Q | 13,293 | 21 | 95.95 | 24 | NA |
| A558R | 1,021,108 | 79 | 98.22 | 37 | 0.90 |
| A558S | 12,647 | 27 | 96.13 | 21 | NA |
| A558T | 1,312 | 27 | 0.00 | 5 | NA |
| A558V | 115,307 | 39 | 97.16 | 29 | 1.61 |
| A558Y | 101,890 | 39 | 97.05 | 38 | 1.58 |

FIG. 22

| Mutant | AQ20 total basecount | AQ20 mean | Raw read acccuracy% | Target bases with no strand bias% | Systematic error% |
|---|---|---|---|---|---|
| D559A | 1,463,945 | 116 | 98.65 | 57 | 0.96 |
| D559C | 58,630 | 37 | 97.18 | 45 | 0.75 |
| D559E | 90,762 | 35 | 97.03 | 44 | 2.00 |
| D559F | 752,380 | 68 | 98.09 | 39 | 1.49 |
| D559G | 2,800,882 | 114 | 98.67 | 55 | 1.27 |
| D559H | 3,773,476 | 123 | 98.79 | 64 | 0.88 |
| D559I | 1,135,864 | 85 | 98.31 | 41 | 1.50 |
| D559K | 3,442,101 | 109 | 98.65 | 55 | 0.96 |
| D559L | 1,699,849 | 91 | 98.36 | 43 | 1.51 |
| D559M | 2,809,618 | 117 | 98.72 | 54 | 1.04 |
| D559N | 2,060,371 | 104 | 98.53 | 48 | 1.49 |
| D559P | 2,511,347 | 117 | 98.73 | 55 | 1.12 |
| D559Q | 2,726,033 | 119 | 98.73 | 58 | 1.08 |
| D559R | 2,738,109 | 116 | 98.71 | 66 | 0.81 |
| D559S | 1,927,179 | 101 | 98.51 | 50 | 1.39 |
| D559T | 2,325,137 | 116 | 98.66 | 58 | 1.30 |
| D559V | 1,261,187 | 92 | 98.37 | 43 | 1.32 |
| D559Y | 2,034,056 | 99 | 98.46 | 49 | 1.24 |

FIG. 23

| Mutant | AQ20 Mean | Raw Read Accuracy (%) | AQ20 total basecount | Systematic Error (%) |
|---|---|---|---|---|
| 559A | 206 | 99.0 | 71,868,061 | 0.61 |
| 559A | 247 | 99.0 | 92,820,468 | 0.48 |
| 559A | 220 | 98.8 | 91,573,349 | 0.53 |
|  |  |  |  |  |
| 559R | 210 | 98.6 | 129,800,448 | 0.67 |
| 559R | 206 | 98.6 | 121,923,702 | 0.66 |

FIG. 24

| Mutant | AQ20 total basecount | AQ20 mean | Raw read acccuracy% | Target bases with no strand bias% | Systematic error% |
|---|---|---|---|---|---|
| H823D | 598,888 | 56 | 97.84 | 32 | 2.07 |
| H823F | 897,197 | 60 | 98.07 | 26 | 2.07 |
| H823I | 569,661 | 53 | 97.93 | 29 | 1.99 |
| H823K | 806,499 | 57 | 98.03 | 26 | 2.04 |
| H823L | 619,032 | 55 | 97.98 | 31 | 2.13 |
| H823M | 669,262 | 57 | 97.99 | 29 | 2.16 |
| H823N | 793,388 | 58 | 97.94 | 27 | 2.17 |
| H823P | 868,970 | 54 | 97.95 | 28 | 2.36 |
| H823Q | 575,966 | 59 | 98.05 | 34 | 1.88 |
| H823R | 215,689 | 57 | 98.08 | 39 | 1.08 |
| H823S | 867,801 | 59 | 98.07 | 28 | 2.10 |
| H823T | 852,190 | 57 | 97.98 | 26 | 2.26 |
| H823W | 585,296 | 55 | 97.92 | 34 | 2.04 |
| H823Y | 867,436 | 55 | 98.01 | 27 | 2.29 |

FIG. 25

| Mutant | AQ20 total basecount | AQ20 mean | Raw read acccuracy% | Target bases with no strand bias% | Systematic error% |
|---|---|---|---|---|---|
| H568A | 1,177,875 | 41 | 97.43 | 29 | 3.09 |
| H568C | 147,296 | 24 | 96.76 | 33 | 1.96 |
| H568D | 91,564 | 33 | 96.83 | 37 | 1.90 |
| H568E | 92,667 | 30 | 96.97 | 35 | 1.87 |
| H568F | 550,087 | 40 | 97.27 | 29 | 2.54 |
| H568G | 516,460 | 46 | 97.46 | 32 | 2.28 |
| H568I | 17,987 | 21 | 96.22 | 21 | NA |
| H568K | 260,614 | 42 | 97.34 | 38 | 1.86 |
| H568L | 12,365 | 20 | 96.83 | 10 | 0.95 |
| H568N | 1,068,726 | 51 | 97.75 | 31 | 2.55 |
| H568P | 4,738 | 24 | 96.63 | 15 | NA |
| H568Q | 301,825 | 42 | 97.40 | 38 | 2.04 |
| H568R | 247,447 | 36 | 97.14 | 38 | 1.84 |
| H568S | 736,466 | 46 | 97.50 | 31 | 2.59 |
| H568T | 250,961 | 38 | 97.20 | 40 | 2.09 |
| H568V | 92,335 | 25 | 96.65 | 33 | 1.85 |
| H568W | 650,881 | 38 | 97.28 | 30 | 2.70 |
| H568Y | 579,252 | 40 | 97.28 | 33 | 2.64 |

FIG. 26

| Pol/Conditions | Run | aq17bases | q17mean | snr | Raw Read Acc | 50bp error | 100bp error | 200bp error | Systematic Error | 200q17/ 100q17 |
|---|---|---|---|---|---|---|---|---|---|---|
| 782R | B7-577 | 1,294,750,985 | 228 | 24.39 | 99.6423 | 0.165 | 0.198 | 0.707 | 0.067% | 90.06% |
| | BEA-1054 | 1,245,655,996 | 223 | 23.799 | 99.5803 | 0.178 | 0.223 | 0.923 | 0.081% | 86.34% |
| 782R/718K | B7-576 | 1,178,525,546 | 232 | 24.905 | 99.7546 | 0.214 | 0.236 | 0.29 | 0.065% | 95.02% |
| | BEA-1053 | 1,284,194,284 | 232 | 23.448 | 99.737 | 0.229 | 0.239 | 0.323 | 0.039% | 94.89% |
| 718K | SAN-782 | 1,168,221,010 | 229 | 22.467 | 99.6626 | 0.276 | 0.327 | 0.403 | 0.181% | 93.50% |
| | SAN-783 | 1,167,563,825 | 227 | 22.166 | 99.6621 | 0.273 | 0.323 | 0.403 | 0.172% | 92.91% |
| 515K/529R/718K | C19-710 | 189,228,238 | 225 | 20.216 | 99.6209 | 0.368 | 0.385 | 0.396 | 0.162% | 92.00% |
| | C18-651 | 145,439,692 | 210 | 19.379 | 99.3208 | 0.695 | 0.653 | 0.684 | 0.263% | 85.65% |

FIG. 27

| polymeraseused | runname | a.aq20bases | a.loading density | a.peaksignal | a.q20mean | a.q47mean | a.snr | raw read accuracy | systematic Error (5) | a.200q17/ 100q17 |
|---|---|---|---|---|---|---|---|---|---|---|
| n782r-718k-568n | R26-98 | 241,440,070 | 0.8 | 69 | 364 | 301 | 23.31 | 99.5731 | 0.11% | 96% |
| n782r-718k-568n | SN2-137 | 244,243,059 | 0.81 | 66 | 363 | 299 | 23.2 | 99.5554 | 0.12% | 96% |
| n782r-718k-568n | R24-160 | 266,601,512 | 0.88 | 66 | 364 | 305 | 21.16 | 99.6282 | 0.07% | 96% |
|  |  |  |  |  |  |  |  |  |  |  |
| 718K | C19-759 | 249,602,505 | 0.85 | 68 | 346 | 274 | 23.36 | 99.4871 | 0.24% | 93% |
| 718K | C18-700 | 188,338,533 | 0.8 | 69 | 306 | 231 | 23.13 | 99.2294 | 0.42% | 90% |
| 718K | BEA-1099 | 228,705,327 | 0.89 | 68 | 322 | 249 | 23.41 | 99.3668 | 0.32% | 91% |
| 718K | B7--618 | 210,984,770 | 0.79 | 69 | 321 | 247 | 22.43 | 99.3568 | 0.35% | 92% |
| 718K | SNA-728 | 216,215,417 | 0.8 | 68 | 327 | 251 | 23.86 | 99.3567 | 0.35% | 92% |
| 718K | R25-14 | 195,724,093 | 0.81 | 70 | 310 | 235 | 23.83 | 99.2844 | 0.41% | 90% |

FIG. 28

| polymerase used | runname | a.aq17bases | a.aq20bases | a.loading density | a.peak signal | a.q17mean | a.q20mean | a.raw Accuracy | a.snr | a.total reads |
|---|---|---|---|---|---|---|---|---|---|---|
| n782r-h576m-lot1 | P23-186 | 1,989,065,851 | 1,496,289,329 | 0.64 | 50 | 75 | 63 | 97.2 | 8.02 | 37,391,972 |
| n782r-h576m-lot1 | P23-185 | 2,333,342,621 | 1,792,380,249 | 0.65 | 52 | 79 | 67 | 97.5 | 8.29 | 39,591,427 |
| | | | | | | | | | | |
| d718k plt2 1357981 | P19-224 | 994,889,331 | 754,871,206 | 0.72 | 44 | 60 | 50 | 96.7 | 6.84 | 30,212,587 |
| d718k plt2 1357981 | P17-213 | 1,157,838,581 | 866,041,720 | 0.7 | 42 | 62 | 52 | 96.7 | 6.74 | 34,326,440 |
| | | | | | | | | | | |

318 Chips

| POLYMERASE | a.aq47bases | a.loading density | a.peak signal | a.q20 mean | a.total reads | raw read accuracy | consensus phredq | VariantQC filtered | SSF | sse_115 |
|---|---|---|---|---|---|---|---|---|---|---|
| LR2 | 1,207,205,156 | 0.84 | 71 | 223 | 6,611,307 | 99.5751 | 37.5 | 9933 | 0.292% | 0.009% |
| LR2 | 1,166,877,375 | 0.84 | 70 | 222 | 6,484,553 | 99.5376 | 37.07 | 10,484 | 0.313% | 0.012% |
| AVERAGE | | | | | | 99.56 | 37.3 | 10,209 | 0.303% | 0.010% |
| SEQ ID NO: 35 | 1,469,855,706 | 0.91 | 80 | 232 | 7,185,406 | 99.7634 | 53.7 | 981 | 0.027% | 0.004% |
| SEQ ID NO: 35 | 1,324,104,067 | 0.87 | 76 | 230 | 6,609,130 | 99.7245 | 52.08 | 1042 | 0.024% | 0.005% |
| SEQ ID NO: 35 | 1,326,359,278 | 0.86 | 74 | 231 | 6,495,389 | 99.7565 | 52.24 | 1061 | 0.027% | 0.005% |
| AVERAGE | | | | | | 99.75 | 52.67 | 1028 | 0.026% | 0.005% |

314 Chips

| POLYMERASE | a.aq47bases | a.loading density | a.peak signal | a.q20 mean | a.total reads | raw read accuracy | consensus phredq | VariantQC filtered | SSF | sse_115 |
|---|---|---|---|---|---|---|---|---|---|---|
| LR2 | 114,042,974 | 0.81 | 85 | 224 | 614,632 | 99.6391 | 36.35 | 11,608 | 0.224% | 0.015% |
| LR2 | 97,200,857 | 0.75 | 76 | 221 | 530,724 | 99.6281 | 36.41 | 12,155 | 0.236% | 0.012% |
| AVERAGE | | | | | | 99.63 | 36.4 | 11,832 | 0.230% | 0.013% |
| SEQ ID NO: 35 | 142,031,636 | 0.84 | 100 | 231 | 690,805 | 99.7555 | 48.2 | 1545 | 0.020% | 0.005% |
| SEQ ID NO: 35 | 140,189,703 | 0.88 | 104 | 230 | 685,650 | 99.7543 | 48.93 | 1560 | 0.020% | 0.005% |
| SEQ ID NO: 35 | 144,115,054 | 0.84 | 103 | 231 | 698,612 | 99.7715 | 52.08 | 1536 | 0.023% | 0.005% |
| SEQ ID NO: 35 | 147,325,630 | 0.89 | 92 | 231 | 724,839 | 99.7435 | 48.07 | 1456 | 0.020% | 0.007% |
| AVERAGE | | | | | | 99.75 | 49.32 | 1524 | 0.021% | 0.005% |

US 9,657,281 B2

POLYMERASE COMPOSITIONS, METHODS OF MAKING AND USING SAME

CROSS REFERENCE TO RELATED APPLICATIONS

This application claims the benefit of priority under 35 U.S.C. §119(e) to U.S. Provisional Application No. 61/884,921, filed Sep. 30, 2013, entitled "POLYMERASE COMPOSITIONS, METHODS OF MAKING AND USING SAME", the disclosure of which is incorporated herein by reference in its entirety.

SEQUENCE LISTING

This application hereby incorporates by reference the material of the electronic Sequence Listing filed concurrently herewith. The material in the electronic Sequence Listing is submitted as a text (.txt) file entitled "2014-09-29 LT00858_ST25.txt" created on Sep. 29, 2014, which has a file size of 148 KB, and is herein incorporated by reference in its entirety.

TECHNICAL FIELD

In some embodiments, the disclosure relates generally to polymerase compositions, methods of making and using the same. In some embodiments, the disclosure relates generally to one or more modified polymerases, where the one or more modified polymerases contain at least one amino acid mutation (e.g., substitution, deletion or addition) as compared to a reference polymerase. In some embodiments, the disclosure relates generally to compositions comprising a modified DNA or RNA polymerase. In some embodiments, the disclosure relates generally to compositions comprising a modified DNA polymerase having lowered systematic error as compared to a reference DNA polymerase. In some embodiments, the compositions can include a modified polymerase from an A family DNA polymerase, B family DNA polymerase or a C family DNA polymerase. In some embodiments, the disclosure relates generally to the transfer of a homologous amino acid mutation (e.g., substitution, deletion or addition) across a class or family of polymerases. In some embodiments, the disclosure relates generally to a polymerase composition for nucleic acid sequencing, including next-generation sequencing. In some embodiments, the disclosure relates generally to a modified polymerase composition for the generation of nucleic acid libraries or nucleic acid templates. In some embodiments, the disclosure relates generally to a modified polymerase composition for the amplification of nucleic acid libraries or nucleic acid templates. In some embodiments, the disclosure relates to systems, apparatuses and kits that contain one or more of the modified polymerases. In some embodiments, the compositions, systems, apparatuses and kits can be used for synthesizing a DNA strand. In some embodiments, the compositions, systems, apparatuses and kits can be used for performing polymerization. In some embodiments, the compositions, systems, apparatuses and kits can be used for amplifying a DNA molecule. In some embodiments, the compositions, systems, apparatuses and kits can be used for amplifying at least 10, 50, 100, 500, 1000, 2500, 5000, 7500, 10000, 25000, 50000, 100000, or more nucleic acid templates in a single reaction. In some embodiments, the compositions, systems, apparatuses and kits can be used for amplifying at least 10, 50, 100, 500, 1000, 2500, 5000, 7500, 10000, 25000, 50000, 100000, or more nucleic acid templates in a single reaction vessel.

BACKGROUND

The ability of enzymes to catalyze biological reactions is fundamental to life. A range of biological applications use enzymes to synthesize various biomolecules in vitro. One particularly useful class of enzymes is the polymerases, which can catalyze the polymerization of biomolecules (e.g., nucleotides or amino acids) into biopolymers (e.g., nucleic acids or peptides). For example, polymerases that can polymerize nucleotides into nucleic acids, particularly in a template-dependent fashion, are useful in recombinant DNA technology and nucleic acid sequencing applications. Many nucleic acid sequencing methods monitor nucleotide incorporations during in vitro template-dependent nucleic acid synthesis catalyzed by a polymerase. Single Molecule Sequencing (SMS) and Paired-End Sequencing (PES) typically include a polymerase for template-dependent nucleic acid synthesis. Polymerases are also useful for the generation of nucleic acid libraries, such as libraries created during emulsion PCR or bridge PCR. Nucleic acid libraries created using such polymerases can be used in a variety of downstream processes, such as genotyping, nucleotide polymorphism (SNP) analysis, copy number variation analysis, epigenetic analysis, gene expression analysis, hybridization arrays, analysis of gene mutations including but not limited to detection, prognosis and/or diagnosis of disease states, detection and analysis of rare or low frequency allele mutations, and nucleic acid sequencing including but not limited to de novo sequencing or targeted resequencing.

When performing polymerase-dependent nucleic acid synthesis or amplification, it can be useful to modify the polymerase (for example via mutation or chemical modification) so as to alter its catalytic properties. In some instances, it can be useful to modify the polymerase to enhance its catalytic properties. In some embodiments, it can be useful to enhance a polymerase's catalytic properties via site-directed amino acid substitution or deletion. Polymerase performance in various biological assays involving nucleic acid synthesis can be limited by the kinetic behavior of the polymerase towards nucleotide substrates. For example, analysis of polymerase activity can be complicated by undesirable behavior such as the tendency of a given polymerase to dissociate from the template; to bind and/or incorporate the incorrect, e.g., non Watson-Crick base-paired, nucleotide; or to release the correct, e.g., Watson-Crick based paired, nucleotide without incorporation. These and other desirable properties can be enhanced via suitable selection, engineering and/or modification of a polymerase of choice. For example, such modification can be performed to favorably alter the polymerase's rate of nucleotide incorporation, affinity of binding to template, processivity, average read length, accuracy of nucleotide incorporation, strand bias, systematic error, total sequencing throughput; such alterations can increase the amount of sequence information and/or quality of sequencing information obtained from a single sequencing reaction. There remains a need in the art for improved polymerase compositions exhibiting altered properties, e.g., increased processivity, increased read length (including error-free read length), increased raw accuracy and/or affinity for DNA template, increased sequencing throughput, decreased strand bias and/or decreased systematic error. Such polymerase compositions can be useful in a wide variety of assays involving polymerase-dependent nucleic acid synthesis, including nucleic acid sequencing, qPCR, PCR, bridge PCR, isothermal amplification, clonal amplification and production of nucleic acid libraries.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIG. 3 is a table providing exemplary template affinity data obtained for a modified polymerase obtained according to the disclosure, as compared to a reference polymerase.

FIG. 4 is a table providing exemplary nucleic acid sequencing data obtained using exemplary modified polymerases according to the disclosure.

FIG. 5 is a table providing exemplary nucleic acid sequencing data obtained using exemplary modified polymerases according to the disclosure.

FIG. 13 is a table providing exemplary nucleic acid sequencing data obtained using an exemplary modified polymerase according to the disclosure.

FIG. 14 is a table providing exemplary nucleic acid sequencing data obtained using an exemplary modified polymerase according to the disclosure.

FIG. 15 is a table providing exemplary nucleic acid sequencing data obtained using an exemplary modified polymerase according to the disclosure.

FIG. 16 is a table providing exemplary nucleic acid sequencing data obtained using an exemplary modified polymerase according to the disclosure.

FIG. 17 is a table providing exemplary nucleic acid sequencing data obtained using an exemplary modified polymerase according to the disclosure.

FIG. 18 is a table providing exemplary nucleic acid sequencing data obtained using an exemplary modified polymerase according to the disclosure.

FIG. 19 is a table providing exemplary nucleic acid sequencing data obtained using an exemplary modified polymerase according to the disclosure.

FIG. 20 is a table providing exemplary nucleic acid sequencing data obtained using an exemplary modified polymerase according to the disclosure.

FIG. 21 is a table providing exemplary nucleic acid sequencing data obtained using an exemplary modified polymerase according to the disclosure.

FIG. 22 is a table providing exemplary nucleic acid sequencing data obtained using an exemplary modified polymerase according to the disclosure.

FIG. 23 is a table providing exemplary nucleic acid sequencing data obtained using an exemplary modified polymerase according to the disclosure.

FIG. 24 is a table providing exemplary nucleic acid sequencing data obtained using an exemplary modified polymerase according to the disclosure.

FIG. 25 is a table providing exemplary nucleic acid sequencing data obtained using an exemplary modified polymerase according to the disclosure.

FIG. 26 is a table providing exemplary nucleic acid sequencing data obtained using an exemplary modified polymerase according to the disclosure.

FIG. 27 is a table providing exemplary nucleic acid sequencing data obtained using an exemplary modified polymerase according to the disclosure.

FIG. 28 is a table providing exemplary nucleic acid sequencing data obtained using an exemplary modified polymerase according to the disclosure.

FIG. 29 is a table providing exemplary nucleic acid sequencing data obtained using an exemplary modified polymerase according to the disclosure.

FIG. 32 is a table providing exemplary nucleic acid sequencing data obtained using an exemplary modified polymerase according to the disclosure.

FIG. 35 is a table providing exemplary nucleic acid sequencing data obtained using an exemplary modified polymerase according to the disclosure.

SUMMARY

Figure 1:
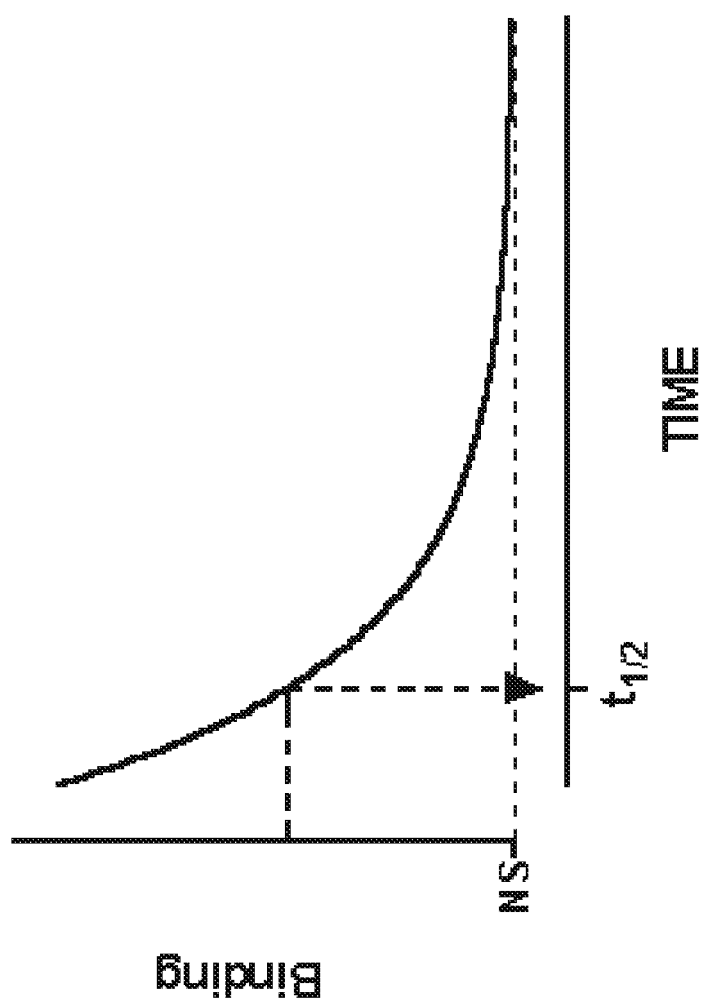
FIG. 1 is a schematic outlining an exemplary dissociation rate curve according to the disclosure.

In some embodiments, the disclosure relates generally to a method for performing a nucleotide polymerization reaction comprising or consisting of contacting a modified polymerase or a biologically active fragment thereof with a nucleic acid template in the presence of one or more nucleotides, where the modified polymerase or the biologically active fragment thereof includes one or more amino acid modifications relative to a reference polymerase and where the modified polymerase or the biologically active fragment thereof has a lowered systematic error, decreased strand bias, increased raw read accuracy and/or increased total sequencing throughput as compared to the reference polymerase, and polymerizing at least one of the one or more nucleotides using the modified polymerase or the biologically active fragment thereof. In some embodiments, the disclosure relates generally to a method for performing a nucleotide polymerization reaction comprising or consisting of contacting a modified polymerase or a biologically active fragment thereof with a nucleic acid template in the presence of one or more nucleotides, where the modified polymerase or the biologically active fragment thereof includes one or more amino acid modifications relative to a reference polymerase and where the modified polymerase or the biologically active fragment thereof has an increased dissociation time constant relative to the reference polymerase, and polymerizing at least one of the one or more nucleotides using the modified polymerase or the biologically active fragment thereof. In some embodiments, the method includes polymerizing at least one of the one or more nucleotides using the modified polymerase or the biologically active fragment thereof in the presence of a high ionic strength solution. In some embodiments, the method can further include polymerizing the at least one nucleotide in a template-dependent fashion. In some embodiments, the method can further including hybridizing a primer to the template prior to, during or after the contacting, and where the polymerizing includes polymerizing the at least one nucleotide onto an end of the primer using the modified polymerase or the biologically active fragment thereof. In some embodiments, the polymerizing is performed in the proximity of a sensor that is capable of detecting the polymerization of the at least one nucleotide by the modified polymerase or the biologically active fragment thereof. In some embodiments, the method can further include detecting a signal indicating the polymerization of the at least one of the one or more nucleotides by the modified polymerase or the biologically active fragment thereof using a sensor. In some embodiments, the sensor can be an ISFET.

In some embodiments, the modified polymerase or the biologically active fragment thereof comprises or consists of at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises or consists of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises or consists of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises or consists of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises or consists of at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises or consists of an isolated polypeptide having at least 90% identity to a Family A DNA polymerase containing an amino acid sequence selected from the group consisting of: SEQ ID NO: 2, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37. In some embodiments, the modified polymerase or the biologically active fragment thereof comprises at least 25 contiguous amino acids from the polymerase catalytic domain. In some embodiments, the modified polymerase or the biologically active fragment thereof comprises at least 25 contiguous amino acids from the polymerase DNA binding domain. In some embodiments, the modified polymerase or the biologically active fragment thereof comprises or consists of at least 100 amino acid residues having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises or consists of at least 150 amino acid residues of the polymerase catalytic domain having at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the disclosure generally relates to a method for performing nucleic acid amplification comprising or consisting of generating an amplification reaction mixture having a modified polymerase or a biologically active fragment thereof, a primer, a nucleic acid template, and one or more nucleotides, where the modified polymerase or the biologically active fragment thereof includes one or more amino acid modifications relative to a reference polymerase and has a lowered systematic error relative to the reference polymerase; and subjecting the amplification reaction mixture to amplifying conditions, where at least one of the one or more nucleotides is polymerized onto the end of the primer using the modified polymerase or the biologically active fragment thereof. In some embodiments, the method includes a modified polymerase or a biologically active fragment thereof having lowered systematic error comprising or consisting of at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof having lowered systematic error comprising or consisting of at least 85% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof having lowered systematic error comprising or consisting of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof having lowered systematic error comprising or consisting of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof having lowered systematic error comprising or consisting of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof having lowered systematic error comprising or consisting of at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the disclosure generally relates to a method for performing nucleic acid amplification comprising or consisting of generating an amplification reaction mixture having a modified polymerase or a biologically active fragment thereof, a primer, a nucleic acid template, and one or more nucleotides, where the modified polymerase or the biologically active fragment thereof includes one or more amino acid modifications (e.g., amino acid substitutions, deletions and/or additions) relative to a reference polymerase and has an increased dissociation time constant relative to the reference polymerase; and subjecting the amplification reaction mixture to amplifying conditions, where at least one of the one or more nucleotides is polymerized onto the end of the primer using the modified polymerase or the biologically active fragment thereof. In some embodiments, the method includes a modified polymerase or a biologically active fragment thereof comprising or consisting of at least 80% identity SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 85% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises at least 25 contiguous amino acids of the polymerase catalytic domain. In some embodiments, the modified polymerase or the biologically active fragment thereof comprises at least 25 contiguous amino acid residues of the polymerase DNA binding domain. In some embodiments, the modified polymerase or the biologically active fragment thereof comprises or consists of at least 100 contiguous amino acid residues of the polymerase catalytic domain having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises or consists of at least 150 contiguous amino acid residues of the polymerase catalytic domain having at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises or consists of at least 150 contiguous amino acid residues of the polymerase catalytic domain having at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes amplifying conditions having a high ionic strength solution. In some embodiments, amplifying conditions having a high ionic strength solution include at least 120 mM salt. In some embodiments, amplifying conditions having a high ionic strength solution include 125 mM salt. In some embodiments, amplifying conditions having a high ionic strength solution include 125 mM to 200 mM salt. In some embodiments, the salt can include KCl and/or NaCl.

In some embodiments, the disclosure generally relates to a method for performing polymerization comprising or consisting of providing a reaction mixture including a nucleic acid hybridized to a primer and bound to a modified polymerase; and contacting the nucleic acid with at least one type of nucleotide, wherein the contacting includes incorporating at least one nucleotide onto the primer thereby generating an extended primer product. In some embodiments, the method further includes detecting the presence of the extended primer product in the reaction mixture, thereby determining whether nucleotide incorporation has occurred. In some embodiments, the method further includes repeating the contacting and detecting steps more than once, thereby detecting a plurality of nucleotide incorporations. In some embodiments, the method further includes identifying at least one of the plurality of nucleotide incorporations. In some embodiments, the polymerization method can include PCR, qPCR, bridge PCR, RT-PCR, ligation mediated PCR, isothermal amplification or emulsion PCR. In some embodiments, the method includes a modified polymerase or a biologically active fragment thereof comprising or consisting of at least 80% identity SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 85% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase comprising an isolated polypeptide having at least 90% identity to a Family A DNA polymerase containing an amino acid sequence selected from the group consisting of: SEQ ID NO: 2 SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 SEQ ID NO: 35, SEQ ID NO: 36 and SEQ ID NO: 37.

In some embodiments, the disclosure generally relates to a method for performing a nucleotide polymerization reaction comprising or consisting of mixing a modified polymerase or a biologically active fragment thereof with a nucleic acid template in the presence of one or more nucleotides, where the modified polymerase or the biologically active fragment thereof includes one or more amino acid modifications relative to a reference polymerase and has increased accuracy relative to a reference polymerase; and polymerizing at least one of the one or more nucleotides using the modified polymerase or the biologically active fragment thereof in the mixture. In some embodiments, the method includes a modified polymerase or a biologically active fragment thereof having increased accuracy as determined by measuring increased accuracy in the presence of a high ionic strength solution. In some embodiments, the method includes a modified polymerase or a biologically active fragment thereof comprising or consisting of at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof having increased accuracy comprises or consists of at least 150 amino acid residues of the polymerase catalytic domain having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof having increased accuracy comprises or consists of at least 150 amino acid residues of the polymerase catalytic domain having at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof having increased accuracy comprises or consists of at least 150 amino acid residues of the polymerase catalytic domain having at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the disclosure generally relates to a method of detecting nucleotide incorporation comprising or consisting of performing a nucleotide incorporation using a modified polymerase or a biologically active fragment thereof having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, a nucleic acid template, and one or more nucleotide triphosphates; generating one or more byproducts of the nucleotide incorporation, detecting the presence of at least one of the one or more byproducts of the nucleotide incorporation, and thereby detecting the nucleotide incorporation. In some embodiments, the method includes a modified polymerase or a biologically active fragment thereof comprising or consisting of at least 85% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29 SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes or consists of detecting nucleotide incorporation by a modified polymerase or a biologically active fragment thereof that includes at least 25 contiguous amino acid residues of the polymerase catalytic domain or the polymerase DNA binding domain. In some embodiments, the method comprises or consists of determining the identity of one or more nucleotides in the nucleotide incorporation. In some embodiments, the byproduct of the nucleotide incorporation can include a hydrogen ion. In some embodiments, the byproduct of nucleotide incorporation can include a pyrophosphate or phosphate ion.

In some embodiments, the disclosure generally relates to a method of detecting a change in ion concentration during a nucleotide polymerization reaction comprising or consisting of performing a nucleotide polymerization reaction using a modified polymerase or a biologically active fragment thereof having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, where the concentration of at least one type of ion changes during the course of the nucleotide polymerization reaction and detecting a signal indicating the change in concentration of the at least one type of ion. In some embodiments, the method includes a modified polymerase or a biologically active fragment thereof comprising or consisting of at least 85% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28 SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:

29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the ion can include a hydrogen ion. In some embodiments, the modified polymerase or the biologically active fragment thereof detecting a change in ion concentration comprises or consists of at least 150 contiguous amino acid residues of the polymerase catalytic domain having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the modified polymerase or the biological active fragment thereof detecting a change in ion concentration comprises or consists of at least 200 contiguous amino acid resides of the polymerase having at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biological active fragment thereof detecting a change in ion concentration comprises or consists of at least 200 contiguous amino acid resides of the polymerase having at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the disclosure generally relates to a method for amplifying a nucleic acid comprising or consisting of contacting a nucleic acid with a modified polymerase or a biologically active fragment thereof comprising at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, under suitable conditions for amplification of the nucleic acid, and amplifying the nucleic acid. In some embodiments, the amplifying can be performed by polymerase chain reaction, emulsion polymerase chain reaction, isothermal amplification, recombinase polymerase amplification, proximity ligation amplification, rolling circle amplification, loop-mediated isothermal amplification or strand displacement amplification. In some embodiments, the method includes amplification of the nucleic acid using a modified polymerase or a biologically active fragment thereof comprising or consisting of at least 85% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes amplifying a nucleic acid using a modified polymerase or a biologically active fragment thereof comprising or consisting of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes amplifying a nucleic acid using a modified polymerase or a biologically active fragment thereof comprising or consisting of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes amplifying a nucleic acid using a modified polymerase or a biologically active fragment thereof for amplifying the nucleic acid comprising or consisting of at least 150 contiguous amino acid residues having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof for amplifying the nucleic acid comprises or consists of at least 150 contiguous amino acid residues having at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof for amplifying the nucleic acid comprises or consists of at least 150 contiguous amino acid residues having at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the modified polymerase or the biologically active fragment thereof for amplifying the nucleic acid comprises or consists of at least 150 contiguous amino acid residues having at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof for amplifying the nucleic acid comprises or consists of at least 150 contiguous amino acid residues having at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the disclosure relates generally to a composition comprising or consisting of an isolated polymerase or a biologically active fragment thereof having at least 25 contiguous amino acid resides of the polymerase catalytic domain having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the isolated polymerase or the biologically active fragment thereof has detectable polymerase activity. In some embodiments, the isolated polymerase or the biologically active fragment thereof can include a DNA polymerase. In some embodiments, the isolated polymerase comprises a genetically engineered polymerase that is not naturally occurring. In some embodiments, the isolated polymerase comprises a fusion of one or more genetically engineered polymerases that retain polymerase activity. In some embodiments, the polymerase activity is measured as raw read accuracy, systematic error, strand bias, average read length or total sequencing throughput. In some embodiments, the isolated or modified polymerases as disclosed herein can include a fusion of a first naturally occurring polymerase domain (e.g., a catalytic domain) with a first genetically engineered polymerase domain (e.g., a binding domain). In some embodiments, the isolated or modified polymerases disclosed herein can include a fusion of a first genetically engineered polymerase domain (e.g., a catalytic domain) to a second genetically engineered polymerase domain (e.g., a binding domain), thereby forming an isolated or modified polymerase retaining polymerase activity.

In some embodiments, the disclosure is generally related to an isolated and purified polypeptide comprising or consisting of at least 90% identity to SEQ ID NO: 25 and includes an amino acid substitution at one or more positions corresponding to positions selected from the group consisting of: N780, E788, A558, D559, H823, H568, D718, D775, H576, E515 and N529, wherein the numbering is relative to SEQ ID NO: 25.

In some embodiments, the disclosure is generally related to an isolated and purified polypeptide having at least 90% identity to SEQ ID NO: 2 and includes an amino acid substitution at one or more positions corresponding to positions selected from the group consisting of: N487, N485, E493, A263, D264, H528, H273, D423, D480, H281, E220 and N234, wherein the numbering is relative to SEQ ID NO: 2.

In some embodiments, the disclosure is generally related to an isolated and purified polypeptide comprising at least 90% identity to SEQ ID NO: 28 and includes an amino acid substitution at one or more positions corresponding to positions selected from the group consisting of: N780, E788, A558, D559, H823, H568, D775 and D718, wherein the numbering is relative to SEQ ID NO: 28.

In some embodiments, the disclosure is generally related to an isolated and purified polypeptide comprising at least 90% identity to SEQ ID NO: 37 and includes an amino acid substitution at one or more positions corresponding to positions selected from the group consisting of: N485, E493, A263, D264, H528, H273, D423 and D480, wherein the numbering is relative to SEQ ID NO: 37.

In some embodiments, the disclosure is generally related to an isolated and purified polypeptide comprising or consisting of at least 80% identity to SEQ ID NO: 1 or a biologically active fragment thereof and having one or more amino acid mutations (e.g., substitutions) selected from the group consisting of N31R, N31K, H46R, D77K, D77H, D113N, D114R, D130A, D130H, D144M, D144K, L212A, E220K, N234R, N234K, V241K, V251K, A263K, D264A, D264R, D264Q, D264S, D264K, Y272R, H273N, H273R, L280R, H281A, H281M, E294S, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, E446Q, F448K, N457T, A462T, H473R, Y477F, D480R, D480F, D480H, D480A, D480S, D480N, D480Q, N485K N485W, N485Y, N487H, N487R N487W, N487F, N487I, V488R, E493Q, E493R, M495Q, H528A, H528F, H528S, V533I, H572R, W577Y and D579F, wherein the numbering is relative to the amino acid sequence of SEQ ID NO: 1.

In some embodiments, the disclosure is generally related to an isolated and purified polypeptide comprising or consisting of at least 80% identity to SEQ ID NO: 2 or a biologically active fragment thereof and having one or more amino acid mutations (e.g., substitutions) selected from the group consisting of N31R, N31K, D77K, D77H, D113N, D114R, D130A, D130H, D144M, D144K, L212A, E220K, N234R, N234K, V241K, V251K, D264A, D264R, D264Q, D264S, D264K, Y272R, H273N, H273R, L280R, H281A, H281M, E294S, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, F448K, N457T, A462T, H473R, Y477F, D480R, D480F, D480H, D480A, D480S, D480N, D480Q, N485K N485W, N485Y, N487H, N487R N487W, N487F, N487I, V488R, E493Q, E493R, M495Q, H528A, H528F, H528S, V533I, W577Y and D579F, wherein the numbering is relative to the amino acid sequence of SEQ ID NO: 2.

In some embodiments, the disclosure is generally related to an isolated and purified polypeptide comprising or consisting of at least 80% identity to SEQ ID NO: 16 or a biologically active fragment thereof and having one or more amino acid mutations (e.g., substitutions) selected from the group consisting of N782R, N780K, E788R, A558K, D559A, D559R, H823S, H823F, H568N, D718K, D775R, H576M, E515K and N529R, wherein the numbering is relative to the amino acid sequence of SEQ ID NO: 16. In some embodiments, the disclosure is generally related to an isolated and purified polypeptide comprising or consisting of at least 80% identity to SEQ ID NO: 16 or a biologically active fragment thereof, where the polypeptide comprises a mutation or combination of mutations relative to SEQ ID NO: 16 selected from any one or more of: N782, N780, E788, A558, D559, H823, H568, D718, D775, H576, E515 and N529, wherein the numbering is relative to the amino acid sequence of SEQ ID NO: 16.

In some embodiments, the disclosure is generally related to an isolated and purified polypeptide comprising or consisting of at least 80% identity to SEQ ID NO: 16 or a biologically active fragment thereof having one or more amino acid substitutions selected from the group consisting of N782R and D718K, wherein the numbering is relative to the amino acid sequence of SEQ ID NO: 16. In some embodiments, the disclosure is generally related to an isolated and purified polypeptide comprising or consisting of at least 80% identity to SEQ ID NO: 16 or a biologically active fragment thereof having one or more amino acid substitutions selected from the group consisting of H576M, N782R and D718K, wherein the numbering is relative to the amino acid sequence of SEQ ID NO: 16.

In some embodiments, the disclosure is generally related to an isolated and purified polypeptide comprising or consisting of at least 80% identity to SEQ ID NO: 16 or a biologically active fragment thereof having one or more amino acid substitutions selected from the group consisting of D559A, H568N, H576M, E788R, and N782R, wherein the numbering is relative to the amino acid sequence of SEQ ID NO: 16.

In some embodiments, the disclosure is generally related to an isolated and purified polypeptide comprising or consisting of at least 90% identity to SEQ ID NO: 16 or a biologically active fragment thereof and further comprising amino acid substitutions D559A, H568N, H576M, E788R, and N782R, wherein the numbering is relative to the amino acid sequence of SEQ ID NO: 16.

In some embodiments, the disclosure is generally related to an isolated and purified polypeptide comprising or consisting of at least 95% identity to SEQ ID NO: 16 or a biologically active fragment thereof and further comprising amino acid substitutions D559A, H568N, H576M, E788R, and N782R, wherein the numbering is relative to the amino acid sequence of SEQ ID NO: 16. In some embodiments, the disclosure is generally related to an isolated and purified polypeptide comprising or consisting of at least 98% identity to SEQ ID NO: 16 or a biologically active fragment thereof and further comprising amino acid substitutions D559A, H568N, H576M, E788R, and N782R, wherein the numbering is relative to the amino acid sequence of SEQ ID NO: 16.

In some embodiments, the disclosure is generally related to an isolated and purified polypeptide comprising or consisting of at least 90% identity to SEQ ID NO: 16 or a biologically active fragment thereof and further comprising amino acid substitutions H576M, N782R and D718K, wherein the numbering is relative to the amino acid sequence of SEQ ID NO: 16.

In some embodiments, the disclosure is generally related to an isolated and purified polypeptide comprising or consisting of at least 95% identity to SEQ ID NO: 16 or a biologically active fragment thereof and further comprising amino acid substitutions H576M, N782R and D718K, wherein the numbering is relative to the amino acid sequence of SEQ ID NO: 16.

In some embodiments, the disclosure is generally related to an isolated and purified polypeptide comprising or consisting of at least 98% identity to SEQ ID NO: 16 or a biologically active fragment thereof and further comprising amino acid substitutions H576M, N782R and D718K, wherein the numbering is relative to the amino acid sequence of SEQ ID NO: 16.

In some embodiments, the disclosure is generally related to an isolated and purified polypeptide comprising or consisting of at least 90% identity to SEQ ID NO: 16 or a biologically active fragment thereof and further comprising amino acid substitution D718K, wherein the numbering is relative to the amino acid sequence of SEQ ID NO: 16.

In some embodiments, the disclosure is generally related to an isolated and purified polypeptide comprising or consisting of at least 90% identity to SEQ ID NO: 16 or a biologically active fragment thereof and further comprising amino acid substitutions N782R and H576M, wherein the numbering is relative to the amino acid sequence of SEQ ID NO: 16.

In some embodiments, the disclosure is generally related to an isolated and purified polypeptide comprising or consisting of at least 80% identity to SEQ ID NO: 25 or a biologically active fragment thereof and having one or more amino acid mutations selected from the group consisting of N780K, E788R, A558K, D559A, D559R, H823S, H823F, H568N, D718K, D775R, H576M, E515K and N529R wherein the numbering is relative to the amino acid sequence of SEQ ID NO: 25.

In some embodiments, the disclosure is generally related to an isolated and purified polypeptide comprising or consisting of at least 80% identity to SEQ ID NO: 26 or a biologically active fragment thereof and having one or more amino acid mutations selected from the group consisting of N780K, E788R, A558K, D559A, D559R, H823S, H823F, D775R, H576M, H568N, E515K and N529R, wherein the numbering is relative to the amino acid sequence of SEQ ID NO: 26.

In some embodiments, the disclosure is generally related to an isolated and purified polypeptide comprising or consisting of at least 80% identity to SEQ ID NO: 27 or a biologically active fragment thereof and having one or more amino acid mutations selected from the group consisting of N780K, E788R, A558K, D559A, D559R, H823S, H823F, D775R, H576M, E515K and N529R, wherein the numbering is relative to the amino acid sequence of SEQ ID NO: 27.

In some embodiments, the disclosure is generally related to an isolated and purified polypeptide comprising or consisting of at least 80% identity to SEQ ID NO: 28 or a biologically active fragment thereof and having one or more amino acid mutations selected from the group consisting of N780K, E788R, A558K, D559A, D559R, H823S, H823F, D718K, D775R, H568N, E515K and N529R, wherein the numbering is relative to the amino acid sequence of SEQ ID NO: 28.

In some embodiments, the disclosure is generally related to an isolated and purified polypeptide comprising or consisting of at least 80% identity to SEQ ID NO: 29 or a biologically active fragment thereof and having one or more amino acid mutations selected from the group consisting of N780K, E788R, A558K, D559A, D559R, D718K, D775R, H576M, H568N, E515K and N529R, wherein the numbering is relative to the amino acid sequence of SEQ ID NO: 29.

In some embodiments, the disclosure relates generally to an isolated and purified polypeptide comprising or consisting of at least 90% identity to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, or a biologically active fragment thereof and can optionally further include one or more amino acid mutations selected from the group consisting of E515K and N529R, wherein the numbering is relative to the amino acid sequence of SEQ ID NO: 16.

In some embodiments, the disclosure is generally related to an isolated and purified polypeptide comprising or consisting of at least 80% identity to SEQ ID NO: 15 or a biologically active fragment thereof and having one or more amino acid mutations selected from the group consisting of E471K, N485R, R492K, D513K, A675K, D732R, S739W, V740R and E745Q, wherein the numbering is relative to the amino acid sequence of SEQ ID NO: 15.

In some embodiments, the disclosure is generally related to an isolated and purified polypeptide comprising or consisting of at least 80% identity to SEQ ID NO: 18 or a biologically active fragment thereof and having one or more amino acid mutations selected from the group consisting of E245K, S259R, T266K, E290K, A448K, D505R, A512W, R513R and E518Q, wherein the numbering is relative to SEQ ID NO: 18.

In some embodiments, the disclosure is generally related to an isolated nucleic acid sequence comprising or consisting of a nucleic acid sequencing encoding a polypeptide having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the isolated nucleic acid sequence comprising or consisting of the nucleic acid sequencing encoding the modified polymerase or the biologically active fragment thereof comprises or consists of at least 85% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the isolated nucleic acid sequence comprising or consisting of the nucleic acid sequencing encoding the modified polymerase or the biologically active fragment thereof comprises or consists of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the isolated nucleic acid sequence comprising or consisting of the nucleic acid sequencing encoding the modified polymerase or the biologically active fragment thereof comprises or consists of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the isolated nucleic acid sequence comprising or consisting of the nucleic acid sequencing encoding the modified polymerase or the biologically active fragment thereof comprises or consists of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the isolated nucleic acid sequence comprising or consisting of the nucleic acid sequencing encoding the modified polymerase or the biologically active fragment thereof comprises or consists of at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the disclosure is generally related to a vector comprising an isolated nucleic sequence encoding a polypeptide having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the vector comprising an isolated nucleic sequence encoding the modified polymerase or the biologically active fragment thereof comprises or consists of at least 85% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the vector comprising an isolated nucleic sequence encoding the modified polymerase or the biologically active fragment thereof comprises or consists of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the vector comprising an isolated nucleic sequence encoding the modified polymerase or the biologically active fragment thereof comprises or consists of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the vector comprising an isolated nucleic sequence encoding the modified polymerase or the biologically active fragment thereof comprises or consists of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the vector comprising an isolated nucleic sequence encoding the modified polymerase or the biologically active fragment thereof comprises or consists of at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the disclosure is generally related to a kit comprising an isolated polypeptide having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the kit comprises an isolated polypeptide comprising or consisting of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the kit comprises an isolated polypeptide comprising or consisting of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the kit comprises an isolated polypeptide comprising or consisting of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the kit comprises an isolated polypeptide comprising or consisting of at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the kit comprises an isolated polypeptide comprising or consisting of at least 150 contiguous amino acid residues having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the kit comprises an isolated polypeptide comprising or consisting of at least 150 contiguous amino acid residues having at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the kit comprises an isolated polypeptide comprising or consisting of at least 150 contiguous amino acid residues having at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the isolated polypeptide comprises at least 25 contiguous amino acid residues from the polypeptide catalytic and/or DNA binding domain.

In some embodiments, the disclosure generally relates to a method for identifying one or more mutations in a gene, comprising amplifying said one or more mutations in said gene using a modified polymerase or a biologically active fragment thereof having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, under conditions that allow amplification, and detecting said one or more mutations in said gene. In some embodiments, the method includes a modified polymerase or a biologically active fragment thereof comprising or consisting of at least 90% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method includes a modified polymerase or a biologically active fragment thereof comprising or consisting of at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the disclosure generally relates to a method for identifying one or more mutations in a gene (e.g., deletions, insertions, substitutions, rearrangements, splices, and/or fusions), comprising amplifying at least a portion of the gene spanning the one or more mutations using a modified polymerase or a biologically active fragment thereof having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, under conditions that allow amplification, and detecting the one or more mutations in the gene. In some embodiments, the gene can be clinically associated with cancer or an inherited disease. In some embodiments, the gene can be associated with pre-natal or newborn genetic abnormalities. In some embodiments, the disease can be associated with pathogenicity. In some embodiments, the gene can be associated with infectious disease. In some embodiments, the gene can be associated with disease resistance in plants or animals. In some embodiments, the gene can be associated with a pathology associated with a human or animal disease. In some embodiments, the gene can be associated with bacterial resistance to one or more antibiotics. In some embodiments, the gene can be associated with a genetically modified plant or food. In some embodiments, the gene can be associated with predictive or prognostic drug treatment of a disease in an animal or human. In some embodiments, the conditions that allow amplification of the one or more mutations within the gene include polymerase chain reaction, emulsion polymerase chain reaction, isothermal amplification, loop-mediated isothermal amplification, recombinase polymerase amplification, proximity ligation amplification, rolling-circle amplification or strand displacement amplification. In some embodiments, the method includes using a modified polymerase or a biologically active fragment thereof comprising or consisting of at least 150 contiguous amino acid residues having at least 80% identity to SEQ ID NO: 2, SEQ ID NO:

3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises at least 25 contiguous amino acid residues from the polymerase catalytic and/or DNA binding domain.

In some embodiments, the disclosure generally relates to a polymerase or a biologically active fragment thereof having DNA polymerase activity and at least 80% identity to SEQ ID NO: 1, SEQ ID NO: 2, SEQ ID NO: 15, SEQ ID NO: 16, SEQ ID NO: 18, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, where the polymerase or the biologically active fragment thereof includes at least one amino acid mutation as compared to SEQ ID NO: 1, SEQ ID NO: 2, SEQ ID NO: 15, SEQ ID NO: 16, SEQ ID NO: 18, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the polymerase or biologically active fragment thereof comprises at least one amino acid mutation located in the polymerase DNA binding or catalytic domain. In some embodiments, the polymerase or the biologically active fragment thereof comprises substantial identity over at least 150 contiguous amino acid residues with respect to any part of SEQ ID NO: 1, SEQ ID NO: 15, SEQ ID NO: 16, SEQ ID NO. 18, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the polymerase or the biologically active fragment thereof comprises or consists of 150 contiguous amino acid residues of any part of the polymerase DNA binding or catalytic domain. In some embodiments, the polymerase or the biologically active fragment thereof comprises at least 90% identity over the 150 contiguous amino acid residues with respect to any part of SEQ ID NO: 15, SEQ ID NO: 16, SEQ ID NO: 18, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the disclosure generally relates to a substantially purified polymerase or a biologically active fragment thereof having an amino acid sequence comprising or consisting of at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the disclosure generally relates to a substantially purified polymerase or a biologically active fragment thereof having an amino acid sequence comprising or consisting of a sequence variant having at least 95% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the disclosure generally relates to a substantially purified polymerase or a biologically active fragment thereof having an amino acid sequence comprising or consisting of a sequence variant having at least 98% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the disclosure generally relates to a substantially purified polymerase or a biologically active fragment thereof having an amino acid sequence comprising or consisting of a sequence variant having at least 99% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the disclosure generally relates to a substantially purified polymerase having an amino acid sequence comprising or consisting of a fragment of SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37 that retains polymerase activity. In some embodiments, the polymerase activity is selected from DNA binding activity, primer extension activity, strand displacement activity, proofreading activity, nick-initiated polymerase activity, reverse transcriptase activity accuracy, mean read length, thermostability, systematic error, total sequencing throughput, strand bias or nucleotide polymerization activity. In some embodiments, the polymerase activity is selected from one or more sequencing based metrics selected from raw read accuracy, mean read length, systematic error, total sequencing throughput, or strand bias. In some embodiments, the disclosure generally relates to a substantially purified polymerase having an amino acid sequence comprising or consisting of a biologically active fragment of SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37 having polymerase activity selected from increased accuracy, increased mean read length, lowered systematic error, increased total sequencing throughput, or decreased strand bias as compared to polymerase activity of SEQ ID NO. 1 or SEQ ID NO: 16. In some embodiments, the polymerase activity is determined in the presence of a high ionic strength solution.

In some embodiments, the disclosure relates generally to a composition comprising a recombinant polymerase homologous to SEQ ID NO: 1 or a biologically active fragment thereof having at least 80% identity to SEQ ID NO: 1 or a biologically active fragment thereof and where the recombinant polymerase homologous to SEQ ID NO: 1 comprises a mutation or combination of mutations relative to SEQ ID NO: 1 selected from H46R, and where the polymerase further includes a mutation at one or more of E446Q, H572R, H273R, H281A, H473R, Y477F, D480R, or H528A, wherein the numbering is relative to SEQ ID NO: 1.

In some embodiments, the disclosure relates generally to a composition comprising a recombinant polymerase homologous to SEQ ID NO: 1 or a biologically active fragment thereof having at least 80% identity to SEQ ID NO: 1 or a biologically active fragment thereof and where the recombinant polymerase homologous to SEQ ID NO: 1 comprises a mutation or combination of mutations relative to SEQ ID NO: 1 selected from E446Q, where the polymerase further includes a mutation at one or more of H46R, H572R, H273R, H281A, H473R, Y477F, D480R, or H528A, wherein the numbering is relative to SEQ ID NO: 1.

In some embodiments, the disclosure relates generally to a composition comprising a recombinant polymerase homologous to SEQ ID NO: 1 or a biologically active fragment thereof having at least 80% identity to SEQ ID NO: 1 or a biologically active fragment thereof and where the recombinant polymerase homologous to SEQ ID NO: 1 comprises a mutation or combination of mutations relative to SEQ ID NO: 1 selected from H572R, where the polymerase further includes a mutation at one or more of H46R, E446Q, H572R, H273R, H281A, H473R, Y477F, D480R, or H528A, wherein the numbering is relative to SEQ ID NO: 1.

In some embodiments, the disclosure relates generally to a composition comprising a recombinant polymerase homologous to SEQ ID NO: 1 or a biologically active fragment thereof having at least 80% identity to SEQ ID NO: 1 or a biologically active fragment thereof and where the recombinant polymerase homologous to SEQ ID NO: 1 comprises a C93 mutation, wherein the numbering is relative to SEQ ID NO: 1.

In some embodiments, the disclosure relates generally to a composition comprising a recombinant polymerase homologous to SEQ ID NO: 1 or a biologically active fragment thereof having at least 80% identity to SEQ ID NO: 1 or a biologically active fragment thereof and where the recombinant polymerase homologous to SEQ ID NO: 1 comprises a Q238 mutation, wherein the numbering is relative to SEQ ID NO: 1.

In some embodiments, the disclosure relates generally to a composition comprising a recombinant polymerase homologous to SEQ ID NO: 1 or a biologically active fragment thereof having at least 80% identity to SEQ ID NO: 1 or a biologically active fragment thereof and where the recombinant polymerase homologous to SEQ ID NO: 1 comprises a H273 mutation, wherein the numbering is relative to SEQ ID NO: 1.

In some embodiments, the disclosure relates generally to a composition comprising a recombinant polymerase homologous to SEQ ID NO: 1 or a biologically active fragment thereof having at least 80% identity to SEQ ID NO: 1 or a biologically active fragment thereof and where the recombinant polymerase homologous to SEQ ID NO: 1 comprises a H281 mutation, wherein the numbering is relative to SEQ ID NO: 1.

In some embodiments, the disclosure relates generally to a composition comprising a recombinant polymerase homologous to SEQ ID NO: 1 or a biologically active fragment thereof having at least 80% identity to SEQ ID NO: 1 or a biologically active fragment thereof and where the recombinant polymerase homologous to SEQ ID NO: 1 comprises a H473 mutation, wherein the numbering is relative to SEQ ID NO: 1.

In some embodiments, the disclosure relates generally to a composition comprising a recombinant polymerase homologous to SEQ ID NO: 1 or a biologically active fragment thereof having at least 80% identity to SEQ ID NO: 1 or a biologically active fragment thereof and where the recombinant polymerase homologous to SEQ ID NO: 1 comprises a H528 mutation, wherein the numbering is relative to SEQ ID NO: 1.

In some embodiments, the recombinant polymerase homologous to SEQ ID NO: 1 comprises a mutation that increases dissociation time constant, increases processivity, increases accuracy, increases average read length, increases minimum read length, increases AQ20 or increase 200Q17 value as compared to a reference polymerase lacking a mutation or combination of mutations relative to the recombinant polymerase homologous to SEQ ID NO: 1. In some embodiments, the recombinant polymerase homologous to SEQ ID NO: 1 comprises increased accuracy as compared to a reference polymerase lacking a mutation or combination of mutations relative to the recombinant polymerase homologous to SEQ ID NO: 1. In some embodiments, the recombinant polymerase homologous to SEQ ID NO: 1 comprises increased average read length as compared to a reference polymerase lacking a mutation or combination of mutations relative to the recombinant polymerase homologous to SEQ ID NO: 1. In some embodiments, the recombinant polymerase homologous to SEQ ID NO: 1 comprises increased sequencing throughput in the presence of a high ionic strength solution as compared to a reference polymerase lacking a mutation or combination of mutations relative to the recombinant polymerase homologous to SEQ ID NO: 1. In some embodiments, the recombinant polymerase homologous to SEQ ID NO: 1 comprises increased dissociation time constant as compared to a reference polymerase lacking a mutation or combination of mutations relative to the recombinant polymerase homologous to SEQ ID NO: 1. In some embodiments, the increased dissociation time constant, increased processivity, increased accuracy, increased average read length, increased minimum read length, increased AQ20 or increased 200Q17 value is measured using an ISFET. In some embodiments, the ISFET is coupled to a semiconductor based sequencing platform. In some embodiments, the semiconductor based sequencing platform is a Personal Genome Machine or a Proton Sequencer. In some embodiments, the disclosure relates generally to a composition comprising a recombinant polymerase homologous to SEQ ID NO: 2 or a biologically active fragment thereof having at least 80% identity to SEQ ID NO: 2 or a biologically active fragment thereof and where the recombinant polymerase homologous to SEQ ID NO: 2 comprises a mutation or combination of mutations relative to SEQ ID NO: 2 selected from N487R, and where the recombinant polymerase further includes a mutation at one or more of H281M, D423K, H273N, E493R, and D264A, wherein the numbering is relative to SEQ ID NO: 2.

In some embodiments, the disclosure relates generally to a composition comprising a recombinant polymerase homologous to SEQ ID NO: 2 or a biologically active fragment thereof having at least 80% identity to SEQ ID NO: 2 or a biologically active fragment thereof and where the recombinant polymerase homologous to SEQ ID NO: 2 comprises a mutation or combination of mutations relative to SEQ ID NO: 2 selected from H281M, where the recombinant polymerase further includes a mutation at one or more of N487R, D264A, H273N and E493R, wherein the numbering is relative to SEQ ID NO: 2.

In some embodiments, the disclosure relates generally to a composition comprising a recombinant polymerase homologous to SEQ ID NO: 2 or a biologically active fragment thereof having at least 80% identity to SEQ ID NO: 2 or a biologically active fragment thereof and where the recombinant polymerase homologous to SEQ ID NO: 2 comprises a mutation or combination of mutations relative to SEQ ID NO: 2 selected from E493R where the recombinant polymerase further includes a mutation at one or more of N487R, H281M, D423K, D264A, or H273N, wherein the numbering is relative to SEQ ID NO: 2.

In some embodiments, the disclosure relates generally to a composition comprising a recombinant polymerase homologous to SEQ ID NO: 2 or a biologically active fragment thereof having at least 80% identity to SEQ ID NO: 2 or a biologically active fragment thereof and where the recombinant polymerase homologous to SEQ ID NO: 2 comprises a D264A or D264R mutation, wherein the numbering is relative to SEQ ID NO: 2.

In some embodiments, the disclosure relates generally to a composition comprising a recombinant polymerase homologous to SEQ ID NO: 2 or a biologically active fragment thereof having at least 80% identity to SEQ ID NO: 2 or a biologically active fragment thereof and where the recombinant polymerase homologous to SEQ ID NO: 2 comprises a H273N mutation, wherein the numbering is relative to SEQ ID NO: 2.

In some embodiments, the disclosure relates generally to a composition comprising a recombinant polymerase homologous to SEQ ID NO: 2 or a biologically active fragment thereof having at least 80% identity to SEQ ID NO: 2 or a biologically active fragment thereof and where the recombinant polymerase homologous to SEQ ID NO: 2 comprises a D423K mutation, wherein the numbering is relative to SEQ ID NO: 2.

In some embodiments, the disclosure relates generally to a composition comprising a recombinant polymerase homologous to SEQ ID NO: 2 or a biologically active fragment thereof having at least 80% identity to SEQ ID NO: 2 or a biologically active fragment thereof and where the recombinant polymerase homologous to SEQ ID NO: 2 comprises a H281M mutation, wherein the numbering is relative to SEQ ID NO: 2.

In some embodiments, the disclosure relates generally to a composition comprising a recombinant polymerase containing an amino acid sequence that is at least 80% identical to SEQ ID NO: 2 or a biologically active fragment thereof, wherein the recombinant polymerase includes one or more amino acid substitutions at positions corresponding to positions selected from the group consisting of: N487, N485, E493, A263, D264, H528, H273, D423, D480 and H281, wherein the numbering is relative to SEQ ID NO: 2. In some embodiments, the recombinant polymerase includes one or more amino acid substitutions at positions corresponding to positions selected from the group consisting of: N487R, N485K, E493R, A263K, D264A, D264R, H528S, H528F, H273N, D423K, D480R and H281M, wherein the numbering is relative to SEQ ID NO: 2. In some embodiments, the modified polymerase comprises a recombinant polymerase having an amino acid sequence that corresponds to one or more amino acid substitutions at positions corresponding to positions selected from the group consisting of: N487, N485, E493, A263, D264, H528, H273, D423, D480 and H281, wherein the numbering is relative to SEQ ID NO: 2.

In some embodiments, the recombinant polymerase homologous to SEQ ID NO: 2 comprises a mutation that increases accuracy, increases average read length, increases minimum read length, increases AQ20, increases 200Q17, increases total sequencing throughput, reduces strand bias or lowers systematic errors as compared to a reference polymerase lacking a mutation (or combination of mutations) relative to the recombinant polymerase homologous to SEQ ID NO: 2. In some embodiments, the recombinant polymerase homologous to SEQ ID NO: 2 comprises increased raw read accuracy as compared to a reference polymerase lacking a mutation or combination of mutations relative to the recombinant polymerase homologous to SEQ ID NO: 2. In some embodiments, the recombinant polymerase homologous to SEQ ID NO: 2 comprises increased average read length as compared to a reference polymerase lacking a mutation or combination of mutations relative to the recombinant polymerase homologous to SEQ ID NO: 2. In some embodiments, the recombinant polymerase homologous to SEQ ID NO: 2 comprises increased total sequencing throughput as compared to a reference polymerase lacking a mutation or combination of mutations relative to the recombinant polymerase homologous to SEQ ID NO: 2. In some embodiments, the recombinant polymerase homologous to SEQ ID NO: 2 comprises increased sequencing throughput in the presence of a high ionic strength solution as compared to a reference polymerase lacking a mutation or combination of mutations relative to the recombinant polymerase homologous to SEQ ID NO: 2. In some embodiments, the recombinant polymerase homologous to SEQ ID NO: 2 comprises decreased strand bias as compared to a reference polymerase lacking a mutation or combination of mutations relative to the recombinant polymerase homologous to SEQ ID NO: 2. In some embodiments, the recombinant polymerase homologous to SEQ ID NO: 2 comprises lowered systematic error as compared to a reference polymerase lacking a mutation or combination of mutations relative to the recombinant polymerase homologous to SEQ ID NO: 2. In some embodiments, the increased accuracy, increased average read length, increased minimum read length, increased sequencing throughput, reduced strand bias or lowered systematic error is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corporation (CA).

In some embodiments, the recombinant polymerase homologous to SEQ ID NO: 2 comprises a mutation that increases dissociation time constant, increases processivity, increases AQ20 or increases 200Q17 value as compared to a reference polymerase lacking a mutation (or combination of mutations) relative to the recombinant polymerase homologous to SEQ ID NO: 2. In some embodiments, the recombinant polymerase homologous to SEQ ID NO: 2 comprises increased dissociation time constant as compared to a reference polymerase lacking a mutation or combination of mutations relative to the recombinant polymerase homologous to SEQ ID NO: 2. In some embodiments, the increased dissociation time constant, increased processivity, increased AQ20 or increased 200Q17 value is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corporation (CA).

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase homologous to SEQ ID NO: 16 comprises a mutation or combination of mutations relative to SEQ ID NO: 16 selected from N782R, and where the recombinant polymerase further includes a mutation at one or more of N780K, E788R, A558K, D559A, D559R, H823S, H823F, H568N, D718K, D775R, E515K, N529R, or H576M, wherein the numbering is relative to SEQ ID NO: 16.

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase comprises a mutation or combination of mutations relative to SEQ ID NO: 16 selected from N780K, where the recombinant polymerase further includes a mutation at one or more of N782R, E788R, A558K, D559A, D559R, H823S, H823F, H568N, D718K, D775R, E515K, N529R, or H576M, wherein the numbering is relative to SEQ ID NO: 16.

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase homologous to SEQ ID NO: 16 comprises a mutation or combination of mutations relative to SEQ ID NO: 16 selected from E788R where the recombinant polymerase further includes a mutation at one or more of N782R, N780K, A558K, D559A, D559R, H823S, H823F, H568N, D718K, D775R, E515K, N529R, or H576M, wherein the numbering is relative to SEQ ID NO: 16.

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase homologous to SEQ ID NO: 16 comprises an A558K mutation, wherein the numbering is relative to SEQ ID NO: 16.

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase homologous to SEQ ID NO: 16 comprises a D559A or D559R mutation, wherein the numbering is relative to SEQ ID NO: 16.

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase homologous to SEQ ID NO: 16 comprises a H568N mutation, wherein the numbering is relative to SEQ ID NO: 16.

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase homologous to SEQ ID NO: 16 comprises a H823S or H823F mutation, wherein the numbering is relative to SEQ ID NO: 16.

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase homologous to SEQ ID NO: 16 comprises a D718K mutation, wherein the numbering is relative to SEQ ID NO: 16.

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase homologous to SEQ ID NO: 16 comprises a D775R mutation, wherein the numbering is relative to SEQ ID NO: 16.

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase homologous to SEQ ID NO: 16 comprises a H576M mutation, wherein the numbering is relative to SEQ ID NO: 16.

In some embodiments, the disclosure relates generally to a composition comprising a recombinant polymerase homologous to SEQ ID NO: 16 or a biologically active fragment thereof having at least 80% identity to SEQ ID NO: 16 or a biologically active fragment thereof and where the recombinant polymerase homologous to SEQ ID NO: 16 optionally includes one or more amino acid mutations selected from the group consisting of E515K and N529R, wherein the numbering is relative to SEQ ID NO: 16.

In some embodiments, the recombinant polymerase homologous to SEQ ID NO: 16 comprises a mutation that increases accuracy, increases average read length, increases minimum read length, increases AQ20, increases 200Q17, increases total sequencing throughput, reduces strand bias or lowers systematic errors as compared to a reference polymerase lacking a mutation (or combination of mutations) relative to the recombinant polymerase homologous to SEQ ID NO: 16. In some embodiments, the recombinant polymerase homologous to SEQ ID NO: 16 comprises increased raw read accuracy as compared to a reference polymerase lacking a mutation or combination of mutations relative to the recombinant polymerase homologous to SEQ ID NO: 16. In some embodiments, the recombinant polymerase homologous to SEQ ID NO: 16 comprises increased average read length as compared to a reference polymerase lacking a mutation or combination of mutations relative to the recombinant polymerase homologous to SEQ ID NO: 16. In some embodiments, the recombinant polymerase homologous to SEQ ID NO: 16 comprises increased total sequencing throughput as compared to a reference polymerase lacking a mutation or combination of mutations relative to the recombinant polymerase homologous to SEQ ID NO: 16. In some embodiments, the recombinant polymerase homologous to SEQ ID NO: 16 comprises increased sequencing throughput in the presence of a high ionic strength solution as compared to a reference polymerase lacking a mutation or combination of mutations relative to the recombinant polymerase homologous to SEQ ID NO: 16. In some embodiments, the recombinant polymerase homologous to SEQ ID NO: 16 comprises decreased strand bias as compared to a reference polymerase lacking a mutation or combination of mutations relative to the recombinant polymerase homologous to SEQ ID NO: 16. In some embodiments, the recombinant polymerase homologous to SEQ ID NO: 16 comprises lowered systematic error as compared to a reference polymerase lacking a mutation or combination of mutations relative to the recombinant polymerase homologous to SEQ ID NO: 16. In some embodiments, the increased accuracy, increased average read length, increased minimum read length, increased sequencing throughput, reduced strand bias or lowered systematic error is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corporation (CA).

In some embodiments, the recombinant polymerase homologous to SEQ ID NO: 16 comprises a mutation that increases dissociation time constant, increases processivity, increases AQ20 or increase 200Q17 value as compared to a reference polymerase lacking a mutation (or combination of mutations) relative to the recombinant polymerase homologous to SEQ ID NO: 16. In some embodiments, the recombinant polymerase homologous to SEQ ID NO: 16 comprises increased dissociation time constant as compared to a reference polymerase lacking a mutation or combination of mutations relative to the recombinant polymerase homologous to SEQ ID NO: 16. In some embodiments, the increased dissociation time constant, increased processivity, increased AQ20 or increased 200Q17 value is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corporation (CA).

In some embodiments, the disclosure generally relates to a composition comprising a recombinant polymerase homologous to SEQ ID NO: 15 or a biologically active fragment thereof having at least 80% identity to SEQ ID NO: 15 or a biologically active fragment thereof and where the recombinant polymerase homologous to SEQ ID NO: 15 comprises a mutation or combination of mutations relative to SEQ ID NO: 15 selected from E471K, wherein the polymerase further includes a mutation at one or more of: N485R, R492K, D513K, A675K, D732R, S739W, V740R and E745Q, wherein the numbering is relative to SEQ ID NO: 15.

In some embodiments, the disclosure generally relates to a composition comprising a recombinant polymerase homologous to SEQ ID NO: 15 or a biologically active fragment thereof having at least 80% identity to SEQ ID NO: 15 or a biologically active fragment thereof and where the recombinant polymerase homologous to SEQ ID NO: 15 comprises a mutation or combination of mutations relative to SEQ ID NO: 15 selected from V740R, wherein the polymerase further includes a mutation at one or more of: E471K, N485R, D513K and E745Q, wherein the numbering is relative to SEQ ID NO: 15.

In some embodiments, the disclosure generally relates to a composition comprising a recombinant polymerase homologous to SEQ ID NO: 15 or a biologically active fragment thereof having at least 80% identity to SEQ ID NO: 15 or a biologically active fragment thereof and where the recombinant polymerase homologous to SEQ ID NO: 15 comprises a N485 mutation, wherein the numbering is relative to SEQ ID NO: 15. In some embodiments, the disclosure generally relates to a composition comprising a recombinant polymerase homologous to SEQ ID NO: 15 or a biologically active fragment thereof having at least 80% identity to SEQ ID NO: 15 or a biologically active fragment thereof and where the recombinant polymerase homologous to SEQ ID NO: 15 comprises a mutation or combination of mutations relative to SEQ ID NO: 15 selected from a D513 mutation, wherein the numbering is relative to SEQ ID NO: 15.

In some embodiments, the disclosure generally relates to a composition comprising a recombinant polymerase homologous to SEQ ID NO: 15 or a biologically active fragment thereof having at least 80% identity to SEQ ID NO: 15 or a biologically active fragment thereof and where the recombinant polymerase homologous to SEQ ID NO: 15 comprises a mutation or combination of mutations relative to SEQ ID NO: 15 selected from a D732 mutation, wherein the numbering is relative to SEQ ID NO: 15.

In some embodiments, the disclosure generally relates to a composition comprising a recombinant polymerase homologous to SEQ ID NO: 15 or a biologically active fragment thereof having at least 80% identity to SEQ ID NO: 15 or a biologically active fragment thereof and where the recombinant polymerase homologous to SEQ ID NO: 15 comprises a mutation or combination of mutations relative to SEQ ID NO: 15 selected from an E745 mutation, wherein the numbering is relative to SEQ ID NO: 15.

In some embodiments, the recombinant polymerase homologous to SEQ ID NO: 15 or the biologically active fragment thereof comprises increased accuracy as compared to a reference polymerase lacking a mutation or combination of mutations relative to SEQ ID NO: 15 or increased dissociation time constant as compared to a reference polymerase lacking a mutation or combination of mutations relative to SEQ ID NO: 15 or increased minimum read length as compared to a reference polymerase lacking a mutation or combination of mutations relative to SEQ ID NO: 15 or increased sequencing performance in the presence of a high ionic strength solution as compared to a reference polymerase lacking a mutation or combination of mutations relative to the recombinant polymerase homologous to SEQ ID NO: 15 or increased average read length as compared to a reference polymerase lacking a mutation or combination of mutations relative to SEQ ID NO: 15.

In some embodiments, the disclosure is generally related to a composition comprising a recombinant polymerase homologous to SEQ ID NO: 18 or a biologically active fragment thereof having at least 80% identity to SEQ ID NO: 18 or a biologically fragment thereof and where the recombinant polymerase homologous to SEQ ID NO: 18 comprises a mutation or combination of mutations relative to SEQ ID NO: 18 selected from E245K, where the polymerase further includes a mutation at one or more of: S259R, T266K, E290K, A448K, D505R, A512W, R513R and E518Q, wherein the numbering is relative to SEQ ID NO: 18.

In some embodiments, the disclosure is generally related to a composition comprising a recombinant polymerase homologous to SEQ ID NO: 18 or a biologically active fragment thereof having at least 80% identity to SEQ ID NO: 18 or a biologically fragment thereof and where the recombinant polymerase homologous to SEQ ID NO: 18 comprises a mutation or combination of mutations relative to SEQ ID NO: 18 selected from E245K, where the polymerase further includes a mutation at one or more of: S259R, T266K, E290K, A448K, D505R, A512W, R513R and E518Q, wherein the numbering is relative to SEQ ID NO: 18.

In some embodiments, the disclosure is generally related to a composition comprising a recombinant polymerase homologous to SEQ ID NO: 18 or a biologically active fragment thereof having at least 80% identity to SEQ ID NO: 18 or a biologically fragment thereof and where the recombinant polymerase homologous to SEQ ID NO: 18 comprises a mutation or combination of mutations relative to SEQ ID NO: 18 selected from D505R, where the polymerase further includes a mutation at one or more of: E245K, S259R, T266K, E290K, A448K, A512W, R513R and E518Q, wherein the numbering is relative to SEQ ID NO: 18.

In some embodiments, the disclosure is generally related to a composition comprising a recombinant polymerase homologous to SEQ ID NO: 18 or a biologically active fragment thereof having at least 80% identity to SEQ ID NO: 18 or a biologically fragment thereof and where the recombinant polymerase homologous to SEQ ID NO: 18 comprises an E290 mutation, wherein the numbering is relative to SEQ ID NO: 18.

In some embodiments, the disclosure is generally related to a composition comprising a recombinant polymerase homologous to SEQ ID NO: 18 or a biologically active fragment thereof having at least 80% identity to SEQ ID NO: 18 or a biologically fragment thereof and where the recombinant polymerase homologous to SEQ ID NO: 18 comprises an S259 mutation, wherein the numbering is relative to SEQ ID NO: 18.

In some embodiments, the disclosure is generally related to a composition comprising a recombinant polymerase homologous to SEQ ID NO: 18 or a biologically active fragment thereof having at least 80% identity to SEQ ID NO: 18 or a biologically fragment thereof and where the recombinant polymerase homologous to SEQ ID NO: 18 comprises an R513 mutation, wherein the numbering is relative to SEQ ID NO: 18.

In some embodiments, the disclosure is generally related to a composition comprising a recombinant polymerase homologous to SEQ ID NO: 18 or a biologically active fragment thereof having at least 80% identity to SEQ ID NO: 18 or a biologically fragment thereof and where the recombinant polymerase homologous to SEQ ID NO: 18 comprises an A512 mutation, wherein the numbering is relative to SEQ ID NO: 18.

In some embodiments, the recombinant polymerase homologous to SEQ ID NO: 18 or the biologically active fragment thereof comprises increased accuracy as compared to a reference polymerase lacking a mutation or combination of mutations relative to SEQ ID NO: 18 or increased dissociation time constant activity as compared to a reference polymerase lacking a mutation or combination of mutations relative to SEQ ID NO: 18 or increased minimum read length as compared to a reference polymerase lacking a mutation or combination of mutations relative to SEQ ID NO: 18 or increased sequencing performance in the presence of high ionic strength as compared to a reference polymerase lacking a mutation or combination of mutations relative to the recombinant polymerase homologous to SEQ ID NO: 18 or increased average read length as compared to a reference polymerase lacking a mutation or combination of mutations relative to SEQ ID NO: 18. In some embodiments, the disclosure generally relates to a composition comprising a recombinant polymerase homologous to SEQ ID NO: 25 or a biologically active fragment thereof having at least 80% identity to SEQ ID NO: 25 or a biologically active fragment thereof and where the recombinant polymerase homologous to SEQ ID NO: 25 comprises a mutation or combination of mutations relative to SEQ ID NO: 25 selected from D718K, wherein the polymerase further includes a mutation at one or more of: N780K, E788R, A558K, D559A, D559R, H823S, H823F, H568N, D775R, and H576M, wherein the numbering is relative to SEQ ID NO: 25.

In some embodiments, the disclosure generally relates to a composition comprising a recombinant polymerase homologous to SEQ ID NO: 25 or a biologically active fragment thereof having at least 80% identity to SEQ ID NO: 25 or a biologically active fragment thereof and where the recombinant polymerase homologous to SEQ ID NO: 25 comprises a mutation or combination of mutations relative to SEQ ID NO: 25 selected from H568N, wherein the polymerase further includes a mutation at one or more of: N780K, E788R, A558K, D559A, D559R, H823S, H823F, D718K, D775R, or H576M, wherein the numbering is relative to SEQ ID NO: 25.

In some embodiments, the disclosure generally relates to a composition comprising a recombinant polymerase homologous to SEQ ID NO: 25 or a biologically active fragment thereof having at least 80% identity to SEQ ID NO: 25 or a biologically active fragment thereof and where the recombinant polymerase homologous to SEQ ID NO: 25 comprises a D718K mutation, wherein the numbering is relative to SEQ ID NO: 25.

In some embodiments, the disclosure generally relates to a composition comprising a recombinant polymerase homologous to SEQ ID NO: 25 or a biologically active fragment thereof having at least 80% identity to SEQ ID NO: 25 or a biologically active fragment thereof and where the recombinant polymerase homologous to SEQ ID NO: 25 comprises a mutation or combination of mutations relative to SEQ ID NO: 25 comprising a H823S or H823F mutation, wherein the numbering is relative to SEQ ID NO: 25.

In some embodiments, the disclosure generally relates to a composition comprising a recombinant polymerase homologous to SEQ ID NO: 25 or a biologically active fragment thereof having at least 80% identity to SEQ ID NO: 25 or a biologically active fragment thereof and where the recombinant polymerase homologous to SEQ ID NO: 25 comprises a mutation or combination of mutations relative to SEQ ID NO: 25 selected from a N780K mutation, wherein the numbering is relative to SEQ ID NO: 25.

In some embodiments, the disclosure generally relates to a composition comprising a recombinant polymerase homologous to SEQ ID NO: 25 or a biologically active fragment thereof having at least 80% identity to SEQ ID NO: 25 or a biologically active fragment thereof and where the recombinant polymerase homologous to SEQ ID NO: 25 comprises a mutation or combination of mutations relative to SEQ ID NO: 25 selected from an E788R mutation, wherein the numbering is relative to SEQ ID NO: 25.

In some embodiments, the disclosure relates generally to a composition comprising a recombinant polymerase homologous to SEQ ID NO: 25 or a biologically active fragment thereof having at least 80% identity to SEQ ID NO: 25 or a biologically active fragment thereof and where the recombinant polymerase homologous to SEQ ID NO: 25 optionally includes one or more amino acid mutations selected from the group consisting of E515K and N529R, wherein the numbering is relative to SEQ ID NO: 25.

In some embodiments, the disclosure relates to a recombinant polymerase homologous to SEQ ID NO: 25 or a biologically active fragment thereof which comprises increased accuracy as compared to a reference polymerase lacking a mutation or combination of mutations relative to SEQ ID NO: 25 or increased read length as compared to a reference polymerase lacking a mutation or combination of mutations relative to SEQ ID NO: 25 or increased total sequencing throughput as compared to a reference polymerase lacking a mutation or combination of mutations relative to SEQ ID NO: 25 or decreased systematic error as compared to a reference polymerase lacking a mutation or combination of mutations relative to SEQ ID NO: 25 or decreased strand bias as compared to a reference polymerase lacking a mutation or combination of mutations relative to the recombinant polymerase homologous to SEQ ID NO: 25 or increased average read length as compared to a reference polymerase lacking a mutation or combination of mutations relative to SEQ ID NO: 25. In some embodiments, the composition comprising a recombinant polymerase homologous to SEQ ID NO: 25 or a biologically active fragment thereof comprises at least 90% identity to SEQ ID NO: 25 or a biologically active fragment thereof.

In some embodiments, the recombinant polymerase homologous to SEQ ID NO: 25 comprises a mutation that increases accuracy, increases average read length, increases minimum read length, increases AQ20, increases 200Q17, increases total sequencing throughput, reduces strand bias or lowers systematic errors as compared to a reference polymerase lacking a mutation (or combination of mutations) relative to the recombinant polymerase homologous to SEQ ID NO: 25. In some embodiments, the recombinant polymerase homologous to SEQ ID NO: 25 comprises increased accuracy as compared to a reference polymerase lacking a mutation or combination of mutations relative to the recombinant polymerase homologous to SEQ ID NO: 25. In some embodiments, the recombinant polymerase homologous to SEQ ID NO: 25 comprises increased average read length as compared to a reference polymerase lacking a mutation or combination of mutations relative to the recombinant polymerase homologous to SEQ ID NO: 25. In some embodiments, the recombinant polymerase homologous to SEQ ID NO: 25 comprises increased total sequencing throughput as compared to a reference polymerase lacking a mutation or combination of mutations relative to the recombinant polymerase homologous to SEQ ID NO: 25. In some embodiments, the recombinant polymerase homologous to SEQ ID NO: 25 comprises decreased strand bias as compared to a reference polymerase lacking a mutation or combination of mutations relative to the recombinant polymerase homologous to SEQ ID NO: 25. In some embodiments, the recombinant polymerase homologous to SEQ ID NO: 25 comprises lowered systematic error as compared to a reference polymerase lacking a mutation or combination of mutations relative to the recombinant polymerase homologous to SEQ ID NO: 25. In some embodiments, the increased accuracy, increased average read length, increased minimum read length, increased sequencing throughput, reduced strand bias or lowered systematic error is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corporation (CA).

In some embodiments, the recombinant polymerase homologous to SEQ ID NO: 25 comprises a mutation that increases dissociation time constant, increases processivity, increases AQ20 or increase 200Q17 value as compared to a reference polymerase lacking a mutation (or combination of mutations) relative to the recombinant polymerase homologous to SEQ ID NO: 25. In some embodiments, the recombinant polymerase homologous to SEQ ID NO: 25 comprises increased dissociation time constant as compared to a reference polymerase lacking a mutation or combination of mutations relative to the recombinant polymerase homologous to SEQ ID NO: 25.

In some embodiments, the disclosure generally relates to a recombinant polymerase containing an amino acid sequence that is at least 80% identical to SEQ ID NO: 25 or a biologically active fragment thereof, wherein the recombinant polymerase includes one or more amino acid substitutions at positions corresponding to positions selected from the group consisting of: N780, E788, A558, D559, H823, H568, D718, D775 and H576, wherein the numbering is relative to SEQ ID NO: 25. In some embodiments, the recombinant polymerase contains an amino acid sequence that is at least 80% identical to SEQ ID NO: 25 or a biologically active fragment thereof, wherein the recombinant polymerase includes one or more amino acid substitutions at positions corresponding to positions selected from the group consisting of: N780, E788, A558, D559, H823, H568, D718, D775 and H576, wherein the numbering is relative to SEQ ID NO: 25. In some embodiments, the recombinant polymerase exhibits increased raw read accuracy, decreased systematic error, decreased strand bias, increased average read length or increased total sequencing throughput as compared to a reference polymerase lacking the one or more amino acid substitutions at positions corresponding to positions selected from the group consisting of: N780, E788, A558, D559, H823, H568, D718, D775 and H576, wherein the numbering is relative to SEQ ID NO: 25.

In some embodiments, the disclosure relates generally to a composition comprising a recombinant polymerase homologous to SEQ ID NO: 26 or a biologically active fragment thereof having at least 80% identity to SEQ ID NO: 26 or a biologically active fragment thereof. In some embodiments, the disclosure relates generally to a composition comprising a recombinant polymerase homologous to SEQ ID NO: 26 or a biologically active fragment thereof having at least 95% identity to SEQ ID NO: 26 or a biologically active fragment thereof. In some embodiments, the disclosure relates generally to a composition comprising a recombinant polymerase homologous to SEQ ID NO: 26 or a biologically active fragment thereof having at least 80% identity to SEQ ID NO: 26 or a biologically active fragment thereof and where the recombinant polymerase homologous to SEQ ID NO: 26 comprises a mutation or combination of mutations relative to SEQ ID NO: 26 selected from H568N, where the polymerase further includes a mutation at one or more of N780K, E788R, A558K, D559A, D559R, H823S, H823F, D775R, or H576M, wherein the numbering is relative to SEQ ID NO: 26.

In some embodiments, the disclosure relates generally to a composition comprising a recombinant polymerase homologous to SEQ ID NO: 26 or a biologically active fragment thereof having at least 80% identity to SEQ ID NO: 26 or a biologically active fragment thereof and where the recombinant polymerase homologous to SEQ ID NO: 26 comprises an A558K mutation, wherein the numbering is relative to SEQ ID NO: 26.

In some embodiments, the disclosure relates generally to a composition comprising a recombinant polymerase homologous to SEQ ID NO: 26 or a biologically active fragment thereof having at least 80% identity to SEQ ID NO: 26 or a biologically active fragment thereof and where the recombinant polymerase homologous to SEQ ID NO: 26 comprises a D559A or D559R mutation, wherein the numbering is relative to SEQ ID NO: 26.

In some embodiments, the disclosure relates generally to a composition comprising a recombinant polymerase homologous to SEQ ID NO: 26 or a biologically active fragment thereof having at least 80% identity to SEQ ID NO: 26 or a biologically active fragment thereof and where the recombinant polymerase homologous to SEQ ID NO: 26 comprises a H568N mutation, wherein the numbering is relative to SEQ ID NO: 26.

In some embodiments, the disclosure relates generally to a composition comprising a recombinant polymerase homologous to SEQ ID NO: 26 or a biologically active fragment thereof having at least 80% identity to SEQ ID NO: 26 or a biologically active fragment thereof and where the recombinant polymerase comprises a H823S or H823F mutation, wherein the numbering is relative to SEQ ID NO: 26.

In some embodiments, the disclosure relates generally to a composition comprising a recombinant polymerase homologous to SEQ ID NO: 26 or a biologically active fragment thereof having at least 80% identity to SEQ ID NO: 26 or a biologically active fragment thereof and where the recombinant polymerase homologous to SEQ ID NO: 26 comprises a D775R mutation, wherein the numbering is relative to SEQ ID NO: 26.

In some embodiments, the disclosure relates generally to a composition comprising a recombinant polymerase homologous to SEQ ID NO: 26 or a biologically active fragment thereof having at least 80% identity to SEQ ID NO: 26 or a biologically active fragment thereof and where the recombinant polymerase homologous to SEQ ID NO: 26 comprises a H576M mutation, wherein the numbering is relative to SEQ ID NO: 26.

In some embodiments, the disclosure relates generally to a composition comprising a recombinant polymerase homologous to SEQ ID NO: 26 or a biologically active fragment thereof having at least 80% identity to SEQ ID NO: 26 or a biologically active fragment thereof and where the recombinant polymerase homologous to SEQ ID NO: 26 optionally includes one or more amino acid mutations selected from the group consisting of E515K and N529R, wherein the numbering is relative to SEQ ID NO: 26.

In some embodiments, the recombinant polymerase homologous to SEQ ID NO: 26 or the biologically active fragment thereof comprises increased accuracy as compared to a reference polymerase lacking a mutation or combination of mutations relative to SEQ ID NO: 26 or increased read length as compared to a reference polymerase lacking a mutation or combination of mutations relative to SEQ ID NO: 26 or increased total sequencing throughput as compared to a reference polymerase lacking a mutation or combination of mutations relative to the recombinant polymerase homologous to SEQ ID NO: 26 or reduced strand bias as compared to a reference polymerase lacking a mutation or combination of mutations relative to SEQ ID NO: 26 or lowered systematic error as compared to a reference polymerase lacking a mutation or combination of mutations relative to SEQ ID NO: 26.

In some embodiments, the increased accuracy increased read length, increased sequencing throughput, reduced strand bias or lowered systematic error is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corporation (CA).

In some embodiments, the disclosure is generally related to a composition comprising a recombinant polymerase homologous to SEQ ID NO: 28 or a biologically active fragment thereof having at least 80% identity to SEQ ID NO: 28 or a biologically fragment thereof. In some embodiments, the disclosure is generally related to a composition comprising a recombinant polymerase homologous to SEQ ID NO: 28 or a biologically active fragment thereof having at least 80% identity to SEQ ID NO: 28 or a biologically fragment thereof and where the recombinant polymerase homologous to SEQ ID NO: 28 comprises a mutation or combination of mutations relative to SEQ ID NO: 28 selected from D718K, where the polymerase further includes a mutation at one or more of: A558K, H823S, H823F, D559A, D559R, D568N, D775R, E788R, N780K, E515K and N529R, wherein the numbering is relative to SEQ ID NO: 28.

In some embodiments, the recombinant polymerase homologous to SEQ ID NO: 28 or the biologically active fragment thereof comprises increased accuracy as compared to a reference polymerase lacking a mutation or combination of mutations relative to SEQ ID NO: 28 or increased read length as compared to a reference polymerase lacking a mutation or combination of mutations relative to SEQ ID NO: 28 or increased total sequencing throughput as compared to a reference polymerase lacking a mutation or combination of mutations relative to the recombinant polymerase homologous to SEQ ID NO: 28 or reduced strand bias as compared to a reference polymerase lacking a mutation or combination of mutations relative to SEQ ID NO: 28 or decreased systematic error as compared to a reference polymerase lacking a mutation or combination of mutations relative to SEQ ID NO: 28.

In some embodiments, the increased accuracy increased read length, increased sequencing throughput, reduced strand bias or lowered systematic error is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corporation (CA).

In some embodiments, the disclosure is generally related to a composition comprising a recombinant polymerase homologous to SEQ ID NO: 29 or a biologically active fragment thereof having at least 80% identity to SEQ ID NO: 29 or a biologically fragment thereof. In some embodiments, the disclosure is generally related to a composition comprising a recombinant polymerase homologous to SEQ ID NO: 29 or a biologically active fragment thereof having at least 80% identity to SEQ ID NO: 29 or a biologically fragment thereof and where the recombinant polymerase comprises a mutation or combination of mutations relative to SEQ ID NO: 29 selected from D718K, where the polymerase further includes a mutation at one or more of: A558K, D559A, D559R, D568N, D775R, E788R, H576M, N780K, E515K and N529R, wherein the numbering is relative to SEQ ID NO: 29. In some embodiments, the recombinant polymerase homologous to SEQ ID NO: 29 or the biologically active fragment thereof comprises increased accuracy as compared to a reference polymerase lacking a mutation or combination of mutations relative to SEQ ID NO: 29 or increased read length as compared to a reference polymerase lacking a mutation or combination of mutations relative to SEQ ID NO: 29 or increased total sequencing throughput as compared to a reference polymerase lacking a mutation or combination of mutations relative to the recombinant polymerase homologous to SEQ ID NO: 29 or reduced strand bias as compared to a reference polymerase lacking a mutation or combination of mutations relative to SEQ ID NO: 29 or lowered systematic error as compared to a reference polymerase lacking a mutation or combination of mutations relative to SEQ ID NO: 29.

In some embodiments, the disclosure generally relates to a composition comprising a recombinant polymerase homologous to SEQ ID NO: 30 or a biologically active fragment thereof having at least 80% identity to SEQ ID NO: 30 or a biologically active fragment thereof and where the recombinant polymerase homologous to SEQ ID NO: 30 comprises a mutation or combination of mutations relative to SEQ ID NO: 30 selected from N782R, wherein the polymerase further includes a mutation at one or more of A558K, D559A, D559R, H823S, H823F, H568N, and H576M, wherein the numbering is relative to SEQ ID NO: 30.

In some embodiments, the disclosure generally relates to a composition comprising a recombinant polymerase homologous to SEQ ID NO: 30 or a biologically active fragment thereof having at least 80% identity to SEQ ID NO: 30 or a biologically active fragment thereof and where the recombinant polymerase homologous to SEQ ID NO: 30 comprises a mutation or combination of mutations relative to SEQ ID NO: 30 selected from H568N, wherein the polymerase further includes a mutation at one or more of: N780K, E788R, A558K, D559A, D559R, H823S, H823F, D775R, or H576M, wherein the numbering is relative to SEQ ID NO: 30.

In some embodiments, the disclosure generally relates to a composition comprising a recombinant polymerase homologous to SEQ ID NO: 30 or a biologically active fragment thereof having at least 80% identity to SEQ ID NO: 30 or a biologically active fragment thereof and where the recombinant polymerase homologous to SEQ ID NO: 30 comprises a mutation or combination of mutations relative to SEQ ID NO: 30 comprising a H823S or H823F mutation, wherein the numbering is relative to SEQ ID NO: 30.

In some embodiments, the disclosure generally relates to a composition comprising a recombinant polymerase homologous to SEQ ID NO: 30 or a biologically active fragment thereof having at least 80% identity to SEQ ID NO: 30 or a biologically active fragment thereof and where the recombinant polymerase homologous to SEQ ID NO: 30 comprises a mutation or combination of mutations relative to SEQ ID NO: 30 selected from a N782R mutation, wherein the numbering is relative to SEQ ID NO: 30.

In some embodiments, the disclosure generally relates to a composition comprising a recombinant polymerase homologous to SEQ ID NO: 30 or a biologically active fragment thereof having at least 80% identity to SEQ ID NO: 30 or a biologically active fragment thereof and where the recombinant polymerase homologous to SEQ ID NO: 30 comprises a mutation or combination of mutations relative to SEQ ID NO: 30 selected from an H668N mutation, wherein the numbering is relative to SEQ ID NO: 30.

In some embodiments, the disclosure relates to a recombinant polymerase homologous to SEQ ID NO: 30 or a biologically active fragment thereof which comprises increased accuracy as compared to a reference polymerase lacking a mutation or combination of mutations relative to SEQ ID NO: 30 or increased read length as compared to a reference polymerase lacking a mutation or combination of mutations relative to SEQ ID NO: 30 or increased total sequencing throughput as compared to a reference polymerase lacking a mutation or combination of mutations relative to SEQ ID NO: 30 or decreased systematic error as compared to a reference polymerase lacking a mutation or combination of mutations relative to SEQ ID NO: 30 or decreased strand bias as compared to a reference polymerase lacking a mutation or combination of mutations relative to the recombinant polymerase homologous to SEQ ID NO: 30 or increased average read length as compared to a reference polymerase lacking a mutation or combination of mutations relative to SEQ ID NO: 30. In some embodiments, the composition comprising a recombinant polymerase homologous to SEQ ID NO: 30 or a biologically active fragment thereof comprises at least 90% identity to SEQ ID NO: 30 or a biologically active fragment thereof.

In some embodiments, the recombinant polymerase homologous to SEQ ID NO: 30 comprises a mutation that increases accuracy, increases average read length, increases minimum read length, increases AQ20, increases 200Q17, increases total sequencing throughput, reduces strand bias or lowers systematic errors as compared to a reference polymerase lacking a mutation (or combination of mutations) relative to the recombinant polymerase homologous to SEQ ID NO: 30. In some embodiments, the recombinant polymerase homologous to SEQ ID NO: 30 comprises increased accuracy as compared to a reference polymerase lacking a mutation or combination of mutations relative to the recombinant polymerase homologous to SEQ ID NO: 30. In some embodiments, the recombinant polymerase homologous to SEQ ID NO: 30 comprises increased average read length as compared to a reference polymerase lacking a mutation or combination of mutations relative to the recombinant polymerase homologous to SEQ ID NO: 30. In some embodiments, the recombinant polymerase homologous to SEQ ID NO: 30 comprises increased total sequencing throughput as compared to a reference polymerase lacking a mutation or combination of mutations relative to the recombinant polymerase homologous to SEQ ID NO: 30. In some embodiments, the recombinant polymerase homologous to SEQ ID NO: 30 comprises decreased strand bias as compared to a reference polymerase lacking a mutation or combination of mutations relative to the recombinant polymerase homologous to SEQ ID NO: 30. In some embodiments, the recombinant polymerase homologous to SEQ ID NO: 30 comprises lowered systematic error as compared to a reference polymerase lacking a mutation or combination of mutations relative to the recombinant polymerase homologous to SEQ ID NO: 30. In some embodiments, the increased accuracy, increased average read length, increased minimum read length, increased sequencing throughput, reduced strand bias or lowered systematic error is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corporation (CA).

In some embodiments, the disclosure relates generally to a composition comprising a recombinant polymerase homologous to SEQ ID NO: 31 or a biologically active fragment thereof having at least 80% identity to SEQ ID NO: 31 or a biologically active fragment thereof. In some embodiments, the disclosure relates generally to a composition comprising a recombinant polymerase homologous to SEQ ID NO: 31 or a biologically active fragment thereof having at least 95% identity to SEQ ID NO: 31 or a biologically active fragment thereof. In some embodiments, the disclosure relates generally to a composition comprising a recombinant polymerase homologous to SEQ ID NO: 31 or a biologically active fragment thereof having at least 80% identity to SEQ ID NO: 31 or a biologically active fragment thereof and where the recombinant polymerase homologous to SEQ ID NO: 31 comprises a mutation or combination of mutations relative to SEQ ID NO: 31 selected from H568N, where the polymerase further includes a mutation at one or more of N780K, E788R, A558K, D559A, D559R, H823S, H823F, D775R, or H576M, wherein the numbering is relative to SEQ ID NO: 31.

In some embodiments, the disclosure relates generally to a composition comprising a recombinant polymerase homologous to SEQ ID NO: 31 or a biologically active fragment thereof having at least 80% identity to SEQ ID NO: 31 or a biologically active fragment thereof and where the recombinant polymerase homologous to SEQ ID NO: 31 comprises an D559A mutation, wherein the numbering is relative to SEQ ID NO: 31.

In some embodiments, the disclosure relates generally to a composition comprising a recombinant polymerase homologous to SEQ ID NO: 31 or a biologically active fragment thereof having at least 80% identity to SEQ ID NO: 31 or a biologically active fragment thereof and where the recombinant polymerase homologous to SEQ ID NO: 31 comprises a E788R mutation, wherein the numbering is relative to SEQ ID NO: 31.

In some embodiments, the disclosure relates generally to a composition comprising a recombinant polymerase homologous to SEQ ID NO: 31 or a biologically active fragment thereof having at least 80% identity to SEQ ID NO: 31 or a biologically active fragment thereof and where the recombinant polymerase homologous to SEQ ID NO: 31 comprises a H568N mutation, wherein the numbering is relative to SEQ ID NO: 31.

In some embodiments, the disclosure relates generally to a composition comprising a recombinant polymerase homologous to SEQ ID NO: 31 or a biologically active fragment thereof having at least 80% identity to SEQ ID NO: 31 or a biologically active fragment thereof and where the recombinant polymerase comprises a H823S or H823F mutation, wherein the numbering is relative to SEQ ID NO: 31.

In some embodiments, the disclosure relates generally to a composition comprising a recombinant polymerase homologous to SEQ ID NO: 31 or a biologically active fragment thereof having at least 80% identity to SEQ ID NO: 31 or a biologically active fragment thereof and where the recombinant polymerase homologous to SEQ ID NO: 31 comprises a D775R mutation, wherein the numbering is relative to SEQ ID NO: 31.

In some embodiments, the recombinant polymerase homologous to SEQ ID NO: 31 or the biologically active fragment thereof comprises increased accuracy as compared to a reference polymerase lacking a mutation or combination of mutations relative to SEQ ID NO: 31 or increased read length as compared to a reference polymerase lacking a mutation or combination of mutations relative to SEQ ID NO: 31 or increased total sequencing throughput as compared to a reference polymerase lacking a mutation or combination of mutations relative to the recombinant polymerase homologous to SEQ ID NO: 31 or reduced strand bias as compared to a reference polymerase lacking a mutation or combination of mutations relative to SEQ ID NO: 31 or lowered systematic error as compared to a reference polymerase lacking a mutation or combination of mutations relative to SEQ ID NO: 31.

In some embodiments, the increased accuracy increased read length, increased sequencing throughput, reduced strand bias or lowered systematic error is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corporation (CA).

In some embodiments, the disclosure relates generally to a composition comprising a recombinant polymerase homologous to SEQ ID NO: 32 or a biologically active fragment thereof having at least 80% identity to SEQ ID NO: 32 or a biologically active fragment thereof. In some embodiments, the disclosure relates generally to a composition comprising a recombinant polymerase homologous to SEQ ID NO: 32 or a biologically active fragment thereof having at least 95% identity to SEQ ID NO: 32 or a biologically active fragment thereof. In some embodiments, the disclosure relates generally to a composition comprising a recombinant polymerase homologous to SEQ ID NO: 32 or a biologically active fragment thereof having at least 80% identity to SEQ ID NO: 32 or a biologically active fragment thereof and where the recombinant polymerase homologous to SEQ ID NO: 32 comprises a mutation or combination of mutations relative to SEQ ID NO: 32 selected from D718K, where the polymerase further includes a mutation at one or more of N780K, A558K, H823S, H823F, or D775R, wherein the numbering is relative to SEQ ID NO: 32.

In some embodiments, the disclosure relates generally to a composition comprising a recombinant polymerase homologous to SEQ ID NO: 32 or a biologically active fragment thereof having at least 80% identity to SEQ ID NO: 32 or a biologically active fragment thereof and where the recombinant polymerase homologous to SEQ ID NO: 32 comprises an D718K mutation, wherein the numbering is relative to SEQ ID NO: 32.

In some embodiments, the disclosure relates generally to a composition comprising a recombinant polymerase homologous to SEQ ID NO: 32 or a biologically active fragment thereof having at least 80% identity to SEQ ID NO: 32 or a biologically active fragment thereof and where the recombinant polymerase homologous to SEQ ID NO: 32 comprises a E788R mutation, wherein the numbering is relative to SEQ ID NO: 32.

In some embodiments, the disclosure relates generally to a composition comprising a recombinant polymerase homologous to SEQ ID NO: 32 or a biologically active fragment thereof having at least 80% identity to SEQ ID NO: 32 or a biologically active fragment thereof and where the recombinant polymerase comprises a H823S or H823F mutation, wherein the numbering is relative to SEQ ID NO: 32.

In some embodiments, the disclosure relates generally to a composition comprising a recombinant polymerase homologous to SEQ ID NO: 32 or a biologically active fragment thereof having at least 80% identity to SEQ ID NO: 32 or a biologically active fragment thereof and where the recombinant polymerase homologous to SEQ ID NO: 32 comprises a D775R mutation, wherein the numbering is relative to SEQ ID NO: 32.

In some embodiments, the recombinant polymerase homologous to SEQ ID NO: 32 or the biologically active fragment thereof comprises increased accuracy as compared to a reference polymerase lacking a mutation or combination of mutations relative to SEQ ID NO: 32 or increased read length as compared to a reference polymerase lacking a mutation or combination of mutations relative to SEQ ID NO: 32 or increased total sequencing throughput as compared to a reference polymerase lacking a mutation or combination of mutations relative to the recombinant polymerase homologous to SEQ ID NO: 32 or reduced strand bias as compared to a reference polymerase lacking a mutation or combination of mutations relative to SEQ ID NO: 32 or lowered systematic error as compared to a reference polymerase lacking a mutation or combination of mutations relative to SEQ ID NO: 32.

In some embodiments, the increased accuracy increased read length, increased sequencing throughput, reduced strand bias or lowered systematic error is measured using an ISFET. In some embodiments, the ISFET is coupled to a semiconductor based sequencing platform. In some embodiments, the semiconductor based sequencing platform is a Personal Genome Machine or a Proton Sequencer available from Life Technologies Corporation (CA).

In some embodiments, the recombinant polymerase homologous to SEQ ID NO: 16, SEQ ID NO: 25, SEQ ID NO: 26, SEQ ID NO: 27, SEQ ID NO: 28, SEQ ID NO: 29, SEQ ID NO: 30, SEQ ID NO: 31, or SEQ ID NO: 32 can optionally further include one or more mutations selected from the group consisting of E515K and N529R, wherein the numbering is relative to SEQ ID NO: 16.

In some embodiments, the disclosure relates generally to a composition comprising a recombinant polymerase homologous to SEQ ID NO: 1 or a biologically active fragment thereof, where the recombinant polymerase comprises a mutation or combination of mutations relative to SEQ ID NO: 1 selected from any one or more of: N31, D77, D113, D114, D130, D144, L212, E220, N234, V241, V251, A263K, D264, Y272, H273, L280, H281, E294, V299, D303, I331, E325, L335, E336, I354, I370, Q409, G416, V418, G420, D423, G425, Q428, N429, E446, F448, N457, A462, H473, Y477, D480, N485, N487, V488, E493, M495, H528, V533, H572, W577 and D579. In some embodiments, the disclosure relates generally to a composition comprising a recombinant polymerase homologous to SEQ ID NO: 1 or biologically active fragment thereof comprises a mutation or combination of mutations relative to SEQ ID NO: 1 selected from any one or more of: N31R, N31K, D77K, D77H, D113N, D114R, D130A, D130H, D144M, D144K, L212A, E220K, N234R, N234K, V241K, V251K, A263K, D264A, D264R, D264Q, D264S, D264K, Y272R, H273N, H273R, L280R, H281A, H281M, E294S, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, E446Q, F448K, N457T, A462T, H473R, Y477F, D480R, D480F, D480H, D480A, D480S, D480N, D480Q, N485K, N485W, N485Y, N487R, N487H, N487W, N487F, N487I, V488R, E493Q, E493R, M495Q, H528A, H528F, H528S, H528R, H528K, V533I, H572R, W577Y and D579F.

In some embodiments, the recombinant polymerase homologous to SEQ ID NO: 1 and comprising a mutation or combination of mutations relative to SEQ ID NO: 1 includes any biologically active fragment of the recombinant polymerase that retains polymerase activity.

In some embodiments, the disclosure relates generally to a composition comprising a recombinant polymerase homologous to SEQ ID NO: 16 or a biologically active fragment thereof, where the recombinant polymerase homologous to SEQ ID NO: 16 comprises a mutation or combination of mutations relative to SEQ ID NO: 16 selected from any one or more of: H341, C388, Q533, H568, H576, E741, H768, Y772, H823, C845, H867, N782, N780, E788, A558, D559, D718, D775, E515 and N529.

In some embodiments, the recombinant polymerase homologous to SEQ ID NO: 16, comprises a mutation or combination of mutations relative to SEQ ID NO: 16 selected from any one or more of: H341R, C388R, Q533C, H568R, H576A, E741Q, H768R, Y772F, H823A, C845Q, H867R, N782R, N780K, E788R, A558K, D559A, D559R, H823S, H568N, D718K, D775R, H576M, E515K and N529R. In some embodiments, the recombinant polymerase homologous to SEQ ID NO: 16 and comprising a mutation or combination of mutations relative to SEQ ID NO: 16 includes any biological fragment of the recombinant polymerase that retains polymerase activity.

In some embodiments, the disclosure relates generally to a composition comprising a recombinant polymerase homologous to SEQ ID NO: 15, where the recombinant polymerase comprises a mutation or combination of mutations relative to SEQ ID NO: 15 selected from any one or more of: E471, N485, R492, D513, A675, D732, S739, V740 and E745. In some embodiments, the recombinant polymerase homologous to SEQ ID NO: 15, comprises a mutation or combination of mutations relative to SEQ ID NO: 15 selected from any one or more of: E471K, N485R, R492K, D513K, A675K, D732R, S739W, V740R and E745Q. In some embodiments, the recombinant polymerase homologous to SEQ ID NO: 15 and comprising a mutation or combination of mutations relative to SEQ ID NO: 1 include any biological fragment of the recombinant polymerase that retains polymerase activity.

In some embodiments, the disclosure relates generally to a composition comprising a recombinant polymerase homologous to SEQ ID NO: 18, wherein the recombinant polymerase comprises a mutation or combination of mutations relative to SEQ ID NO: 18 selected from any one or more of: E245, S259, T266, E290, A448, D505, A512, and E518. In some embodiments, the recombinant polymerase homologous to SEQ ID NO: 18, comprises a mutation or combination of mutations relative to SEQ ID NO: 18 selected from any one of or more of: E245K, S259R, T266K, E290K, A448K, D505R, A512W, and E518Q. In some embodiments, the recombinant polymerase homologous to SEQ ID NO: 18 and comprising a mutation or combination of mutations relative to SEQ ID NO: 1 include any biological fragment of the recombinant polymerase that retains polymerase activity.

In some embodiments, the disclosure relates generally to a composition comprising an isolated polypeptide having at least 90% identity to a Family A DNA polymerase containing an amino acid sequence selected from the group consisting of: SEQ ID NO: 2, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37. In some embodiments, the isolated polypeptide comprises at least 90% identity to SEQ ID NO: 25 and includes an amino acid substitution at one or more positions corresponding to positions selected from the group consisting of: N780, E788, A558, D559, H823, H568, D718, D775, H576, E515 and N529, wherein the numbering is relative to SEQ ID NO: 25. In some embodiments, the composition comprises an isolated polypeptide comprises at least 90% identity to SEQ ID NO: 2 and includes an amino acid substitution at one or more positions corresponding to positions selected from the group consisting of: N487, N485, E493, A263, D264, H528, H273, D423, D480, H281, E220 and N234, wherein the numbering is relative to SEQ ID NO: 2. In some embodiments, the composition comprises an isolated polypeptide comprises at least 90% identity to SEQ ID NO: 28 and includes an amino acid substitution at one or more positions corresponding to positions selected from the group consisting of: N780, E788, A558, D559, H823, H568, D775 and D718, wherein the numbering is relative to SEQ ID NO: 28. In some embodiments, the composition comprises an isolated polypeptide comprises at least 90% identity to SEQ ID NO: 37 and includes an amino acid substitution at one or more positions corresponding to positions selected from the group consisting of: N485, E493, A263, D264, H528, H273, D423 and D480, wherein the numbering is relative to SEQ ID NO: 37.

In some embodiments, the disclosure generally relates to a composition comprising a recombinant polymerase containing an amino acid sequence that is at least 80% identical to SEQ ID NO: 25 or a biologically active fragment thereof, wherein the recombinant polymerase includes one or more amino acid substitutions at positions corresponding to positions selected from the group consisting of: N780, E788, A558, D559, H823, H568, D718, D775 and H576, wherein the numbering is relative to SEQ ID NO: 25. In some embodiments, the recombinant polymerase includes one or more amino acid substitutions at positions corresponding to positions selected from the group consisting of: N780K, E788R, A558K, D559A, D559R, H823S, H823F, H568N, D718K, D775R and H576M, wherein the numbering is relative to SEQ ID NO: 25.

In some embodiments, the disclosure generally relates to a composition comprising a recombinant polymerase containing an amino acid sequence that is at least 80% identical to SEQ ID NO: 2 or a biologically active fragment thereof, wherein the recombinant polymerase includes one or more amino acid substitutions at positions corresponding to positions selected from the group consisting of: N487, N485, E493, A263, D264, H528, H273, D423, D480 and H281, wherein the numbering is relative to SEQ ID NO: 2. In some embodiments, the recombinant polymerase includes one or more amino acid substitutions at positions corresponding to positions selected from the group consisting of: N487R, N485K, E493R, A263K, D264A, D264R, H528S, H528F, H273N, D423K, D480R and H281M, wherein the numbering is relative to SEQ ID NO: 2.

In some embodiments, the disclosure relates generally to a composition comprising an isolated polypeptide containing an amino acid sequence that has at least 80% homology to SEQ ID NO: 37 or a biologically active fragment thereof, wherein the isolated polypeptide includes one or more amino acid substitutions at positions corresponding to positions selected from the group consisting of: D423, D264, H273 and E493, wherein the numbering is relative to SEQ ID NO: 37, and wherein the isolated polypeptide exhibits a decreased dissociation rate constant relative to SEQ ID NO: 2.

In some embodiments, the disclosure relates generally to a composition comprising a recombinant polymerase containing an amino acid sequence that has at least 80% homology to SEQ ID NO: 2 or a biologically active fragment thereof, wherein the recombinant polymerase comprises a Family A DNA polymerase having one or more amino acid substitutions at positions corresponding to positions selected from the group consisting of: N487, N485, E493, A263, D264, H528, H273, D423, D480 and H281, wherein the numbering is relative to SEQ ID NO: 2, and wherein the recombinant polymerase exhibits a decreased dissociation rate constant as compared to SEQ ID NO: 2.

In some embodiments, the composition comprises a recombinant polymerase homologous to SEQ ID NO: 2 or a biologically active fragment thereof having at least 90% identity to SEQ ID NO: 2 or a biologically active fragment thereof, wherein the recombinant polymerase homologous to SEQ ID NO: 2 or the biologically active fragment thereof comprises a Family A or Family B DNA polymerase having an amino acid substitution or combination of amino acid substitutions corresponding to amino acid positions N487, N485, E493, A263, D264, H528, H273, D423, D480 and H281, wherein the numbering is relative to SEQ ID NO:2.

In some embodiments, the disclosure relates generally to a method for performing polymerization comprising: (a) providing a reaction mixture including a nucleic acid hybridized to a primer and bound to a modified polymerase; and (b) contacting the nucleic acid with at least one type of nucleotide, wherein the contacting includes incorporating at least one nucleotide onto the primer thereby generating an extended primer product.

In some embodiments, the disclosure relates generally to a method for obtaining sequence information from a nucleic acid template, comprising: (a) providing a reaction mixture including a template nucleic acid hybridized to a sequencing primer and bound to a modified polymerase; (b) contacting the template nucleic acid with at least one type of nucleotide, wherein the contacting includes incorporating one or more nucleotides from the at least one type of nucleotide onto the 3' end of the sequencing primer and generating an extended primer product; (c) detecting the presence of the extended primer product in the reaction mixture, thereby determining whether nucleotide incorporation has occurred; and (d) identifying at least one of the one or more nucleotides incorporated from the at least one type of nucleotide. In some embodiments, the method further includes detecting the presence of the extended primer product in the reaction mixture, thereby determining whether nucleotide incorporation has occurred. In some embodiments, the method repeating the contacting and the detecting more than once, thereby detecting a plurality of nucleotide incorporations. In some embodiments, the method further includes identifying at least one of the plurality of nucleotide incorporations. In some embodiments, the methods of polymerization can include PCR, qPCR, bridge PCR, RT-PCR, ligation mediated PCR, isothermal amplification or emulsion PCR. In some embodiments, the methods of obtaining sequence information can include PCR, qPCR, bridge PCR, RT-PCR, ligation mediated PCR, isothermal amplification or emulsion PCR.

In some embodiments, the composition (and related methods, kits, systems, and apparatuses) further includes at least one type of chain-terminating nucleotide analog. In some embodiments the at least one type of chain-terminating nucleotide analog is incorporated into a primer by a recombinant polymerase containing an amino acid sequence that is at least 80% identical to SEQ ID NO: 2 or a biologically active fragment thereof, wherein the recombinant polymerase includes one or more amino acid substitutions at positions corresponding to positions selected from the group consisting of: N487, N485, E493, A263, D264, H528, H273, D423, D480 and H281, wherein the numbering is relative to SEQ ID NO: 2.

In some embodiments, the chain-terminating nucleotide analog is incorporated into the primer in a template-dependent manner. In some embodiments, the chain-terminating nucleotide analog is labeled with a first detectable label.

In some embodiments, the composition (and related methods, kits, systems, and apparatuses) includes more than one type of chain-terminating nucleotide analog. In some embodiments, the composition further comprises a different detectable label for each type of chain-terminating nucleotide analog. In some embodiments, the chain-terminating nucleotide analog includes a dideoxynucleotide. In some embodiments, the dideoxynucleotide is selected from the group consisting of ddATP, ddTTP, ddCTP and ddGTP. It will be readily apparent to the skilled artisan that other types of chain-terminating nucleotide analogs can be used, for example 3'-O-blocked and 3'-unblocked reversible terminators, 3'-O—N3 reversible terminators, 3'-ONH2 reversible terminators, 3'O-allyl reversible terminators and/or virtual terminators (See Chen et al., Genomics Proteomics and Bioinformatics (2013) 11: 34-40, hereby incorporated by reference in its entirety). In some embodiments, the primer can be labeled with a second detectable label. In some embodiments, the composition further includes a ligase.

In some embodiments, the disclosure relates generally to a method for performing nucleic acid sequencing comprising contacting a modified polymerase or a biologically active fragment thereof with a nucleic acid template in the presence of one or more nucleotides, where the modified polymerase or the biologically active fragment thereof includes one or more amino acid modifications relative to a reference polymerase, and where the modified polymerase or the biologically active fragment thereof has an increased dissociation time constant or lowered systematic error relative to the reference polymerase; and polymerizing at least one of the one or more nucleotides using the modified polymerase or the biologically active fragment thereof. In some embodiments, the nucleic acid template can be a DNA template. In some embodiments, the nucleic acid template can include cDNA. In some embodiments, the nucleic acid template can include cDNA derived from a RNA sample. In some embodiments, the one or more nucleotides do not contain a detectable label. In some embodiments, the modified polymerase or the biologically active fragment thereof is a family A or family B DNA polymerase. In some embodiments, the modified polymerase is a DNA or RNA polymerase. In some embodiments, the disclosure relates generally to a modified DNA polymerase comprising at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the disclosure relates generally to a modified polymerase comprising or consisting of a sequence variant at least 95% identical to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the disclosure relates generally to a modified polymerase comprising or consisting of a sequence variant at least 98% identical to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the disclosure relates generally to a modified polymerase comprising or consisting of a sequence variant at least 99% identical to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the disclosure relates generally to a modified polymerase comprising a biologically active fragment of SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37 that retains polymerase activity. In some embodiments, the modified polymerase comprises a biologically active fragment having at least 80% identity and retaining polymerase activity to any fragment of SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase comprises a biologically active fragment having at least 25 contiguous amino acids of the polymerase catalytic domain and at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the biologically active fragment includes at least 100 contiguous amino acid residues having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the method further includes determining the identity of the one or more nucleotides polymerized by the modified polymerase. In some embodiments, the method further includes determining the number of nucleotides polymerized by the modified polymerase. In some embodiments, at least 50% of the one or more nucleotides polymerized by the modified polymerase are identified. In some embodiments, substantially all of the one or more nucleotides polymerized by the modified polymerase are identified. In some embodiments, the polymerization occurs in the presence of a high ionic strength solution. In some embodiments the high ionic strength solution comprises about 125 mM to about 200 mM salt. In some embodiments, the polymerization occurs in the presence of an ionic strength solution of at least 125 mM salt. In some embodiments, the high ionic strength solution comprises KCl and/or NaCl.

In some embodiments, the disclosure relates generally to a method for performing a nucleotide polymerization reaction comprising contacting a modified polymerase or a biologically active fragment thereof with a nucleic acid template in the presence of one or more nucleotides, where the modified polymerase or the biologically active fragment thereof includes one or more amino acid modifications (e.g., substitutions, additions, deletions, rearrangements, fusions and/or splices) relative to a reference polymerase and has an increased accuracy relative to the reference polymerase, and polymerizing at least one of the one or more nucleotides using the modified polymerase. In some embodiments, the modified polymerase or the biologically active fragment thereof having increased accuracy comprises or consists of at least 150 contiguous amino acid residues having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof having increased accuracy comprises at least 25 contiguous amino acid residues having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37 from the polymerase catalytic or DNA binding domain. In some embodiments, the modified polymerase or the biologically active fragment thereof having increased accuracy comprises at least 25 contiguous amino acid residues from the polymerase catalytic or DNA binding domain of SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the polymerizing is performed in the presence of a high ionic strength solution. In some embodiments, the high ionic strength solution can include at least 125 mM KCl.

In some embodiments, the disclosure relates generally to a method for performing nucleic acid sequencing comprising or consisting of contacting a modified polymerase with a nucleic acid template in the presence of one or more nucleotides, where the modified polymerase includes one or more amino acid modifications relative to a reference polymerase and has an increased accuracy relative to the reference polymerase, and polymerizing at least one of the one or more nucleotides using the modified polymerase. In some embodiments, the modified polymerase or the biologically active fragment thereof comprises or consists of at least 150 contiguous amino acid residues having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof comprises at least 25 contiguous amino acid residues having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37 from the polymerase catalytic or DNA binding domain. In some embodiments, the modified polymerase or the biologically active fragment thereof comprises at least 25 contiguous amino acid residues from the polymerase catalytic or DNA binding domain of SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the polymerizing can be performed in the presence of a high ionic strength solution. In some embodiments, the modified polymerase or the biologically active fragment thereof can include a DNA or RNA polymerase.

In some embodiments, the disclosure relates generally to a method for performing nucleic acid sequencing comprising or consisting of contacting a modified polymerase with a nucleic acid template in the presence of one or more nucleotides, where the modified polymerase includes one or more amino acid modifications relative to a reference polymerase and has an increased signal to noise ratio relative to the reference polymerase, and polymerizing at least one of the one or more nucleotides using the modified polymerase. In some embodiments, the modified polymerase or the biologically active fragment thereof having increased signal to noise ratio comprises or consists of at least 150 contiguous amino acid residues having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof having increased signal to noise ratio comprises at least 25 contiguous amino acid residues having at least 80% identity to SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37 from the polymerase catalytic or DNA binding domain. In some embodiments, the modified polymerase or the biologically active fragment thereof having increased signal to noise ratio comprises at least 25 contiguous amino acid residues from the polymerase catalytic or DNA binding domain of SEQ ID NO: 2, SEQ ID NO: 3, SEQ ID NO: 4, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase or the biologically active fragment thereof having increased signal to noise ratio is a DNA polymerase.

DETAILED DESCRIPTION

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is explicitly or implicitly set forth herein that is contrary to or otherwise inconsistent with any definition set forth in the patents, patent applications, published applications, and other publications that are herein incorporated by reference, the definition and/or description set forth herein prevails over the definition that is incorporated by reference.

The practice of the disclosure will employ, unless otherwise indicated, conventional techniques of molecular biology, microbiology and recombinant DNA techniques, which are within the skill of the art. Such techniques are explained fully in the literature. See, for example, Sambrook, J., and Russell, D. W., 2001, Molecular Cloning: A Laboratory Manual, Third Edition; Ausubel, F. M., et al., eds., 2002, Short Protocols In Molecular Biology, Fifth Edition.

Note that not all of the activities described in the general description or the examples are required, that a portion of a specific activity may not be required, and that one or more further activities may be performed in addition to those described. Still further, the order in which activities are listed are not necessarily the order in which they are performed.

In some instances, some concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprising" (and any form or variant of comprising, such as "comprise" and "comprises"), "having" (and any form or variant of having, such as "have" and "has"), "including" (and any form or variant of including, such as "includes" and "include"), or "containing" (and any form or variant of containing, such as "contains" and "contain"), are inclusive or open-ended and do not exclude additional, unrecited additives, components, integers, elements or method steps. For example, a process, method, article, or apparatus that comprises a list of features is not necessarily limited only to those features but may include other features not expressly listed or inherent to such process, method, article, or apparatus.

Unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Benefits, other advantages, and solutions to problems have been described with regard to specific embodiments. However, such benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features that are, for clarity, described herein in the context of separate embodiments can also be provided in combination in a single embodiment. Conversely, various features that are, for brevity, described in the context of a single embodiment can also be provided separately or in any subcombination. Further, references to values stated in ranges include each and every value within that range.

Also, the use of articles such as "a", "an" or "the" are employed to describe elements and components described herein. This is done merely for convenience and to give a general sense of the scope of the invention. This description should be read to include one or at least one and the singular also includes the plural unless it is obvious that it is meant otherwise. Accordingly, the terms "a," "an," and "the" and similar referents used herein are to be construed to cover both the singular and the plural unless their usage in context indicates otherwise. Accordingly, the use of the word "a" or "an" or "the" when used in the claims or specification, including when used in conjunction with the term "comprising", may mean "one," but it is also consistent with the meaning of "one or more," "at least one," and "one or more than one."

As used herein, the term "polymerase" and its variants comprise any enzyme that can catalyze the polymerization of nucleotides (including analogs thereof) into a nucleic acid strand. Typically but not necessarily such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, homologs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases (such as for example Phi-29 DNA polymerase, reverse transcriptases and *E. coli* DNA polymerase) and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain.

As used herein, the terms "link", "linked", "linkage" and variants thereof comprise any type of fusion, bond, adherence or association that is of sufficient stability to withstand use in the particular biological application of interest. Such linkage can comprise, for example, covalent, ionic, hydrogen, dipole-dipole, hydrophilic, hydrophobic, or affinity bonding, bonds or associations involving van der Waals forces, mechanical bonding, and the like. Optionally, such linkage can occur between a combination of different molecules, including but not limited to: between a nanoparticle and a protein; between a protein and a label; between a linker and a functionalized nanoparticle; between a linker and a protein; between a nucleotide and a label; and the like. Some examples of linkages can be found, for example, in Hermanson, G., Bioconjugate Techniques, Second Edition (2008); Aslam, M., Dent, A., Bioconjugation: Protein Coupling Techniques for the Biomedical Sciences, London: Macmillan (1998); Aslam, M., Dent, A., Bioconjugation: Protein Coupling Techniques for the Biomedical Sciences, London: Macmillan (1998).

The terms "modification" or "modified" and their variants, as used herein with reference to polypeptide or protein, for example a polymerase, comprise any change in the structural, biological and/or chemical properties of the protein. In some embodiments, the modification can include a change in the amino acid sequence of the protein. For example, the modification can optionally include one or more amino acid mutations, including without limitation amino acid additions, deletions and substitutions (including both conservative and non-conservative substitutions).

The term "conservative" and its variants, as used herein with reference to any change in amino acid sequence, refers to an amino acid mutation wherein one or more amino acids is substituted by another amino acid having highly similar properties. For example, one or more amino acids comprising nonpolar or aliphatic side chains (for example, glycine, alanine, valine, leucine, or isoleucine) can be substituted for each other. Similarly, one or more amino acids comprising polar, uncharged side chains (for example, serine, threonine, cysteine, methionine, asparagine or glutamine) can be substituted for each other. Similarly, one or more amino acids comprising aromatic side chains (for example, phenylalanine, tyrosine or tryptophan) can be substituted for each other. Similarly, one or more amino acids comprising positively charged side chains (for example, lysine, arginine or histidine) can be substituted for each other. Similarly, one or more amino acids comprising negatively charged side chains (for example, aspartic acid or glutamic acid) can be substituted for each other. In some embodiments, the modified polymerase is a variant that comprises one or more of these conservative amino acid substitutions, or any combination thereof. In some embodiments, conservative substitutions for leucine include: alanine, isoleucine, valine, phenylalanine, tryptophan, methionine, and cysteine. In other embodiments, conservative substitutions for asparagine include: arginine, lysine, aspartate, glutamate, and glutamine.

Throughout this disclosure, various amino acid mutations, including, for example, amino acid substitutions are referenced using the amino acid single letter code, and indicating the position of the residue within a reference amino acid sequence. In the case of amino acid substitutions, the identity of the substituent is also indicated using the amino acid single letter code. For example, a reference to the hypothetical amino acid substitution "D166A, wherein the numbering is relative to the amino acid sequence of SEQ ID NO: 7" indicates an amino acid substitution wherein an alanine (A) residue is substituted for the normally occurring aspartic acid (D) residue at amino acid position 166 of the amino acid sequence of SEQ ID NO: 7. Many of the amino acid sequences disclosed herein begin with a methionine residue ("M"), which is typically introduced at the beginning of nucleic acid sequences encoding peptides desired to be expressed in bacterial host cells. However, it is to be understood that the disclosure also encompasses all such amino acid sequences beginning from the second amino acid residue onwards, without the inclusion of the first methionine residue.

As used herein, the terms "identical" or "percent identity," and their variants, when used in the context of two or more nucleic acid or polypeptide sequences, refer to two or more sequences or subsequences that are the same or have a specified percentage of amino acid residues or nucleotides that are the same, when compared and aligned for maximum correspondence, as measured using any one or more of the following sequence comparison algorithms: Needleman-Wunsch (see, e.g., Needleman, Saul B.; and Wunsch, Christian D. (1970). "A general method applicable to the search for similarities in the amino acid sequence of two proteins" Journal of Molecular Biology 48 (3):443-53); Smith-Waterman (see, e.g., Smith, Temple F.; and Waterman, Michael S., "Identification of Common Molecular Subsequences" (1981) Journal of Molecular Biology 147:195-197); or BLAST (Basic Local Alignment Search Tool; see, e.g., Altschul S F, Gish W, Miller W, Myers E W, Lipman D J, "Basic local alignment search tool" (1990) J Mol Biol 215 (3):403-410).

As used herein, the terms "substantially identical" or "substantial identity", and their variants, when used in the context of two or more nucleic acid or polypeptide sequences, refer to two or more sequences or subsequences (such as biologically active fragments) that have at least 60%, at least 70%, at least 75%, at least 80%, at least 85%, at least 90%, at least 95%, at least 96%, at least 97%, at least 98%, or at least 99% nucleotide or amino acid residue identity, when compared and aligned for maximum correspondence, as measured using a sequence comparison algorithm or by visual inspection. Substantially identical sequences are typically considered to be homologous without reference to actual ancestry. In some embodiments, "substantial identity" exists over a region of the sequences being compared. In some embodiments, substantial identity exists over a region of at least 25 residues in length, at least 50 residues in length, at least 100 residues in length, at least 150 residues in length, at least 200 residues in length, or greater than 200 residues in length. In some embodiments, the sequences being compared are substantially identical over the full length of the sequences being compared. Typically, substantially identical nucleic acid or protein sequences include less than 100% nucleotide or amino acid residue identity as such sequences would generally be considered "identical".

Proteins and/or protein subsequences (such as biologically active fragments) are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or biologically active fragments or sequences thereof). The precise percentage of similarity between sequences that is useful in establishing homology varies with the nucleic acid and protein at issue, but as little as 25% sequence similarity over 25, 50, 100, 150, or more nucleic acids or amino acid residues, is routinely used to establish homology. Higher levels of sequence similarity, e.g., 30%, 40%, 50%, 60%, 70%, 80%, 85%, 90%, 95%, 98% or 99%, can also be used to establish homology.

Methods for determining homology or sequence similarity percentages (e.g., BLASTP and BLASTN using default parameters) are described herein and are generally available. For sequence comparison and homology determination, typically one sequence acts as a reference sequence to which test sequences are compared. Table 1 provided herein provides an exemplary list of homologous amino acid mutations across four different classes of DNA polymerase, namely a full length Bst DNA polymerase (SEQ ID NO: 16), the large fragment of Bst DNA polymerase (SEQ ID NO: 1), Taq DNA polymerase (SEQ ID NO: 15) and Klenow fragment polymerase (SEQ ID NO: 18). Table 1 provides an exemplary list of several amino acid positions that may be mutated in SEQ ID NO: 1 and identifies the corresponding amino acid position in each of the other polymerases presented (i.e., a homolog). For example, amino acid substitution E220K in SEQ ID NO: 1 was found to be homologous to E515K in SEQ ID 16, E245K in SEQ ID NO: 18 and E471K in SEQ ID NO: 15. It will be readily apparent to the skilled artisan that a variety of publically available alignment tools can be used to identify homologous amino acid mutations (such as amino acid substitutions) across a polymerase amino acid sequence, for example the NCBI alignment and BLAST tools. Generally, when using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2004). One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length "W" in the query sequence, which either match or satisfy some positive-valued threshold score "T" when aligned with a word of the same length in a database sequence. "T" is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (reward score for a pair of matching residues; always >0) and "N" (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters "W", "T", and "X" determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, less than about 0.01, or less than about 0.001.

The term "primer extension activity" and its variants, as used herein, when used in reference to a given polymerase, comprise any in vivo or in vitro enzymatic activity characteristic of a given polymerase that relates to catalyzing nucleotide incorporation onto the terminal 3'OH end of an extending nucleic acid molecule. Typically but not necessarily such nucleotide incorporation occurs in a template-dependent fashion. In some embodiments, the primer extension activity of a given polymerase can be quantified as the total number of nucleotides incorporated (as measured by, e.g., radiometric or other suitable assay) by a unit amount of polymerase (in moles) per unit time (seconds) under a particular set of reaction conditions.

The term "DNA binding activity" and its variants, as used herein, when used in reference to a given polymerase, comprise any in vivo or in vitro enzymatic activity characteristic of a given polymerase that relates to interaction of the polymerase with a DNA sequence in a recognition-based manner. Typically but not necessarily such interaction includes binding of the polymerase, and more specifically binding of the DNA-binding domain of the polymerase, to the recognized DNA sequence. In some embodiments, recognition includes binding of the polymerase to a sequence-specific or non-sequence specific DNA sequence. In some embodiments, the DNA binding activity of a given polymerase can be quantified as the affinity of the polymerase to recognize and bind to the recognized DNA sequence. For example, DNA binding activity can be monitored and determined using an anisotropy signal change (or other suitable assay) as a protein-DNA complex is formed under a particular set of reaction conditions.

As used herein, the term "biologically active fragment" and its variants, when used in reference to a given biomolecule, refers to any fragment, derivative, homolog or analog of the biomolecule that possesses an in vivo or in vitro activity that is characteristic of the biomolecule itself. For example, a polymerase can be characterized by various biological activities, for example DNA binding activity, nucleotide polymerization activity, primer extension activity, strand displacement activity, reverse transcriptase activity, nick-initiated polymerase activity, 3'-5' exonuclease (proofreading) activity, and the like. In some embodiments, a "biologically active fragment" of a polymerase is any fragment, derivative, homolog or analog of the polymerase that can catalyze the polymerization of nucleotides (including homologs and analogs thereof) into a nucleic acid strand. In some embodiments, the biologically active fragment, derivative, homolog or analog of the polymerase possesses 10%, 20%, 30%, 40%, 50%, 60%, 70%, 75%, 80%, 85%, or 90% or greater of the biological activity of the polymerase in any in vivo or in vitro assay of interest such as, for example, DNA binding assays, nucleotide polymerization assays (which may be template-dependent or template-independent), primer extension assays, strand displacement assays, reverse transcriptase assays, proofreading assays, and the like. In some embodiments, the biological activity of a polymerase fragment can be assayed by measuring the primer extension activity in vitro of the fragment under defined reaction conditions. In some embodiments, the biological activity of a polymerase fragment can be assayed by measuring the polymerization activity in vitro of the fragment under defined reaction conditions. In some embodiments, the biological activity of a polymerase fragment can be assayed by measuring the DNA binding activity in vitro of the fragment under defined reaction conditions. In some embodiments, the biological activity of a polymerase fragment can be assayed by measuring the strand displacement activity in vitro of the fragment under defined reaction conditions. In some embodiments, the biological activity of a polymerase fragment can be assayed by measuring the reverse transcriptase activity in vitro of the fragment under defined reaction conditions. In some embodiments, the biological activity of a polymerase fragment can be assayed by measuring the nick-initiated polymerase activity in vitro of the fragment under defined reaction conditions. In some embodiments, the biological activity of a polymerase fragment can be assayed by measuring the proofreading activity in vitro of the fragment under defined reaction conditions. In some embodiments, the biologically active fragment of a polymerase can include measuring the biological activity of any one or more of the polymerase biological activities outlined herein.

In some embodiments, a biologically active fragment can include any part of the DNA binding domain or any part of the catalytic domain of the modified polymerase. In some embodiments, the biologically active fragment can optionally include any 25, 50, 75, 100, 150 or more contiguous amino acid residues of the DNA binding or catalytic domain. In some embodiments, a biologically active fragment of the modified polymerase can include at least 25 contiguous amino acid residues of the catalytic domain or the DNA binding domain having at least 80%, 85%, 90%, 95%, 98%, or 99% identity to any one or more of the polymerases encompassed by the disclosure. In some embodiments, a biologically active fragment of a modified polymerase can include at least 25 contiguous amino acid residues of the catalytic domain or the DNA binding domain having at least 80%, 85%, 90%, 95%, 98%, or 99% identity to any one or more of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

Biologically active fragments can optionally exist in vivo, such as, for example, fragments which arise from post transcriptional processing or which arise from translation of alternatively spliced RNAs, or alternatively can be created through engineering, bulk synthesis, or other suitable manipulation. Biologically active fragments include fragments expressed in native or endogenous cells as well as those made in expression systems such as, for example, in bacterial, yeast, insect or mammalian cells.

In some embodiments, the disclosure relates generally to not only the specific polymerases disclosed herein, but also to any biologically active fragment of such polymerases, which are encompassed within the scope of the present disclosure. In some embodiments, a biologically active fragment of any polymerase of the disclosure includes any fragment that exhibits primer extension activity in vitro.

In some embodiments, the disclosure relates generally to not only the specific polymerases disclosed herein, but also to any biologically active fragment of such polymerases, which are encompassed within the scope of the present disclosure. In some embodiments, a biologically active fragment of any polymerase of the disclosure includes any fragment that exhibits DNA binding activity in vitro.

In some embodiments, the disclosure relates generally to not only the specific polymerases disclosed herein, but also to any biologically active fragment of such polymerases, which are encompassed within the scope of the present disclosure. In some embodiments, a biologically active fragment of any polymerase of the disclosure includes any fragment that retains polymerase activity in vitro. Polymerase activity can be determined by any method known in art. For example, determination of polymerase activity can be based on the activity of extending a primer on a template.

In some embodiments, the disclosure generally relates to a modified polymerase having one or more amino acid mutations (such as a deletion, substitution or addition) relative to a reference polymerase lacking the one or more amino acid mutations, and wherein the modified polymerase retains polymerase activity in vitro, exhibits DNA binding activity in vitro or exhibits primer extension activity in vitro. In some embodiments, the modified polymerase includes any biologically active fragment of such polymerase that retains polymerase activity in vitro, exhibits DNA binding activity in vitro or exhibits primer extension activity in vitro.

In some embodiments, the disclosure generally relates to a modified polymerase having one or more amino acid mutations (such as a deletion, substitution or addition) relative to a reference polymerase lacking the one or more amino acid mutations, and wherein the modified polymerase retains proofreading activity in vitro. In some embodiments, the disclosure generally relates to a modified polymerase having one or more amino acid mutations (such as a deletion, substitution or addition) relative to a reference polymerase lacking the one or more amino acid mutations, and wherein the modified polymerase retains proofreading activity in vitro, exhibits nick-initiated polymerase activity in vitro or reverse transcriptase activity in vitro. In some embodiments, the modified polymerase includes any biologically active fragment of such polymerase that retains proofreading activity in vitro, exhibits nick-initiated polymerase activity in vitro or exhibits reverse transcriptase activity in vitro. Determination of whether a polymerase exhibits exonuclease activity or exhibits reduced exonuclease activity, can be readily determined by standard methods. For example, polynucleotides can be synthesized such that a detectable proportion of the nucleotides are radioactively labeled. These polynucleotides can be incubated in an appropriate buffer in the presence of the polypeptide to be tested. After incubation, the polynucleotide is precipitated and exonuclease activity is detectable as radioactive counts due to free nucleotides in the supernatant. As will be appreciated by the skilled artisan, an appropriate polymerase or biologically active fragment may be selected from those described herein based on any of the above biological activities, or combinations thereof, depending on the application of interest.

As used herein, the term "nucleotide" and its variants comprise any compound that can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally-occurring nucleotides but also any analogs, regardless of their structure, that can bind selectively to, or can be polymerized by, a polymerase. While naturally-occurring nucleotides typically comprise base, sugar and phosphate moieties, the nucleotides of the disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, CNH2, C(O), C(CH2), CH2CH2, or C(OH)CH2R (where R can be a 4-pyridine or 1-imidazole). In one embodiment, the phosphorus atoms in the chain can have side groups having O, BH3, or S. In the phosphorus chain, a phosphorus atom with a side group other than O can be a substituted phosphate group. Some examples of nucleotide analogs are described in Xu, U.S. Pat. No. 7,405,281. In some embodiments, the nucleotide comprises a label (e.g., reporter moiety) and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group or substitute phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof.

As used herein, the term "nucleotide incorporation" and its variants comprise polymerization of one or more nucleotides to form a nucleic acid strand including at least two nucleotides linked to each other, typically but not necessarily via phosphodiester bonds, although alternative linkages may be possible in the context of particular nucleotide analogs.

As used herein, the term "processivity" and its variants comprise the ability of a polymerase to remain bound to a single primer/template hybrid. In some embodiments, processivity can be measured by the number of nucleotides that a polymerase incorporates into a nucleic acid (such as a sequencing primer) prior to dissociation of the polymerase from the primer/template hybrid. In some embodiments, the polymerase has a processivity of at least 100 nucleotides, although in other embodiments it can include a processivity of at least 200 nucleotides, at least 300 nucleotides, at least 400 nucleotides, at least 500 nucleotides or greater. It will be understood by those of ordinary skill in the art that the higher the processivity of the polymerase, the more nucleotides that can be incorporated prior to dissociation and therefore the longer the sequence (read-length) that can be obtained. In other words, polymerases having low processivity will typically provide shorter average read-lengths than will polymerases having higher processivity. In one embodiment, polymerases of the instant disclosure containing one or more amino acid mutations can possess enhanced processivity as compared to a parent polymerase lacking the one or more amino acid mutations.

In one exemplary assay, the processivity of a given polymerase can be measured by incubating the polymerase with a primer:template duplex under nucleotide incorporation conditions, and resolving the resulting primer extension products using any suitable method, for example via gel electrophoresis. The primer can optionally include a label to enhance detectability of the primer extension products. The nucleotide incorporation reaction mixture typically includes a vast excess of unlabeled competitor template, thereby ensuring that virtually all of the extension products are produced through a single template binding event. Following such resolution, the average amount of full-length extension products can be quantified using any suitable means, including fluorimetric or radiometric detection of full-length extension products. To compare the processivity of two or more different enzymes (e.g., reference and modified polymerases), each enzyme can be employed in a parallel and separate reaction, following which the resulting full-length primer extension products can be resolved and measured, and such measurements compared.

In other exemplary embodiments, the processivity of a given polymerase can be measured using any suitable assay known in the art, including but not limited to the assays described in Von Hippel, P. H., Faireld, F. R. and Dolejsi, M. K., On the processivity of polymerases, Ann. NY Acad. Sci., 726:118-131 (1994); Bambara, R. A., Uyemura, D. and Choi, T., On the processive mechanism of *Escherichia coli* DNA polymerase I. Quantitative assessment of processivity, J. Biol. Chem., 253:413-423 (1978); Das, S. K. and Fujimura, R. K., Processiveness of DNA polymerases. A comparative study using a simple procedure, J. Biol. Chem., 254: 1227-1232 (1979); Nasir, M. S. and Jolley, M. E., Fluorescence polarization: An Analytical Tool for Immunoassay and Drug Discovery, Combinational Chemistry and High Throughput Screening, 2:177-190 (1999); Mestas, S. P., Sholders, A. J., and Peersen, O. B., A Fluorescence Polarization Based Screening Assay for Nucleic Acid Polymerase Elongation Activity, Anal. Biochem., 365:194-200 (2007); Nikiforov, T. T., Fluorogenic polymerase, endonuclease, and ligase assays based on DNA substrates labeled with a single fluorophore, Analytical Biochemistry 412: 229-236; and Yan Wang, Dennis E. Prosen, Li Mei, John C. Sullivan, Michael Finney and Peter B. Vander Horn, Nucleic Acids Research, 32(3):1197-1207 (2004).

The terms "read length" or "read-length" and their variants, as used herein, refer to the number of nucleotides that are polymerized (or incorporated into an existing nucleic acid strand) in a template-dependent manner by a polymerase prior to dissociation from a template nucleic acid strand. In some embodiments, a polymerase that dissociates from the template nucleic acid strand after five incorporations will typically provide a sequence having a read length of 5 nucleotides, while a polymerase that dissociates from the template nucleic acid strand after 500 nucleotide incorporations will typically provide a sequence having a read length of about 500 nucleotides. While the actual or absolute processivity of a given polymerase (or the actual read length of polymerization products produced by the polymerase) can vary from reaction to reaction (or even within a single reaction mixture wherein the polymerase produces different products having different read lengths), the polymerase can be characterized by the average processivity (or average read length of polymerization products) observed under a defined set of reaction conditions. The "error-free read length" comprises the number of nucleotides that are consecutively and contiguously incorporated without error (i.e., without mismatch and/or deviation from an established and predictable set of base pairing rules) into the newly synthesized nucleic acid strand.

The terms "systematic error" or "SE" and its variants, as used herein, refers to the percentage of errors in sequence motifs containing homopolymers (HPs) of a defined length, with systematic deletion occurring on strand at a specified minimum frequency, and with sequencing coverage of a specified minimum frequency. For example, in some embodiments the systematic error can be measured as the percentage of errors in sequence motifs containing homopolymers of length 1-6, with systematic deletion occurring on strand with a frequency greater than 15%, when coverage (of the sequencing run) is equal to or greater than 20×. In some embodiments, the systematic error is estimated as the percentage of stochastic errors in sequence motifs containing homopolymers of length 1-6, with systematic deletion occurring on strand with a frequency greater than 15%, when coverage (of the sequencing run) is equal to or greater than 20×; such embodiments are the focus of several of the working examples disclosed herein. In some embodiments, the percentage of systematic error is lowered when using a modified polymerase as disclosed herein as compared to a reference polymerase (e.g., a wild-type polymerase) that does not contain the one or more amino acid modifications. While the actual systematic error of a given polymerase can vary from reaction to reaction (or even within a single reaction mixture) the polymerase can be characterized by the percentage systematic error observed under a defined set of reaction conditions. In some embodiments, the modified polymerases of the instant application have a lowered systematic error percentage as compared to a corresponding reference polymerase not having the one or more amino acid modifications. In some embodiments, the modified polymerases, as disclosed herein, contain a systematic error percentage of less than 3%. In some embodiments, the modified polymerases, as disclosed herein, contain a systematic error percentage of less than 1%. In some embodiments, the modified polymerases as disclosed herein contain a systematic error percentage of less than 0.9%. In some embodiments, the modified polymerases as disclosed herein contain a systematic error percentage of less than 0.8%. In some embodiments, the modified polymerases as disclosed herein contain a systematic error percentage of less than 0.7%. In some embodiments, the modified polymerases as disclosed herein contain a systematic error percentage of less than 0.6%. In some embodiments, the modified polymerases as disclosed herein contain a systematic error percentage of less than 0.5%. In some embodiments, the modified polymerases as disclosed herein contain a systematic error percentage of less than 0.4%. In some embodiments, the modified polymerases as disclosed herein contain a systematic error percentage of less than 0.3%. In some embodiments, the modified polymerases as disclosed herein contain a systematic error percentage of less than 0.2%. In some embodiments, the modified polymerases as disclosed herein contain a systematic error percentage of less than 0.1%. In some embodiments, the modified polymerases as disclosed herein contain a systematic error percentage of less than 0.09%. In some embodiments, the modified polymerases as disclosed herein contain a systematic error percentage of less than 0.08%. In some embodiments, the modified polymerases as disclosed herein contain a systematic error percentage of less than 0.05%. In some embodiments, the modified polymerases as disclosed herein contain a systematic error percentage of less than 0.04%.

The term "strand bias" as used herein, refers to the percentage of target bases in a sequencing run where the read (genotype) from one strand (e.g., positive) is different from the read (genotype) inferred from the other (e.g., negative) strand. The coverage of a given target base is computed by counting the number of read bases mapped to it in an alignment. The mean coverage is computed by averaging this value across every base in the target. Then the relative coverage for a particular base is computed as the ratio of these values. A relative coverage of 1 indicates that a particular base is covered at the expected average rate. A relative coverage above 1 indicates higher than expected coverage and below 1 indicates lower than expected coverage. Generally, the probability of ambiguous mapping increases as reads become shorter or less accurate. Ambiguous mapping is also more likely for reads that derive from repetitive or low complexity regions of the genome, including some regions with extreme GC content. In some embodiments, the percentage of strand bias is lowered when using a modified polymerase as disclosed herein, as compared to a reference polymerase (e.g., a wild-type polymerase) that does not contain the corresponding one or more amino acid modifications. In some embodiments, the modified polymerases of the instant application have a decreased strand bias as compared to the corresponding non-modified polymerase. While the actual strand bias of a given polymerase can vary from reaction to reaction (or even within a single reaction mixture) the polymerase can be characterized by the percentage of target bases with no strand bias, observed under a defined set of reaction conditions. In some embodiments, the modified polymerases as disclosed herein comprise a percentage of target bases with no strand bias of above 25%. In some embodiments, the modified polymerases as disclosed herein comprise a percentage of target bases with no strand bias of about 30%. In some embodiments, the modified polymerases as disclosed herein comprise a percentage of target bases with no strand bias of about 40%. In some embodiments, the modified polymerases as disclosed herein comprise a percentage of target bases with no strand bias of about 45%. In some embodiments, the modified polymerases as disclosed herein comprise a percentage of target bases with no strand bias of about 50%. In some embodiments, the modified polymerases as disclosed herein comprise a percentage of target bases with no strand bias of about 60%. In some embodiments, the modified polymerases as disclosed herein comprise a percentage of target bases with no strand bias of about 70%. In some embodiments, the modified polymerases as disclosed herein comprise a percentage of target bases with no strand bias of about 75%. In some embodiments, the modified polymerases as disclosed herein comprise a percentage of target bases with no strand bias of about 80%. In some embodiments, the modified polymerases as disclosed herein comprise a percentage of target bases with no strand bias of about 85%. Conversely, in some embodiments the modified polymerases as disclosed herein can include about 15% percent of target bases with strand bias. In another embodiment, the modified polymerases as disclosed herein can include about 20%, 25%, 30%, 35%, 40%, 45% or 50% percent of target bases with strand bias.

The terms "signal to noise ratio" or "SNR" refer to the ratio of signal power to noise power. Generally, SNR is a method of measuring a desired signal compared to the level of background noise. In some embodiments, "signal to noise ratio" can refer to the ratio of signal power obtained during a sequencing run as compared to background noise of the same sequencing run. In some embodiments, the instant application discloses methods, kits, apparatuses, and compositions that provide a means to increase the signal to noise ratio. In some embodiments, the disclosure relates generally to a method for performing nucleic acid sequencing comprising contacting a modified polymerase with a nucleic acid template in the presence of one or more nucleotides, where the modified polymerase includes one or more amino acid modifications relative to a reference polymerase and has an increased signal to noise ratio relative to the reference polymerase not having the one or more amino acid mutations, and polymerizing at least one of the one or more nucleotides using the modified polymerase.

In some embodiments, the disclosure relates generally to compositions, methods, systems, apparatuses and kits comprising modified polymerases that are characterized by increased processivity, read length (including error-free read length), total sequencing throughput and/or accuracy as compared to their unmodified counterparts (e.g., reference polymerase), as well as to methods for making and using such modified polymerases in a wide range of biological and chemical reactions such as nucleotide polymerization, primer extension, generation of nucleic acid libraries and nucleic acid sequencing reactions. In some embodiments, the disclosure relates generally to compositions, methods, systems, apparatuses and kits comprising modified polymerases that are characterized decreased strand bias and/or systematic error as compared to their unmodified counterparts (e.g., reference polymerase), as well as to methods for making and using such modified polymerases in a wide range of biological and chemical reactions such as nucleotide polymerization, primer extension, generation of nucleic acid libraries and nucleic acid sequencing reactions. In some embodiments, the modified polymerases include one or more amino acid mutations (e.g., amino acid substitutions, additions or deletions) relative to their corresponding unmodified counterparts. In some embodiments, the term accuracy as used herein can be measured by determining the rate of incorporation of a correct nucleotide during polymerization as compared to the rate of incorporation of an incorrect nucleotide during polymerization. In some embodiments, the rate of incorporation of an incorrect nucleotide can be greater than 0.3, 0.4, 0.5, 0.6, 0.7 seconds or more under elevated salt conditions (high ionic strength solution) as compared to standard (lower) salt conditions. While not wishing to be bound by any particular theory, it has been found by the applicants that the presence of elevated salt during polymerization slows down the rate of incorporation of the incorrect nucleotide, thereby producing a slower incorporation constant for the incorrect nucleotide. In some embodiments, a modified polymerase of the disclosure has enhanced accuracy compared to a relative polymerase, optionally the modified polymerase or a biological fragment thereof has enhanced accuracy (as compared to a relative polymerase) in the presence of a high ionic strength solution.

In some embodiments, the disclosure relates generally to a modified polymerase that retains polymerase activity in the presence of a high ionic strength solution. In some embodiments, the high ionic strength solution can be about 120 mM to about 300 mM salt. In some embodiments, the high ionic strength solution can be 130 mM salt. In some embodiments, the high ionic strength solution can be at least 125 mM salt, such as KCl and/or NaCl. In some embodiments, the high ionic strength solution can be about 225 mM to about 250 mM salt. In some embodiments, the salt can include a potassium and/or sodium salt, such as KCl and/or NaCl. It will be apparent to the skilled artisan that various other suitable salts can be used in place, or in combination with KCl and/or NaCl. In some embodiments, the ionic strength solution can further include a sulfate.

In some embodiments, the modified polymerase can amplify and/or sequence a nucleic acid molecule in the presence of a high ionic strength solution. In some embodiments, a modified polymerase is capable of amplifying (and/or sequencing) a nucleic acid molecule in the presence of a high ionic strength solution to a greater extent (for example as measured by accuracy) than a reference polymerase lacking one or more of the same mutations (or homologous mutations) under identical conditions. In some embodiments, a modified polymerase is capable of amplifying (and/or sequencing) a nucleic acid molecule in the presence of a high ionic strength solution to a greater capacity (for example as measured by accuracy) than a reference polymerase lacking one or more of the mutations (or homologous mutations) under standard ionic strength conditions (i.e., lower ionic strength as compared to a high ionic strength solution).

In some embodiments, the disclosure generally relates to a modified polymerase or a biologically active fragment thereof that can perform nucleotide polymerization or nucleotide incorporation in the presence of elevated salt conditions (in excess of 120 mM salt) as compared to a reference polymerase.

In some embodiments, the disclosure generally relates to a modified polymerase or a biologically active fragment thereof that has increased accuracy or increased dissociation time constant in the presence of elevated salt conditions (in excess of 120 mM salt) as compared to a reference polymerase.

In some embodiments, the disclosure generally relates to a modified polymerase or a biologically fragment thereof that can detect a change in ion concentration during nucleotide polymerization in the presence of elevated salt conditions (in excess of 120 mM salt) as compared to a reference polymerase.

In some embodiments, the disclosure generally relates to a modified polymerase or a biologically active fragment thereof that can amplify or sequence a nucleic acid molecule in the presence of elevated salt conditions (in excess of 120 mM salt).

In some embodiments, the disclosure generally relates to a modified polymerase or a biologically active fragment thereof that has increased accuracy as compared to a reference polymerase.

In some embodiments, the disclosure relates generally to methods, compositions, systems and kits comprising the use of such modified polymerases in nucleotide polymerization reactions, including nucleotide polymerization reactions wherein sequence information is obtained from a nucleic acid molecule. In some embodiments, the disclosure relates generally to methods, compositions, systems and kits comprising the use of such modified polymerases in clonal amplification reactions, including nucleic acid library synthesis. In some embodiments, the disclosure relates to methods for using such modified polymerases in ion-based nucleic acid sequencing reactions, wherein sequence information is obtained from a template nucleic acid using an ion-based sequencing system. In some embodiments, the disclosure relates generally to compositions, methods, systems, kits and apparatuses for carrying out a plurality of label-free DNA sequencing reactions (e.g., ion-based sequencing reactions) using a large-scale array of electronic sensors, for example field effect transistors ("FETs").

In some embodiments, the disclosure relates to methods for using such modified polymerases during amplification of nucleic acids in a sequencing reaction, wherein sequence information is obtained from the amplification of the nucleic acids using a solid support based sequencing system (e.g., bridge PCR based sequencing). In some embodiments, the disclosure generally relates to methods of amplifying one or more nucleic acids using a solid support system thereby clonally amplifying the nucleic acids on the solid support.

In some embodiments, the disclosure relates generally to compositions (as well as related methods, systems, kits and apparatuses using such compositions) comprising a modified polymerase including at least one amino acid modification (e.g., amino acid substitution, addition, deletion or chemical modification) relative to a reference polymerase (where the reference polymerase does not include the at least one modification), where the modified polymerase is optionally characterized by a change (e.g., increase or decrease) in any one or more of the following properties relative to the reference polymerase: dissociation time constant, rate of dissociation of polymerase from a given nucleic acid template (also referred to herein as "off-rate"), binding affinity of the polymerase for a given nucleic acid template, average read length, minimum read length, accuracy, strand bias, raw read accuracy, systematic error, total sequencing throughput, performance in salt (i.e., ionic strength), AQ20, average error-free read length, 100Q17 value, 200Q17 value and processivity.

As used herein, the terms "Q17" or "Q20" and their variants, when used in reference to a given polymerase, refer to certain aspects of polymerase performance, particularly accuracy, in a given polymerase reaction, for example in a polymerase-based sequencing by synthesis reaction. For example, in a particular sequencing reaction, accuracy metrics can be calculated either through prediction algorithms or through actual alignment to a known reference genome. Predicted quality scores ("Q scores") can be derived from algorithms that look at the inherent properties of the input signal and make fairly accurate estimates regarding if a given single base included in the sequencing "read" will align. In some embodiments, such predicted quality scores can be useful to filter and remove lower quality reads prior to downstream alignment. In some embodiments, the accuracy can be reported in terms of a Phred-like Q score that measures accuracy on logarithmic scale such that: $Q10=90\%$, $Q17=98\%$, $Q20=99\%$, $Q30=99.9\%$, $Q40=99.99\%$, and $Q50=99.999\%$. Phred quality scores ("Q") are defined as a property which is logarithmically related to the base-calling error probabilities ("P"). Often the formula given for calculating "Q" is $Q=10*\log 10(1/\text{error rate})$. In some embodiments, the data obtained from a given polymerase reaction can be filtered to measure only polymerase reads measuring "N" nucleotides or longer and having a Q score that passes a certain threshold, e.g., Q10, Q17, Q100 (referred to herein as the "NQ17" score). For example, the 100Q20 score can indicate the number of reads obtained from a given reaction that are at least 100 nucleotides in length and have Q scores of Q20 (99%) or greater. Similarly, the 200Q20 score can indicate the number of reads that are at least 200 nucleotides in length and have Q scores of Q20 (99%) or greater.

In some embodiments, the accuracy can also be calculated based on proper alignment using a reference genomic sequence, referred to herein as the "raw" accuracy. This is single pass accuracy, involving measurement of the "true" per base error associated with a single read, as opposed to consensus accuracy, which measures the error rate from the consensus sequence which is the result of multiple reads. Raw accuracy measurements can be reported in terms of "AQ" scores (for aligned quality). In some embodiments, the data obtained from a given polymerase reaction can be filtered to measure only polymerase reads measuring "N" nucleotides or longer having a AQ score that passes a certain threshold, e.g., AQ10, AQ17, AQ100 (referred to herein as the "NAQ17" score). For example, the 100AQ20 score can indicate the number of reads obtained from a given polymerase reaction that are at least 100 nucleotides in length and have AQ scores of AQ20 (99%) or greater. Similarly, the 200AQ20 score can indicate the number of reads that are at least 200 nucleotides in length and have AQ scores of AQ20 (99%) or greater.

In some embodiments, the accuracy of the polymerase, (including for example accuracy in a given sequencing reaction) can be measured in terms of the total number of "perfect" (i.e., zero-error) reads obtained from a polymerase reaction that are greater than 100, 200, 300, 400, 500, 750, 1000, 5000, 10000, 100000, or more nucleotides in length.

In some embodiments, the accuracy of the polymerase can be measured in terms of the longest perfect read (typically measured in terms of number of nucleotides included in the read) that is obtained from the polymerase reaction.

In some embodiments, the accuracy of the polymerase can be measured in terms of fold-increase in sequencing throughput obtained in a given sequencing reaction. For example, in some embodiments an exemplary modified polymerase of the instant application may have an increased accuracy of 2-fold, 5-fold, 10-fold, 20-fold, 50-fold, 75-fold, 100-fold, 150-fold, 200-fold, 400-fold, 500-fold, or greater, accuracy than a reference polymerase.

Some exemplary non-limiting descriptions of accuracy metrics can be found in: Ewing B, Hillier L, Wendl M C, Green P. (1998): Base-calling of automated sequencer traces using phred. I. Accuracy assessment. Genome Res. 8(3): 175-185; Ewing B, Green P. (1998): Base-calling of automated sequencer traces using phred. II. Error probabilities. Genome Res. 8(3):186-194; Dear S, Staden R (1992): A standard file format for data from DNA sequencing instruments. DNA Sequence, 3, 107-110; Bonfield J K, Staden R (1995): The application of numerical estimates of base calling accuracy to DNA sequencing projects. Nucleic Acids Res. 1995 Apr. 25; 23(8):1406-10, herein incorporated by reference in their entireties.

In some embodiments, the sequencing accuracy of a given set of polymerases (including any of the reference or modified polymerases described herein) can be measured in an ion based sequencing reaction run; such accuracies can optionally be compared with each other to determine whether a given amino acid mutation increases or decreases the sequencing accuracy relative to a reference or unmodified polymerase. In some embodiments, the sequencing accuracy of one or more polymerases can be measured using any ion-based sequencing apparatus supplied by Ion Torrent Technologies (Ion Torrent Systems, Life Technologies, Carlsbad, Calif.), including for example the Ion Torrent PGM™ Sequencer (Ion Torrent Systems, Life Technologies, Part No. 4462917), optionally using the sequencing protocols and reagents provided by Ion Torrent Systems. Some examples of calculation of accuracy metrics of a given polymerase using such ion-based sequencing systems is described further in the Ion Torrent Application Note titled "Ion Torrent: Ion Personal Genome Machine™ Performance Overview, Performance Spring 2011", hereby incorporated by reference.

As used herein, the terms "dissociation rate constant" and "dissociation time constant", when used in reference to a given polymerase, refer to the time constant for dissociation ("koff") of a polymerase from a nucleic acid template under a defined set of reaction conditions. Some exemplary assays for measuring the dissociation time constant of a polymerase are described further below. In some embodiments, the dissociation time constant can be measured in units of inverse time, e.g., sec-1 or min-1.

In some embodiments, the disclosure relates generally to an isolated modified polymerase including at least one amino acid modification relative to a reference polymerase and providing an increased average read length of primer extension products in a primer extension reaction using the modified polymerase, relative to the average read length of primer extension products obtained using the reference polymerase. In some embodiments, the isolated modified polymerase provides an increased average error-free read length of primer extension products in a primer extension reaction using the modified polymerase, relative to the average error-free read length of primer extension products obtained using the reference polymerase. Optionally, the modified polymerase includes two or more amino acid substitutions relative to the reference polymerase.

In some embodiments, the primer extension reaction is an ion-based sequencing reaction.

In some embodiments, the isolated modified polymerase provides an increased 100Q17 or 200Q17 value in a nucleic acid sequencing reaction (for example in an ion-based sequencing reaction) relative to the 100Q17 or 200Q17 value obtained using a reference polymerase.

In some embodiments, the reference polymerase includes a naturally occurring or wild type polymerase. In other embodiments, the reference polymerase includes a derivative, truncated, mutant or variant form of a naturally occurring polymerase that is different from the modified polymerase, for example having one or more amino acid mutations omitted as compared to the modified polymerase.

In some embodiments, the disclosure relates generally to methods for performing a nucleotide polymerization reaction, comprising: contacting a modified polymerase with a nucleic acid template in the presence of one or more nucleotides; and polymerizing at least one of the one or more nucleotides using the modified polymerase. The polymerizing optionally further includes polymerizing the at least one nucleotide in a template-dependent fashion. In some embodiments, the modified polymerase includes one or more amino acid substitutions relative to a reference polymerase that does not include the one or more amino acid substitutions.

In some embodiments, the method further includes hybridizing a primer to the template prior to, during, or after the contacting. The polymerizing can include polymerizing the at least one nucleotide onto an end of the primer using the modified polymerase.

In some embodiments, the polymerizing is performed in the proximity of a sensor that is capable of detecting the polymerization of the at least one nucleotide by the modified polymerase.

In some embodiments, the method further includes detecting a signal indicating the polymerization of the at least one of the one or more nucleotides by the modified polymerase using the sensor.

In some embodiments, the modified polymerase, the reference polymerase, or both the modified and reference polymerase is a DNA polymerase. The DNA polymerase can include, without limitation, a bacterial DNA polymerase, prokaryotic DNA polymerase, eukaryotic DNA polymerase, archaeal DNA polymerase, viral DNA polymerase or phage DNA polymerase.

In some embodiments, the DNA polymerase is selected from the group consisting of an A family DNA polymerase; a B family DNA polymerase; a mixed-type polymerase; an unclassified DNA polymerase and RT family polymerase; and variants and derivatives thereof.

In some embodiments, the DNA polymerase is an A family DNA polymerase selected from the group consisting of a Pol I-type DNA polymerase such as E. coli DNA polymerase, the Klenow fragment of E. coli DNA polymerase, Bst DNA polymerase, Taq DNA polymerase, Platinum Taq DNA polymerase series, Omni Klen Taq DNA polymerase series, Klen Taq DNA polymerase series, T7 DNA polymerase, and Tth DNA polymerase. In some embodiments, the DNA polymerase is Bst DNA polymerase. In other embodiments, the DNA polymerase is E. coli DNA polymerase I. In some embodiments, the DNA polymerase is the Klenow fragment of E. coli DNA polymerase. In some embodiments, the polymerase is Taq DNA polymerase. In some embodiments, the polymerase is T7 DNA polymerase.

In other embodiments, the DNA polymerase is a B family DNA polymerase selected from the group consisting of Tli polymerase, Pfu polymerase, Pfu turbo polymerase, Pyrobest polymerase, Pwo polymerase, KOD polymerase, Sac polymerase, S so polymerase, Poc polymerase, Pab polymerase, Mth polymerase, Pho polymerase, ES4 polymerase, VENT polymerase, DEEPVENT polymerase, Therminator™ polymerase, phage Phi29 polymerase, and phage B103 polymerase. In some embodiments, the polymerase is KOD polymerase. In some embodiments, the polymerase is Therminator™ polymerase. In some embodiments, the polymerase is phage Phi29 DNA polymerase. In some embodiments the polymerase is phage B103 polymerase, including, for example, the variants disclosed in U.S. Patent Publication No. 20110014612 which is incorporated by reference herein.

In other embodiments, the DNA polymerase is a mixed-type polymerase selected from the group consisting of EX-Taq polymerase, LA-Taq polymerase, Expand polymerase series, and Hi-Fi polymerase. In yet other embodiments, the DNA polymerase is an unclassified DNA polymerase selected from the group consisting of Tbr polymerase, Tfl polymerase, Tru polymerase, Tac polymerase, Tne polymerase, Tma polymerase, Tih polymerase, and Tfi polymerase.

In other embodiments, the DNA polymerase is an RT polymerase selected from the group consisting of HIV reverse transcriptase, M-MLV reverse transcriptase and AMV reverse transcriptase. In some embodiments, the polymerase is HIV reverse transcriptase or a fragment thereof having DNA polymerase activity.

Suitable bacterial DNA polymerases include without limitation E. coli DNA polymerases I, II and III, IV and V, the Klenow fragment of E. coli DNA polymerase, Clostridium stercorarium (Cst) DNA polymerase, Clostridium thermocellum (Cth) DNA polymerase, Bacillus stearothermophilus (Bst) DNA polymerase and Sulfolobus solfataricus (Sso) DNA polymerase.

Suitable eukaryotic DNA polymerases include without limitation the DNA polymerases $\alpha$, $\delta$, $\epsilon$, $\eta$, $\zeta$, $\gamma$, $\beta$, $\sigma$, $\lambda$, $\mu$, $\iota$, and $\kappa$, as well as the Rev1 polymerase (terminal deoxycytidyl transferase) and terminal deoxynucleotidyl transferase (TdT).

Suitable viral and/or phage DNA polymerases include without limitation T4 DNA polymerase, T5 DNA polymerase, T7 DNA polymerase, Phi-15 DNA polymerase, Phi-29 DNA polymerase (see, e.g., U.S. Pat. No. 5,198,543; also referred to variously as Φ29 polymerase, phi29 polymerase, phi 29 polymerase, Phi 29 polymerase, and Phi29 polymerase); Φ15 polymerase (also referred to herein as Phi-15 polymerase); Φ21 polymerase (Phi-21 polymerase); PZA polymerase; PZE polymerase, PRD1 polymerase; Nf polymerase; M2Y polymerase; SF5 polymerase; f1 DNA polymerase, Cp-1 polymerase; Cp-5 polymerase; Cp-7 polymerase; PR4 polymerase; PR5 polymerase; PR722 polymerase; L17 polymerase; M13 DNA polymerase, RB69 DNA polymerase, G1 polymerase; GA-1 polymerase, BS32 polymerase; B103 polymerase; a polymerase obtained from any phi-29 like phage or derivatives thereof, etc. See, e.g., U.S. Pat. No. 5,576,204, filed Feb. 11, 1993; U.S. Pat. Appl. No. 2007/0196846, published Aug. 23, 2007.

Suitable archaeal DNA polymerases include without limitation the thermostable and/or thermophilic DNA polymerases such as, for example, DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavus* (Tfl) DNA polymerase, *Pyrococcus woesei* (Pwo) DNA polymerase, *Pyrococcus furiosus* (Pfu) DNA polymerase as well as Turbo Pfu DNA polymerase, *Thermococcus litoralis* (Tli) DNA polymerase or Vent DNA polymerase, *Pyrococcus* sp. GB-D polymerase, "Deep Vent" DNA polymerase, New England Biolabs), *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. 9° N-7 DNA polymerase; *Thermococcus* sp. NA1; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; the heterodimeric DNA polymerase DP1/DP2, etc.

In some embodiments, the modified polymerase is an RNA polymerase. Suitable RNA polymerases include, without limitation, T3, T5, T7, and SP6 RNA polymerases.

In some embodiments, the polymerase is a reverse transcriptase. Suitable reverse transcriptases include without limitation reverse transcriptases from HIV, HTLV-I, HTLV-II, FeLV, FIV, SIV, AMV, MMTV and MoMuLV, as well as the commercially available "Superscript" reverse transcriptases, (Life Technologies Corp., Carlsbad, Calif.) and telomerases.

In some embodiments, the modified polymerase is derived from a known DNA polymerase. The DNA polymerases have been classified into seven different families, based upon both amino acid sequence comparisons and three-dimensional structure analyses. The DNA polymerase I (pol I) or type A polymerase family includes the repair polymerases *E. coli* DNA pol I, *Thermus aquaticus* pol I, and *Bacillus stearothermophilus* pol I, replicative DNA polymerases from some bacteriophages (T3, T5 and T7) and eukaryotic mitochondrial DNA polymerases. The DNA polymerase α (pol α) or type B polymerase family includes all eukaryotic replicating DNA polymerases as well as archaebacterial DNA polymerases, viral DNA polymerases, DNA polymerases encoded in mitochondrial plasmids of various fungi and plants, and the polymerases from bacteriophages T4 and RB69. Family C polymerases are the primary bacterial chromosome replicative enzymes. These are sometimes considered a subset of family Y, which contains the eukaryotic polymerase pol β, as well as other eukaryotic polymerases such as pol σ, pol λ, pol μ, and terminal deoxynucleotidyl transferase (TdT). Family D polymerases are all found in the Euryarchaeota subdomain of Archaea and are thought to be replicative polymerases. The family Y polymerases are called translesion synthesis (TLS) polymerases due to their ability to replicate through damaged DNA. They are also known as error-prone polymerases since they have a low fidelity on undamaged templates. This family includes Pol η, Polζ, Pol ι (iota), Pol κ (kappa), and Rev1, and Pol IV and PolV from *E coli*. Finally, the reverse transcriptase family includes reverse transcriptases from retroviruses and eukaryotic polymerases, usually restricted to telomerases. These polymerases use an RNA template to synthesize the DNA strand, and are also known as RNA-dependent DNA polymerases.

In some embodiments, a modified polymerase or biologically active fragment thereof can be prepared using any suitable method or assay known to one of skill in the art. In some embodiments, any suitable method of protein engineering to obtain a modified polymerase or biologically active fragment thereof is encompassed by the disclosure. For example, site-directed mutagenesis is a technique that can be used to introduce one or more known or random mutations within a DNA construct. The introduction of the one or more amino acid mutations can be verified for example, against a standard or reference polymerase or via nucleic acid sequencing. Once verified, the construct containing the one or more of the amino acid mutations can be transformed into bacterial cells and expressed.

Typically, colonies containing mutant expression constructs are inoculated in media, induced, and grown to a desired optical density before collection (often via centrifugation) and purification of the supernatant. It will be readily apparent to the skilled artisan that the supernatant can be purified by any suitable means. Typically, a column for analytical or preparative protein purification is selected. In some embodiments, a modified polymerase or biologically active fragment thereof prepared using the methods can be purified, without limitation, over a heparin column essentially according to the manufacturer's instructions.

Once purified, the modified polymerase or biologically active fragment thereof can be assessed using any suitable method for various polymerase activities. In some embodiments, the polymerase activity being assessed will depend on the application of interest. For example a polymerase used to amplify or sequence a nucleic acid molecule of about 400 bp in length may include polymerase activities such as increased processivity and/or increased dissociation time constant relative to a reference polymerase. In another example, an application requiring deep targeted-resequencing of a nucleic acid molecule of about 100 bp in length may include a polymerase with increased proofreading activity, increased raw accuracy, increased total sequencing throughput, decreased strand bias, lowered systematic error or increased minimum read length. In some embodiments, the one or more polymerase activities assessed can be related to polymerase performance or polymerase activity in the presence of high ionic strength solution (e.g., high salt conditions).

In some embodiments, a modified polymerase or biologically active fragment thereof prepared according to the methods can be assessed for DNA binding activity, nucleotide polymerization activity, primer extension activity, strand displacement activity, reverse transcriptase activity, 3'-5' exonuclease (proofreading) activity, and the like.

In some embodiments, a modified polymerase or biologically active fragment thereof prepared according to the methods can be assessed for increased accuracy, increase processivity, increased average read length, increased minimum read length, increased total sequencing throughput, reduced strand bias, lowered systematic error, increased AQ20, increased 200Q17 value or the ability to perform nucleotide polymerization as compared to a reference polymerase. In some embodiments, the modified polymerase or the biologically active fragment thereof can be assessed for any one of the polymerase activities in the presence of a high ionic strength solution.

In some embodiments, a modified polymerase or biologically active fragment thereof is optionally characterized by a change (e.g., increase or decrease) in any one or more of the following properties (often, relative to a polymerase lacking the one or more amino acid mutations): dissociation time constant, rate of dissociation of polymerase from a given nucleic acid template, binding affinity of the polymerase for a given nucleic acid template, average read length, minimum read length, accuracy, total number of perfect reads, total sequencing throughput, strand bias, systematic error, fold-increase in throughput of a sequencing reaction, performance in salt (i.e., ionic strength), AQ20, average error-free read length, error-rate, 100Q17 value, 200Q17 value, Q score, raw read accuracy, and processivity.

In some embodiments, a modified polymerase or biologically active fragment thereof can be assessed individually with respect to known values in the art for an analogous polymerase. In some embodiments, a modified polymerase or biologically active fragment thereof prepared according to the methods can be assessed against a known or reference polymerase under similar or identical conditions. In some embodiments, the conditions can include amplifying or sequencing a nucleic acid molecule in the presence of a high ionic strength solution.

In some embodiments, the disclosure relates generally to methods for producing a plurality of modified polymerases or biologically active fragments. In some embodiments, the disclosure relates generally to methods for producing a plurality of modified polymerases or biologically active fragments using a high-throughput or automated system. In some embodiments, the methods comprise mixing a plurality of modified polymerases or biologically active fragments with a series of reagents necessary for protein purification and extracting the purified polymerases or biologically active fragments from the mixture. In one example, a plurality of random or site-directed mutagenesis reactions can be prepared in a 96- or 384-well plate. Optionally, the contents of the 96- or 384-well plate can undergo an initial screen to identify polymerase mutant constructs. The contents of each individual well (or the contents of each well from an initial screen) can be delivered to a series of flasks, tubes or shakers for inoculation and induction. Once at the required optical density, the flask, tubes or shakers can be centrifuged and the supernatants recovered. Each supernatant can undergo protein purification, for example via fully automated column purification (for example see, Camper and Viola, Analytical Biochemistry, 2009, p 176-181). The purified modified polymerases or biologically active fragments can be assessed for one, or a combination of polymerase activities, such as DNA binding, primer extension, strand displacement, reverse transcriptase activity, and the like. It is envisaged that the skilled artisan can use the method (or variations of the methods that are within the scope of the disclosure) to identify a plurality of modified polymerases or biologically active fragments. In some aspects, the methods can be used to identify a plurality of modified polymerases or biologically active fragments having enhanced accuracy as compared to a reference polymerase. In some embodiments, the methods can be used to identify a plurality of modified polymerases or biologically active fragments thereof having enhanced accuracy in the presence of a high ionic strength solution. In some embodiments, the high ionic strength solution can include a KCl and/or NaCl salt. In some embodiments, the high ionic strength solution can be about 120 to 300 mM salt. In some embodiments, the high ionic strength solution can be about 120 mM to about 200 mM salt. In some embodiments, the high ionic strength solution can be at least 125 mM salt. It will be apparent to the skilled artisan that various other suitable salts can be used in place, or in combination with KCl and/or NaCl. In some embodiments, the ionic strength solution can further include a sulfate.

As will be readily apparent to the skilled artisan, the disclosure outlines an exemplary automated and high-throughput method (and related apparatus and systems) to generate a library of modified polymerases or biological active fragments. The disclosure also outlines methods (and related kits, compositions, apparatus and systems) to assess such modified polymerases or biologically active fragments for polymerase activity. It is also encompassed by the disclosure that the skilled artisan can readily produce a mutagenized library of constructs wherein every amino acid within the polymerase of interest can be mutated. In some embodiments, a mutagenized library can be prepared wherein each amino acid within the polymerase is mutated by every possible amino acid combination. In some embodiments, a mutagenized library can be prepared where each amino acid within the polymerase is mutated, and where the combination of possible amino acid mutations is limited to conservative or non-conservative amino acid substitutions. In both examples, mutagenized libraries can be created containing vast numbers of mutant constructs that can be applied through an automated or high-throughput system for purification or for initial screening. In some embodiments, plates of 96- or 384-library constructs representing a mutagenized library can be assessed for one or more polymerase activities using an On-PGM polymerase screen, using a Personal Genome Machine and Ion PGM Sequencing Chips (Life Technologies Corp, CA). In one example, the On-PGM polymerase screen can include one or more 96- or 384-plates representing a mutagenized library; where each well of the plate consists of a different construct (modified polymerase) containing at least one, or more, amino acid mutations as compared to a reference polymerase in at least one well on the same plate (lacking the at least one or more amino acid mutations). In some embodiments, the reference polymerase acts as a control sample within the 96- or 384-plate to assess polymerase activity of each modified polymerase within the wells of the plate. In some embodiments, the library of constructs and reference polymerase within the plate can further include a unique barcode for each modified polymerase within the plate. Thus, a 96-well plate may contain 96 barcodes if each well in the plate contains either a reference polymerase or a modified polymerase construct. Once purified, the mutagenized library of proteins can be assessed for one, or a combination of polymerase activities, such as DNA binding, primer extension, strand displacement, reverse transcriptase, nick-initiated polymerase activity, raw accuracy, increase total sequencing throughput, reduced strand bias, lowered systematic error, read length and the like. In some embodiments, the libraries can further include template libraries that are known to perform well under the proposed amplification conditions, so that the well-performing template libraries can act as a baseline or control reading.

Optionally, the purified modified polymerases or biologically active fragments thereof can be further assessed for other properties such as the ability to amplify or sequence a nucleic acid molecule in the presence of high salt (ionic strength). The source or origin of the polymerase to be mutated is generally not considered critical. For example, eukaryotic, prokaryotic, archaeal, bacterial, phage or viral polymerases can be used in the methods. In some embodiments, the polymerase can be a DNA or RNA polymerase. In some embodiments, the DNA polymerase can include a family A or family B DNA polymerase. The exemplary methods provided herein are to be considered illustrative in view of the field of protein engineering and enzymatics and should not be construed as in any way limiting.

In some embodiments, the modified polymerase or a biologically active fragment thereof, includes one or more amino acid mutations that are located inside the catalytic domain of the modified polymerase. In some embodiments, the modified polymerase or biologically active fragment thereof can include at least 25, 50, 75, 100, 150, or more amino acid residues of the catalytic domain. In some embodiments, the modified polymerase or biologically active fragment thereof can include any part of the catalytic domain that comprises at least 25, 50, 75, 100, 150, or more contiguous amino acid residues. In some embodiments, the modified polymerase or biologically active fragment thereof can include at least 25 contiguous amino acid residues of the catalytic domain and can optionally include one or more amino acid residues at the C-terminal or the N-terminal that are outside the catalytic domain. In some embodiments, the modified polymerase or a biologically active fragment can include any 25, 50, 75, 100, 150, or more contiguous amino acid residues of the catalytic domain coupled to any one or more non-catalytic domain amino acid residues.

In some embodiments, the modified polymerase (or biologically active fragment thereof) includes one or more amino acid mutations that are located inside the catalytic domain of the modified polymerase, and wherein the polymerase has at least 80%, 85%, 90%, 95%, 96%, 97%, 98%, 99%, or more identity to any one of the modified polymerases disclosed herein. In some embodiments, the modified polymerase (or biologically active fragment thereof) includes one or more amino acid mutations that are located inside the catalytic domain of the modified polymerase, and wherein the polymerase has at least 80%, 85%, 90%, 95%, 96%, 97%, 98%, 99% or more identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues of the catalytic domain and has at least 80% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues of the catalytic domain and has at least 85% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37. In some embodiments, the modified polymerase or biologically active fragment thereof includes at least 25 contiguous amino acid residues of the catalytic domain and has at least 90% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues of the catalytic domain and has at least 90% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues of the catalytic domain and has at least 95% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues of the catalytic domain and has at least 98% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues of the catalytic domain and has at least 80% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues of the catalytic domain and has at least 85% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues of the catalytic domain and has at least 90% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues of the catalytic domain and has at least 97% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues of the catalytic domain and has at least 98% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or a biologically active fragment thereof, includes one or more amino acid mutations that are located inside the DNA binding domain of the polymerase. In some embodiments, the modified polymerase or biologically active fragment thereof can include at least 25, 50, 75, 100, 150, or more amino acid residues of the DNA binding domain of the modified polymerase. In some embodiments, the modified polymerase or biologically active fragment thereof can include any part of the DNA binding domain that comprises at least 25, 50, 75, 100, 150, or more contigiuous amino acid residues. In some embodiments, the modified polymerase or biologically active fragment thereof can include at least 25 contiguous amino acid residues of the binding domain and can optionally include one or more amino acid residues at the C-terminal or the N-terminal that are outside of the binding domain. In some embodiments, the modified polymerase or a biologically active fragment can include any 25, 50, 75, 100, 150 or more contiguous amino acid residues of the binding domain coupled to any one or more non-binding domain amino acid residues. In some embodiments, the modified polymerase (or biologically active fragment thereof) includes one or more amino acid mutations that are located inside the DNA binding domain of the modified polymerase, and wherein the polymerase has at least 80%, 85%, 90%, 95%, 96%, 97%, 98%, 99%, or more identity to any one of the modified polymerases disclosed herein. In some embodiments, the modified polymerase (or biologically active fragment thereof) includes one or more amino acid mutations that are located inside the DNA binding domain of the modified polymerase, and wherein the polymerase has at least 80%, 85%, 90%, 95%, 96%, 97%, 98%, 99% or more identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues of the DNA binding domain and has at least 80% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues of the DNA binding domain and has at least 85% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues of the DNA binding domain and has at least 90% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues of the DNA binding domain and has at least 95% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28 and SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues of the DNA binding domain and has at least 98% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues of the DNA binding domain and has at least 80% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, and SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues of the DNA binding domain and has at least 85% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues of the DNA binding domain and has at least 90% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues of the DNA binding domain and has at least 95% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the modified polymerase or biologically active fragment thereof includes at least 50 contiguous amino acid residues of the DNA binding domain and has at least 98% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the modified polymerase or a biologically active fragment thereof, includes one or more amino acid mutations that are located outside the catalytic domain (also referred to herein as the DNA binding cleft) of the polymerase. The catalytic domains of the A family DNA polymerases, B family DNA polymerases and reverse transcriptases, as well as the RNA-dependent RNA polymerases are well known; all share a common overall structure and catalytic mechanism. The catalytic domains of all these polymerases have a shape that has been compared to a right hand and consists of "palm", "thumb" and "finger" domains. The palm domain typically contains the catalytic site for the phosphoryl transfer reaction. The thumb is thought to play a role positioning the duplex DNA and in processivity and translocation. The fingers interact with the incoming nucleotide as well as the template base with which it is paired. The palm domains are homologous in the A, B and RT families, but the arrangements of the fingers and thumb are different. The thumb domains of the different polymerase families do share common features, containing parallel or anti-parallel α-helices, with at least one α-helix interacting with the minor groove of the primer-template complex. The fingers domain also conserves an α-helix positioned at the blunt end of the primer-template complex. This helix contains highly conserved side chains (the B motif).

Three conserved motifs, A, B, and C have been identified for the A family polymerases. The A and C motifs are typically conserved in both the B family polymerases and the RT polymerases. (Delarue et al., Protein Engineering 3: 461-467 (1990)).

In some embodiments, for the A family polymerases, the A motif comprises the consensus sequence:

DXSXXE. (SEQ ID NO: 5)

In some embodiments, for the A family polymerases, the B motif comprises the consensus sequence:

KXXXXXXYG (SEQ ID NO: 6)

In some embodiments, for the A family polymerases, the C motif comprises the consensus sequence:

VHDE (SEQ ID NO: 7)

In some embodiments, the polymerase optionally comprises any A family polymerase, or biologically active fragment, mutant, variant or truncation thereof, wherein the linking moiety is linked to any amino acid residue of the A family polymerase, or biologically active fragment mutant, variant or truncation thereof, that is situated outside the A, B or C motifs. In some embodiments, the linking moiety is linked to any amino acid residue of the A family polymerase, or biologically active fragment, that is situated outside the A motif, the B motif or the C motif.

The A and C motifs typically form part of the palm domain, and each motif typically contains a strictly conserved aspartic acid residue, which are involved in the catalytic mechanism common to all the DNA polymerases. DNA synthesis can be mediated by transfer of a phosphoryl group from the incoming nucleotide to the 3' OH of the DNA, releasing a polyphosphate moiety and forming a new DNA phosphodiester bond. This reaction is typically catalyzed by a mechanism involving two metal ions, normally Mg2+, and the two conserved aspartic acid residues.

In some embodiments, the conserved glutamic acid residue in motif A of the A family DNA polymerases plays an important role in incorporation of the correct nucleotide, as does the corresponding conserved tyrosine in B family members (Minnick et al., Proc. Natl. Acad. Sci. USA 99: 1194-1199 (2002); Parsell et al, Nucleic Acids Res. 35: 3076-3086 (2002). Mutations at the conserved Leu of motif A affect replication fidelity (Venkatesan et al., J. Biol. Chem. 281: 4486-4494 (2006)).

In some embodiments, the B motif contains conserved lysine, tyrosine and glycine residues. The B motif of *E coli* pol I has been shown to bind nucleotide substrates and contains a conserved tyrosine which has been shown to be in the active site.

In some embodiments, for the B family □polymerases, the A motif comprises the consensus sequence:

DXXSLYPS. (SEQ ID NO: 8)

In some embodiments, for the B family□ polymerases, the B motif comprises the consensus sequence:

KXXXNSXYG (SEQ ID NO: 9)

In some embodiments, for the B family□ polymerases, the C motif comprises the consensus sequence:

YGDTDS (SEQ ID NO: 10)

The residues in bold indicate invariant residues.

In some embodiments, the modified polymerase optionally comprises any B family polymerase, or biologically active fragment, mutant, variant or truncation thereof, wherein the linking moiety is linked to any amino acid residue of the B family polymerase, or biologically active fragment, mutant, variant or truncation thereof that is situated outside the A, B or C motifs. In some embodiments, the linking moiety is linked to any amino acid residue of the B family polymerase, or biologically active fragment, that is situated outside the A motif, the B motif or the C motif.

In some embodiments, the B family polymerases contain six conserved motifs, of which regions I and II correspond to the A and C motifs of the A family. Region III is involved in nucleotide binding and is functionally homologous to motif B. Regions I, II and III converge at the center of the active site from the palm (I), the fingers (II), and base of the thumb (III) to produce a contiguous conserved surface. Within these regions, a set of highly conserved residues form three chemically distinct clusters consisting of exposed aromatic residues, negatively charged residues, and positively charged residues, respectively. For example, in the replication polymerase of the bacteriophage RB69, these three clusters corresponds to the following amino acid residues: Y416, Y567, and Y391 (exposed aromatic residues), D621, D623, D411, D684, and E686 (negatively charged residues), and K560, R482, and K486 (positively charged residues). See Wang et al, Cell 89: 1087-1099 (1997). These three clusters typically encompass the region in which the primer terminus and the incoming nucleotide would be expected to bind. In some embodiments, the modified polymerase optionally comprises any B family polymerase, or biologically active fragment, mutant, variant or truncation thereof, wherein the linking moiety is linked to any amino acid residue of the B family polymerase, or biologically active fragment, mutant, variant or truncation thereof that is situated outside one or more of these conserved amino acid clusters or motifs. In some embodiments, the linking moiety is linked to any amino acid residue of the B family polymerase, or biologically active fragment, mutant, variant or truncation thereof that is situated outside any of these conserved amino acid clusters or motifs.

The RT polymerases contain four conserved sequence motifs (Poch et al., EMBO J. 12: 3867-3874 (1989)), with motifs A and C containing the conserved catalytic aspartates. The integrity of motif B is also required for reverse transcriptase function.

The consensus sequence for motif A is DXXXXF/Y (SEQ ID NO: 11)

The consensus sequence for motif B is FXGXXXS/A (SEQ ID NO: 12)

The consensus sequence for motif C is YXDD (SEQ ID NO: 13)

The consensus sequence for motif D is GXXXXXXXK (SEQ ID NO: 14).

Mutations in the YXDD motif (motif C), the most highly conserved of these motifs, can abolish polymerase activity and alter the processivity and fidelity (Sharma et al., Antiviral Chemistry and Chemotherapy 16: 169-182 (2005)). In addition, the conserved lysine residue in motif D, a loop that is unique to the RT polymerases, is an invariant residue important for nucleotide binding (Canard et al., J. Biol. Chem. 274: 35768-35776 (1999)).

In some embodiments, the modified polymerase optionally comprises any RT polymerase, or biologically active fragment, mutant, variant or truncation thereof, wherein the linking moiety is linked to any amino acid residue of the RT polymerase, or biologically active fragment, mutant, variant or truncation thereof that is situated outside one or more of the A, B, C and D motifs. In some embodiments, the linking moiety is linked to any amino acid residue of the RT polymerase, or biologically active fragment, mutant, variant or truncation thereof that is situated outside any of these motifs.

In some embodiments, the modified polymerase includes one or more modifications (including amino acid substitutions, deletions, additions or chemical modifications) located at any position other than at the conserved or invariant residues.

In some embodiments, the modified polymerase or biologically active fragment thereof includes at least 25 contiguous amino acid residues having at least 80% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues having at least 85% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28. SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues having at least 85% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues having at least 90% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 100 contiguous amino acid residues having at least 90% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 100 contiguous amino acid residues having at least 95% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 150 contiguous amino acid residues having at least 95% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues having at least 98% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 50 contiguous amino acid residues having at least 98% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, the modified polymerase or biologically active fragment thereof includes at least 25 contiguous amino acid residues having at least 99% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28 and SEQ ID NO:29.

In some embodiments, the modified polymerase or biologically active fragment thereof includes at least 50 contiguous amino acid residues having at least 99% identity to any one of SEQ ID NO: 2, SEQ ID NO: 3, SEQ ID NO: 4, SEQ ID NO: 15, SEQ ID NO: 16, SEQ ID NO: 18, SEQ ID NO: 19, SEQ ID NO: 20, SEQ ID NO: 24, SEQ ID NO: 25, SEQ ID NO: 26, SEQ ID NO: 27, SEQ ID NO: 28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 and SEQ ID NO: 37.

In some embodiments, in addition to the polymerase domains, the modified polymerase can include one or more additional functional domains, including domains required for 3'->5' (reverse) exonuclease activity that mediates proofreading of the newly synthesized DNA strand, or for 5'->3' (forward) exonuclease activity that mediates nick translation during DNA repair, or for FLAP endonuclease activity. In some embodiments, the modified polymerase has strand-displacing activity, and can catalyze nucleic acid synthesis by polymerizing nucleotides into the 3' end of a nick within a double stranded nucleic acid template while simultaneously displacing the nucleic acid located downstream of the nick. The modified polymerase optionally has any one or more of these activities as well.

The 3' to 5' exonuclease proofreading domains of both A and B family DNA polymerases contain three conserved motifs, called Exo I, Exo II and Exo III, each of which contains an invariant aspartic acid residue essential for metal binding and exonuclease function. Alterations of these conserved aspartic acid residues result in proteins which retain polymerase activity, but are deficient in exonuclease activity (Hall et al., J. Gen. Virol. 76: 2999-3008 (1995)). Conserved motifs in the 5' to 3' exonuclease domains and amino acid alterations that affect exonuclease activity have also been identified (U.S. Pat. No. 5,466,591).

Representative examples of A family enzymes are E. coli. Pol I, or the Klenow fragment of E coli. Pol I, Bst DNA polymerase, Taq DNA polymerase, T7 DNA polymerase and Tth DNA polymerase. A family enzymes also include the Platinum Taq DNA polymerase series.

In some embodiments, the A family enzymes are characterized by high DNA elongation rates but can have poor fidelity because of the lack of 3'-5' exonuclease activity. In some embodiments, the B family enzymes can have high fidelity owing to their 3'-5' exonuclease activity but can achieve low DNA elongation rates.

Other types of polymerases include, for example, Tbr polymerase, Tfl polymerase, Tru polymerase, Tac polymerase, Tne polymerase, Tma polymerase, Tih polymerase, Tfi polymerase and the like. RT polymerases include HIV reverse transcriptase, Moloney Murine Leukemia Virus (M-MLV) reverse transcriptase, Avian Myeloblastosis Virus (AMV) reverse transcriptase or Rous Sarcoma Virus (RSV) reverse transcriptase. Variants, modified products and derivatives thereof are also usable. Similarly, Taq, Platinum Taq, Tth, Tli, Pfu, Pfutubo, Pyrobest, Pwo and KOD, VENT, DEEPVENT, EX-Taq, LA-Taq, Therminator™, the Expand series and Platinum Taq Hi-Fi are all commercially available. Other enzymes can be readily isolated from specific bacteria by those of ordinary skill in the art.

One exemplary polymerase, E coli DNA polymerase I ("Pol I") possesses three enzymatic activities: a 5' to 3' DNA polymerase activity; a 3' to 5' exonuclease activity that mediates proofreading; and a 5' to 3' exonuclease activity mediating nick translation during DNA repair. The Klenow fragment is a large protein fragment produced when E. coli Pol I is proteolytically cleaved by subtilisin. It retains the polymerase and proofreading exonuclease activities, but lacks the 5' to 3' exonuclease activity. An exo-Klenow fragment which has been mutated to remove the proofreading exonuclease activity is also available. The structure of the Klenow fragment shows that highly conserved residues that interact with DNA include N675, N678, K635, R631, E611, T609, R835, D827, 5562 and N579 (Beese et al, Science 260: 352-355 (1993)).

Arg682 in the Klenow fragment of E. coli DNA polymerase I (pol I) is important for the template-dependent nucleotide-binding function, and appears to maintain high processivity of the DNA polymerase (Pandey et al., European Journal of Biochemistry, 214:59-65 (1993)).

In some embodiments, the modified polymerase is derived from Taq DNA polymerase, which is an A family DNA polymerase derived from the thermophilic bacterium *Thermus aquaticus*. It is best known for its use in the polymerase chain reaction. Taq polymerase lacks a proofreading activity, and thus has a relatively low replication fidelity (Kim et al., Nature 376: 612-616 (2002).

In some embodiments, the modified polymerase is derived from the T7 DNA polymerase of bacteriophage T7, which is an A family DNA polymerase that consists of a 1:1 complex of the viral T7 gene 5 protein (80 k Da) and the *E. coli* thioredoxin (12 k Da). It lacks a 5'->3' exonuclease domain, but the 3'->5' exonuclease activity is approximately 1000-fold greater than that of *E. coli* Klenow fragment. The exonuclease activity appears to be responsible for the high fidelity of this enzyme and prevents strand displacement synthesis. This polymerase typically exhibits high levels of processivity.

In some embodiments, the modified polymerase is derived from KOD DNA polymerase, which is a B family DNA polymerase derived from *Thermococcus* kodakaraensis. KOD polymerase is a thermostable DNA polymerase with high fidelity and processivity.

In some embodiments, the modified polymerase is derived from the Therminator™ DNA polymerase, which is also a B family DNA polymerase. Therminator™ is an A485L point mutation of the DNA polymerase from *Thermococcus* species 9oN-7 (Ichida et al., Nucleic Acids Res. 33: 5214-5222 (2005)). Therminator™ polymerase has an enhanced ability to incorporate modified substrates such as dideoxynucleotides, ribonucleotides, and acyclonucleotides.

In some embodiments, the modified polymerase is derived from a Phi29 polymerase or a Phi29-type polymerase, for example a polymerase derived from the bacteriophage B 103. The Phi29 and B 103 DNA polymerases are B family polymerases from related bacteriophages. In addition to the A, B and C motifs, the Phi29 family of DNA polymerases contain an additional conserved motif, KXY in region Y (Blanco et al., J. Biol. Chem. 268: 16763-16770 (1993). Mutations to Phi29 and B103 polymerases that affect polymerase activity and nucleotide binding affinity are described in U.S. Patent Publication No. 20110014612 and its priority documents U.S. Provisional Application Nos. 61/307,356; 61/299,917; 61/299,919; 61/293,616; 61/293,618; 61/289,388; 61/263,974; 61/245,457; 61/242,771; 61/184,770; and 61/164,324, herein incorporated by reference in their entireties.

In some embodiments, the modified polymerase is derived from the reverse transcriptase from human immunodeficiency virus type 1 (HIV-1), which is a heterodimer consisting of one 66-kDa and one 51-kDa subunit. The p66 subunit contains both a polymerase and an RNase H domain; proteolytic cleavage of p66 removes the RNase H domain to yield the p51 subunit (Wang et al., PNAS 91:7242-7246 (1994)). The structure of the HIV-1 reverse transcriptase shows multiple interactions between the 2'-OH groups of the RNA template and the reverse transcriptase. Residues Ser280 and Arg284 of helix I in the p66 thumb are involved in the RNA-RT interactions, as well as residues Glu89 and Gln91 of the template grip in the p66 palm. The p51 subunit also plays a role in the interactions between the RNA-DNA duplex and the RT, with residues Lys395, Glu396, Lys22 and Lys390 of the p51 subunit also interacting with the DNA: RNA duplex (Kohlstaedt et al, Science 256: 1783-1790 (1992) and Safarianos et al, The EMBO Journal 20:1449-1461 (2001)).

In some embodiments, the modified polymerase is derived from the Bst DNA polymerase of *Bacillus stearothermophilus*, or any biologically active fragment thereof. The Bst polymerase can be a family A DNA polymerase. The large fragment of the naturally occurring Bst DNA polymerase is equivalent to the Klenow fragment of *E. coli* Pol I, retaining the polymerase and proofreading exonuclease activities while lacking the 5' to 3' exonuclease activity. In some embodiments, the polymerase derived from Bst DNA polymerase can lack 3' to 5' exonuclease activity. As used herein, the term "Bst DNA polymerase" may refer to a full length protein or to a Bst large fragment.

In some embodiments, the reference polymerase, the modified polymerase or both the reference and modified polymerase consist of, or comprise, an isolated variant of a Bst DNA polymerase having, or comprising, the amino acid sequence of SEQ ID NO: 1, which is the amino acid sequence of the large fragment (C-terminal portion) of the Bst DNA polymerase:

SEQ ID NO: 1 corresponds to the large fragment of Bst DNA polymerase and includes the DNA polymerase motifs A, B, and C (see, e.g., Delarue, supra) at residues 358-363, 411-420 and 533-536, respectively, as shown in SEQ ID NO: 1. The motifs are underlined, and the invariant residues within each motif are indicated in bold. In some embodiments, to retain the polymerase activity of a Bst polymerase, any substitutions, deletions or chemical modifications can be made to amino acid residues that are not highly conserved within motifs A, B or C, such as the invariant aspartic acid residues D358 and D535 required for polymerase activity. In some embodiments, the modified polymerase includes a mutant or variant form of a Bst DNA polymerase that retains a detectable level of polymerase activity.

In some embodiments, the reference polymerase, the modified polymerase or both the reference and modified polymerase consists of or comprises an isolated variant of a polymerase having or comprising an amino acid sequence that is at least 80% identical to the amino acid sequence of SEQ ID NO: 1. In some embodiments, the reference polymerase or the modified polymerase is an isolated variant of a Bst DNA polymerase comprising the amino acid sequence of SEQ ID NO: 1, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 1.

In some embodiments, the reference polymerase is a Bst DNA polymerase having, or comprising, the amino acid sequence of SEQ ID NO: 1, and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 1.

In some embodiments, the reference polymerase and/or the modified polymerase can include the amino acid sequence of any biologically active fragment of a polymerase having or comprising the amino acid sequence of SEQ ID NO: 1. In some embodiments, the modified polymerase can include the amino acid sequence of any biologically active fragment of a polymerase having or comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 1.

In some embodiments, the modified polymerase consists of or comprises an isolated variant of a Bst DNA polymerase having or comprising the amino acid sequence of SEQ ID NO: 2:

SEQ ID NO: 2 includes three amino acid substitutions relative to SEQ ID NO: 1, namely: His46Arg (H46R), Glu446Gln (E446Q), and His572Arg (H572R), wherein the numbering is relative to the amino acid sequence of SEQ ID NO: 1.

In some embodiments, the modified polymerase consists of or comprises an isolated variant of a polymerase having or comprising an amino acid sequence that is at least 90% identical to the amino acid sequence of SEQ ID NO: 2. In some embodiments, the polymerase is a variant of a Bst DNA polymerase comprising the amino acid sequence of SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

In some embodiments, the reference polymerase is a Bst DNA polymerase having, or comprising, the amino acid sequence of SEQ ID NO: 2, and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 2.

In some embodiments, the reference polymerase and/or the modified polymerase can include the amino acid sequence of any biologically active fragment of a polymerase having the amino acid sequence of SEQ ID NO: 2 and further including any one or more amino acid mutations selected from the group consisting of: D264S, D423K, and D480R.

In some embodiments, the modified polymerase can include the amino acid sequence of SEQ ID NO: 2 or any biologically active fragment thereof including any one or more amino acid substitutions selected from the group consisting of E220K, N234R, A263K, D264A, D264R, H273N, H281M, D423K, D480R, N485K, N487R, E493R, H528F and H528S, wherein the numbering is relative to the amino acid residues of SEQ ID NO: 2.

In some embodiments, the modified polymerase comprises or consists of the amino acid sequence of SEQ ID NO: 2 or any biologically active fragment thereof and further comprises amino acid substitution E220K, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution N234R, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution A263K, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution D264A, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution D264R, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution H273N, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution H281M, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution D423K, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitutions D423K and N487R, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitutions H281M and N487R, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution D480R, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution N485K, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution N487R, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution E493R, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution H528F, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitution H528S, wherein the numbering is relative to the amino acid sequence of SEQ ID NO: 2.

In some embodiments, the modified polymerase comprises or consists of the amino acid sequence of SEQ ID NO: 2 or any biologically active fragment thereof and further comprises amino acid substitutions E220K, N234R, and D423K, wherein the numbering is relative to the amino acid sequence of SEQ ID NO: 2.

In some embodiments, the modified polymerase can include the amino acid sequence of SEQ ID NO: 2 or any biologically fragment thereof further comprising any one or more amino acid substitutions selected from the group consisting of: D264A, H273N, H281M, D423K, N487R and E493R, wherein the numbering is relative to the amino acid residues of SEQ ID NO: 2.

In some embodiments, the modified polymerase consists of or comprises a modified polymerase having amino acid sequence SEQ ID NO: 2 and further comprising amino acid substitutions D264A, H273N, H281M, D423K, N487R and E493R, wherein the numbering is relative to amino acid residues of SEQ ID NO: 2. In some embodiments, the modified polymerase can include the amino acid sequence of SEQ ID NO: 2 or any biologically fragment thereof further comprising any one or more amino acid substitutions selected from the group consisting of: H281M, D423K, and N487R, wherein the numbering is relative to amino acid residues of SEQ ID NO: 2.

In some embodiments, the modified polymerase consists of or comprises a modified polymerase having amino acid sequence SEQ ID NO: 2 and further comprising amino acid substitutions H281M, D423K, and N487R, wherein the numbering is relative to amino acid residues of SEQ ID NO: 2.

In some embodiments, the modified polymerase can include the amino acid sequence of any biologically active fragment of a polymerase having or comprising the amino acid sequence of SEQ ID NO: 2. In some embodiments, the modified polymerase can include the amino acid sequence of any biologically active fragment of a polymerase having or comprising an amino acid sequence that is at least 90% identical to the amino acid sequence of SEQ ID NO: 2.

In some embodiments, the reference polymerase, the modified polymerase or both the reference and modified polymerase consists of or comprises an isolated variant of a Bst DNA polymerase having or comprising the amino acid sequence of SEQ ID NO: 3:

SEQ ID NO: 3 includes two further amino acid substitutions as compared to SEQ ID NO: 2, namely: His473Arg (H473R) and His528Ala (H528A), wherein the numbering is relative to the amino acid sequence of SEQ ID NO: 2. Thus SEQ ID NO: 3 contains a total of five amino acid substitutions as compared to the large fragment wild-type sequence of SEQ ID NO:1. The substituted amino acids as compared to SEQ ID NO: 1 are underlined and in bold.

In some embodiments, the modified polymerase consists of or comprises an isolated variant of a polymerase having or comprising an amino acid sequence that is at least 90% identical to the amino acid sequence of SEQ ID NO: 3. In some embodiments, the polymerase is a variant of a Bst DNA polymerase comprising the amino acid sequence of SEQ ID NO: 3, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 3.

In some embodiments, the reference polymerase is a Bst DNA polymerase having, or comprising, the amino acid sequence of SEQ ID NO: 3, and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 3.

In some embodiments, the modified polymerase can include the amino acid sequence of any biologically active fragment of a polymerase having or comprising the amino acid sequence of SEQ ID NO: 3. In some embodiments, the modified polymerase can include the amino acid sequence of any biologically active fragment of a polymerase having or comprising an amino acid sequence that is at least 90% identical to the amino acid sequence of SEQ ID NO: 3.

In some embodiments, the modified polymerase consists of or comprises an isolated variant of a Bst DNA polymerase having or comprising the amino acid sequence of SEQ ID NO: 4:

SEQ ID NO: 4 contains three additional amino acid substitutions as compared to SEQ ID NO: 3, namely: H281A, H273R and Y477F, wherein the numbering is relative to the amino acid sequence of SEQ ID NO: 3. Thus SEQ ID NO: 4 contains a total of eight amino acid substitutions as compared to the large fragment wild-type sequence of SEQ ID NO: 1. The substituted amino acids as compared to SEQ ID NO: 1 are underlined and in bold.

In some embodiments, the reference polymerase, the modified polymerase consists of or comprises an isolated variant of a polymerase having or comprising an amino acid sequence that is at least 90% identical to the amino acid sequence of SEQ ID NO: 4. In some embodiments, the polymerase is a variant of a Bst DNA polymerase comprising the amino acid sequence of SEQ ID NO: 4, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 4.

In some embodiments, the reference polymerase is a Bst DNA polymerase having, or comprising, the amino acid sequence of SEQ ID NO: 4, and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 4.

In some embodiments, the modified polymerase can include the amino acid sequence of any biologically active fragment of a polymerase having or comprising the amino acid sequence of SEQ ID NO: 4. In some embodiments, modified polymerase can include the amino acid sequence of any biologically active fragment of a polymerase having or comprising an amino acid sequence that is at least 90% identical to the amino acid sequence of SEQ ID NO: 4.

In some embodiments, the modified polymerase consists of or comprises an isolated variant of a Bst DNA polymerase having or comprising the amino acid sequence of SEQ ID NO: 33:

SEQ ID NO: 33 includes one amino acid substitution relative to SEQ ID NO:2, namely: D423K, wherein the numbering is relative to the amino acid sequence of SEQ ID NO: 2.

In some embodiments, the modified polymerase consists of or comprises an isolated variant of a polymerase having or comprising an amino acid sequence that is at least 90% identical to the amino acid sequence of SEQ ID NO: 33. In some embodiments, the polymerase is a variant of a Bst DNA polymerase comprising the amino acid sequence of SEQ ID NO: 33, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 33.

In some embodiments, the reference polymerase is a Bst DNA polymerase having, or comprising, the amino acid sequence of SEQ ID NO: 33 and the modified polymerase further include one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 2.

In some embodiments, the modified polymerase consists of or comprises an isolated variant of a Bst DNA polymerase having or comprising the amino acid sequence of SEQ ID NO: 34:

SEQ ID NO: 34 includes six amino acid substitutions relative to SEQ ID NO:2, namely: D423K N487R, H281M, D264A, H273N and E493R, wherein the numbering is relative to the amino acid sequence of SEQ ID NO: 2.

In some embodiments, the modified polymerase consists of or comprises an isolated variant of a polymerase having or comprising an amino acid sequence that is at least 90% identical to the amino acid sequence of SEQ ID NO: 34. In some embodiments, the modified polymerase is a variant of a Bst DNA polymerase comprising the amino acid sequence of SEQ ID NO: 34, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 34.

In some embodiments, the reference polymerase is a Bst DNA polymerase having, or comprising, the amino acid sequence of SEQ ID NO: 34 and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 34. In some embodiments, the modified polymerase consists of or comprises an isolated variant of a Bst DNA polymerase having or comprising the amino acid sequence of SEQ ID NO: 35:

SEQ ID NO: 35 includes three amino acid substitutions relative to SEQ ID NO:2, namely: D423K, N487R and H281M, wherein the numbering is relative to the amino acid sequence of SEQ ID NO: 2.

In some embodiments, the modified polymerase consists of or comprises an isolated variant of a polymerase having or comprising an amino acid sequence that is at least 90% identical to the amino acid sequence of SEQ ID NO: 35. In some embodiments, the polymerase is a variant of a Bst DNA polymerase comprising the amino acid sequence of SEQ ID NO: 35, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 35.

In some embodiments, the reference polymerase is a Bst DNA polymerase having, or comprising, the amino acid sequence of SEQ ID NO: 35 and the modified polymerase further include one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 2.

In some embodiments, the modified polymerase consists of or comprises an isolated variant of a Bst DNA polymerase having or comprising the amino acid sequence of SEQ ID NO: 36:

SEQ ID NO: 36 includes two amino acid substitutions relative to SEQ ID NO:2, namely: D423K, and N487R, wherein the numbering is relative to the amino acid sequence of SEQ ID NO: 2.

In some embodiments, the modified polymerase consists of or comprises an isolated variant of a polymerase having or comprising an amino acid sequence that is at least 90% identical to the amino acid sequence of SEQ ID NO: 36. In some embodiments, the polymerase is a variant of a Bst DNA polymerase comprising the amino acid sequence of SEQ ID NO: 36, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 36.

In some embodiments, the reference polymerase is a Bst DNA polymerase having, or comprising, the amino acid sequence of SEQ ID NO: 36 and the modified polymerase further include one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 2.

In some embodiments, the modified polymerase consists of or comprises an isolated variant of a Bst DNA polymerase having or comprising the amino acid sequence of SEQ ID NO: 37:

SEQ ID NO: 37 includes two amino acid substitutions relative to SEQ ID NO:2, namely: N487R and H281M, wherein the numbering is relative to the amino acid sequence of SEQ ID NO: 2.

In some embodiments, the modified polymerase consists of or comprises an isolated variant of a polymerase having or comprising an amino acid sequence that is at least 90% identical to the amino acid sequence of SEQ ID NO: 37. In some embodiments, the polymerase is a variant of a Bst DNA polymerase comprising the amino acid sequence of SEQ ID NO: 37, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 37.

In some embodiments, the reference polymerase is a Bst DNA polymerase having, or comprising, the amino acid sequence of SEQ ID NO: 37 and the modified polymerase further include one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 2.

In some embodiments, the disclosure relates generally to a modified polymerase that includes an isolated variant of a Bst DNA polymerase comprising an amino acid sequence selected from the group consisting of SEQ ID NO: 1, SEQ ID NO: 2, SEQ ID NO: 3, SEQ ID NO: 4, SEQ ID NO: 16, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, or SEQ ID NO: 37, and further including one or more amino acid modifications. Optionally, the modified polymerase includes one, two, three, four or more amino acid substitutions relative to the amino acid sequence of SEQ ID NO: 1, SEQ ID NO:2, SEQ ID NO:3, SEQ ID NO:4, SEQ ID NO:16, SEQ ID NO:25, SEQ ID NO:26, SEQ ID NO:27, SEQ ID NO:28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the reference polymerase is a Bst DNA polymerase having, or comprising the amino acid sequence of SEQ ID NO: 1, SEQ ID NO:2, SEQ ID NO:3, SEQ ID NO:4, SEQ ID NO:16, SEQ ID NO:25, SEQ ID NO:26, SEQ ID NO:27, SEQ ID NO:28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37 and the modified polymerase is a mutant or variant of the reference polymerase and further includes one or more amino acid mutations relative to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. The one or more amino acid substitutions present in the modified polymerase relative to the reference polymerase can include at least one conservative amino acid substitution.

In some embodiments, the reference polymerase can have or comprise the amino acid sequence of SEQ ID NO: 1, SEQ ID NO: 2, SEQ ID NO: 3, SEQ ID NO:4, SEQ ID NO:16, SEQ ID NO:25, SEQ ID NO:26, SEQ ID NO:26, SEQ ID NO:27, SEQ ID NO:28, SEQ ID NO:29 SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, and the modified polymerase can have or comprise the amino acid sequence of the reference polymerase, further including one or more amino acid mutations as compared to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase.

In some embodiments, the modified polymerase can further include any one or more amino acid mutations selected from the group consisting of: H46R, C93R, Q238C, H273R, H281A, E446Q, H473R, Y477F, H528A, C550Q, H572R, E220K, N234R, A263K, D264A, D264R, H273N, H281M, D423K, D480R, N485K, N487R, E493R, H528F and H528S, wherein the numbering is relative to the amino acid sequence of SEQ ID NO: 1. In some embodiments, the modified polymerase has a reduced buffering capacity relative to the reference polymerase. Without being bound to any particular theory of operation, it can be observed that in some embodiments one or more of the aforementioned mutations can alter, e.g., increase or decrease the buffering capacity of the modified polymerase relative to the unmodified polymerase. Such mutations can therefore be referred to as "buffering" mutations. In some embodiments, such increase or decrease in buffering capacity can increase the observed signal in an ion-based sequencing reaction. Further information about such mutations and their possible effect on the buffering capacity of the polymerase can be found, for example, in U.S. Provisional Appl. No. 60/308,863 filed Feb. 26, 2010; U.S. patent application Ser. No. 13/035,081 filed Feb. 25, 2011; Ser. No. 13/035,177 filed Feb. 25, 2011; Ser. No. 13/036,526 filed Feb. 28, 2011; and Ser. No. 13/036,623 filed Feb. 25, 2011; as well as in International PCT Appl. Nos. PCT/US2011/026219 filed Feb. 25, 2011; PCT/US2011/026228 filed Feb. 25, 2011; PCT/US2011/026450 filed Feb. 28, 2011; and PCT/US2011/026468 filed Feb. 28, 2011; all of which aforementioned applications are hereby incorporated by reference in their entireties. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 1. Optionally, the reference polymerase, the modified polymerase, or both the reference and modified polymerases can further include one or more amino acid mutations that decrease or eliminate exonuclease activity. Some exemplary mutations that can reduce or eliminate the exonuclease activity of the polymerase are described further herein.

In some embodiments, the reference polymerase has or comprises the amino acid sequence of SEQ ID NO: 1, SEQ ID NO:2, SEQ ID NO:3, SEQ ID NO:4, SEQ ID NO: 33, SEQ ID NO: 34, SEQ ID NO: 35, SEQ ID NO: 36 or SEQ ID NO: 37 and the modified polymerase has or comprises the amino acid sequence of the reference polymerase, further including one or more amino acid mutations as compared to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase further includes one or more amino acid substitutions at any one or more positions selected from the group consisting of: 46, 93, 220, 234, 238, 263, 264, 273, 281, 423, 446, 473, 477, 480, 485, 487, 493, 528, 550 and 572, wherein the numbering is relative of the amino acid sequence of SEQ ID NO: 1. In some embodiments one or more of the aforementioned amino acid substitutions can alter, e.g., increase or decrease the buffering capacity of the modified polymerase relative to the corresponding reference polymerase having the amino acid sequence of SEQ ID NO: 1, SEQ ID NO: 2, SEQ ID NO: 3 SEQ ID NO: 4 SEQ ID NO: 34, SEQ ID NO: 35, or SEQ ID NO: 37. Such mutations can therefore be referred to as "buffering" mutations. In some embodiments, such increase or decrease in buffering capacity can increase the observed signal in an ion-based sequencing reaction. In some embodiments, the amino acid substitutions include the substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 1. In some embodiments, the modified polymerase exhibits a change in any one or more parameters selected from the group consisting of: average read length, accuracy, total sequencing throughput, strand bias, lowered systematic error, minimum read length, enhanced performed in higher ionic strength solution, improved processivity, performance in polymerase chain reaction, performance in emulsion polymerase chain reaction, buffering capacity, off-rate, dissociation time constant, AQ20, 100Q17 value and 200Q17 value, relative to the reference polymerase. Optionally, the change is observed by comparing the performance of the reference and modified polymerases in an ion-based sequencing reaction. Optionally, the reference polymerase, the modified polymerase, or both the reference and modified polymerases can further include one or more amino acid mutations that decrease or eliminate exonuclease activity.

In some embodiments, the reference polymerase has or comprises the amino acid sequence of SEQ ID NO: 1, SEQ ID NO: 2, SEQ ID NO: 3 or SEQ ID NO: 4, SEQ ID NO:25, SEQ ID NO:26, SEQ ID NO:27, SEQ ID NO:28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, and the modified polymerase has or comprises the amino acid sequence of the reference polymerase and further comprising one or more additional amino acid substitutions. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase comprises the amino acid sequence of SEQ ID NO: 1 and further includes any one or more amino acid mutations selected from the group consisting of: N31R, N31K, D77K, D77H, D113N, D114R, D130A, D130H, D144M, D144K, L212A, E220K, N234R, N234K, V241K, V251K, A263K, D264A, D264R, D264Q, D264S, D264K, Y272R, H273N, H273R, L280R, H281A, H281M, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, E446Q, F448K, N457T, A462T, H473R, Y477F, D480R, D480F, D480H, D480A, D480S, D480N, D480Q, N485K, N485W, N485Y, N487H, N487R, N487W, N487F, N487I, V488R, E493Q, E493R, M495Q, H528A, H528F, H528S H528R, H528K, V533I, F1572R, W577Y and D579F, wherein the numbering is relative of the amino acid sequence of SEQ ID NO: 1. Without being bound to any particular theory of operation, it can be observed that in some embodiments a modified polymerase including one or more of the above amino acid mutations exhibits an altered (e.g., increased or decreased) binding affinity for a nucleic acid template relative to an unmodified polymerase, or an altered (e.g., increased or decreased) rate of dissociation from the nucleic acid template ("off-rate") relative to the unmodified polymerase, or relative to a reference polymerase having the amino acid sequence of SEQ ID NO: 1, SEQ ID NO: 2, SEQ ID NO: 3 SEQ ID NO: 4, SEQ ID NO:25, SEQ ID NO:26, SEQ ID NO:27, SEQ ID NO:28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, wherein the modified polymerase contains at least one additional amino acid substitution relative to the reference or unmodified polymerase. In some embodiments, the modified polymerase exhibits an altered, e.g., increased or decreased average read length, or an altered minimum read length, or an altered average error-free read length, or altered (e.g., increased or decreased) observed AQ20, 100Q17 or 200Q17 values relative to the reference polymerase. In some embodiments, the modified polymerase exhibits a change in any one or more of the following kinetic parameters: average read length, minimum read length, accuracy, strand bias, systematic error, total sequencing throughput, enhanced performed in higher ionic strength solution, improved processivity, performance in polymerase chain reaction, performance in emulsion polymerase chain reaction, dissociation time constant, off-rate, AQ20, 100Q17 value, and 200Q17 value, relative to the reference polymerase. Optionally, the change is observed by comparing the performance of the reference and modified polymerases in an ion-based sequencing reaction. The Examples provided herein illustrate the change in off-rate and in dissociation time constant observed in various exemplary modified polymerase having the amino acid sequence of SEQ ID NO: 2 and further including various exemplary amino acid substitutions from the list above, relative to the off-rate and dissociation time constant of a reference polymerase having the amino acid sequence of SEQ ID NO: 2. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 1. Optionally, the reference polymerase, the modified polymerase, or both the reference and modified polymerases can further include one or more amino acid mutations that decrease or eliminate exonuclease activity.

In some embodiments, the reference polymerase has or comprises the amino acid sequence of SEQ ID NO: 1, SEQ ID NO: 2, SEQ ID NO: 3 or SEQ ID NO: 4, SEQ ID NO:25, SEQ ID NO:26, SEQ ID NO:27, SEQ ID NO:28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37 and the modified polymerase has or comprises the amino acid sequence of the reference polymerase and further includes one or more amino acid substitutions relative to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase further includes one or more amino acid substitutions at any one or more positions selected from the group consisting of: 31, 77, 113, 114, 130, 144, 212, 220, 234, 241, 251, 263, 264, 272, 273, 280, 281, 294, 299, 303, 331, 325, 335, 336, 354, 370, 409, 416, 418, 420, 423, 425, 428, 429, 448, 457, 462, 480, 485, 487, 488, 493, 495, 528, 533, 577 and 579, wherein the numbering is relative of the amino acid sequence of SEQ ID NO: 1.

In some embodiments a modified polymerase including one or more of these mutations exhibits an altered (e.g., increased or decreased) binding affinity for a nucleic acid template relative to the corresponding unmodified polymerase or to a reference polymerase. In some embodiments, the modified polymerase has an altered (e.g., increased or decreased) rate of dissociation from the nucleic acid template ("off-rate") relative to the unmodified polymerase or to a reference polymerase. In some embodiments, the modified polymerase exhibits an altered, e.g., increased or decreased read length, or an altered average error-free read length, or altered (e.g., increased or decreased) observed 100Q17 or 200Q17 values relative to the reference polymerase. In some embodiments, the modified polymerase exhibits a change in any one or more of the following kinetic parameters: average read length, minimum read length, enhanced performed in higher ionic strength solution, improved processivity, performance in polymerase chain reaction, performance in emulsion polymerase chain reaction, dissociation time constant, off-rate, AQ20, 100Q17 value, and 200Q17 value, relative to the reference polymerase. Optionally, the change is observed by comparing the performance of the reference and modified polymerases in an ion-based sequencing reaction. In some embodiments, the amino acid substitutions include the substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 1. In some embodiments, the modified polymerase exhibits a change in any one or more parameters selected from the group consisting of: average read length, minimum read length, enhanced performed in higher ionic strength solution, improved processivity, performance in polymerase chain reaction, performance in emulsion polymerase chain reaction, buffering capacity, off-rate, 100Q17 value, AQ20 and 200Q17 value, relative to the reference polymerase. Optionally, the change is observed by comparing the performance of the reference and modified polymerases in an ion-based sequencing reaction. Optionally, the reference polymerase, the modified polymerase, or both the reference and modified polymerases can further include one or more amino acid mutations that decrease or eliminate exonuclease activity.

In some embodiments, the reference polymerase has or comprises the amino acid sequence of SEQ ID NO: 1, SEQ ID NO: 2, SEQ ID NO: 3, SEQ ID NO: 4, SEQ ID NO:25, SEQ ID NO:26, SEQ ID NO:27, SEQ ID NO:28, SEQ ID NO:29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37 and the modified polymerase has or comprises the amino acid sequence of the reference polymerase and further includes at least one amino acid substitution relative to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase further includes amino acid substitutions at any one or more positions selected from the group consisting of: 31, 46, 77, 93, 113, 114, 130, 144, 212, 220, 234, 238, 241, 251, 263, 264, 272, 273, 280, 281, 294, 299, 303, 331, 325, 335, 336, 354, 370, 409, 416, 418, 420, 423, 425, 428, 429, 446, 448, 457, 462, 473, 477, 480, 485, 487, 488, 493, 495, 528, 533, 550, 572, 577 and 579, wherein the numbering is relative of the amino acid sequence of SEQ ID NO: 1. In some embodiments, the amino acid substitutions include the substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 1. In some embodiments, the modified polymerase exhibits a change in any one or more parameters selected from the group consisting of: binding affinity for a nucleic acid template, buffering capacity, average read length, minimum read length, enhanced performed in higher ionic strength solution, improved processivity, performance in polymerase chain reaction, performance in emulsion polymerase chain reaction, AQ20, dissociation time constant, off-rate, 100Q17 value and 200Q17 value, relative to the reference polymerase. Optionally, the change is observed by comparing the performance of the reference and modified polymerases in an ion-based sequencing reaction. Optionally, the reference polymerase, the modified polymerase, or both the reference and modified polymerases can further include one or more amino acid mutations that decrease or eliminate exonuclease activity.

In some embodiments, the reference polymerase has or comprises the amino acid sequence of SEQ ID NO: 1, SEQ ID NO: 2, SEQ ID NO: 3 or SEQ ID NO: 4, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, and the modified polymerase has or comprises the amino acid sequence of the reference polymerase and further including at least one amino acid substitution relative to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase further includes any one or more amino acid mutations selected from the group consisting of: N31R, N31K, H46A, H46R, D77K, D77H, C93R, D113N, D114R, D130A, D130H, D144M, D144K, L212A, E220K, N234R, N234K, Q238C, V241K, V251K, A263K, D264A, D264R, D264Q, D264S, D264K, Y272R, H273A, H273N, H273R, L280R, H281A, H281R, H281M, E294S, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, E446Q, F448K, N457T, A462T, H473A, H473R, Y477F, D480R, D480F, D480H, D480A, D480S, D480N, D480Q, N485K, N485W, N485Y, N487H, N487R, N487W, N487F, N487I, V488R, E493R, E493Q, M495Q, H528A, H528F, H528S H528R, H528K, V533I, C550Q, H572A, H572R, W577Y and D579F, wherein the numbering is relative of the amino acid sequence of SEQ ID NO: 1.

Without being bound to any particular theory of operation, it can be observed that in some embodiments a modified polymerase including one or more of these mutations exhibits an altered (e.g., increased or decreased) binding affinity for a nucleic acid template relative to an unmodified polymerase, or an altered (e.g., increased or decreased) rate of dissociation from the nucleic acid template ("off-rate") relative to the unmodified polymerase. In some embodiments, the modified polymerase exhibits an altered (e.g., increased or decreased) buffering capacity relative to the unmodified polymerase. In some embodiments, the modified polymerase exhibits an altered, e.g., increased or decreased read length, or an altered average error-free read length, or altered dissociation time constant, or altered (e.g., increased or decreased) observed 100Q17 or 200Q17 values relative to the reference polymerase. In some embodiments, the modified polymerase exhibits an altered, e.g., increased or decreased read length, or an altered average error-free read length, or altered (e.g., increased or decreased) observed 100Q17 or 200Q17 values relative to the reference polymerase. In some embodiments, the modified polymerase exhibits a change in any one or more parameters selected from the group consisting of: buffering capacity, off-rate, average read length, minimum read length, raw accuracy, total sequencing throughput, systematic error, strand bias, enhanced performed in higher ionic strength solution, improved processivity, performance in polymerase chain reaction, performance in emulsion polymerase chain reaction, AQ20, 100Q17 value and 200Q17 value, relative to the reference polymerase. Optionally, the change is observed by comparing the performance of the reference and modified polymerases in an ion-based sequencing reaction. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 1. Optionally, the reference polymerase, the modified polymerase, or both the reference and modified polymerases can further include one or more amino acid mutations that decrease or eliminate exonuclease activity.

In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase further includes amino acid substitutions at any one or more positions selected from the group consisting of: 46, 93, 238, 273, 281, 446, 473, 477, 528, 550 and 572, as well as one or more amino acid substitutions selected from the group consisting of 31, 77, 113, 114, 130, 144, 212, 220, 234, 241, 251, 263, 264, 272, 280, 294, 299, 303, 331, 325, 335, 336, 354, 370, 409, 416, 418, 420, 423, 425, 428, 429, 448, 457, 462, 480, 485, 487, 488, 493, 495, 533, 577 and 579, wherein the numbering is relative of the amino acid sequence of SEQ ID NO: 1. In some embodiments, the amino acid substitutions include the substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 1. In some embodiments, the modified polymerase exhibits a change in any one or more parameters selected from the group consisting of: binding affinity for a nucleic acid template, buffering capacity, average read length, minimum read length, raw accuracy, total sequencing throughput, systematic error, strand bias, enhanced performed in higher ionic strength solution, improved processivity, performance in polymerase chain reaction, performance in emulsion polymerase chain reaction, AQ20, dissociation time constant, off-rate, 100Q17 value and 200Q17 value, relative to the reference polymerase. Optionally, the change is observed by comparing the performance of the reference and modified polymerases in an ion-based sequencing reaction. Optionally, the reference polymerase, the modified polymerase, or both the reference and modified polymerases can further include one or more amino acid mutations that decrease or eliminate exonuclease activity.

In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase further includes one or more amino acid substitutions selected from the group consisting of: H46A, H46R, C93R, Q238C, H273A, H273R, H281A, H281R, H281M, E446Q, H473A, H473R, Y477F, H528A, H528R, H528K, C550Q, H572A and H572R, as well as one or more amino acid substitutions selected from the group consisting of N31R, N31K, D77K, D77H, D113N, D114R, D130A, D130H, D144M, D144K, L212A, E220K, N234R, N234K, V241K, V251K, D264Q, D264S, D264K, Y272R, L280R, E294S, E294F, E294G, E294K, V299K, V299H, V299F, D303R, E325R, I331Q, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, F448K, N457T, A462T, D480R, D480F, D480H, D480A, D480S, D480N, D480Q, N485W, N485Y, N487H, N487W, N487F, N487I, V488R, E493Q, M495Q, V533I, W577Y and D579F, wherein the numbering is relative of the amino acid sequence of SEQ ID NO: 1. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 1. In some embodiments, the modified polymerase exhibits a change in any one or more parameters selected from the group consisting of: buffering capacity, average read length, minimum read length, raw accuracy, total sequencing throughput, systematic error, strand bias, enhanced performed in higher ionic strength solution, improved processivity, performance in polymerase chain reaction, performance in emulsion polymerase chain reaction, AQ20, dissociation time constant, off-rate, 100Q17 value and 200Q17 value, relative to the reference polymerase. Optionally, the change is observed by comparing the performance of the reference and modified polymerases in an ion-based sequencing reaction. Optionally, the reference polymerase, the modified polymerase, or both the reference and modified polymerases can further include one or more amino acid mutations that decrease or eliminate exonuclease activity.

In some embodiments, the disclosure relates generally to a modified polymerase having or comprising the amino acid sequence of SEQ ID NO: 1, SEQ ID NO: 2, SEQ ID NO: 3, SEQ ID NO: 4, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, or the amino acid sequence of any biologically active fragment of a polymerase having or comprising the amino acid sequence of SEQ ID NO: 1, SEQ ID NO: 2, SEQ ID NO: 3, SEQ ID NO: 4, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37, and further including at least one amino acid mutation relative to the amino acid sequence of a reference polymerase having the amino acid sequence of SEQ ID NO: 1, SEQ ID NO: 2, SEQ ID NO: 3 or SEQ ID NO: 4, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase.

In some embodiments, the modified polymerase according to the disclosure can include at least amino acid mutation, D480R, wherein the numbering is relative to the amino acid sequence of SEQ ID NO: 2. In some embodiments, the modified polymerase according to the disclosure can include amino acid mutations D264K and E493Q, wherein the numbering is relative to the amino acid sequence of SEQ ID NO: 2. In some embodiments, the modified polymerase according to the disclosure can include amino acid mutations E220K, N234R and D423K, wherein the numbering is relative to the amino acid sequence of SEQ ID NO: 2. In some embodiments, the modified polymerase according to the disclosure can include amino acid mutations E220K, N234R, D423K, and H528A, wherein the numbering is relative to the amino acid sequence of SEQ ID NO: 2. In some embodiments, the modified polymerase according to the disclosure can include amino acid mutations E220K, N234R, D423K, H473R, and H528A, wherein the numbering is relative to the amino acid sequence of SEQ ID NO: 2 (see SEQ ID NO: 20). In some embodiments, the modified polymerase according to the disclosure can include amino acid mutation D423K, wherein the numbering is relative to the amino acid sequence of SEQ ID NO: 2 (see SEQ ID NO: 33). In some embodiments, the modified polymerase according to the disclosure can include amino acid mutations N487R, H281M, D264A, H273N, and E493R, wherein the numbering is relative to the amino acid sequence of SEQ ID NO: 2 (see SEQ ID NO: 34). In some embodiments, the modified polymerase according to the disclosure can include amino acid mutations N487R, H281M, and D423K, wherein the numbering is relative to the amino acid sequence of SEQ ID NO: 2 (see SEQ ID NO: 35). In some embodiments, the modified polymerase according to the disclosure can include amino acid mutations N487R and D423K, wherein the numbering is relative to the amino acid sequence of SEQ ID NO: 2 (see SEQ ID NO: 36). In some embodiments, the modified polymerase according to the disclosure can include amino acid mutations N487R and H281M, wherein the numbering is relative to the amino acid sequence of SEQ ID NO: 2 (see SEQ ID NO: 37).

In some embodiments, the modified polymerase according to the disclosure can include any one or more amino acid mutations selected from the group consisting of: E220K, N234R, V241K, A263K, D264R, D264K, H273N, H281M, D423K, D480R, N485K, N487R N487W, V488R, H473R, E493R, H528F, H528S, H528A and E493Q, wherein the numbering is relative to the amino acid sequence of SEQ ID NO: 2. In some embodiments a modified polymerase including one or more of these mutations exhibits an altered (e.g., increased or decreased) binding affinity and/or lowered systematic error and/or decreased strand bias for a nucleic acid template relative to the corresponding unmodified polymerase or to a reference polymerase. In some embodiments, the modified polymerase has an altered (e.g., increased or decreased) rate of dissociation from the nucleic acid template ("off-rate") relative to the unmodified polymerase or to a reference polymerase. In some embodiments, the modified polymerase exhibits an altered, e.g., increased or decreased read length, or an altered average error-free read length, or altered (e.g., increased or decreased) observed 100Q17 or 200Q17 values relative to the reference polymerase. In some embodiments, the modified polymerase exhibits a change in any one or more of the following kinetic parameters: average read length, minimum read length, raw accuracy, total sequencing throughput, systematic error, strand bias, enhanced performed in higher ionic strength solution, improved processivity, performance in polymerase chain reaction, performance in emulsion polymerase chain reaction, dissociation time constant, off-rate, AQ20, 100Q17 value, and 200Q17 value, relative to the reference polymerase. Optionally, the change is observed by comparing the performance of the reference and modified polymerases in an ion-based sequencing reaction. In some embodiments, the amino acid substitutions include the substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified polymerase, or both the reference and modified polymerases can further include a deletion of the methionine residue at position 1, or a substitution of the methionine residue at position 1 with any other amino acid residue. In some embodiments, the modified polymerase exhibits a change in any one or more parameters selected from the group consisting of: buffering capacity, average read length, minimum read length, enhanced performed in higher ionic strength solution, improved processivity, performance in polymerase chain reaction, performance in emulsion polymerase chain reaction, off-rate, AQ20, 100Q17 value and 200Q17 value, relative to the reference polymerase. Optionally, the change is observed by comparing the performance of the reference and modified polymerases in an ion-based sequencing reaction. Optionally, the reference polymerase, the modified polymerase, or both the reference and modified polymerases can further include one or more amino acid mutations that decrease or eliminate exonuclease activity.

In some embodiments, the modified polymerase includes the amino acid sequence of SEQ ID NO: 2, or the amino acid sequence of any biologically active fragment of a polymerase having the amino acid sequence of SEQ ID NO: 2.

The modified polymerase can further include one or more amino acid mutations relative to the amino acid sequence of SEQ ID NO: 2.

In some embodiments, the modified polymerase includes the amino acid sequence of SEQ ID NO: 3, or the amino acid sequence of any biologically active fragment of a polymerase having the amino acid sequence of SEQ ID NO: 3. The modified polymerase can further include one or more amino acid mutations relative to the amino acid sequence of SEQ ID NO: 3.

In some embodiments, the modified polymerase includes the amino acid sequence of SEQ ID NO: 4, or the amino acid sequence of any biologically active fragment of a polymerase having the amino acid sequence of SEQ ID NO: 4. The modified polymerase can further include one or more amino acid mutations relative to the amino acid sequence of SEQ ID NO: 4.

In some embodiments, the modified polymerase includes the amino acid sequence of SEQ ID NO: 33, or the amino acid sequence of any biologically active fragment of a polymerase having the amino acid sequence of SEQ ID NO: 33. The modified polymerase can further include one or more amino acid mutations relative to the amino acid sequence of SEQ ID NO: 33.

In some embodiments, the modified polymerase includes the amino acid sequence of SEQ ID NO: 34, or the amino acid sequence of any biologically active fragment of a polymerase having the amino acid sequence of SEQ ID NO: 34. The modified polymerase can further include one or more amino acid mutations relative to the amino acid sequence of SEQ ID NO: 34.

In some embodiments, the modified polymerase includes the amino acid sequence of SEQ ID NO: 35, or the amino acid sequence of any biologically active fragment of a polymerase having the amino acid sequence of SEQ ID NO: 35. The modified polymerase can further include one or more amino acid mutations relative to the amino acid sequence of SEQ ID NO: 35.

In some embodiments, the modified polymerase includes the amino acid sequence of SEQ ID NO: 36, or the amino acid sequence of any biologically active fragment of a polymerase having the amino acid sequence of SEQ ID NO: 36. The modified polymerase can further include one or more amino acid mutations relative to the amino acid sequence of SEQ ID NO: 36.

In some embodiments, the modified polymerase includes the amino acid sequence of SEQ ID NO: 37, or the amino acid sequence of any biologically active fragment of a polymerase having the amino acid sequence of SEQ ID NO: 37. The modified polymerase can further include one or more amino acid mutations relative to the amino acid sequence of SEQ ID NO: 37. In some embodiments, the modified polymerase includes one or more amino acid mutations selected from an amino acid substitution, deletion, or addition.

In some embodiments, the modified polymerase has polymerase activity. The polymerase or biologically active fragment can have primer extension activity in vivo or in vitro.

In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 2, SEQ ID NO: 3, SEQ ID NO: 4, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37.

In some embodiments, the one or more mutations in the modified polymerase can include at least one amino acid substitution. In some embodiments, the at least one amino acid substitution can optionally occur at any one or more positions selected from the group consisting of: 46, 220, 234, 263, 264, 273, 281, 423, 446, 473, 477, 480, 485, 487, 493, 528 and 572, wherein the numbering is relative to the amino acid sequence of SEQ ID NO: 1. In some embodiments, the modified polymerase includes at least two, three, four, five, or more amino acid substitutions occurring at positions selected from this group. Without intending to be bound to any particular theory of action, it can be observed that in some embodiments, amino acid substitution at such positions can alter, e.g., increase or decrease the buffering capacity of the modified polymerase relative to the corresponding unmodified polymerase, or relative to a reference polymerase. Such mutations can therefore be referred to as "buffering" mutations. In some embodiments, such increase or decrease in buffering capacity can increase the observed signal in an ion-based sequencing reaction.

In some embodiments, the modified polymerase includes the amino acid sequence of SEQ ID NO: 1, or includes the amino acid sequence of a biologically active fragment of a polymerase having the amino acid sequence of SEQ ID NO: 1, or includes an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 1, and further includes at least one amino acid substitution selected from the group consisting of: H46A, H46R, H273A, H273R, H281A, H281R, E446Q, H473A, H473R, Y477F, H528A, H528R, H572A and H572R, wherein the numbering is relative of the amino acid sequence of SEQ ID NO: 1. In some embodiments, the modified polymerase includes any two, three, four, five or more of these amino acid substitutions.

In some embodiments, the one or more mutations in the modified polymerase can include at least one amino acid substitution. The at least one amino acid substitution can optionally occur at any one or more positions selected from the group consisting of: 31, 77, 113, 114, 130, 144, 212, 220, 234, 241, 251, 264, 272, 280, 294, 299, 303, 331, 325, 335, 336, 354, 370, 409, 416, 418, 420, 423, 425, 428, 429, 448, 457, 462, 480, 485, 487, 488, 493, 495, 533, 577 and 579, wherein the numbering is relative to the amino acid sequence of SEQ ID NO: 1. In some embodiments, the modified polymerase includes at least two, three, four, five, or more amino acid substitutions occurring at positions selected from this group. Without being bound to any particular theory of operation, it can be observed that in some embodiments a modified polymerase including any one of such amino acid substitutions exhibits an altered (e.g., increased or decreased) binding affinity for a nucleic acid template relative to an unmodified polymerase, or an altered (e.g., increased or decreased) rate of dissociation from the nucleic acid template ("off-rate") relative to the corresponding unmodified polymerase, or relative to a reference polymerase. In some embodiments, the modified polymerase exhibits an altered (e.g., increased or decreased) read length, or an altered (e.g., increased or decreased) average error-free read length, or altered (e.g., increased or decreased) dissociation time constant, or altered (e.g., increased or decreased) observed 100Q17 or 200Q17 values relative to the reference polymerase. In some embodiments, the modified polymerase exhibits a change (e.g., increase or decrease) in any one or more properties selected from the group consisting of: DNA binding affinity, off-rate, 100Q17 value and 200Q17 value, relative to the reference polymerase. Optionally, the change is observed by comparing the properties of the reference and modified polymerases in an ion-based sequencing reaction.

In some embodiments, the one or more mutations in the modified polymerase can include at least one amino acid substitution. The at least one amino acid substitution can optionally occur at any one or more positions selected from the group consisting of: 31, 46, 77, 113, 114, 130, 144, 212, 220, 234, 241, 251, 263, 264, 272, 273, 280, 281, 294, 299, 303, 331, 325, 335, 336, 354, 370, 409, 416, 418, 420, 423, 425, 428, 429, 446, 448, 457, 462, 473, 477, 480, 485, 487, 488, 493, 495, 528, 533, 572, 577 and 579, wherein the numbering is relative to the amino acid sequence of SEQ ID NO: 1. In some embodiments, the modified polymerase includes at least two, three, four, five, or more amino acid substitutions occurring at positions selected from this group. In some embodiments, the modified polymerase includes the amino acid sequence of SEQ ID NO: 1, or includes the amino acid sequence of a biologically active fragment of a polymerase having the amino acid sequence of SEQ ID NO: 1, or includes the amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 1, and further includes at least one amino acid substitution at any one or more positions selected from the group consisting of: 46, 273, 281, 446, 473, 477, 528 and 572, as well as at least one amino acid substitution at any one or more positions selected from the group consisting of: 31, 77, 113, 114, 130, 144, 212, 220, 234, 241, 251, 264, 272, 280, 294, 299, 303, 331, 325, 335, 336, 354, 370, 409, 416, 418, 420, 423, 425, 428, 429, 448, 457, 462, 480, 485, 487, 488, 493, 495, 533, 577 and 579, wherein the numbering is relative to the amino acid sequence of SEQ ID NO: 1, In some embodiments, the modified polymerase includes at least two, three, four, five, or more amino acid substitutions occurring at positions selected from each of these two groups of amino acid substitutions.

In some embodiments, the modified polymerase includes the amino acid sequence of SEQ ID NO: 1, or includes the amino acid sequence of a biologically active fragment of a polymerase having the amino acid sequence of SEQ ID NO: 1, or includes an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 1, and further includes at least one amino acid substitution selected from the group consisting of: N31R, N31K, D77K, D77H, D113N, D114R, D130A, D130H, D144M, D144K, L212A, E220K, N234R, N234K, V241K, V251K, D264Q, D264S, D264K, Y272R, L280R, E294S, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, F448K, N457T, A462T, D480R, D480F, D480H, D480A, D480S, D480N, D480Q, N485W, N485Y, N487H, N487W, N487F, N487I, V488R, E493Q, M495Q, V533I, W577Y and D579F, wherein the numbering is relative of the amino acid sequence of SEQ ID NO: 1. In some embodiments, the modified polymerase includes any two, three, four, five or more of these amino acid substitutions.

In some embodiments, the modified polymerase includes at least one amino acid substitution designed to replace a preexisting cysteine residue with a different amino acid residue, or to replace a non-cysteine amino acid residue with a cysteine residue. The at least one amino acid substitution optionally includes one or more amino acid substitutions selected from the group consisting of: C93R, Q238C and C550Q, wherein the numbering is relative to the amino acid sequence of SEQ ID NO: 1.

In some embodiments, the modified polymerase includes the amino acid sequence of SEQ ID NO: 2, or includes the amino acid sequence of a biologically active fragment of a polymerase having the amino acid sequence of SEQ ID NO: 2, or includes an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 2, and further includes at least one amino acid substitution selected from the group consisting of: N31R, N31K, D77K, D77H, D113N, D114R, D130A, D130H, D144M, D144K, L212A, E220K, N234R, N234K, V241K, V251K, D264Q, D264S, D264K, Y272R, L280R, E294S, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, F448K, N457T, A462T, D480R, D480F, D480H, D480A, D480S, D480N, D480Q, N485W, N485Y, N487H, N487W, N487F, N487I, V488R, E493Q, M495Q, V533I, W577Y and D579F, wherein the numbering is relative of the amino acid sequence of SEQ ID NO: 2. Optionally, the modified polymerase can further include at least one amino acid substitution selected from the group consisting of: H46A, H46R, H273A, H273R, H281A, H281R, H281M, E446Q, H473A, H473R, Y477F, H528A, H528R, H528K, H572A and H572R, wherein the numbering is relative to the amino acid sequence of SEQ ID NO: 2. In some embodiments, the modified polymerase includes any two, three, four, five or more amino acid substitutions selected from each of these two groups of amino acid substitutions.

In some embodiments, the modified polymerase includes the amino acid sequence of SEQ ID NO: 1, or includes the amino acid sequence of a biologically active fragment of a polymerase having the amino acid sequence of SEQ ID NO: 1, or includes an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 1, and further includes at least one amino acid substitution selected from the group consisting of: N31R, N31K, H46A, H46R, D77K, D77H, D113N, D114R, D130A, D130H, D144M, D144K, L212A, E220K, N234R, N234K, V241K, V251K, D264Q, D264S, D264K, Y272R, H273A, H273R, L280R, H281A, H281R, E294S, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, E446Q, F448K, N457T, A462T, H473A, H473R, Y477F, D480R, D480F, D480H, D480A, D480S, D480N, D480Q, N485W, N485Y, N487H, N487W, N487F, N487I, V488R, E493Q, M495Q, H528A, H528R, V533I, H572R, H578A, W577Y and D579F, wherein the numbering is relative of the amino acid sequence of SEQ ID NO: 1. In some embodiments, the modified polymerase includes any two, three, four, five or more of these amino acid substitutions.

In some embodiments, the modified polymerase has an altered (e.g., increased or decreased) binding affinity for a nucleic acid template relative to a reference polymerase. In some embodiments, the modified polymerase has an altered (e.g., increased or decreased) rate of dissociation from the nucleic acid template ("off-rate") relative to a reference polymerase. In some embodiments, the modified polymerase exhibits an altered (e.g., increased or decreased) read length, or an altered (e.g., increased or decreased) average error-free read length, or an altered (e.g., increased or decreased) observed 100Q17 or 200Q17 value relative to the reference polymerase. In some embodiments, the modified polymerase exhibits a change (e.g., increase or decrease) in any one or more of the following properties: binding affinity for a nucleic acid template, dissociation time constant, off-rate, 100Q17 value, and 200Q17 value, relative to the reference polymerase. In some embodiments, the altered property is increased or decreased by at least 10%, 20%, 30%, 40%, 50%, 75%, 90%, 100%, 200%, 300%, 500%, 750%, 1000%, 3000% or greater, relative to the corresponding unmodified polymerase, or to the reference polymerase. Optionally, the change is observed by comparing the properties of the reference and modified polymerases in an ion-based sequencing reaction.

In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 16.

Optionally, the reference polymerase, the modified polymerase, or both the reference and modified polymerases can further include one or more amino acid mutations that decrease or eliminate any exonuclease activity of the polymerase.

In some embodiments, the reference polymerase, the modified polymerase or both the reference and modified polymerase consists of or comprises an isolated variant of a Bst DNA polymerase having or comprising the amino acid sequence of SEQ ID NO: 16:

SEQ ID NO: 16 comprises the amino acid sequence of a naturally occurring (wild-type) Bst DNA polymerase.

In some embodiments, the reference polymerase is a Bst DNA polymerase having, or comprising the amino acid sequence of SEQ ID NO: 16, and the modified polymerase is a mutant or variant of the reference polymerase and further includes one or more amino acid mutations relative to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. Optionally, the one or more amino acid substitutions present in the modified polymerase relative to the reference polymerase can include at least one conservative amino acid substitution.

In some embodiments, the reference polymerase, the modified polymerase or both the reference and modified polymerase consists of or comprises an isolated variant of a Bst DNA polymerase having or comprising the amino acid sequence of SEQ ID NO: 25. SEQ ID NO: 25 has one amino acid substitution as compared to SEQ ID NO: 16, namely: N782R, wherein the numbering is relative to the amino acid sequence of SEQ ID NO: 16.

In some embodiments, the modified polymerase consists of or comprises an isolated variant of a polymerase having or comprising an amino acid sequence that is at least 90% identical to the amino acid sequence of SEQ ID NO: 25. In some embodiments, the polymerase is a variant of a Bst DNA polymerase comprising the amino acid sequence of SEQ ID NO: 25, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 25.

In some embodiments, the modified polymerase consists of or comprises an isolated variant of a Bst DNA polymerase having or comprising the amino acid sequence of SEQ ID NO: 26.

SEQ ID NO: 26 contains two amino acid substitutions as compared to SEQ ID NO: 16, namely: N782R and D718K, wherein the numbering is relative to the amino acid sequence of SEQ ID NO: 16.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 26. In some embodiments, the modified polymerase is a variant of a Bst DNA polymerase comprising the amino acid sequence of SEQ ID NO: 26, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 26.

In some embodiments, the reference polymerase is a Bst DNA polymerase having, or comprising, the amino acid sequence of SEQ ID NO: 26, and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 26.

In some embodiments, the modified polymerase can include the amino acid sequence of any biologically active fragment of a polymerase having or comprising the amino acid sequence of SEQ ID NO: 26. In some embodiments, the modified polymerase can include the amino acid sequence of any biologically active fragment of a polymerase having or comprising an amino acid sequence that is at least 90% identical to the amino acid sequence of SEQ ID NO: 26.

In some embodiments, the reference polymerase is a Bst DNA polymerase having, or comprising, the amino acid sequence of SEQ ID NO: 27, and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 27.

In some embodiments, the modified polymerase can include the amino acid sequence of any biologically active fragment of a polymerase having or comprising the amino acid sequence of SEQ ID NO: 27. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 27.

SEQ ID NO: 27 contains three amino acid substitutions as compared to SEQ ID NO: 16, namely: N782R, D718K and H568N, wherein the numbering is relative to the amino acid sequence of SEQ ID NO: 16.

In some embodiments, the modified polymerase consists of or comprises an isolated variant of a polymerase having or comprising an amino acid sequence that is at least 90% identical to the amino acid sequence of SEQ ID NO: 27. In some embodiments, the modified polymerase is a variant of a Bst DNA polymerase comprising the amino acid sequence of SEQ ID NO: 27, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 27.

In some embodiments, the modified polymerase can include the amino acid sequence of any biologically active fragment of a polymerase having or comprising the amino acid sequence of SEQ ID NO: 27. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 27.

In some embodiments, the modified polymerase consists of or comprises an isolated variant of a Bst DNA polymerase having or comprising the amino acid sequence of SEQ ID NO: 28.

SEQ ID NO: 28 contains two amino acid substitutions as compared to SEQ ID NO: 16, namely: N782R and H576M, wherein the numbering is relative to the amino acid sequence of SEQ ID NO: 16.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 28. In some embodiments, the modified polymerase is a variant of a Bst DNA polymerase comprising the amino acid sequence of SEQ ID NO: 28, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 28.

In some embodiments, the reference polymerase is a Bst DNA polymerase having, or comprising, the amino acid sequence of SEQ ID NO: 28, and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 28.

In some embodiments, the modified polymerase can include the amino acid sequence of any biologically active fragment of a polymerase having or comprising the amino acid sequence of SEQ ID NO: 28. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 28.

In some embodiments, the modified polymerase consists of or comprises an isolated variant of a Bst DNA polymerase having or comprising the amino acid sequence of SEQ ID NO: 29.

SEQ ID NO: 29 contain two amino acid substitutions as compared to SEQ ID NO: 16, namely: N782R and H823S, wherein the numbering is relative to the amino acid sequence of SEQ ID NO: 16.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 29. In some embodiments, the modified polymerase is a variant of a Bst DNA polymerase comprising the amino acid sequence of SEQ ID NO: 29, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 29.

In some embodiments, the reference polymerase is a Bst DNA polymerase having, or comprising, the amino acid sequence of SEQ ID NO: 29, and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 29.

In some embodiments, the modified polymerase can include the amino acid sequence of any biologically active fragment of a polymerase having or comprising the amino acid sequence of SEQ ID NO: 29. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 29.

In some embodiments, the modified polymerase consists of or comprises an isolated variant of a Bst DNA polymerase having or comprising the amino acid sequence of SEQ ID NO: 30.

SEQ ID NO: 30 contains one amino acid substitution as compared to SEQ ID NO: 16, namely: D718K, wherein the numbering is relative to the amino acid sequence of SEQ ID NO: 16.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 30. In some embodiments, the modified polymerase is a variant of a Bst DNA polymerase comprising the amino acid sequence of SEQ ID NO: 30, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 30.

In some embodiments, the reference polymerase is a Bst DNA polymerase having, or comprising, the amino acid sequence of SEQ ID NO: 30 and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 30.

In some embodiments, the modified polymerase can include the amino acid sequence of any biologically active fragment of a polymerase having or comprising the amino acid sequence of SEQ ID NO: 30. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 30.

In some embodiments, the modified polymerase consists of or comprises an isolated variant of a Bst DNA polymerase having or comprising the amino acid sequence of SEQ ID NO: 31.

SEQ ID NO: 31 contains three amino acid substitutions as compared to SEQ ID NO: 16, namely: D718K, N782R and H576M, wherein the numbering is relative to the amino acid sequence of SEQ ID NO: 16.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 31. In some embodiments, the modified polymerase is a variant of a Bst DNA polymerase comprising the amino acid sequence of SEQ ID NO: 31, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 31.

In some embodiments, the reference polymerase is a Bst DNA polymerase having, or comprising, the amino acid sequence of SEQ ID NO: 31 and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 31.

In some embodiments, the modified polymerase can include the amino acid sequence of any biologically active fragment of a polymerase having or comprising the amino acid sequence of SEQ ID NO: 31. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 31.

In some embodiments, the modified polymerase consists of or comprises an isolated variant of a Bst DNA polymerase having or comprising the amino acid sequence of SEQ ID NO: 32.

SEQ ID NO: 32 contains five amino acid substitutions as compared to SEQ ID NO: 16, namely N782R, H576M, D559A, H568N and E788R, wherein the numbering is relative to the amino acid sequence of SEQ ID NO: 16.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 32. In some embodiments, the modified polymerase is a variant of a Bst DNA polymerase comprising the amino acid sequence of SEQ ID NO: 32, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 32.

In some embodiments, the reference polymerase is a Bst DNA polymerase having, or comprising, the amino acid sequence of SEQ ID NO: 32 and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 32.

In some embodiments, the modified polymerase can include the amino acid sequence of any biologically active fragment of a polymerase having or comprising the amino acid sequence of SEQ ID NO: 32. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 32.

In some embodiments, the modified polymerase consists of or comprises an isolated variant of a Bst DNA polymerase having or comprising the amino acid sequence of SEQ ID NO: 33.

SEQ ID NO: 33 contains one amino acid substitution as compared to SEQ ID NO: 2, namely D423K, wherein the numbering is relative to the amino acid sequence of SEQ ID NO: 2.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 33. In some embodiments, the modified polymerase is a variant of a Bst DNA polymerase comprising the amino acid sequence of SEQ ID NO: 33, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 33.

In some embodiments, the reference polymerase is a Bst DNA polymerase having, or comprising, the amino acid sequence of SEQ ID NO: 33 and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 33.

In some embodiments, the modified polymerase can include the amino acid sequence of any biologically active fragment of a polymerase having or comprising the amino acid sequence of SEQ ID NO: 33. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 33.

In some embodiments, the modified polymerase consists of or comprises an isolated variant of a Bst DNA polymerase having or comprising the amino acid sequence of SEQ ID NO: 34.

SEQ ID NO: 34 contains five amino acid substitutions as compared to SEQ ID NO: 2, namely N487R, H281M, D264A, H273N and E493R, wherein the numbering is relative to the amino acid sequence of SEQ ID NO: 2.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 34. In some embodiments, the modified polymerase is a variant of a Bst DNA polymerase comprising the amino acid sequence of SEQ ID NO: 34, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 34.

In some embodiments, the reference polymerase is a Bst DNA polymerase having, or comprising, the amino acid sequence of SEQ ID NO: 34 and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 34.

In some embodiments, the modified polymerase can include the amino acid sequence of any biologically active fragment of a polymerase having or comprising the amino acid sequence of SEQ ID NO: 34. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 34.

In some embodiments, the modified polymerase consists of or comprises an isolated variant of a Bst DNA polymerase having or comprising the amino acid sequence of SEQ ID NO: 35.

SEQ ID NO: 35 contains three amino acid substitutions as compared to SEQ ID NO: 2, namely N487R, H281M and D423K, wherein the numbering is relative to the amino acid sequence of SEQ ID NO: 2.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 35. In some embodiments, the modified polymerase is a variant of a Bst DNA polymerase comprising the amino acid sequence of SEQ ID NO: 35, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 35.

In some embodiments, the reference polymerase is a Bst DNA polymerase having, or comprising, the amino acid sequence of SEQ ID NO: 35 and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 35.

In some embodiments, the modified polymerase can include the amino acid sequence of any biologically active fragment of a polymerase having or comprising the amino acid sequence of SEQ ID NO: 35. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 35.

In some embodiments, the modified polymerase consists of or comprises an isolated variant of a Bst DNA polymerase having or comprising the amino acid sequence of SEQ ID NO: 36.

SEQ ID NO: 36 contains two amino acid substitutions as compared to SEQ ID NO: 2, namely N487R and D423K, wherein the numbering is relative to the amino acid sequence of SEQ ID NO: 2.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 36. In some embodiments, the modified polymerase is a variant of a Bst DNA polymerase comprising the amino acid sequence of SEQ ID NO: 36, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 36.

In some embodiments, the reference polymerase is a Bst DNA polymerase having, or comprising, the amino acid sequence of SEQ ID NO: 36 and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 36.

In some embodiments, the modified polymerase can include the amino acid sequence of any biologically active fragment of a polymerase having or comprising the amino acid sequence of SEQ ID NO: 36. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 36.

In some embodiments, the modified polymerase consists of or comprises an isolated variant of a Bst DNA polymerase having or comprising the amino acid sequence of SEQ ID NO: 37.

SEQ ID NO: 37 contains two amino acid substitutions as compared to SEQ ID NO: 2, namely N487R and H281M, wherein the numbering is relative to the amino acid sequence of SEQ ID NO: 2.

In some embodiments, the reference polymerase, the modified polymerase or both the reference and modified polymerase consists of or comprises an isolated variant of a polymerase having or comprising an amino acid sequence that is at least 90% identical to the amino acid sequence of SEQ ID NO: 37. In some embodiments, the modified polymerase is a variant of a Bst DNA polymerase comprising the amino acid sequence of SEQ ID NO: 37, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 37.

In some embodiments, the reference polymerase is a Bst DNA polymerase having, or comprising, the amino acid sequence of SEQ ID NO: 37 and the modified polymerase further includes one or more amino acid modifications (e.g., amino acid substitutions, deletions, additions or chemical modifications) relative to the reference polymerase. In some embodiments, the reference polymerase, the modified polymerase, or both the reference and modified polymerases include a deletion or substitution of the methionine residue at position 1, wherein the numbering is relative to the amino acid sequence of SEQ ID NO: 37.

In some embodiments, the modified polymerase can include the amino acid sequence of any biologically active fragment of a polymerase having or comprising the amino acid sequence of SEQ ID NO: 37. In some embodiments, the reference polymerase and/or the modified polymerase can include the amino acid sequence of any biologically active fragment of a polymerase having or comprising an amino acid sequence that is at least 90% identical to the amino acid sequence of SEQ ID NO: 37.

In some embodiments, the modified polymerase comprises a recombinant polymerase containing an amino acid sequence that has at least 80% homology to SEQ ID NO: 2 or a biologically active fragment thereof, wherein the recombinant polymerase comprises a Family A DNA polymerase having one or more amino acid substitutions at positions corresponding to positions selected from the group consisting of: N487, N485, E493, A263, D264, H528, H273, D423, D480 and H281, wherein the numbering is relative to SEQ ID NO: 2, and wherein the recombinant polymerase exhibits a decreased dissociation rate constant as compared to SEQ ID NO: 2. In some embodiments, the recombinant polymerase includes one or more amino acid substitutions at positions corresponding to positions selected from the group consisting of: N487R, N485K, E493R, A263K, D264A, D264R, H528S, H528F, H273N, D423K, D480R and H281M, wherein the numbering is relative to SEQ ID NO: 2.

In some embodiments, the modified polymerase comprises a recombinant polymerase containing an amino acid sequence that is at least 80% identical to SEQ ID NO: 25 or a biologically active fragment thereof, wherein the recombinant polymerase includes one or more amino acid substitutions at positions corresponding to positions selected from the group consisting of: N780, E788, A558, D559, H823, H568, D718, D775 and H576, wherein the numbering is relative to SEQ ID NO: 25. In some embodiments, the modified polymerase comprises a recombinant polymerase containing an amino acid sequence that is at least 80% identical to SEQ ID NO: 25 or a biologically active fragment thereof, wherein the recombinant polymerase includes one or more amino acid substitutions at positions corresponding to positions selected from the group consisting of: N780K, E788R, A558K, D559A, D559R, H823S, H823F, H568N, D718K, D775R and H576M, wherein the numbering is relative to SEQ ID NO: 25. In some embodiments, the modified polymerase comprises a recombinant polymerase exhibiting increased raw read accuracy, decreased systematic error, decreased strand bias, increased average read length or increased total sequencing throughput as compared to a reference polymerase lacking the one or more amino acid substitutions at positions corresponding to positions selected from the group consisting of: N780, E788, A558, D559, H823, H568, D718, D775 and H576, wherein the numbering is relative to SEQ ID NO: 25.

In some embodiments, the modified polymerase comprises an isolated polypeptide containing an amino acid sequence that has at least 80% homology to SEQ ID NO: 37 or a biologically active fragment thereof, wherein the isolated polypeptide includes one or more amino acid substitutions at positions corresponding to positions selected from the group consisting of: D423, D264, H273 and E493, wherein the numbering is relative to SEQ ID NO: 37, and wherein the isolated polypeptide exhibits a decreased dissociation rate constant relative to SEQ ID NO: 2.

In some embodiments, the modified polymerase comprises a recombinant polymerase containing an amino acid sequence that has at least 80% homology to SEQ ID NO: 2 or a biologically active fragment thereof, wherein the recombinant polymerase comprises a Family A DNA polymerase having one or more amino acid substitutions at positions corresponding to positions selected from the group consisting of: N487, N485, E493, A263, D264, H528, H273, D423, D480 and H281, wherein the numbering is relative to SEQ ID NO: 2, and wherein the recombinant polymerase exhibits a decreased dissociation rate constant as compared to SEQ ID NO: 2.

In some embodiments, the reference polymerase can have or comprise the amino acid sequence of SEQ ID NO: 16, and the modified polymerase can have or comprise the amino acid sequence of the reference polymerase and further include at least one amino acid substitution relative to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. The modified polymerase can further include any one or more amino acid mutations selected from the group consisting of: H341R, C388R, E515K, N529R Q533C, A558K, D559A, D559R, H568R, H568N, H576A, H576M, D718K, E741Q, H768R, Y772F, D775R, N780K, N782K, E788R, H823A, H823S, H823F, C845Q and H867R, wherein the numbering is relative to the amino acid sequence of SEQ ID NO: 16.

In some embodiments, the modified polymerase has a reduced buffering capacity relative to the reference polymerase. Without being bound to any particular theory of operation, it can be observed that in some embodiments one or more of the aforementioned mutations can decrease the buffering capacity of the modified polymerase relative to the unmodified polymerase. In some embodiments, such decrease in buffering capacity can increase the observed signal in an ion-based sequencing reaction. Further information about such mutations and their possible effect on the buffering capacity of the polymerase can be found, for example, in U.S. Provisional Appl. No. 60/308,863 filed Feb. 26, 2010; U.S. patent application Ser. No. 13/035,081 filed Feb. 25, 2011; Ser. No. 13/035,177 filed Feb. 25, 2011; Ser. No. 13/036,526 filed Feb. 28, 2011; and Ser. No. 13/036,623 filed Feb. 25, 2011; as well as in International PCT Appl. Nos. PCT/US2011/026219 filed Feb. 25, 2011; PCT/US2011/026228 filed Feb. 25, 2011; PCT/US2011/026450 filed Feb. 28, 2011; and PCT/US2011/026468 filed Feb. 28, 2011; all of which aforementioned applications are hereby incorporated by reference in their entireties. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 16. Optionally, the reference polymerase, the modified polymerase, or both the reference and modified polymerases can further include one or more amino acid mutations that decrease or eliminate exonuclease activity. Some exemplary mutations that can reduce or eliminate the exonuclease activity of the polymerase are described further herein. In some embodiments, the reference polymerase has or comprises the amino acid sequence of SEQ ID NO: 16, and the modified polymerase has or comprises the amino acid sequence of the reference polymerase and further including at least one amino acid substitution relative to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase further includes any one or more amino acid mutations selected from the group consisting of: N326R, N326K, D372K, D372H, D408N, D409R, D425A, D425H, D439M, D439K, L507A, E515K, N529R, N529K, V536K, V546K, A558K, D559A, D559R, D559Q, D559S, Y567R, H568N, L575R, H576M, E589S, E589F, E589G, V594K, V594H, V594F, D598R, 1626Q, L630T, E631P, 1649W, 1649F, 1665A, Q704R, G711K, V713M, V713I, G715K, D718S, D718K, D718N, D718R, D718T, D718G, D718I, D718K, G720R, Q723W, N724R, N724K, F743K, N752T, A757T, D775R, D775F, D775H, D775A, D775S, D775N, D775Q, N780W, N780Y, N780K, N782H, N782W, N782F, N782I, E782Q, V783R, E788R, E788Q, M790Q, H823S, H823F V828I, W872Y and D874F, wherein the numbering is relative of the amino acid sequence of SEQ ID NO: 16. Without being bound to any particular theory of operation, it can be observed that in some embodiments a modified polymerase including one or more of these mutations exhibits an altered (e.g., increased or decreased) rate of dissociation from the nucleic acid template ("off-rate") relative to the unmodified polymerase. In some embodiments, the modified polymerase exhibits an altered, e.g., increased or decreased dissociation time constant relative to the reference polymerase. In some embodiments, the modified polymerase exhibits an altered, e.g., increased or decreased read length, or an altered average error-free read length, or altered (e.g., increased or decreased) observed 100Q17 or 200Q17 values relative to the reference polymerase. In some embodiments, the modified polymerase exhibits a change in any one or more of the following kinetic parameters: average read length, minimum read length, raw accuracy, strand bias, systematic error, total sequencing throughput, enhanced performed in higher ionic strength solution, improved processivity, performance in polymerase chain reaction, performance in emulsion polymerase chain reaction, dissociation time constant, off-rate, AQ20, 100Q17 value, and 200Q17 value, relative to the reference polymerase. Optionally, the change is observed by comparing the performance of the reference and modified polymerases in an ion-based sequencing reaction. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 16. Optionally, the reference polymerase, the modified polymerase, or both the reference and modified polymerases can further include one or more amino acid mutations that decrease or eliminate exonuclease activity.

In some embodiments, the reference polymerase has or comprises the amino acid sequence of SEQ ID NO: 16, and the modified polymerase has or comprises the amino acid sequence of the reference polymerase and further includes at least one amino acid substitution relative to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. In some embodiments, the modified polymerase further includes an amino acid substitution at any one or more positions selected from the group consisting of: 326, 341, 372, 388, 408, 409, 425, 439, 507, 515, 529, 533, 536, 546, 558, 559, 567, 568, 575, 576, 589, 594, 598, 626, 630, 631, 649, 665, 704, 711, 713, 715, 718, 720, 723, 724, 741, 743, 752, 757, 768, 772, 775, 780, 782, 783, 788, 790, 823, 828, 845, 867, 872 and 874, wherein the numbering is relative of the amino acid sequence of SEQ ID NO: 16.

In some embodiments, the modified polymerase can include the amino acid sequence of any biologically active fragment of a polymerase having the amino acid sequence of SEQ ID NO: 16 and further including any one or more amino acid mutations selected from the group consisting of: N782R, D780K, E788R, A588K, H568N, H576M, H823S, H823F, D559A, D559R, D559S, D718K, and D775R.

In some embodiments, the amino acid substitutions include the substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 16. In some embodiments, the modified polymerase exhibits a change in any one or more parameters selected from the group consisting of: average read length, minimum read length, raw accuracy, strand bias, systematic error, total sequencing throughput, enhanced performed in higher ionic strength solution, improved processivity, performance in polymerase chain reaction, performance in emulsion polymerase chain reaction, AQ20, buffering capacity, off-rate, 100Q17 value and 200Q17 value, relative to the reference polymerase. Optionally, the change is observed by comparing the performance of the reference and modified polymerases in an ion-based sequencing reaction. Optionally, the reference polymerase, the modified polymerase, or both the reference and modified polymerases can further include one or more amino acid mutations that decrease or eliminate exonuclease activity.

In some embodiments, the modified polymerase further includes any one or more amino acid mutations selected from the group consisting of: N326R, N326K, H341R, D372K, D372H, C388R, D408N, D409R, D425A, D425H, D439M, D439K, L507A, E515K, N529R, N529K, V536K, V546K, Q533C, D559A, D559Q, D559S, Y567R, H568R, L575R, H576A, H576M, E589S, E589F, E589G, V594K, V594H, V594F, D598R, 1626Q, L630T, E631P, 1649W, 1649F, 1665A, Q704R, G711K, V713M, V713I, G715K, D718S, D718K, D718N, D718R, D718T, D718G, D718I, D718K, G720R, Q723W, N724R, N724K, E741Q, F743K, N752T, A757T, H768R, Y772F, D775R, D775F, D775H, D775A, D775S, D775N, D775Q, N780W, N780Y, N782H, N782R, N782W, N782F, N782I, E782Q, V783R, E788Q, M790Q, H823A, H823S, V828I, C845Q, H867R, W872Y and D874F, wherein the numbering is relative of the amino acid sequence of SEQ ID NO: 16. Without being bound to any particular theory of operation, it can be observed that in some embodiments a modified polymerase including one or more of these mutations exhibits an altered (e.g., increased or decreased) rate of dissociation from the nucleic acid template ("off-rate") relative to the unmodified polymerase. In some embodiments, the modified polymerase exhibits an altered (e.g., increased or decreased) dissociation time constant relative to the unmodified polymerase. In some embodiments, the modified polymerase exhibits an altered (e.g., increased or decreased) buffering capacity relative to the unmodified polymerase. In some embodiments, the modified polymerase exhibits an altered, e.g., increased or decreased read length, or an altered average error-free read length, or altered (e.g., increased or decreased) observed 100Q17 or 200Q17 values relative to the reference polymerase. In some embodiments, the modified polymerase exhibits a change in any one or more parameters selected from the group consisting of: buffering capacity, average read length, minimum read length, raw accuracy, strand bias, systematic error, total sequencing throughput, enhanced performed in higher ionic strength solution, improved processivity, performance in polymerase chain reaction, performance in emulsion polymerase chain reaction, off-rate, AQ20, 100Q17 value and 200Q17 value, relative to the reference polymerase. Optionally, the change is observed by comparing the performance of the reference and modified polymerases in an ion-based sequencing reaction. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 16. Optionally, the reference polymerase, the modified polymerase, or both the reference and modified polymerases can further include one or more amino acid mutations that decrease or eliminate exonuclease activity.

In some embodiments, the reference polymerase has or comprises the amino acid sequence of SEQ ID NO: 16, and the modified polymerase has or comprises the amino acid sequence of the reference polymerase and further includes at least one amino acid substitution relative to the reference polymerase. In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase. The at least one amino acid substitution can optionally occur at any one or more positions selected from the group consisting of: 341, 388, 533, 568, 576, 741, 768, 772, 823, 845 and 867. In some embodiments, the modified polymerase can further include at least one amino acid substitution at one or more positions selected from the group consisting of: 326, 372, 408, 409, 425, 439, 507, 515, 529, 536, 546, 559, 567, 575, 589, 594, 598, 626, 630, 631, 649, 665, 704, 711, 713, 715, 718, 720, 723, 724, 743, 752, 757, 775, 780, 782, 783, 788, 790, 828, 872 and 874, wherein the numbering is relative of the amino acid sequence of SEQ ID NO: 16. In some embodiments, the amino acid substitutions include the substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 16. In some embodiments, the modified polymerase exhibits a change in any one or more parameters selected from the group consisting of: buffering capacity, average read length, minimum read length, raw accuracy, strand bias, systematic error, total sequencing throughput, enhanced performed in higher ionic strength solution, improved processivity, performance in polymerase chain reaction, performance in emulsion polymerase chain reaction, dissociation time constant, off-rate, AQ20, 100Q17 value and 200Q17 value, relative to the reference polymerase. Optionally, the change is observed by comparing the performance of the reference and modified polymerases in an ion-based sequencing reaction. Optionally, the reference polymerase, the modified polymerase, or both the reference and modified polymerases can further include one or more amino acid mutations that decrease or eliminate exonuclease activity.

In some embodiments, the modified polymerase further includes one or more amino acid substitutions selected from the group consisting of: H341A, H341R, C388R, Q533C, H568A, H568R, H576A, H576M, H576R, E741Q, H768A, H768R, Y772F, H823A, H823R, H823K, C845Q, H867A and H867R, as well as one or more amino acid substitutions selected from the group consisting of: N326R, N326K, D372K, D372H, D408N, D409R, D425A, D425H, D439M, D439K, L507A, E515K, N529R, N529K, V536K, V546K, D559Q, D559S, D559K, Y567R, L575R, E589S, E589F, E589G, E589K, V594K, V594H, V594F, D598R, 1626Q, L630T, E631P, 1649W, 1649F, 1665A, Q704R, G711K, V713M, V713I, G715K, D718S, D718K, D718N, D718R, D718T, D718G, D718I, D718K, G720R, Q723W, N724R, N724K, F743K, N752T, A757T, D775R, D775F, D775H, D775A, D775S, D775N, D775Q, N780W, N780Y, N782H, N782W, N782F, N782I, E782Q, V783R, E788Q, M790Q, V828I, W872Y and D874F, wherein the numbering is relative of the amino acid sequence of SEQ ID NO: 16.

In some embodiments, the disclosure relates generally to a modified polymerase comprising the amino acid sequence of SEQ ID NO: 16, or the amino acid sequence of any biologically active fragment of a polymerase having or comprising the amino acid sequence of SEQ ID NO: 16, and further including at least one amino acid mutation relative to the amino acid sequence of a reference polymerase, where the reference polymerase consists of the amino acid sequence of SEQ ID NO: 16.

In some embodiments, the modified polymerase comprises an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of the reference polymerase.

In some embodiments, the modified polymerase has polymerase activity. The modified polymerase or biologically active fragment can have primer extension activity in vivo or in vitro.

In some embodiments, the one or more mutations in the modified polymerase can include at least one amino acid substitution. The at least one amino acid substitution can optionally occur at any one or more positions selected from the group consisting of: 341, 388, 533, 568, 576, 741, 768, 772, 823, 845 and 867, wherein the numbering is relative to the amino acid sequence of SEQ ID NO: 16. In some embodiments, the modified polymerase includes at least two, three, four, five, or more amino acid substitutions occurring at positions selected from this group. Without intending to be bound to any particular theory of action, it can be observed that in some embodiments, amino acid substitution at such positions can alter, e.g., increase or decrease the buffering capacity of the modified polymerase relative to the corresponding unmodified polymerase, or relative to a reference polymerase. Such mutations can therefore be referred to as "buffering" mutations. In some embodiments, such increase or decrease in buffering capacity can increase the observed signal in an ion-based sequencing reaction.

In some embodiments, the one or more mutations in the modified polymerase can include at least one amino acid substitution. The at least one amino acid substitution can optionally occur at any one or more positions selected from the group consisting of: 326, 372, 408, 409, 425, 439, 507, 515, 529, 536, 546, 559, 567, 575, 589, 594, 598, 626, 630, 631, 649, 665, 704, 711, 713, 715, 718, 720, 723, 724, 743, 752, 757, 775, 780, 782, 783, 788, 790, 828, 872 and 874, wherein the numbering is relative to the amino acid sequence of SEQ ID NO: 16. In some embodiments, the modified polymerase includes at least two, three, four, five, or more amino acid substitutions occurring at positions selected from this group. Without being bound to any particular theory of operation, it can be observed that in some embodiments a modified polymerase including any one of such amino acid substitutions exhibits an altered (e.g., increased or decreased) binding affinity for a nucleic acid template relative to an unmodified polymerase, or an altered (e.g., increased or decreased) rate of dissociation from the nucleic acid template ("off-rate") relative to the corresponding unmodified polymerase, or relative to a reference polymerase. In some embodiments, the modified polymerase exhibits an altered (e.g., increased or decreased) read length, or an altered (e.g., increased or decreased) average error-free read length, or altered (e.g., increased or decreased) dissociation time constant, or altered (e.g., increased or decreased) observed 100Q17 or 200Q17 values relative to the reference polymerase. In some embodiments, the modified polymerase exhibits a change (e.g., increase or decrease) in any one or more properties selected from the group consisting of: DNA binding affinity, raw accuracy, strand bias, systematic error, total sequencing throughput, off-rate, 100Q17 value and 200Q17 value, relative to the reference polymerase. Optionally, the change is observed by comparing the properties of the reference and modified polymerases in an ion-based sequencing reaction.

In some embodiments, the one or more mutations in the modified polymerase can include at least one amino acid substitution. The at least one amino acid substitution can optionally occur at any one or more positions selected from the group consisting of: 326, 341, 372, 408, 409, 425, 439, 507, 515, 529, 536, 546, 559, 567, 568, 575, 576, 589, 594, 598, 626, 630, 631, 649, 665, 704, 711, 713, 715, 718, 720, 723, 724, 741, 743, 752, 757, 768, 772, 775, 780, 782, 783, 788, 790, 823, 828, 867, 872 and 874, wherein the numbering is relative to the amino acid sequence of SEQ ID NO: 16. In some embodiments, the modified polymerase includes at least two, three, four, five, or more amino acid substitutions occurring at positions selected from this group.

In some embodiments, the modified polymerase includes the amino acid sequence of SEQ ID NO: 16, or the amino acid sequence of a biologically active fragment of a polymerase having the amino acid sequence of SEQ ID NO: 16 and further includes at least one amino acid substitution at any one or more positions selected from the group consisting of: 341, 568, 576, 741, 768, 772, 823, 845 and 867, as well as at least one amino acid substitution at any one or more positions selected from the group consisting of: 326, 372, 408, 409, 425, 439, 507, 515, 529, 536, 546, 559, 567, 575, 589, 594, 598, 626, 630, 631, 649, 665, 704, 711, 713, 715, 718, 720, 723, 724, 743, 752, 757, 775, 780, 782, 783, 788, 790, 828, 872 and 874, wherein the numbering is relative to the amino acid sequence of SEQ ID NO: 16, In some embodiments, the modified polymerase includes at least two, three, four, five, or more amino acid substitutions occurring at positions selected from each of these two groups of amino acid substitutions.

In some embodiments, the modified polymerase includes the amino acid sequence of SEQ ID NO: 16, or the amino acid sequence of a biologically active fragment of a polymerase having the amino acid sequence of SEQ ID NO: 16. In some embodiments, the modified polymerase further includes at least one amino acid substitution selected from the group consisting of: H341A, H341R, H568A, H568R, H576A, H576R, E741Q, H768A, H768R, Y772F, H823A, H823R, H867A and H867R, wherein the numbering is relative of the amino acid sequence of SEQ ID NO: 16. In some embodiments, the modified polymerase includes any two, three, four, five or more of these amino acid substitutions.

In some embodiments, the modified polymerase includes at least one amino acid substitution designed to replace a preexisting cysteine residue with a different amino acid residue, or to replace a non-cysteine amino acid residue with a cysteine residue. The at least one amino acid substitution optionally includes one or more amino acid substitutions selected from the group consisting of: C388R, Q533C, C845Q, wherein the numbering is relative to the amino acid sequence of SEQ ID NO: 16.

In some embodiments, the modified polymerase further includes at least one amino acid substitution selected from the group consisting of: H341A, H341R, H568A, H568R, H576A, H576R, H576M, E741Q, H768A, H768R, Y772F, H823A, H823R, H823K, H867A and H867R, wherein the numbering is relative of the amino acid sequence of SEQ ID NO: 16. In some embodiments, the modified polymerase includes any two, three, four, five or more of these amino acid substitutions.

In some embodiments, the modified polymerase further includes at least one amino acid substitution selected from the group consisting of: N326R, N326K, D372K, D372H, D408N, D409R, D425A, D425H, D439M, D439K, L507A, E515K, N529R, N529K, V536K, V546K, D559Q, D559S, D559K, Y567R, L575R, E589S, E589F, E589G, E589K, V594K, V594H, V594F, D598R, I626Q, L630T, E631P, I649W, I649F, I665A, Q704R, G711K, V713M, V713I, G715K, D718S, D718K, D718N, D718R, D718T, D718G, D718I, D718K, G720R, Q723W, N724R, N724K, F743K, N752T, A757T, D775R, D775F, D775H, D775A, D775S, D775N, D775Q, N780W, N780Y, N782H, N782W, N782F, N782I, E782Q, V783R, E788Q, M790Q, V828I, W872Y and D874F, wherein the numbering is relative of the amino acid sequence of SEQ ID NO: 16. Optionally, the modified polymerase can further include at least one amino acid substitution selected from the group consisting of: H341A, H341R, H568A, H568R, H576A, H576R, H576M, E741Q, H768A, H768R, Y772F, H823A, H823R, H823K, H867A and H867R, wherein the numbering is relative to the amino acid sequence of SEQ ID NO: 16. In some embodiments, the modified polymerase includes any two, three, four, five or more amino acid substitutions selected from each of these two groups of amino acid substitutions.

In some embodiments, the modified polymerase further includes at least one amino acid substitution selected from the group consisting of: N326R, N326K, H341A, H341R, D372K, D372H, D408N, D409R, D425A, D425H, D439M, D439K, L507A, E515K, N529R, N529K, V536K, V546K, D559Q, D559S, D559K, Y567R, H568A, H568R, L575R, H576A, H576R, E589S, E589F, E589G, E589K, V594K, V594H, V594F, D598R, I626Q, L630T, E631P, I649W, I649F, I665A, Q704R, G711K, V713M, V713I, G715K, D718S, D718K, D718N, D718R, D718T, D718G, D718I, D718K, G720R, Q723W, N724R, N724K, E741Q, F743K, N752T, A757T, H768A, H768R, Y772F, D775R, D775F, D775H, D775A, D775S, D775N, D775Q, N780W, N780Y, N782H, N782W, N782F, N782I, E782Q, V783R, E788Q, M790Q, H823A, H823R, V828I, H867A, H867R, W872Y and D874F, wherein the numbering is relative of the amino acid sequence of SEQ ID NO: 16. In some embodiments, the modified polymerase includes any two, three, four, five or more of these amino acid substitutions.

In some embodiments, the modified polymerase according to the disclosure can include at least amino acid mutation, D775R, wherein the numbering is relative to the amino acid sequence of SEQ ID NO: 16. In some embodiments, the modified polymerase according to the disclosure can include amino acid mutations D559K and E788Q, wherein the numbering is relative to the amino acid sequence of SEQ ID NO: 16. In some embodiments, the modified polymerase according to the disclosure can include amino acid mutations E515K, N529R and D718K, wherein the numbering is relative to the amino acid sequence of SEQ ID NO: 16. In some embodiments, the modified polymerase according to the disclosure can include amino acid mutations E515K, N529R, D718K, and H823A, wherein the numbering is relative to the amino acid sequence of SEQ ID NO: 16. In some embodiments, the modified polymerase according to the disclosure can include amino acid mutations E515K, N529R, D718K, H768R and H823A, wherein the numbering is relative to the amino acid sequence of SEQ ID NO: 16. In some embodiments, the modified polymerase according to the disclosure can include any one or more amino acid mutations selected from the group consisting of: E515K, N529R, V536K, D559K, D718K, H768R, D775R, N782W, V783R, E788Q, and H823A) wherein the numbering is relative to the amino acid sequence of SEQ ID NO: 16. In some embodiments, the modified polymerase according to the disclosure can include amino acid mutations N782R, wherein the numbering is relative to the amino acid sequence of SEQ ID NO: 16. In some embodiments, the modified polymerase according to the disclosure can include amino acid mutations N782R and D718K, wherein the numbering is relative to the amino acid sequence of SEQ ID NO: 16. In some embodiments, the modified polymerase according to the disclosure can include amino acid mutations N782R, D718K and H568N wherein the numbering is relative to the amino acid sequence of SEQ ID NO: 16. In some embodiments, the modified polymerase according to the disclosure can include amino acid mutations N782R and H576M wherein the numbering is relative to the amino acid sequence of SEQ ID NO: 16. In some embodiments, the modified polymerase according to the disclosure can include amino acid mutations N782R and H823S, wherein the numbering is relative to the amino acid sequence of SEQ ID NO: 16. In some embodiments, the modified polymerase according to the disclosure can include amino acid mutations D718K, wherein the numbering is relative to the amino acid sequence of SEQ ID NO: 16. In some embodiments, the modified polymerase according to the disclosure can include amino acid mutations N782R, D718K and H576M, wherein the numbering is relative to the amino acid sequence of SEQ ID NO: 16. In some embodiments, the modified polymerase according to the disclosure can include amino acid mutations N782R, D718K, H576M, D559A, H5678N and E788R, wherein the numbering is relative to the amino acid sequence of SEQ ID NO: 16.

In some embodiments a modified polymerase including one or more of these mutations exhibits an altered (e.g., increased or decreased) binding affinity for a nucleic acid template relative to the corresponding unmodified polymerase or to a reference polymerase. In some embodiments, the modified polymerase has an altered (e.g., increased or decreased) rate of dissociation from the nucleic acid template ("off-rate") relative to the unmodified polymerase or to a reference polymerase. In some embodiments, the modified polymerase exhibits an altered, e.g., increased or decreased read length, or increased raw accuracy, or decreased strand bias, or lowered systematic error, or increased total sequencing throughput, or an altered average error-free read length, or altered (e.g., increased or decreased) observed 100Q17 or 200Q17 values relative to the reference polymerase. In some embodiments, the modified polymerase exhibits a change in any one or more of the following kinetic parameters: average read length, minimum read length, raw accuracy, strand bias, systematic error, total sequencing throughput, enhanced performed in higher ionic strength solution, improved processivity, performance in polymerase chain reaction, performance in emulsion polymerase chain reaction, dissociation time constant, off-rate, AQ20, 100Q17 value, and 200Q17 value, relative to the reference polymerase. Optionally, the change is observed by comparing the performance of the reference and modified polymerases in an ion-based sequencing reaction. In some embodiments, the amino acid substitutions include the substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 16. In some embodiments, the modified polymerase exhibits a change in any one or more parameters selected from the group consisting of: buffering capacity, average read length, minimum read length, enhanced performed in higher ionic strength solution, improved processivity, performance in polymerase chain reaction, performance in emulsion polymerase chain reaction, off-rate, AQ20, 100Q17 value and 200Q17 value, relative to the reference polymerase. Optionally, the change is observed by comparing the performance of the reference and modified polymerases in an ion-based sequencing reaction. Optionally, the reference polymerase, the modified polymerase, or both the reference and modified polymerases can further include one or more amino acid mutations that decrease or eliminate exonuclease activity.

In some embodiments, the modified polymerase has an altered (e.g., increased or decreased) binding affinity for a nucleic acid template relative to a reference polymerase. In some embodiments, the modified polymerase has an altered (e.g., increased or decreased) rate of dissociation from the nucleic acid template ("off-rate") relative to a reference polymerase. In some embodiments, the modified polymerase exhibits an altered (e.g., increased or decreased) read length, or an altered (e.g., increased or decreased) average error-free read length, or an altered (e.g., increased or decreased) observed 100Q17 or 200Q17 value relative to the reference polymerase. In some embodiments, the modified polymerase exhibits a change (e.g., increase or decrease) in any one or more of the following properties: binding affinity for a nucleic acid template, dissociation time constant, off-rate, 100Q17 value, and 200Q17 value, relative to the reference polymerase. In some embodiments, the altered property is increased or decreased by at least 10%, 20%, 30%, 40%, 50%, 75%, 90%, 100%, 200%, 300%, 500%, 750%, 1000%, 3000% or greater, relative to the corresponding reference polymerase. Optionally, the change is observed by comparing the properties of the reference and modified polymerases in an ion-based sequencing reaction.

Optionally, the reference polymerase, the modified polymerase, or both the reference and modified polymerases can further include one or more amino acid mutations that decrease or eliminate any exonuclease activity of the polymerase. In some embodiments, the reference polymerase, the modified polymerase, or both the reference and modified polymerase is a Bst DNA polymerase that has proofreading exonuclease activity. In various embodiments, the proofreading exonuclease activity of a modified Bst DNA polymerase is at least about 40%, 50%, 60%, 70%, 80% or 90% that of the corresponding wild type protein. In order to retain the proofreading exonuclease activity of a modified Bst DNA polymerase, the skilled artisan will understand that any substitutions, deletions or chemical modifications should be made to amino acid residues that are not highly conserved within the Exo I, Exo II and Exo III motifs.

In some embodiments, the modified polymerase is a Taq DNA polymerase. In some embodiments, the polymerase is a Taq DNA polymerase commercially available as Platinum Taq High Fidelity DNA polymerase (Life Technologies, CA), that includes one or more amino acid mutations as compared to the reference Platinum Taq High Fidelity DNA polymerase. In some embodiments, the modified polymerase is a Taq DNA polymerase having, or comprising, the amino acid sequence of SEQ ID NO: 15, which is the amino acid sequence of the large fragment of the Taq Pol A polymerase:

In some embodiments, the modified polymerase includes a mutant or variant form of a Taq DNA polymerase that retains a detectable level of polymerase activity. In order to retain the polymerase activity of the Taq DNA polymerase, any substitutions, deletions or chemical modifications will be made to amino acid residues that are not highly conserved, such as the invariant aspartic acid residues required for polymerase activity. In some embodiments, the modified polymerase can include Taq DNA polymerase, a hot-start Taq DNA polymerase, a chemical hot-start Taq DNA polymerase, Platinium Taq DNA polymerase and the like.

In some embodiments, the modified polymerase can include an isolated variant of a polymerase having or comprising an amino acid sequence that is at least 90% identical to the amino acid sequence of SEQ ID NO: 15. In some embodiments, the modified polymerase is a variant of a Taq DNA polymerase comprising the amino acid sequence of SEQ ID NO: 15, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 15.

In some embodiments, the modified polymerase includes a mutant or variant form of Taq DNA polymerase having amino acid mutation, E471K, wherein the numbering is relative to the amino acid sequence of SEQ ID NO: 15. In some embodiments, the modified Taq DNA polymerase can include amino acid mutation, N485R, wherein the numbering is relative to the amino acid sequence of SEQ ID NO: 15. In some embodiments, the modified Taq DNA polymerase can include amino acid mutation, R492K, wherein the numbering is relative to the amino acid sequence of SEQ ID NO: 15. In some embodiments, the modified Taq DNA polymerase can include amino acid mutation, D513K, wherein the numbering is relative to the amino acid sequence of SEQ ID NO: 15. In some embodiments, the modified Taq DNA polymerase can include amino acid mutation, A675K, wherein the numbering is relative to the amino acid sequence of SEQ ID NO: 15. In some embodiments, the modified Taq DNA polymerase can include amino acid mutation, D732R, wherein the numbering is relative to the amino acid sequence of SEQ ID NO: 15. In some embodiments, the modified Taq DNA polymerase can include amino acid mutation S739W, wherein the numbering is relative to the amino acid sequence of SEQ ID NO: 15. In some embodiments, the modified Taq DNA polymerase can include amino acid mutation V740R, wherein the numbering is relative to the amino acid sequence of SEQ ID NO: 15. In some embodiments, the modified Taq DNA polymerase can include amino acid mutation E745Q, wherein the numbering is relative to the amino acid sequence of SEQ ID NO: 15. In some embodiments, the modified polymerase can include a variant or mutant of Taq DNA polymerase having or comprising one or more of the following amino acid mutations selected from the group consisting of: E471K, N485R, R492K, D513K, A675K, D732R, S739W, V740R and E745Q, wherein the numbering is relative to the amino acid sequence of SEQ ID NO: 15.

In some embodiments a modified polymerase including one or more of these mutations exhibits an altered (e.g., increased or decreased) binding affinity for a nucleic acid template relative to the corresponding unmodified polymerase or to a reference polymerase. In some embodiments, the modified Taq polymerase has an altered (e.g., increased or decreased) rate of dissociation from the nucleic acid template ("off-rate") relative to the unmodified polymerase or to a reference polymerase. In some embodiments, the modified Taq polymerase exhibits an altered, e.g., increased or decreased read length, or an altered average error-free read length, or altered (e.g., increased or decreased) observed 100Q17 or 200Q17 values relative to the reference polymerase. In some embodiments, the modified Taq polymerase exhibits a change in any one or more of the following kinetic parameters: average read length, minimum read length, enhanced performed in higher ionic strength solution, improved processivity, performance in polymerase chain reaction, performance in emulsion polymerase chain reaction, dissociation time constant, off-rate, AQ 20, 100Q17 value, and 200Q17 value, relative to the reference polymerase. Optionally, the change is observed by comparing the performance of the reference and modified polymerases in an ion-based sequencing reaction. In some embodiments, the amino acid substitutions include the substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified Taq polymerase, or both the reference and modified Taq polymerases can further include a deletion of the methionine residue at position 1, or a substitution of the methionine residue at position 1 with any other amino acid residue, wherein the numbering is relative to the amino acid sequence of SEQ ID NO: 15. In some embodiments, the modified Taq polymerase exhibits a change in any one or more parameters selected from the group consisting of: buffering capacity, average read length, mininmum read length, enhanced performed in higher ionic strength solution, improved processivity, performance in polymerase chain reaction, performance in emulsion polymerase chain reaction, AQ20, off-rate, 100Q17 value and 200Q17 value, relative to the reference polymerase. Optionally, the change is observed by comparing the performance of the reference and modified Taq polymerases in an ion-based sequencing reaction. Optionally, the reference polymerase, the modified Taq polymerase, or both the reference and modified Taq polymerases can further include one or more amino acid mutations that decrease or eliminate exonuclease activity.

In some embodiments, the modified polymerase is a Taq DNA polymerase having, or comprising, the amino acid sequence of SEQ ID NO: 15 except for the first residue (N-terminal methionine) of SEQ ID NO: 15, which is not included in the modified polymerase.

As the skilled artisan will readily appreciate, the scope of the present disclosure encompasses not only the specific amino acid and/or nucleotide sequences disclosed herein, but also, for example, many related sequences encoding genes and/or peptides with the functional properties described herein. For example, the scope and spirit of the disclosure encompasses any nucleotide and amino acid sequences encoding conservative variants of the various polymerases disclosed herein. It will also be readily apparent to the skilled artisan that the modified polymerases disclosed herein by amino acid sequence can be converted to the corresponding nucleotide sequence without undue experimentation, for example using a number of freely available sequence conversion applications (e.g. "in-silco").

In some embodiments, the modified polymerase is the Klenow Fragment of E. coli DNA polymerase I. DNA polymerase I from E. coli contains a 5' to 3' exonuclease domain (typically corresponding to amino acid resides: 7-252). However, in order to generate the Klenow fragment, these and additional amino acid resides (1-323) are cleaved. Amino acid residues 324-928 of E. coli DNA polymerase I constitute the Klenow fragment (provided herein as SEQ ID NO: 18 which encodes for the Klenow fragment polypeptide). Both E. coli DNA polymerase I and the Klenow fragment contain a 3' to 5' exonuclease (proofreading) domain located at amino acid residues 345-539; and a polymerase domain responsible for polymerization of a new DNA strand (amino acid residues 547-926). Overall, the Klenow fragment as compared to E. coli polymerase I generally lacks amino acids 1-323.

In some embodiments, the modified polymerase is a Klenow Fragment of E. coli DNA polymerase having, or comprising, the amino acid sequence of SEQ ID NO: 18.

In some embodiments, the modified polymerase includes a mutant or variant form of the Klenow fragment of DNA polymerase I that retains a detectable level of polymerase activity. In order to retain the polymerase activity of the Klenow fragment, any substitutions, deletions or chemical modifications will be made to amino acid residues that are not highly conserved, such as the invariant aspartic acid residues required for polymerase activity.

In some embodiments, the modified polymerase can include an isolated variant of a polymerase having or comprising an amino acid sequence that is at least 90% identical to the amino acid sequence of SEQ ID NO: 18. In some embodiments, the modified polymerase is a variant of a Klenow fragment of DNA polymerase I comprising the amino acid sequence of SEQ ID NO: 18, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 18.

In some embodiments, the modified polymerase includes a mutant or variant form of the Klenow fragment of DNA polymerase I having amino acid mutation, E245K, wherein the numbering is relative to the amino acid sequence of SEQ ID NO: 18. In some embodiments, the modified polymerase includes a mutant or variant form of the Klenow fragment of DNA polymerase I having amino acid mutation, S259R, wherein the numbering is relative to the amino acid sequence of SEQ ID NO: 18. In some embodiments, the modified polymerase includes a mutant or variant form of the Klenow fragment of DNA polymerase I having amino acid mutation, T266K, wherein the numbering is relative to the amino acid sequence of SEQ ID NO: 18. In some embodiments, the modified polymerase includes a mutant or variant form of the Klenow fragment of DNA polymerase I having amino acid mutation, E290K, wherein the numbering is relative to the amino acid sequence of SEQ ID NO: 18. In some embodiments, the modified polymerase includes a mutant or variant form of the Klenow fragment of DNA polymerase I having amino acid mutation, A448K, wherein the numbering is relative to the amino acid sequence of SEQ ID NO: 18. In some embodiments, the modified Klenow fragment of DNA polymerase I can include amino acid mutation, D505R, wherein the numbering is relative to the amino acid sequence of SEQ ID NO: 18. In some embodiments, the modified polymerase includes a mutant or variant form of the Klenow fragment of DNA polymerase I having amino acid mutation, A512W, wherein the numbering is relative to the amino acid sequence of SEQ ID NO: 18. In some embodiments, the modified Klenow fragment of DNA polymerase I can include amino acid mutation E518Q, wherein the numbering is relative to the amino acid sequence of SEQ ID NO: 18. In some embodiments, the modified polymerase can include a variant or mutant of Klenow fragment of DNA polymerase I having or comprising one or more of the following amino acid mutations selected from the group consisting of: E245K, S259R, T266K, E290K, A448K, D505R, A512W, and E518Q, wherein the numbering is relative to the amino acid sequence of SEQ ID NO: 18.

In some embodiments a modified Klenow fragment of DNA polymerase I including one or more of the above mutations exhibits an altered (e.g., increased or decreased) binding affinity for a nucleic acid template relative to the corresponding unmodified polymerase or to a reference polymerase. In some embodiments, the modified Klenow fragment of DNA polymerase I has an altered (e.g., increased or decreased) rate of dissociation from the nucleic acid template ("off-rate") relative to the unmodified polymerase or to a reference polymerase. In some embodiments, the modified polymerase exhibits an altered, e.g., increased or decreased read length, or an altered average error-free read length, or altered (e.g., increased or decreased) observed 100Q17 or 200Q17 values relative to the reference polymerase. In some embodiments, the modified polymerase exhibits a change in any one or more of the following kinetic parameters: average read length, mininmum read length, enhanced performed in higher ionic strength solution, improved processivity, performance in polymerase chain reaction, performance in emulsion polymerase chain reaction, dissociation time constant, off-rate, AQ 20, 100Q17 value, and 200Q17 value, relative to the reference polymerase. Optionally, the change is observed by comparing the performance of the reference and modified polymerases in an ion-based sequencing reaction. In some embodiments, the amino acid substitutions include the substitution of the existing amino acid residue at the indicated position with any other amino acid residue (including both naturally occurring and non-natural amino acid residues). In some embodiments, the amino acid substitution is a conservative substitution; alternatively, the amino acid substitution can be a non-conservative substitution. In some embodiments, the reference polymerase, the modified polymerase, or both the reference and modified polymerases can further include a deletion of the methionine residue at position 1, or a substitution of the methionine residue at position 1 with any other amino acid residue, wherein the numbering is relative to the amino acid sequence of SEQ ID NO: 18. In some embodiments, the modified polymerase exhibits a change in any one or more parameters selected from the group consisting of: average read length, mininmum read length, enhanced performed in higher ionic strength solution, improved processivity, performance in polymerase chain reaction, performance in emulsion polymerase chain reaction, buffering capacity, off-rate, 100Q17 value and 200Q17 value, relative to the reference polymerase. Optionally, the change is observed by comparing the performance of the reference and modified polymerases in an ion-based sequencing reaction.

In one aspect of the disclosure, it has been found that amino acids of a polymerase (for example, a reference polymerase) can be mutated to generate modified polymerases with altered catalytic properties. In some embodiments, SEQ ID NO: 16 (corresponding to full-length wild-type Bst DNA polymerase) can be mutated at one or more of the amino acids provided in Table 1 to obtain one or more polymerases with altered catalytic properties as compared to a reference polymerase (e.g., full-length wild-type Bst polymerase). In some embodiments, SEQ ID NO: 1 (corresponding to a truncated version of wild-type Bst DNA polymerase) can be mutated at one or more of the amino acids provided in Table 1 to obtain one or more polymerases with altered catalytic properties as compared to a reference polymerase (e.g., the truncated wild-type Bst polymerase). In some embodiments, SEQ ID NO: 18 (corresponding to the Klenow fragment of DNA polymerase I from E. coli) can be mutated at one or more of the amino acids provided in Table 1 to obtain one or more polymerases with altered catalytic properties as compared to a reference polymerase (e.g., the Klenow fragment of DNA polymerase I). In some embodiments, SEQ ID NO: 15 (corresponding to wild-type Taq DNA polymerase) can be mutated at one or more of the amino acids provided in Table 1 to obtain one or more polymerases with altered catalytic properties as compared to a reference polymerase (e.g., Taq DNA polymerase). In some embodiments, incorporating one or more of the amino acid mutations identified in Table 1 can produce a modified polymerase with enhanced catalytic properties. In some embodiments, the modified polymerase exhibits an altered, e.g., increased or decreased read length, or an altered average error-free read length, or altered (e.g., increased or decreased) observed 100Q17 or 200Q17 values relative to the reference polymerase. In some embodiments, the modified polymerase exhibits a change in any one or more of the following kinetic parameters: average read length, mininmum read length, enhanced performed in higher ionic strength solution, improved processivity, performance in polymerase chain reaction, performance in emulsion polymerase chain reaction, dissociation time constant, off-rate, AQ20 100Q17 value, and 200Q17 value, relative to the reference polymerase.

TABLE 1

| SEQ ID NO: 16 | SEQ ID NO: 1 | SEQ ID NO: 18 | SEQ ID NO: 15 |
| --- | --- | --- | --- |
| E515K | E220K | E245 | E471 |
| N529R | N234R | S259R | N485R |
| V536K | V241K | T266K | R492K |
| D559K | D264 | E290K | D513K |
| D718K | D423K | A448K | A675K |
| D775R | D480R | D505R | D732R |
| N782W | N487W | A512W | S739W |
| V783R | V488R | | V740R |
| E788Q | E493Q | E518 | E745 |

While not wishing to be bound by any particular theory, it was observed that nine different amino acid mutations per polymerase (of Table) were transferable (homologous) among the four polymerases (full length Bst polymerase, large fragment Bst polymerase, Taq DNA polymerase and Klenow Fragment of E. Coli Pol I). As a result, it is reasonably believed that once an amino acid mutation is identified in a polymerase that provides altered catalytic properties, the amino acid mutation can be screened using methods known to one of ordinary skill in the art (such as amino acid or nucleotide sequence alignment), to determine if the amino acid mutation can be transferred to a different polymerase, such as a different species, class or polymerase family (as demonstrated herein). In some embodiments, the transferable (or homologous) amino acid mutation can include an amino acid mutation that enhances catalytic properties such as increased read-length, increased raw accuracy, decreased strand bias, lowered systematic error, improved homopolymer accuracy, increased total sequencing throughput, increased error-free read length, enhanced processivity, increased 100Q17 value, increased 200Q17 value, and the like. In some embodiments, the transferable (or homologous) amino acid mutation can include an amino acid mutation that decrease catalytic properties such as decreased read-length, decreased error-free read length, decreased processivity, decreased 100Q17value, decreased 200Q17 value, and the like. In some embodiments, a transferable (or homologous) amino acid mutation can include transferring one or more amino acid mutations to another polymerase within, or between, DNA polymerase families, such as DNA polymerase family A,DNA polymerase family B, or DNA polymerase family C. It will be readily apparent to the skilled artisan that a transferable (i.e., homologous) amino acid mutation, such as an amino acid substitution present in a first polymerase may be transferred to a corresponding amino acid position in a homologous polymerase. For example, sequence alignment of the first polymerase having the first amino acid substitution against a B family DNA polymerase, A family DNA polymerase, or C family DNA polymerase can result in the identification of the corresponding amino acid residue in the homologous A family, B family or C family DNA polymerase. Examples of B family DNA polymerase alignment are well known in the art and include for example Hopfner et al., Proc. Natl. Acad. Sci. USA (1999), 96: 3600-3605 and Kahler and Antranikian, Bacteriol., (2000), 182: 655-663, which are incorporated herein by reference in their entirety. Examples of A and C family DNA polymerase alignments are also well known in the art and include for example Ito and Braithwaite, Nucleic Acids Research, (1991), Vol. 19, 15: 4045-4057, and Braithwaite and Ito, Nucleic Acids Research, (1993), Vol. 21, 4: 787-802, are incorporated herein by reference in their entirety. In some embodiments, a transferable (or homologous) amino acid mutation can include transferring one or more amnio acid mutations to one or more polymerases within, or between, DNA polymerase families, such as across bacterial, viral, archaeal, eukaryotic or phage DNA polymerases.

In some embodiments, a modified polymerase according to the disclosure can include any polymerase having one or more amino acid mutations (such as a substitution, insertion, or deletion) that are homologous to one or more of the amino acid mutations disclosed herein. For example, the disclosure encompasses modified polymerases that include one or more amino acid mutations that are homologous to one or more amino acid mutations provided herein for Bst DNA polymerase (e.g., SEQ ID NO: 2, SEQ ID NO: 3, SEQ ID NO: 4, SEQ ID NO: 16, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37). In some embodiments, a modified polymerase according to the disclosure can include any polymerase having one or more amino acid mutations that are homologous to one or more amino acid mutations provided herein for Taq DNA polymerase (e.g., one or more homologous amino acid mutations that correspond to one or more amino acid mutations of SEQ ID NO: 15). In some embodiments, a modified polymerase according to the disclosure can include any polymerase having one or more amino acid mutations that are homologous to one or more amino acid mutations provided herein for the Klenow fragment of E. Coli DNA polymerase I (e.g., one or more homologous amino acid mutations that correspond to one or more amino acid mutations of SEQ ID NO: 18).

In some embodiments, the disclosure relates to a modified polymerase or any biologically active fragment of a polymerase having one or more amino acid mutations that are homologous to one or more amino acid mutations of Bst DNA polymerase (e.g., H46R; E446Q; and H572R, wherein the numbering is relative to the amino acid sequence of SEQ ID NO: 1). In some embodiments, the disclosure relates to a modified polymerase or any biologically active fragment of a polymerase having one or more amino acid mutations that are homologous to one or more amino acid mutations of Bst DNA polymerase (H473R and H528A, wherein the numbering is relative to the amino acid sequence of SEQ ID NO: 1). In some embodiments, the disclosure relates to a modified polymerase or any biologically active fragment of a polymerase that contains one or more amino acid mutations that are homologous to one or more amino acid mutations of Bst DNA polymerase (H273R; H281A; and Y477F, wherein the numbering is relative to the amino acid sequence of SEQ ID NO: 1).

In some embodiments, a modified polymerase or any biologically active fragment of a polymerase according to the disclosure can include any polymerase having one or more amino acid mutations that are homologous to one or more amino acid mutations for Bst DNA polymerase including, any one or more amino acid mutations selected from the group consisting of: H46R, C93R, E220K, N234R, Q238C, A263K, D264A, D264R, H273N, H273R, H281A, H281M, D423K, E446Q, H473R, Y477F, D480R, N485K, N487R, E493R, H528A, H528F, H528S, H528N, H528K, C550Q and H572R, wherein the numbering is relative to the amino acid sequence of SEQ ID NO: 1. In some embodiments, a modified polymerase or any biologically active fragment of a polymerase according to the disclosure can include any polymerase having one or more amino acid mutations that are homologous to one or more amino acid mutations for Bst DNA polymerase including, any one or more amino acid mutations selected from the group consisting of: N31R, N31K, D77K, D77H, D113N, D114R, D130A, D130H, D144M, D144K, L212A, E220K, N234R, N234K, V241K, V251K, D264Q, D264S, D264K, Y272R, H273R, L280R, H281A, E294S, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, E446Q, F448K, N457T, A462T, H473R, Y477F, D480R, D480F, D480H, D480A, D480S, D480N, D480Q, N485W, N485Y, N487H, N487W, N487F, N487I, V488R, E493Q, M495Q, H528A, V533I, H572R, W577Y and D579F, wherein the numbering is relative to the amino acid sequence of SEQ ID NO: 1. In some embodiments, a modified polymerase or any biologically active fragment of a polymerase according to the disclosure can include any polymerase having one or more amino acid mutations that are homologous to one or more amino acid mutations for Bst DNA polymerase including, any one or more amino acid mutations selected from the group consisting of: N31R, N31K, H46A, H46R, D77K, D77H, C93R, D113N, D114R, D130A, D130H, D144M, D144K, L212A, E220K, N234R, N234K, Q238C, V241K, V251K, D264Q, D264S, D264K, Y272R, H273A, H273R, L280R, H281A, H281R, E294S, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, E446Q, F448K, N457T, A462T, H473A, H473R, Y477F, D480R, D480F, D480H, D480A, D480S, D480N, D480Q, N485W, N485Y, N487H, N487W, N487F, N487I, V488R, E493Q, M495Q, H528A, H528R, V533I, C550Q, H572A, H572R, W577Y and D579F, wherein the numbering is relative of the amino acid sequence of SEQ ID NO: 1.

In some embodiments, a modified polymerase according to the disclosure can include any polymerase having one or more amino acid mutations that are homologous to one or more amino acid mutations for Bst DNA polymerase including, any one or more amino acid mutations selected from the group consisting of: H46A, H46R, C93R, Q238C, H273A, H273R, H281A, H281R, H281M, E446Q, H473A, H473R, Y477F, H528A, H528R, H528K, C550Q, H572A and H572R, as well as one or more amino acid substitutions selected from the group consisting of N31R, N31K, D77K, D77H, D113N, D114R, D130A, D130H, D144M, D144K, L212A, E220K, N234R, N234K, V241K, V251K, D264Q, D264S, D264K, Y272R, L280R, E294S, E294F, E294G, E294K, V299K, V299H, V299F, D303R, E325R, I331Q, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, F448K, N457T, A462T, D480R, D480F, D480H, D480A, D480S, D480N, D480Q, N485W, N485Y, N487H, N487W, N487F, N487I, V488R, E493Q, M495Q, V533I, W577Y and D579F, wherein the numbering is relative of the amino acid sequence of SEQ ID NO: 1. Optionally, the modified polymerase having one or more amino acid mutations homologous to one or more amino acid mutations of Bst DNA polymerase can further include at least one amino acid substitution that is homologous to an amino acid substitution in Bst DNA polymerase selected from the group consisting of: H46A, H46R, H273A, H273R, H281A, H281R, E446Q, H473A, H473R, Y477F, H528A, H528R, H572A, and H572R, wherein the numbering is relative to the amino acid sequence of SEQ ID NO: 1.

In some embodiments, a modified polymerase according to the disclosure can include any polymerase having one or more amino acid mutations that are homologous to one or more amino acid mutations for Bst DNA polymerase including, any one or more amino acid mutations selected from the group consisting of: H46A, H46R, H273A, H273R, H281A, H281R, E446Q, H473A, H473R, Y477F, H528A, H528R, H572A, and H572R, wherein the numbering is relative to the amino acid sequence of SEQ ID NO: 1.

In some embodiments, a modified polymerase according to the disclosure can include any polymerase having one or more amino acid mutations that are homologous to one or more amino acid mutations for Bst DNA polymerase including, any one or more amino acid mutations selected from the group consisting of: H46R, E446Q, H572R, and D775R, wherein the numbering is relative to the amino acid sequence of SEQ ID NO: 1.

In some embodiments, a modified polymerase or any biologically active fragment of a polymerase according to the disclosure can include any polymerase having at least one amino acid mutation that is homologous to amino acid mutation D775R for Bst DNA polymerase, wherein the numbering is relative to the amino acid sequence of SEQ ID NO: 16.

In some embodiments, a modified polymerase or any biologically active fragment of a polymerase according to the disclosure can include any polymerase having one or more amino acid mutations that are homologous to one or more amino acid mutations for Bst DNA polymerase including, any one or more amino acid mutations selected from the group consisting of: H341R, C388R, E515K, Q533C, A558K, D559A, D559R, H568R, H568N, H576A, H576M, D718K, E741Q, H768R, Y772F, D775R, N780K, E788R, H823A, H823S, H823F, C845Q and H867R, and N529R wherein the numbering is relative to the amino acid sequence of SEQ ID NO: 16.

In some embodiments, a modified polymerase or any biologically active fragment of a polymerase according to the disclosure can include any polymerase having one or more amino acid mutations that are homologous to one or more amino acid mutations for Bst DNA polymerase including, any one or more amino acid mutations selected from the group consisting of: N326R, N326K, D372K, D372H, D408N, D409R, D425A, D425H, D439M, D439K, L507A, E515K, N529R, N529K, V536K, V546K, D559Q, D559S, Y567R, L575R, E589S, E589F, E589G, V594K, V594H, V594F, D598R, 1626Q, L630T, E631P, 1649W, 1649F, 1665A, Q704R, G711K, V713M, V713I, G715K, D718S, D718K, D718N, D718R, D718T, D718G, D718I, D718K, G720R, Q723W, N724R, N724K, F743K, N752T, A757T, D775R, D775F, D775H, D775A, D775S, D775N, D775Q, N780W, N780Y, N782H, N782W, N782F, N782I, E782Q, V783R, E788Q, M790Q, V828I, W872Y and D874F, wherein the numbering is relative of the amino acid sequence of SEQ ID NO: 16.

In some embodiments, a modified polymerase or any biologically active fragment of a polymerase according to the disclosure can include any polymerase having one or more amino acid mutations that are homologous to one or more amino acid mutations for Bst DNA polymerase including, any one or more amino acid mutations selected from the group consisting of: N326R, N326K, H341R, D372K, D372H, C388R, D408N, D409R, D425A, D425H, D439M, D439K, L507A, E515K, N529R, N529K, V536K, V546K, Q533C, D559Q, D559S, Y567R, H568R, L575R, H576A, E589S, E589F, E589G, V594K, V594H, V594F, D598R, 1626Q, L630T, E631P, 1649W, 1649F, 1665A, Q704R, G711K, V713M, V713I, G715K, D718S, D718K, D718N, D718R, D718T, D718G, D718I, D718K, G720R, Q723W, N724R, N724K, E741Q, F743K, N752T, A757T, H768R, Y772F, D775R, D775F, D775H, D775A, D775S, D775N, D775Q, N780W, N780Y, N782H, N782W, N782F, N782I, E782Q, V783R, E788Q, M790Q, H823A, V828I, C845Q, H867R, W872Y and D874F, wherein the numbering is relative of the amino acid sequence of SEQ ID NO: 16.

In some embodiments, a modified polymerase or any biologically active fragment of a polymerase according to the disclosure can include any polymerase having one or more amino acid mutations that are homologous to one or more amino acid mutations for Bst DNA polymerase including, any one or more amino acid mutations selected from the group consisting of: H341A, H341R, C388R, Q533C, H568A, H568R, H576A, H576R, E741Q, H768A, H768R, Y772F, H823A, H823R, C845Q, H867A and H867R, as well as one or more amino acid substitutions selected from the group consisting of: N326R, N326K, D372K, D372H, D408N, D409R, D425A, D425H, D439M, D439K, L507A, E515K, N529R, N529K, V536K, V546K, D559Q, D559S, D559K, Y567R, L575R, E589S, E589F, E589G, E589K, V594K, V594H, V594F, D598R, 1626Q, L630T, E631P, 1649W, 1649F, 1665A, Q704R, G711K, V713M, V713I, G715K, D718S, D718K, D718N, D718R, D718T, D718G, D718I, D718K, G720R, Q723W, N724R, N724K, F743K, N752T, A757T, D775R, D775F, D775H, D775A, D775S, D775N, D775Q, N780W, N780Y, N782H, N782W, N782F, N782I, E782Q, V783R, E788Q, M790Q, V828I, W872Y and D874F, wherein the numbering is relative of the amino acid sequence of SEQ ID NO: 16.

In some embodiments, a modified polymerase or any biologically active fragment of a polymerase according to the disclosure can include any polymerase having one or more amino acid mutations that are homologous to one or more amino acid mutations for Bst DNA polymerase including, any one or more amino acid mutations selected from the group consisting of: H341A, H341R, C388R, Q533C, H568A, H568R, H576A, H576R, E741Q, H768A, H768R, Y772F, H823A, H823R, C845Q, H867A and H867R, wherein the numbering is relative to the amino acid sequence of SEQ ID NO: 16.

In some embodiments, a modified polymerase or any biologically active fragment of a polymerase according to the disclosure can include any polymerase having one or more amino acid mutations that are homologous to one or more amino acid mutations for Bst DNA polymerase including, any one or more amino acid mutations selected from the group consisting of: H341A, H341R, H568A, H568R, H576A, H576R, E741Q, H768A, H768R, Y772F, H823A, H823R, H867A and H867R, wherein the numbering is relative to the amino acid sequence of SEQ ID NO: 16.

In some embodiments, a modified polymerase or any biologically active fragment of a polymerase according to the disclosure can include any polymerase having one or more amino acid mutations that are homologous to one or more amino acid mutations for Bst DNA polymerase including, any one or more amino acid mutations selected from the group consisting of: N326R, N326K, D372K, D372H, D408N, D409R, D425A, D425H, D439M, D439K, L507A, E515K, N529R, N529K, V536K, V546K, D559Q, D559S, D559K, Y567R, L575R, E589S, E589F, E589G, E589K, V594K, V594H, V594F, D598R, 1626Q, L630T, E631P, 1649W, 1649F, 1665A, Q704R, G711K, V713M, V713I, G715K, D718S, D718K, D718N, D718R, D718T, D718G, D718I, D718K, G720R, Q723W, N724R, N724K, F743K, N752T, A757T, D775R, D775F, D775H, D775A, D775S, D775N, D775Q, N780W, N780Y, N782H, N782W, N782F, N782I, E782Q, V783R, E788Q, M790Q, V828I, W872Y and D874F, wherein the numbering is relative of the amino acid sequence of SEQ ID NO: 16. Optionally, the modified polymerase or any biologically active fragment of a polymerase having one or more amino acid mutations that are homologous to one or more amino acid mutations for Bst DNA polymerase can further include at least one amino acid substitution selected from the group consisting of: H341A, H341R, H568A, H568R, H576A, H576R, H576M, E741Q, H768A, H768R, Y772F, H823A, H823R, H823K, H867A and H867R, wherein the numbering is relative to the amino acid sequence of SEQ ID NO: 16. In some embodiments, the modified polymerase or any biologically active fragment of a polymerase having one or more amino acid mutations that are homologous to one or more amino acid mutations for Bst DNA polymerase includes any two, three, four, five or more amino acid substitutions selected from each of these two groups of amino acid substitutions.

In some embodiments, a modified polymerase or any biologically active fragment of a polymerase according to the disclosure can include any polymerase having one or more amino acid mutations that are homologous to one or more amino acid mutations of Taq DNA polymerase including, any one or more amino acid mutations selected from the group consisting of: E471K, N485R, R492K, D513K, A675K, D732R, S739W, V740R and E745Q, wherein the numbering is relative to the amino acid sequence of SEQ ID NO: 15. In some embodiments, the modified polymerase or any biologically active fragment of a polymerase having one or more amino acid mutations that are homologous to one or more amino acid mutations for Taq DNA polymerase includes any two, three, four, five, or more amino acid substitutions.

In some embodiments, a modified polymerase or any biologically active fragment of a polymerase according to the disclosure can include any polymerase having one or more amino acid mutations that are homologous to one or more amino acid mutations of Klenow fragment DNA polymerase I including, any one or more amino acid mutations selected from the group consisting of: E245K, S259K, T266K, E290K, A448K, D505R, A512W, and E518Q, wherein the numbering is relative to the amino acid sequence of SEQ ID NO: 18. In some embodiments, the modified polymerase or any biologically active fragment of a polymerase having one or more amino acid mutations that are homologous to one or more amino acid mutations for Klenow fragment DNA polymerase I includes any two, three, four, five, or more amino acid substitutions.

In some embodiments, a modified polymerase or any biologically active fragment of a polymerase having one or more amino acid mutations that are homologous to an amino acid mutation disclosed herein for Bst DNA polymerase, Taq DNA polymerase, or Klenow fragment DNA polymerase I from *E. coli* can optionally include at least one amino acid substitution designed to replace a non-cysteine amino acid residue with a cysteine residue. For example, Bst DNA polymerase (e.g., SEQ ID NO: 16), can optionally include one or more amino acid substitutions selected from the group consisting of: C388R, Q533C and C845Q, that can optionally be included in any modified polymerase having one or more homologous amino acid substitutions.

In some embodiments, a modified polymerase or any biologically active fragment of a polymerase having one or more amino acid mutations homologous to one or more amino acid mutations of Bst DNA polymerase, Taq DNA polymerase or Klenow fragment of *E. coli* DNA polymerase I can further include a deletion of the methionine residue at position 1, or a substitution at position 1 with any other amino acid residue, wherein the numbering is relative to the amino acid sequences of SEQ ID NO: 1, SEQ ID NO:2, SEQ ID NO: 15, SEQ ID NO: 16, and SEQ ID NO: 18.

In some embodiments, a modified polymerase or any biologically active fragment of a polymerase having one or more amino acid mutations homologous to one or more amino acid mutations of Bst DNA polymerase, Taq DNA polymerase, or Klenow fragment DNA polymerase I can exhibit a change in any one or more parameters selected from the group consisting of: buffering capacity, dissociation time constant, off-rate, 100Q17 value and 200Q17 value, relative to the reference polymerase. Optionally, the change is observed by comparing the performance of a reference and the modified polymerase in an ion-based sequencing reaction. Optionally, the reference polymerase, the modified polymerase, or both the reference and modified polymerases can further include one or more amino acid mutations that decrease or eliminate exonuclease activity.

In some embodiments, the disclosure relates generally to nucleotide sequences encoding proteins comprising any of the specific amino acid sequences disclosed herein. For example, in some embodiments, the disclosure relates generally to nucleotide sequences encoding proteins having, or comprising, the amino acid sequences of SEQ ID NO: 1, SEQ ID NO: 2, SEQ ID NO: 3, SEQ ID NO: 4, SEQ ID NO: 15, SEQ ID NO: 18, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO:

36 or SEQ ID NO: 37 or any other of the specific polymerases (including any modified and reference polymerases) disclosed herein. In some embodiments, the disclosure relates generally to any nucleotide sequence encoding an amino acid sequence that is at least 80%, at least 85%, at least 90%, at least 91%, at least 92%, at least 93%, at least 94%, at least 95%, at least 96%, at least 97%, at least 98%, or at least 99% identical to the amino acid sequence of SEQ ID NO: 1, SEQ ID NO: 2, SEQ ID NO: 3, SEQ ID NO: 4, SEQ ID NO: 15, SEQ ID NO: 18, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36 or SEQ ID NO: 37. The person of ordinary skill will be readily able to determine nucleotide sequences that encode any of the amino acid sequences of the disclosure based on the known correspondence between the nucleotide sequence and a corresponding protein sequence.

In some embodiments, the disclosure relates to a nucleic acid sequence encoding a modified polymerase that is an isolated variant of a Bst DNA polymerase having or comprising the amino acid sequence of SEQ ID NO: 2, wherein the variant comprises an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 2.

For example, the disclosure relates generally to a nucleic acid sequence having, or comprising the nucleic acid sequence of SEQ ID NO: 17:

SEQ ID NO: 17 includes a nucleic acid sequence that encodes an exemplary modified polymerase that has the amino acid sequence of SEQ ID NO: 2 and further includes the mutation D775R. It be readily apparent to the skilled artisan how to modify the nucleic acid sequence of SEQ ID NO: 17 to generate nucleic acid sequences encoding any of the other exemplary reference or modified polymerases disclosed herein.

In some embodiments, the disclosure relates to a nucleic acid sequence that is at least 50%, 60%, 70%, 80%, 90%, 95% or 99% identical to the nucleic acid sequence of SEQ ID NO: 17. In some embodiments, the nucleic acid sequence encodes a polymerase having the amino acid sequence of SEQ ID NO: 2 and further including any one or more mutations selected from the group consisting of: N31R, N31K, H46R, D77K, D77H, C93R, D113N, D114R, D130A, D130H, D144M, D144K, L212A, E220K, N234R, N234K, Q238C, V241K, V251K, D264Q, D264S, Y272R, H273R, L280R, H281A, H281M, E294S, E294F, E294G, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, E446Q, F448K, N457T, A462T, H473R, Y477F, D480R, D480F, D480H, D480A, D480S, D480N, D480Q, N485W, N485Y, N487H, N487W, N487F, N487I, V488R, E493Q, M495Q, H528A, H528K, V533I, C550Q, H572R, W577Y and D579F, wherein the numbering is relative of the amino acid sequence of SEQ ID NO: 2.

In some embodiments, the nucleic acid sequence encodes a polymerase having the amino acid sequence of SEQ ID NO: 16 and further including any one or more mutations selected from the group consisting of: N326R, N326K, H341R, D372K, D372H, C388R, D408N, D409R, D425A, D425H, D439M, D439K, L507A, E515K, N529R, N529K, V536K, V546K, Q533C, D559Q, D559S, Y567R, H568R, L575R, H576A, H576M, E589S, E589F, E589G, V594K, V594H, V594F, D598R, I626Q, L630T, E631P, I649W, 1649F, 1665A, Q704R, G711K, V713M, V7131, G715K, D718S, D718K, D718N, D718R, D718T, D718G, D7181, D718K, G720R, Q723W, N724R, N724K, E741Q, F743K, N752T, A757T, H768R, Y772F, D775R, D775F, D775H, D775A, D775S, D775N, D775Q, N780W, N780Y, N782H, N782W, N782F, N7821, E782Q, V783R, E788Q, M790Q, H823A, H823K, V8281, C845Q, H867R, W872Y and D874F, wherein the numbering is relative of the amino acid sequence of SEQ ID NO: 16.

In some embodiments, the nucleic acid sequence encodes a polymerase having the amino acid sequence of SEQ ID NO: 15 and further including any one or more mutations selected from the group consisting of: E471K, N485R, R492K, D513K, A675K, D732R, S739W, V740R and E745Q, wherein the numbering is relative of the amino acid sequence of SEQ ID NO: 15.

In some embodiments, the nucleic acid sequence encodes a polymerase having the amino acid sequence of SEQ ID NO: 18 and further including any one or more mutations selected from the group consisting of: E245K, S259R, T266K, E290K, A448K, D505R, A512W, R513R and E518Q, wherein the numbering is relative of the amino acid sequence of SEQ ID NO: 18.

In some embodiments, the nucleotide sequence can be designed employing principles of codon preference to increase the levels of protein expression in a given host organism.

In some embodiments, in order to slow the rate of template dissociation from the polymerase (and increase its processivity), the modified polymerase or any biologically active fragment of a polymerase can include one or more amino acid mutations that cause the modified to dissociate more slowly from the nucleic acid template. Such mutations can have the additional effect of increasing the read length (or the error-free read length) of the modified polymerase relative to its unmodified counterpart.

In some embodiments, the modified polymerase or any biologically active fragment of a polymerase can include one or more introduced cysteines. Such introduced cysteines can serve as sites for attachment of the polymerase to another moiety, substrate, or surface. In some embodiments, the cysteine is introduced at least one position selected from the group consisting of: □238 and Q248, wherein the numbering is relative to the amino acid sequence of SEQ ID NO: 2. For example, the polymerase can include one or both of the following amino acid substitutions: Q238C and Q248C.

In some embodiments, the modified polymerase or any biologically active fragment of a polymerase has or includes the amino acid sequence of SEQ ID NO: 2 and further includes replacement of the cysteine residues C93 and C550 with other amino acid residues that do not include a sulfhydryl side chain. For example, the polymerase can include one or both of the following amino acid substitutions: C93R and C550Q.

In some embodiments, the modified polymerase or any biologically active fragment of a polymerase has (or comprises) the amino acid sequence of SEQ ID NO: 2, and further includes the amino acid substitutions C93R, C550Q and Q238C, wherein the numbering is relative to the amino acid sequence of SEQ ID NO: 2. In some embodiments, the introduced cysteine residue (Q238C) is linked to the bridging moiety, either directly or through a linking moiety. The bridging moiety can include an avidin. The linking moiety (when present) can include a biotin. In some embodiments, the introduced cysteine residue at position 238 can be biotinylated.

In some embodiments, the modified polymerase or any biologically active fragment of a polymerase has (or comprises) the amino acid sequence of SEQ ID NO: 2, and further includes the amino acid substitutions C93R, C550Q and Q248C, wherein the numbering is relative to the amino acid sequence of SEQ ID NO: 2. In some embodiments, the introduced cysteine residue (Q248C) is linked to the bridging moiety, either directly or through a linking moiety. The bridging moiety can include an avidin. The linking moiety (when present) can include a biotin. In some embodiments, the introduced cysteine residue at position 248 can be biotinylated.

In some embodiments, the modified polymerase or any biologically active fragment of a polymerase has or includes the amino acid sequence of SEQ ID NO: 2, and further includes the mutations C93R and C550Q, as well as the cysteine replacement substitution Q238C.

In some embodiments, the modified polymerase or any biologically active fragment of a polymerase has or includes the amino acid sequence of SEQ ID NO: 2, and further includes the mutations C93R and C550Q, as well as the cysteine replacement substitution Q248C.

In some embodiments, the modified polymerase or any biologically active fragment of a polymerase can include one or more biotin moieties. As used herein, the terms "biotin" and "biotin moiety" and their variants comprise biotin (cis-hexahydro-2-oxo-1H-thieno[3,4]imidazole-4-pentanoic acid) and any derivatives and analogs thereof, including biotin-like compounds. Such compounds include, for example, biotin-e-N-lysine, biocytin hydrazide, amino or sulfhydryl derivatives of 2-iminobiotin and biotinyl-ε-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin, and the like, as well as any biotin variants that can specifically bind to an avidin moiety. The terms "avidin" and "avidin moiety" and their variants, as used herein, comprise the native egg-white glycoprotein avidin, as well as any derivatives, analogs and other non-native forms of avidin, which can specifically bind to biotin moieties. In some embodiments, the avidin moiety can comprise deglycosylated forms of avidin, bacterial streptavidins produced by selected strains of *Streptomyces*, e.g., *Streptomyces avidinii*, to truncated streptavidins, and to recombinant avidin and streptavidin as well as to derivatives of native, deglycosylated and recombinant avidin and of native, recombinant and truncated streptavidin, for example, N-acyl avidins, e.g., N-acetyl, N-phthalyl and N-succinyl avidin, and the commercial products ExtrAvidin®, Captavidin®, Neutravidin® and Neutralite Avidin®. All forms of avidin-type molecules, including both native and recombinant avidin and streptavidin as well as derivatized molecules, e.g. nonglycosylated avidins, N-acyl avidins and truncated streptavidins, are encompassed within the terms "avidin" and "avidin moiety". Typically, but not necessarily, avidin exists as a tetrameric protein, wherein each of the four tetramers is capable of binding at least one biotin moiety. As used herein, the term "biotin-avidin bond" and its variants refers to a specific linkage formed between a biotin moiety and an avidin moiety. Typically, a biotin moiety can bind with high affinity to an avidin moiety, with a dissociation constant Kd typically in the order of 10-14 to 10-15 mol/L. Typically, such binding occurs via non-covalent interactions.

In some embodiments, the modified polymerase or any biologically active fragment of a polymerase can include one or more modified or substituted amino acids relative to a reference polymerase, and can further include a biotin moiety that is linked to at least one of the one or more modified or substituted amino acids. The biotin moiety can be linked to the modified polymerase using any suitable linking method. In some embodiments, the modified polymerase includes one or more cysteine replacement substitutions, and the linking moiety includes a biotin moiety that is linked to at least one of the one or more cysteine replacement substitutions.

In some embodiments, the modified polymerase is a biotinylated polymerase. The term "biotinylated" and its variants, as used herein, refer to any covalent or non-covalent adduct of biotin with other moieties such as biomolecules, e.g., proteins, nucleic acids (including DNA, RNA, DNA/RNA chimeric molecules, nucleic acid analogs and peptide nucleic acids), proteins (including enzymes, peptides and antibodies), carbohydrates, lipids, etc.

In some embodiments, the disclosure also relates generally to compositions (as well as related methods, kits and apparatuses) comprising a modified polymerase including at least one amino acid modification relative to a reference polymerase, wherein the modified polymerase has a slower rate of dissociation from a nucleic acid template relative to the reference polymerase. In some embodiments, the rate of dissociation can be modified such that the rate of dissociation increases binding affinity, for example in the presence of neutral osmolytes such as betaine, trimethylamine N-oxide, trehalose, sucrose, ethylene glycols, and the like.

As used herein, the terms "dissociation rate" or "off-rate" refer to the rate of dissociation of a given polymerase from a given template nucleic acid. The dissociation rate (off-rate) can vary with reaction conditions including temperature, salt concentrations, relative concentrations of polymerase and template, and the like. In some embodiments, the dissociation rate can be estimated by measuring the decay in total amount of polymerase bound to a template nucleic acid under given reaction conditions. Such assays can optionally be performed using conditions where re-binding of the polymerase to the template after dissociation of the polymerase from the template is prevented. For example, in a typical dissociation binding experiment to measure the "off rate" for polymerase dissociating from the nucleic acid template, the polymerase and nucleic acid template are initially allowed to bind, optionally to equilibrium. Optionally, the polymerase can be labeled using any suitable label (e.g., radioactive or fluorescent labels). At this point, further binding of the polymerase to template can optionally be blocked to simplify measurement of the rate of dissociation from the template. Such blocking can be performed using any suitable method. For example, in embodiments where the template is fixed to a surface and the polymerase is labeled, blocking can be achieved by (1) removing the buffer including labeled polymerase and replacing with buffer that does not include labeled polymerase, or (2) adding to the reaction mixture a very high concentration of unlabeled polymerase; or (3) diluting the reaction mixture by a large factor (e.g., at least 20- or 100-fold), particularly when the initial concentration of labeled polymerase is low. Following such blocking, the total amount of polymerase bound to template can be measured at various times after such blocking to determine how rapidly the polymerase dissociates from the template. The amount of polymerase bound to template can be mapped (Y axis) against time (X axis). In some embodiments, the resulting curve approximates a single exponential decay curve. FIG. 1 depicts a dissociation rate curve from a typical experiment.

In some embodiments, analysis of binding experiments can be based on a simple model derived from the law of mass action. This model assumes that binding is reversible and allows calculation of koff, the dissociation rate constant. (In the following analysis, the polymerase and nucleic acid template are referred to as "ligand" and "receptor"):

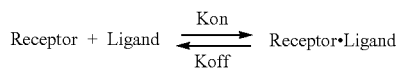

$$\text{Receptor} + \text{Ligand} \underset{\text{Koff}}{\overset{\text{Kon}}{\rightleftharpoons}} \text{Receptor·Ligand}$$

In some embodiments, binding occurs when the polymerase and template nucleic acid collide due to diffusion, and when the collision has the correct orientation and enough energy. The rate of association is:

Number of binding events per unit of time=[Ligand]·[Receptor]·$k$on.

Once binding has occurred, the ligand and receptor can remain bound together for a random amount of time. The probability of dissociation is the same at every instant of time.

The rate of dissociation is:

Number of dissociation events per unit time=[ligand·receptor]·$k$off.

Equilibrium is reached when the rate at which new ligand☐receptor complexes are formed equals the rate at which the ligand☐receptor complexes dissociate. At equilibrium:

[Ligand]·[Receptor]·$k_{on}$=[Ligand·Receptor]·$k_{off}$

This equation can be rearranged to define the equilibrium dissociation constant Kd.

$$\frac{[\text{Ligand}] \cdot [\text{Receptor}]}{[\text{Ligand} \cdot \text{Receptor}]} = \frac{k_{off}}{k_{on}} = K_d$$

If [Ligand] is set as equal to Kd in the equation above, the Kd terms cancel out, and

[Receptor]/[Ligand·Receptor]=1, so [Receptor] equals [Ligand·Receptor]. Since all the receptors are either free or bound to ligand, this means that half the receptors are free and half are bound to ligand. In other words, when the concentration of ligand equals the Kd, half the receptors will be occupied at equilibrium. If the receptors have a high affinity for the ligand, the Kd will be low, as it will take a low concentration of ligand to bind half the receptors.

In such a model, Kd, the equilibrium dissociation constant, is different from koff, the dissociation rate constant (also referred to herein as the "dissociation time constant").

In one exemplary assay, as described in the Examples herein, the dissociation time constant of a given polymerase can be measured by incubating the polymerase with a labeled oligonucleotide including a fluorescent label (referred to herein as "oligonucleotide 221") under defined conditions. When the oligonucleotide is not bound by polymerase, the fluorescence of the fluorescent label on the oligonucleotide is quenched; binding of the polymerase to the oligonucleotide results in de-quencing of the oligonucleotide label and a resulting increase in fluorescence. Blocking is initiated by adding an unlabeled competitor oligonucleotide to the reaction mixture; as polymerase dissociates from the fluorescently labeled oligonucleotide 221, the competitor oligonucleotide hybridizes to oligonucleotide 221 and prevents further binding of the polymerase. Fluorescence is monitored over time. Fluorescence of the reaction mixture is measured at various time points following addition of the competitor oligonucleotide. The observed fluorescence (in RFU or relative fluorescence units) is graphed (Y axis) against time (X axis). To compare the dissociation rates of two or more different enzymes (e.g., a reference and a modified polymerase), each enzyme can be employed in a parallel and separate reaction in which the fluorescence of each reaction mixture is measured at various time points, following which the dissociation rates for each enzyme can be calculated using any suitable method, and compared. In the Examples provided herein, the dissociation rates are calculated according to the following formula:

$Y=(Y0-\text{Plateau})*\exp^{(-K*X)}+\text{Plateau}$

Where:
Y0 is the Y value when X (time) is zero. It is expressed in the same units as Y,
Plateau is the Y value at infinite times, expressed in the same units as Y.
K is the rate constant, expressed in reciprocal of the X axis time units. If X is in minutes, then K is expressed in inverse minutes.
Tau is the time constant, expressed in the same units as the X axis. It is computed as the reciprocal of K.
Half-life is in the time units of the X axis. It is computed as ln(2)/K.
Span, i.e., (Y0–Plateau), is the difference between Y0 and Plateau, expressed in the same units as your Y values.

Figure 2:
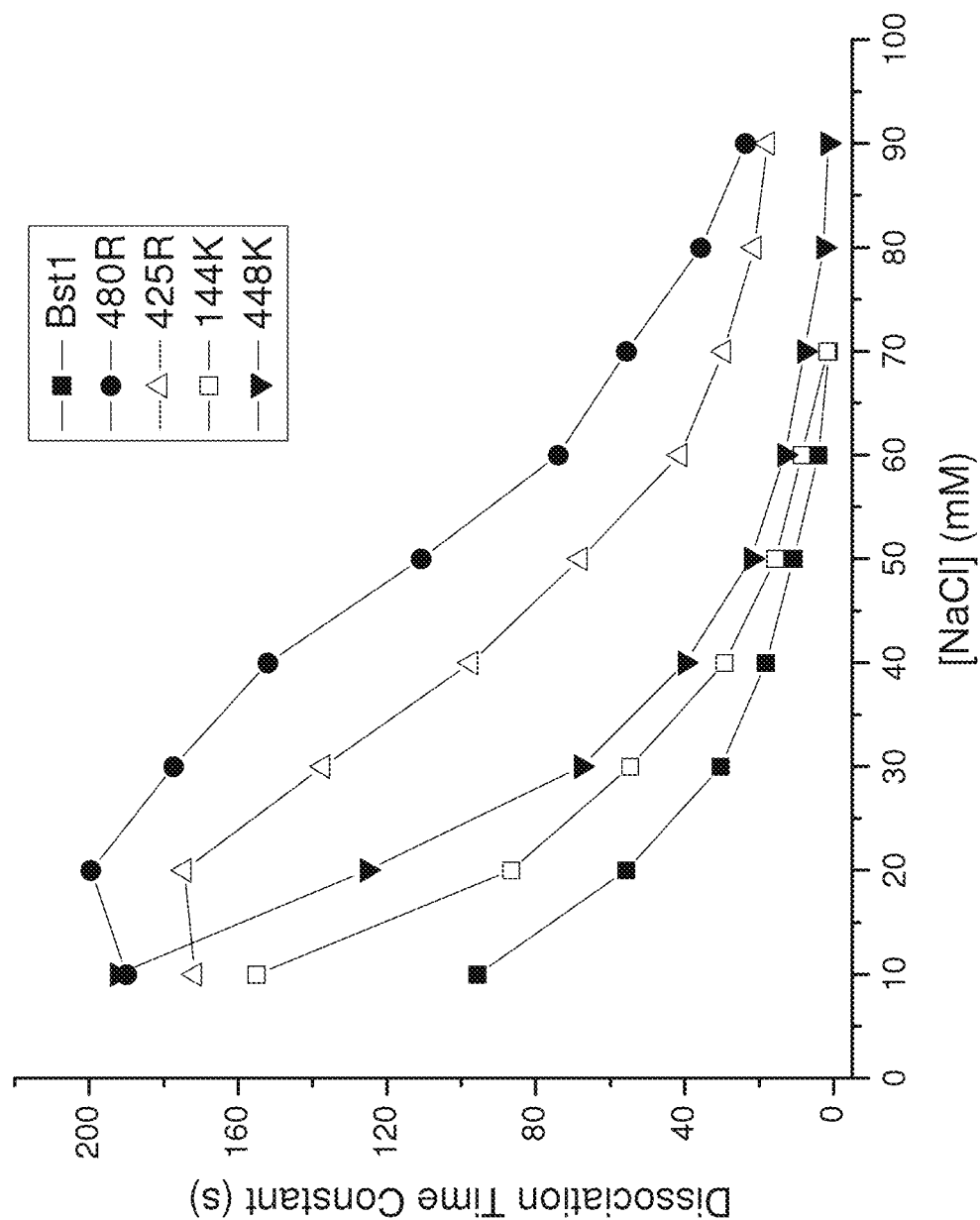
FIG. 2 shows a graph outlining an exemplary dissociation assay performed according to the disclosure.
Figure 6:
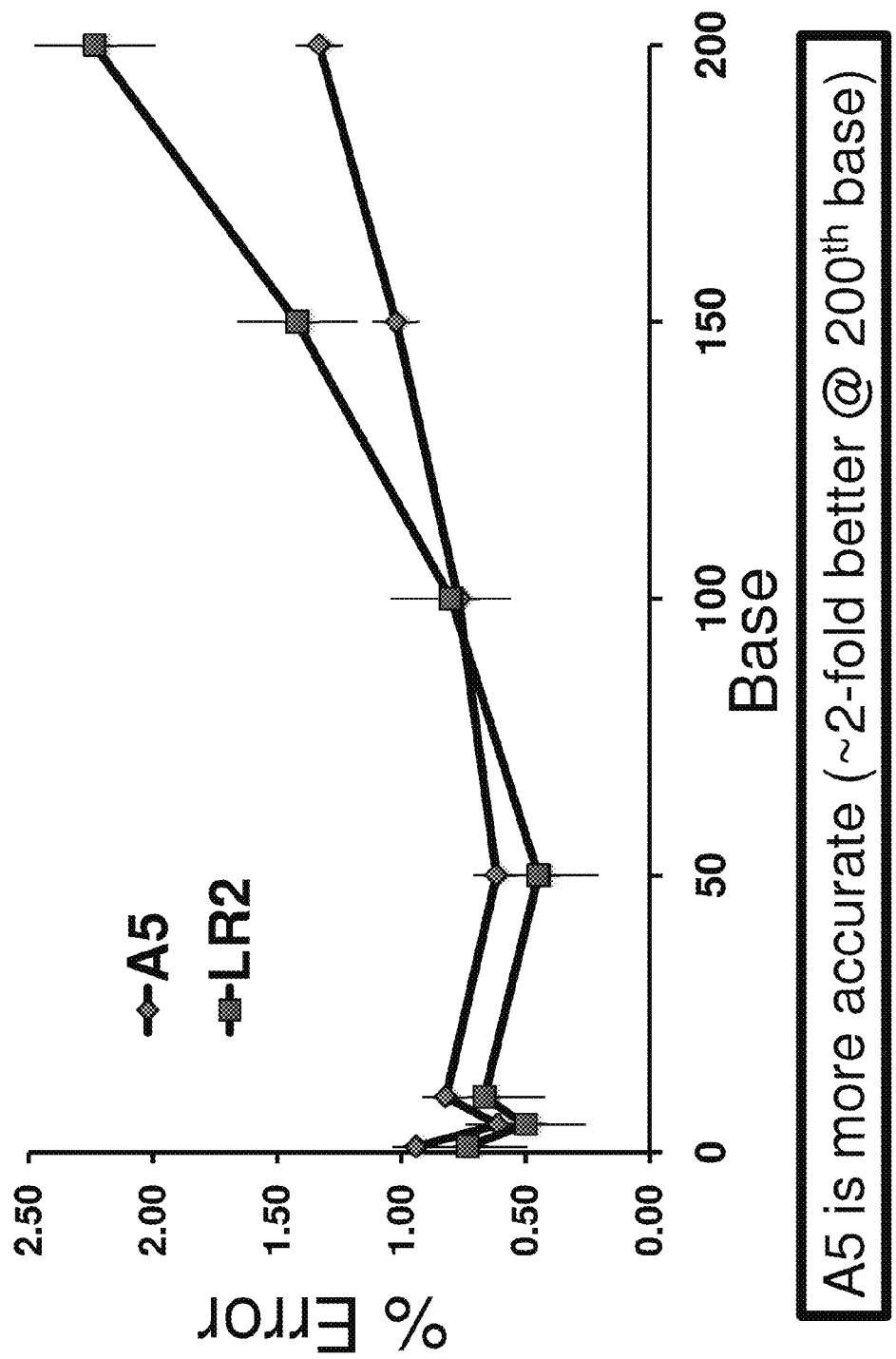
FIG. 6 shows a graph providing exemplary error rate data as measured over base length obtained using exemplary modified polymerases according to the disclosure.
Figure 7:
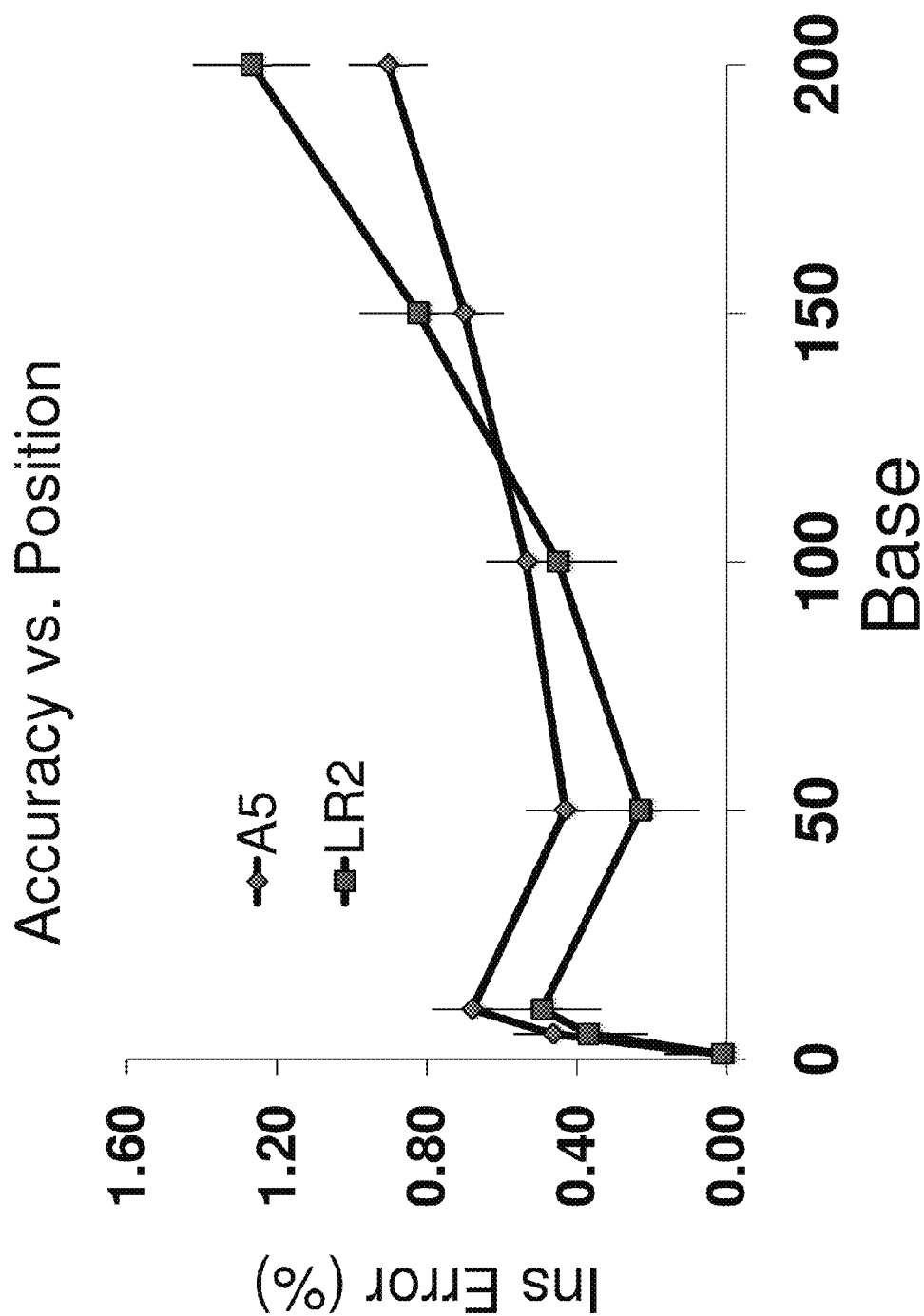
FIG. 7 shows a graph providing exemplary error rate data as measured over base length obtained using exemplary modified polymerases according to the disclosure.

FIG. 2 depicts the results of an exemplary assay performed as described in the Examples, where the dissociation time constants for various exemplary Bst mutants are measured at varying salt concentrations and compared.

In some embodiments, the disclosure relates generally to a method for incorporating at least one nucleotide into a primer, comprising: contacting a nucleic acid complex including a template nucleic acid with primer and a modified polymerase in the presence of one or more nucleotides, and incorporating at least one of the one or more nucleotides into the primer in a template-dependent fashion using said modified polymerase.

Methods for nucleotide incorporation are well known in the art and typically comprise use of a polymerase reaction mixture in which the polymerase is contacted with the template nucleic acid under nucleotide incorporation conditions. When the nucleotide incorporation reaction comprises polymerization of nucleotides onto the end of a primer, the process is typically referred to as "primer extension." Typically but not necessarily such nucleotide incorporation occurs in a template-dependent fashion. Primer extension and other nucleotide incorporation assays are typically performed by contacting the template nucleic acid with a polymerase in the presence of nucleotides in an aqueous solution under nucleotide incorporation conditions. In some embodiments, the nucleotide incorporation reaction can include a primer, which can optionally be hybridized to the template to form a primer-template duplex. Typical nucleotide incorporation conditions are achieved once the template, polymerase, nucleotides and optionally primer are mixed with each other in a suitable aqueous formulation, thereby forming a nucleotide incorporation reaction mixture (or primer extension mixture). The aqueous formulation can optionally include divalent cations and/or salts, particularly $Mg^{++}$ and/or $Ca^{++}$ ions. The aqueous formulation can optionally include divalent anions and/or salts, particularly $SO_4^{2-}$. Typical nucleotide incorporation conditions have included well known parameters for time, temperature, pH, reagents, buffers, reagents, salts, co-factors, nucleotides, target DNA, primer DNA, enzymes such as nucleic acid-dependent polymerase, amounts and/or ratios of the components in the reactions, and the like. The reagents or buffers can include a source of monovalent ions, such as KCl, K-acetate, $NH_4$-acetate, K-glutamate, $NH_4Cl$, or ammonium sulfate. The reagents or buffers can include a source of divalent ions, such as $Mg^{2+}$ and/or $Mn^{2+}$, $MgCl_2$, or Mg-acetate. In some embodiments, the reagents or buffers can include a source of detergent such as Triton and/or Tween. Most polymerases exhibit some levels of nucleotide incorporation activity over pH range of about 5.0 to about 9.5, more typically between about pH 7 and about pH 9, sometimes between about pH 6 to about pH 8, and sometimes between 7 and 8. The buffer can include chelating agents such as EDTA and EGTA, and the like. Although in some embodiments, nucleotide incorporation reactions may include buffering agents, such as Tris, Tricine, HEPES, MOPS, ACES, or MES, which can provide a pH range of about 5.0 to about 9.5, such buffering agents can optionally be reduced or eliminated when performing ion-based reactions requiring detection of ion byproducts. Methods of performing nucleic acid synthesis are well known and extensively practiced in the art and references teaching a wide range of nucleic acid synthesis techniques are readily available. Some exemplary teachings regarding the performance of nucleic acid synthesis (including, for example, template-dependent nucleotide incorporation, as well as primer extension methods) can be found, for example, in Kim et al., Nature 376: 612-616 (2002); Ichida et al., Nucleic Acids Res. 33: 5214-5222 (2005); Pandey et al., European Journal of Biochemistry, 214:59-65 (1993); Blanco et al., J. Biol. Chem. 268: 16763-16770 (1993); U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617; U.S. patent application Ser. No. 12/748,359, now published as U.S. Patent Publication No. 20110014612. Given the ample teaching of primer extension and other nucleotide incorporation reactions in the art, suitable reaction conditions for using the modified polymerases of the disclosure to perform nucleotide incorporation will be readily apparent to the skilled artisan.

In some embodiments, the disclosure relates generally to reagents (e.g., buffer compositions) and kits useful for performance of nucleotide polymerization reactions using modified polymerases, including any of the exemplary modified polymerases described here. The nucleotide polymerization reactions can include without limitation nucleotide incorporation reactions (including both template-dependent and template-independent nucleotide incorporation reactions) as well as primer extension reactions). In some embodiments, the buffer composition can include any one or more of the following: a monovalent metal salt, a divalent metal salt, a divalent anion, and a detergent. For example, the buffer composition can include a potassium or sodium salt. In some embodiments, the buffer composition can include a manganese or magnesium salt. In some embodiments, the buffer composition can include a sulfate such as potassium sulfate and/or magnesium sulfate. In some embodiments, the buffer composition can include a detergent selected from the group consisting of Triton and Tween.

In some embodiments, the buffer composition can include at least one potassium salt, at least one manganese salt, and Triton X-100 (Pierce Biochemicals). The salt can optionally be a chloride salt or a sulfate salt.

In some embodiments, the buffer composition can include at least one potassium salt, at least one magnesium salt, and Triton X-100 (Pierce Biochemicals). The salt can optionally be a chloride salt or a sulfate salt.

In some embodiments, the buffer composition has a pH of about 7.3 to about 8.0, typically about 7.4 to about 7.9.

In some embodiments, the buffer composition includes magnesium or manganese salt at a concentration of between 1 mM and 20 mM, particularly 6-15 mM.

In some embodiments, the buffer composition includes a sulfate at a concentration of between 1 mM and 100 mM, particularly 5-50 mM.

In some embodiments, the buffer composition includes a detergent (e.g., Triton X-100 or Tween-20) at a concentration of between 0.001% to 1%, typically between 0.0025-0.0125%.

In some embodiments, the disclosed modified polymerase compositions, (as well as related methods, systems, apparatuses and kits) can be used to obtain sequence information from a nucleic acid molecule. Many methods of obtaining sequence information from a nucleic acid molecule are known in the art, and it will be readily appreciated that all such methods are within the scope of the present disclosure. Suitable methods of sequencing using the disclosed modified polymerases include without limitation: Sanger sequencing, ligation-based sequencing (also known as sequencing by hybridization) and sequencing by synthesis. Sequencing-by-synthesis methods typically involve template-dependent nucleic acid synthesis (e.g., using a primer that is hybridized to a template nucleic acid or a self-priming template, as will be appreciated by those of ordinary skill), based on the sequence of a template nucleic acid. That is, the sequence of the newly synthesized nucleic acid strand is typically complementary to the sequence of the template nucleic acid and therefore knowledge of the order and identity of nucleotide incorporation into the synthesized strand can provide information about the sequence of the template nucleic acid strand. Sequencing by synthesis using the modified polymerases of the disclosure will typically involve detecting the order and identity of nucleotide incorporation when nucleotides are polymerized in a template-dependent fashion by the modified polymerase. Some exemplary methods of sequence-by-synthesis using labeled nucleotides include single molecule sequencing (see, e.g., U.S. Pat. Nos. 7,329,492 and 7,033,764), which typically involve the use of labeled nucleotides to detecting nucleotide incorporation. In some embodiments, the disclosed polymerase compositions (and related methods, kits, systems and apparatuses) can be used to obtain sequence information for whole genome sequencing, amplicon sequencing, targeted re-sequencing, single molecule sequencing, multiplex or barcoded sequencing, and paired end sequencing applications.

In some embodiments, the disclosed modified polymerase compositions as well as related methods, systems, apparatuses and kits, can be used to amplify nucleic acid molecules. In some embodiments, a nucleic acid molecule can be amplified using a modified polymerase for example by pyrosequencing, polymerase chain reaction, emulsion polymerase chain reaction, bridge polymerase chain reaction, and the like.

In some embodiments, the disclosed modified polymerase compositions (as well as related methods, systems, apparatuses and kits), can be used to generate nucleic acid libraries. In some embodiments, the disclosed modified polymerase compositions can be used to generate nucleic acid libraries for a variety of downstream processes. Many methods for generating nucleic acid libraries are known in the art, and it will be readily appreciated that all such methods are within the scope of the present disclosure. Suitable methods include, without limitation, nucleic acid libraries generated using emulsion PCR, bridge PCR, PCR, qPCR, RT-PCR, and other forms of nucleic acid amplification dependent on polymerization. In some embodiments, the methods can include template-dependent nucleic acid amplification. In some embodiments, the methods can include a primer: template duplex or a nucleic acid template to which the modified polymerase can perform nucleotide incorporation. In some embodiments, the nucleic acid can include a single stranded nucleic acid with a secondary structure such as a hair-pin or stem-loop that can provide a single-stranded overhang to which the modified polymerase can incorporate a nucleotide during polymerization. In some embodiments, methods for generating nucleic acid libraries using one or more of modified polymerases according to the disclosure can include the generation of a nucleic acid library of 50, 100, 200, 300, 400, 500, 600 or more base pairs in length. In some embodiments, the nucleic acid template to which the modified polymerase can perform nucleotide incorporation can be attached, linked or bound to a support, such as a solid support. In some embodiments, the support can include a planar support such as slide. In some embodiments, the support can include a particle, such as an Ion Sphere™ particle (sold by Life Technologies Corp, CA).

In some embodiments, the disclosure relates generally to a method for generating a nucleic acid library comprising contacting a nucleic acid template with a modified polymerase and one or more dNTPs under polymerizing conditions; thereby incorporating one or more dNTPs into the nucleic acid template to generate a nucleic acid library. In some embodiments, the method can further include generating a nucleic acid library or sequencing a nucleic acid library in the presence of a high ionic strength solution. In some embodiments, the disclosure relates generally to a modified polymerase that retains polymerase activity in the presence of high ionic strength solution. In some embodiments, the high ionic strength solution can be about 150 mM Salt150. In some embodiments, the high ionic strength solution can be about 120 mM to about 200 mM salt. In some embodiments, the high ionic strength solution can be about 130 mM salt. In some embodiments, the high ionic strength solution can be at least 125 mM salt. In some embodiments, the salt can include a potassium and/or sodium salt. In some embodiments, the ionic strength solution can further include a sulfate. In some embodiments, a modified polymerase is capable of amplifying (and/or sequencing) a nucleic acid molecule in the presence of a high ionic strength solution to a greater capacity (for example as measured by raw accuracy or homopolymer accuracy) than a reference polymerase lacking one or more of the same mutations (or homologous mutations) under identical conditions. In some embodiments, a modified polymerase is capable of amplifying (and/or sequencing) a nucleic acid molecule in the presence of a high ionic strength solution to a greater capacity (for example as measured by raw accuracy of homopolymer accuracy) than a reference polymerase lacking one or more of the mutations (or homologous mutations) under standard ionic strength conditions (i.e., lower than the higher ionic strength solution, for example 50 mM salt).

Optionally, the method further includes repeating the addition of one or more dNTPs under polymerizing conditions to incorporate a plurality of dNTPs into the nucleic acid template to generate the nucleic acid library. In some embodiments, the method includes detecting the addition of the one or more dNTPs under polymerizing conditions. In some embodiment, the method includes identifying the addition of the one or more dNTPs under polymerizing conditions (e.g., A, G, C, T, A nucleotide flow and nucleotide incorporation).

In some embodiments, the method can further include detecting a nucleotide incorporation by-product during the polymerization. In some embodiments, the nucleotide incorporation by-product can include a hydrogen, pyrophosphate or phosphate ion.

In some embodiments, the method further includes determining the identity of the incorporated dNTPs in the nucleic acid library. In some embodiments, the method further includes determining the number of incorporated nucleotides in the nucleic acid library. In some embodiments, the detecting can further include sequencing the nucleic acid library.

In some embodiments, the disclosed modified polymerase compositions, (as well as related methods, systems, apparatuses and kits) can be used to detect nucleotide incorporation through the generation of by-product formation during the nucleotide incorporation event. Many methods of detecting nucleotide incorporation by-products are known in the art, and it will be readily appreciated that all such methods are within the scope of the present disclosure. Suitable methods of nucleotide by-product detection include without limitation, detection of hydrogen ion, inorganic phosphate, inorganic pyrophosphate, and the like. Several of these by-product detection methods typically involve template-dependent nucleotide incorporation.

In some embodiments, the modified polymerases can be used to perform label-free nucleic acid sequencing, and in particular, ion-based nucleic acid sequencing. The concept of label-free nucleic acid sequencing, including ion-based nucleic acid sequencing, including the following references that are incorporated by reference: Rothberg et al, U.S. Patent Publication Nos. 2009/0026082, 2009/0127589, 2010/0301398, 2010/0300895, 2010/0300559, 2010/0197507, and 2010/0137143, which are incorporated by reference herein in their entireties. Briefly, in such nucleic acid sequencing applications, nucleotide incorporations are determined by detecting the presence of natural byproducts of polymerase-catalyzed nucleic acid synthesis reactions, including hydrogen ions, polyphosphates, PPi, and Pi (e.g., in the presence of pyrophosphatase).

In a typical embodiment of ion-based nucleic acid sequencing, nucleotide incorporations are detected by detecting the presence and/or concentration of hydrogen ions generated by polymerase-catalyzed nucleic acid synthesis reactions, including for example primer extension reactions. In one embodiment, templates that are operably bound to a primer and a polymerase and that are situated within reaction chambers (such as the microwells disclosed in Rothberg et al, cited above), are subjected to repeated cycles of polymerase-catalyzed nucleotide addition to the primer ("adding step") followed by washing ("washing step"). In some embodiments, such templates may be attached as clonal populations to a solid support, such as a microparticle, bead, or the like, and said clonal populations are loaded into reaction chambers. As used herein, "operably bound" means that a primer is annealed to a template so that the primer can be extended by a polymerase and that a polymerase is bound to such primer-template duplex, or in close proximity thereof so that primer extension takes place whenever nucleotides are supplied.

In each adding step of the cycle, the polymerase extends the primer by incorporating added nucleotide in a template-dependent fashion, such that the nucleotide is incorporated only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. In some embodiments, the production of hydrogen ions is proportional to (e.g., monotonically related) to the number of contiguous complementary bases in the template (as well as the total number of template molecules with primer and polymerase that participate in an extension reaction). Thus, when there are a number of contiguous identical complementary bases in the template (i.e. a homopolymer (HP) region), the number of hydrogen ions generated, and therefore the magnitude of the local pH change, is proportional to the number of contiguous identical complementary bases. If the next base in the template is not complementary to the added nucleotide, then no incorporation occurs and no hydrogen ion is released. In some embodiments, after each step of adding a nucleotide, a washing step is performed, in which an unbuffered wash solution at a predetermined pH is used to remove the nucleotide of the previous step in order to prevent misincorporations in later cycles. In some embodiments, after each step of adding a nucleotide, an additional step may be performed wherein the reaction chambers are treated with a nucleotide-destroying agent, such as apyrase, to eliminate any residual nucleotides remaining in the chamber, thereby minimizing the probability of spurious extensions in subsequent cycles. In some embodiments, the treatment may be included as part of the washing step itself.

In one exemplary embodiment, different kinds (or "types") of nucleotides are added sequentially to the reaction chambers, so that each reaction is exposed to the different nucleotide types one at a time. For example, nucleotide types can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired. In some embodiments, the time taken to apply each nucleotide sequentially to the reaction chamber (i.e. flow cycle) can be varied depending on the sequencing information desired. For example, the flow cycle can in some instances be reduced when sequencing long nucleic acid molecules to reduce the overall time needed to sequence the entire nucleic acid molecule. In some embodiments, the flow cycle can be increased, for example when sequencing short nucleic acids or amplicons. In some embodiments, the flow cycle can be about 0.3 seconds to about 3 seconds, and more typically about 0.5 second to about 1.5 seconds.

In one exemplary embodiment, the disclosure relates generally to a method for obtaining sequence information from a nucleic acid template, comprising:

(a) providing a reaction mixture including a template nucleic acid hybridized to a sequencing primer and bound to a modified polymerase, wherein the modified polymerase comprises a polymerase linked to a bridging moiety through one or more attachment sites within the polymerase;

(b) contacting the template nucleic acid with a nucleotide, wherein the contacting includes incorporating the nucleotide into the sequencing primer and generating a sequencing byproduct if the nucleotide is complementary to a corresponding nucleotide in the template nucleic acid; and (c) detecting the presence of sequencing byproduct in the reaction mixture, thereby determining whether nucleotide incorporation has occurred.

In some embodiments, the method can further include repeating the contacting and detecting steps at least once.

In some embodiments, the polymerase of the modified polymerase includes a single attachment site, and the bridging moiety is linked to the polymerase through the single attachment site, either directly or through a linking moiety. In some embodiments, the single attachment site can be linked to a biotin moiety, and the bridging moiety can include an avidin moiety. In some embodiments, the modified polymerase exhibits increased read length and/or processivity relative to an unmodified form of the polymerase under otherwise similar or identical reaction conditions.

In some embodiments, detecting the presence of the sequencing byproduct includes contacting the reaction mixture with a sensor capable of sensing the presence of the sequencing byproduct. The sensor can include a field effect transistor, for example a chemFET or an ISFET.

In some embodiments, the sequencing byproduct includes a hydrogen ion, a dye-linked moiety, a polyphosphate, a pyrophosphate or a phosphate moiety, and detecting the presence of the sequencing byproduct includes using an ISFET to detect the sequencing byproduct. In some embodiments, the detecting the sequencing byproduct includes detecting a hydrogen ion using the ISFET.

In a further embodiment, the disclosure relates generally to a method of detecting a nucleotide incorporation, comprising:

(a) performing a nucleotide incorporation using a modified polymerase and generating one or more byproducts of the nucleotide incorporation; and (b) detecting the presence of at least one of the one or more byproducts of the nucleotide incorporation, thereby detecting the nucleotide incorporation.

In some embodiments, the modified polymerase includes a polymerase linked to a bridging moiety. The bridging moiety is optionally linked to the polymerase through one or more attachment sites within the modified polymerase. In some embodiments, the bridging moiety is linked to the polymerase through a linking moiety. The linking moiety can be linked to at least one of the one or more attachment sites of the polymerase. In some embodiments, the polymerase of the modified polymerase includes a single attachment site, and the bridging moiety is linked to the polymerase through the single attachment site, either directly or through a linking moiety. In some embodiments, the single attachment site can be linked to a biotin moiety, and the bridging moiety can include an avidin moiety. In some embodiments, the bridging moiety is linked to the polymerase through at least one biotin-avidin bond. In some embodiments, the modified polymerase exhibits increased read length and/or processivity and/or read accuracy, increased total throughput, reduced strand bias, lowered systematic error, increased relative to a reference polymerase under otherwise similar or identical reaction conditions.

In some embodiments, the method can further include repeating the performing and detecting steps at least once.

In some embodiments, detecting the presence of the at least one byproduct of nucleotide incorporation includes using a sensor capable of sensing the presence of the byproduct. The sensor can include a field effect transistor, for example a chemFET or an ISFET.

In some embodiments, the at least one byproduct of nucleotide incorporation includes a hydrogen ion, a dye-linked moiety, a polyphosphate, a pyrophosphate or a phosphate moiety, and detecting the presence of the at least one byproduct includes using an ISFET to detect the at least one byproduct. In some embodiments, the at least one byproduct includes a hydrogen ion, and detecting the presence of the sequencing byproduct includes detecting the hydrogen ion using an ISFET.

In some embodiments, the disclosure relates generally to a method of detecting a change in ion concentration during a nucleotide polymerization reaction, comprising:
(a) performing a nucleotide polymerization reaction using a modified polymerase including a polymerase linked to a bridging moiety, wherein the concentration of at least one type of ion changes during the course of the nucleotide polymerization reaction; and
(b) detecting a signal indicating the change in concentration of the at least one type of ion.

In some embodiments, the bridging moiety is linked to the polymerase through one or more attachment sites within the modified polymerase. In some embodiments, the bridging moiety is linked to the polymerase through a linking moiety. The linking moiety can be linked to at least one of the one or more attachment sites of the polymerase. In some embodiments, the polymerase of the modified polymerase includes a single attachment site, and the bridging moiety is linked to the polymerase through the single attachment site, either directly or through a linking moiety. In some embodiments, the single attachment site can be linked to a biotin moiety, and the bridging moiety can include an avidin moiety. In some embodiments, the bridging moiety is linked to the polymerase through at least one biotin-avidin bond. In some embodiments, the modified polymerase exhibits increased read length and/or processivity relative to a reference form of the polymerase under otherwise similar or identical reaction conditions.

In some embodiments, the method can further include repeating the performing and detecting steps at least once.

In some embodiments, detecting the change in concentration of the at least one type of ion includes using a sensor capable of sensing the presence of the byproduct. The sensor can include a field effect transistor, for example a chemFET or an ISFET.

In some embodiments, the at least type of ion includes a hydrogen ion, a dye-linked moiety, a polyphosphate, a pyrophosphate or a phosphate moiety, and detecting the change in concentration of the at least one type of ion includes using an ISFET to detect the at least one type of ion. In some embodiments, the at least one type of ion includes a hydrogen ion, and detecting the presence of the at least one type of ion includes detecting the hydrogen ion using an ISFET.

In one exemplary embodiment, the disclosure relates generally to a method for obtaining sequence information from a nucleic acid template, comprising:

(a) providing a reaction mixture including a template nucleic acid hybridized to a sequencing primer and bound to a modified polymerase;
(b) contacting the template nucleic acid with a nucleotide, wherein the contacting includes incorporating the nucleotide into the sequencing primer and generating a extended primer product; and
(c) detecting the presence of the extended primer product in the reaction mixture, thereby determining whether nucleotide incorporation has occurred. In some embodiments, the modified polymerase comprises SEQ ID NO: 2, SEQ ID NO: 24, SEQ ID NO: 26, SEQ ID NO:28, SEQ ID NO: 31, SEQ ID NO: 32, SEQ ID NO: 34, SEQ ID NO; 35, SEQ ID NO: 36 or SEQ ID NO: 37.

In one exemplary embodiment, the disclosure relates generally to a method for amplifying a nucleic acid template, comprising:
(a) providing a reaction mixture including a nucleic acid template hybridized to a primer and bound to a modified polymerase;
(b) contacting the nucleic acid template with a nucleotide, wherein the contacting includes incorporating the nucleotide into the primer and generating a extended primer product; and
(c) detecting the presence of the extended primer product in the reaction mixture, thereby determining whether nucleotide incorporation has occurred. In some embodiments, the modified polymerase comprises SEQ ID NO: 2, SEQ ID NO: 24, SEQ ID NO: 26, SEQ ID NO: 28, SEQ ID NO: 31, SEQ ID NO: 32, SEQ ID NO: 34, SEQ ID NO: 35; SEQ ID NO: 36 or SEQ ID NO: 37.

The following non-limiting examples are provided purely by way of illustration of exemplary embodiments, and in no way limit the scope and spirit of the present disclosure. Furthermore, it is to be understood that any inventions disclosed or claimed herein encompass all variations, combinations, and permutations of any one or more features described herein. Any one or more features may be explicitly excluded from the claims even if the specific exclusion is not set forth explicitly herein. It should also be understood that disclosure of a reagent for use in a method is intended to be synonymous with (and provide support for) that method involving the use of that reagent, according either to the specific methods disclosed herein, or other methods known in the art unless one of ordinary skill in the art would understand otherwise. In addition, where the specification and/or claims disclose a method, any one or more of the reagents disclosed herein may be used in the method, unless one of ordinary skill in the art would understand otherwise.

EXAMPLES

Example 1

Purification of Exemplary Modified Polymerases

Various exemplary mutations were introduced via site-directed mutagenesis into an exemplary reference polymerase having the amino acid sequence of SEQ ID NO: 2. Recombinant expression constructs encoding these modified polymerases were transformed into bacteria. Colonies containing expression constructs were inoculated into BRM media, grown to OD=0.600 and induced by adding IPTG to a final concentration of 1 mM. The cells were then grown for a further 3 hours at 37° C.

The induced cells were centrifuged for 10 minutes at 6000 rpm, supernatant was discarded, and the cells were resuspended in resuspension buffer (10 mM Tris, pH 7.5, 100 mM NaCl). The resuspended cells were sonicated at a setting of 60 (amplitude) for one minute, and then placed on ice for 1 minute. The sonication was repeated in this manner for a total of 5 times.

The samples were incubated at 65° C. for 10 minutes. The samples were centrifuged at 9000 rpm for 30 minutes. The supernatant was recovered and further purified over a Heparin column. Purified polymerase was assayed to measure the dissociation rate constant as described in the following Example.

Example 2

Measuring Off-Rate of Exemplary Modified and Reference Polymerases

The samples of modified polymerases, as well as a reference polymerase having the amino acid sequence of SEQ ID NO: 2, prepared according to Example 1, were assayed to measure the dissociation rate constants. The goal of this assay was to measure the dissociation rate of a polymerase from a fluorescently labeled DNA template (oligo 221) having the following nucleotide sequence:

(SEQ ID NO: 21)
TTTTTTTGCAGGTGACAGGTTTTTCCTGTCACCNGC, where N is flourescein-dT.

Dissociation is measured by the decrease in fluorescence that occurs when the Bst polymerase dissociates from the template. Dissociation is initiated by adding a vast excess of unlabeled, competitor DNA (hairpin oligo 173) having the following nucleotide sequence:

(SEQ ID NO: 22)
TTTTTTTCCCTTTCCTTTCGGGTGACAGGTTTTTCCTGTCACCC.

As the polymerase dissociates from oligo 221, it is bound by the competitor and thus, cannot rebind the original 221 template.

To perform the assay, reactions (75 µl) containing 30 mM Tris (pH 7.5), 20 mM NaCl, 50 nM oligo 221, and ~10-200 nM partially polymerase samples (prepared according to Example 1) were assembled in 96-well plates. Baseline readings were then taken on the spectrophotometer using 490 nm excitation and 525 nm emission wavelengths. The 173 competitor oligo (2 µM final concentration) was then rapidly added to each well and plates were rapidly returned to the spectrophotometer for readings every 30 seconds for 5 minutes. The dissociation rate was calculated by fitting the data to a one-phase exponential decay equation using Prism-Graph® according to the following formula:

$$Y=(Y0-\text{Plateau})*\exp^{(-K*X)}+\text{Plateau}$$

where:

Y0 is the Y value when X (time) is zero. It is expressed in the same units as Y, Plateau is the Y value at infinite times, expressed in the same units as Y.

K is the rate constant, expressed in reciprocal of the X axis time units. If X is in minutes, then K is expressed in inverse minutes.

Tau is the time constant, expressed in the same units as the X axis. It is computed as the reciprocal of K.

Half-life is in the time units of the X axis. It is computed as $\ln(2)/K$.

Span, i.e., (Y0−Plateau)) is the difference between Y0 and Plateau, expressed in the same units as your Y values.

Representative results of an assay where the dissociation rate constant (also referred to as the "dissociation time constant") of various modified polymerases, as well as a reference polymerase having the amino acid sequence of SEQ ID NO: 2, was measured at varying concentrations of salt, are depicted in FIG. 2. The polymerases included in the assay are represented in FIG. 2 as follows: Bst 1=Reference polymerase having the amino acid sequence of SEQ ID NO: 2; 480R=modified polymerase having the amino acid sequence of SEQ ID NO: 2 and further including the mutation D480R; 425R=modified polymerase having the amino acid sequence of SEQ ID NO: 2 and further including the mutation G425R; 144K=modified polymerase having the amino acid sequence of SEQ ID NO: 2 and further including the mutation D144K; and 488K=modified polymerase having the amino acid sequence of SEQ ID NO: 2 and further including the mutation F448K. As indicated in FIG. 2, some of the modified polymerases exhibited significantly higher dissociation time constants at a given salt concentration as compared with the reference polymerase of SEQ ID NO: 2.

FIG. 3 provides a table listing the relative template affinity observed for various modified polymerases prepared according to example 1 and 2, relative to the template affinity observed for a reference polymerase having the amino acid sequence of SEQ ID NO: 2 (referred to in FIG. 3 as "BST"). Each modified polymerase had the amino acid sequence of SEQ ID NO: 2, plus the amino acid substitution listed in the first column of the table. As indicated in FIG. 3, some of the modified polymerases exhibited significantly increased template affinity relative to the reference polymerase Bst; in some cases, the increase in template affinity was 20×, 30×, 100×, or greater.

Example 3

Comparing Performance of Modified and Reference Polymerases in Nucleic Acid Sequencing A modified polymerase comprising a mutant Bst polymerase having the amino acid sequence of SEQ ID NO: 2 and further including the amino acid substitution D480R (wherein the numbering is relative to the amino acid sequence of SEQ ID NO: 2) was purified essentially as described in Example 1. Both the modified polymerase and a reference polymerase (having the amino acid sequence of SEQ ID NO: 2) (control reaction) were then evaluated for performance in an ion-based sequencing reaction using the Ion Torrent PGM™ Sequencing system (Ion Torrent Systems, Part No. 4462917). Briefly, genomic DNA was purified, adapter-ligated and size selected as described in User Guide for the Ion Fragment Library Kit (Ion Torrent Systems, Part No. 4466464; Publication Part No. 4467320 Rev B). The DNA fragments were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463).

The amplified DNA was then loaded into a PGM™ 314 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923). Ion Torrent Systems is a subsidiary of Life Technologies Corp., Carlsbad, Calif.).

The resulting sets of sequencing reads using either the reference or modified polymerase were analyzed to measure the number of 50Q17 reads, 100Q17 reads, and 200Q17 reads. Using the standard software supplied with the PGM™ sequencing system, the total number of 100Q17 or 200Q17 reads obtained in sequencing reactions using reference and modified polymerases were measured and compared. The exemplary modified polymerase including the mutation D480R provided significantly increased numbers of 50Q17 reads, 100Q17 reads, and 200Q17 reads relative to the reference polymerase (data not shown).

Example 4

Comparing Performance of Modified and Reference Polymerases in Nucleic Acid Sequencing A modified polymerase comprising a mutant Bst polymerase having the amino acid sequence of SEQ ID NO: 2 and further including the amino acid substitutions D264K and E493Q (wherein the numbering is relative to the amino acid sequence of SEQ ID NO: 2) was purified essentially as described in Example 1. Both the modified polymerase and a reference polymerase (having the amino acid sequence of SEQ ID NO: 2)(control reaction) were then evaluated for performance in an ion-based sequencing reaction using the Ion Torrent PGM™ Sequencing system (Ion Torrent Systems, Part No. 4462917). Briefly, genomic DNA was purified, adapter-ligated and size selected as described in User Guide for the Ion Fragment Library Kit (Ion Torrent Systems, Part No. 4466464; Publication Part No. 4467320 Rev B). The DNA fragments were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463). The amplified DNA was then loaded into a PGM™ 314 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923).

The resulting sets of sequencing reads using reference and modified polymerase were analyzed to measure the number of 50Q17 reads, 100Q17 reads, and 200Q17 reads. Using the standard software supplied with the PGM™ sequencing system, the total number of 100Q17 or 200Q17 reads obtained in sequencing reactions using reference and modified polymerases were measured and compared. The exemplary modified polymerase including the mutations D264K and E493Q provided significantly increased numbers of 50Q17 reads, 100Q17 reads, and 200Q17 reads relative to the reference polymerase (data not shown).

Example 5

Comparing Performance of Modified and Reference Polymerases in Nucleic Acid Sequencing A modified polymerase comprising a mutant Bst polymerase having the amino acid sequence of SEQ ID NO: 2 and further including the amino acid substitutions E220K, N234R and D423K (wherein the numbering is relative to the amino acid sequence of SEQ ID NO: 2) was purified essentially as described in Example 1. Both the modified polymerase and a reference polymerase having the amino acid sequence of SEQ ID NO: 2 (control reaction) were then evaluated for performance in an ion-based sequencing reaction using the Ion Torrent PGM™ Sequencing system (Ion Torrent Systems, Part No. 4462917). Briefly, genomic DNA was purified, adapter-ligated and size selected as described in User Guide for the Ion Fragment Library Kit (Ion Torrent Systems, Part No. 4466464; Publication Part No. 4467320 Rev B). The DNA fragments were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463). The amplified DNA was then loaded into a PGM™ 314 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923).

The resulting sets of sequencing reads using reference and modified polymerases were analyzed to measure the number of 50Q17 reads, 100Q17 reads, and 200Q17 reads. Using the standard software supplied with the PGM™ sequencing system, the total number of 100Q17 or 200Q17 reads obtained in sequencing reactions using reference and modified polymerases were measured and compared. The exemplary modified polymerase including the mutations E220K, N234R and D423K provided significantly increased numbers of 50Q17 reads, 100Q17 reads, and 200Q17 reads relative to the reference polymerase (data not shown).

Example 6

Comparing Performance of Exemplary Modified and Reference Polymerases in an Ion-Based Nucleic Acid Sequencing System Exemplary modified polymerases comprising a mutant Bst polymerase having the amino acid sequence of SEQ ID NO: 2 and further including three of the following exemplary amino acid substitutions: N31R, N31K, D77K, D77H, D113N, D114R, D130A, D130H, D144M, D144K, L212A, E220K, N234R, N234K, V241K, V251K, D264Q, D264S, D264R, Y272R, H273R, L280R, H281A, E294S, E294F, E294G, E294K, V299K, V299H, V299F, D303R, I331Q, E325R, L335T, E336P, I354W, I354F, I370A, Q409R, G416K, V418M, V418I, G420K, D423S, D423K, D423N, D423R, D423T, D423G, D423I, D423K, G425R, Q428W, N429R, N429K, E446Q, F448K, N457T, A462T, H473R, Y477F, D480R, D480F, D480H, D480A, D480S, D480N, D480Q, N485W, N485Y, N487H, N487W, N487F, N487I, V488R, E493Q, M495Q, H528A, V5331, H572R, W577Y and D579F, wherein the numbering is relative of the amino acid sequence of SEQ ID NO: 2, were purified essentially as described in Example 1. Both the modified polymerases and a reference polymerase (having the amino acid sequence of SEQ ID NO: 2) (control reaction) were then evaluated for performance in an ion-based sequencing reaction using the Ion Torrent PGM™ Sequencing system, (Ion Torrent Systems, Part No. 4462917). Briefly, genomic DNA was purified, adapter-ligated and size selected as described in User Guide for the Ion Fragment Library Kit (Ion Torrent Systems, Part No. 4466464; Publication Part No. 4467320 Rev B). The DNA fragments were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463). The amplified DNA was then loaded into a PGM™ 314 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923).

The resulting sets of sequencing reads using reference and modified polymerases were analyzed to measure the raw read accuracy of the resulting sequencing reads (as reported by the Ion Torrent standard software provided with the Ion Torrent Sequencing System), the number of 50Q17 reads, 100Q17 reads, and 200Q17 reads. Using the standard software supplied with the PGM™ sequencing system, the total number of 100Q17 or 200Q17 reads obtained in sequencing reactions using reference and modified polymerases were measured and compared.

FIGS. 4-7 depict the increase in accuracy obtained using an exemplary modified polymerase (A5) comprising the amino acid sequence of SEQ ID NO: 2 and further including amino acid substitutions: E220K, N234R, and D423K, wherein the numbering is relative to SEQ ID NO: 2, compared to the accuracy obtained using a reference polymerase comprising the amino acid sequence of SEQ ID NO: 2 (i.e., an exemplary Bst polymerase), and further including a different set of amino acid substitutions (LR2). As shown in FIGS. 4-7, the exemplary modified polymerase (A5) including the mutations provided significantly increased accuracy (as measured by error rate and raw read accuracy) relative to the reference polymerase (LR2). The amino acid sequence of the modified polymerase shown as A5 in FIGS. 4-7 is provided below, as SEQ ID NO: 19.

The corresponding nucleic acid sequence encoding the modified polymerase (A5) (i.e., SEQ ID NO: 19) is provided below as SEQ ID NO: 23. It will be readily apparent to one of ordinary skill in the art, that any one or more of the reference or modified polymerases disclosed, or suggested, by the disclosure can be readily converted (e.g., reverse translated) to the corresponding nucleic acid sequence encoding the reference or modified polymerase. It will also be apparent to the skilled artisan that the nucleic acid sequence for each polypeptide is variable due to the degenerate nature of codons. For example, there are six codons that code for leucine (CTT, CTC, CTA, CTG, TTA and TTG). Thus, the base at position 1 of this codon can be a C or T, position 2 of this codon is always a T, and the base at position 3 can be T, C, A or G. Accordingly, any reference or modified polymerase disclosed or suggested by the disclosure can be translated to any one or more of the degenerate codon nucleic acid sequences.

Example 7

Transfer of Mutations from One Modified Polymerase to Another Polymerase

Various exemplary mutations were introduced via site-directed mutagenesis into exemplary reference polymerases having the amino acid sequences of SEQ ID NO: 2, SEQ ID NO: 16, SEQ ID NO: 15 and SEQ ID NO: 18 (See Table 1). After sequence verification, the modified polymerases containing amino acid mutations (e.g., a Taq DNA polymerase having amino acid mutation D732R, wherein the numbering corresponds to SEQ ID NO. 15; and a Klenow fragment DNA polymerase having amino acid mutation D505R, wherein the numbering corresponds to SEQ ID NO. 18) were transformed into bacterial cells for expression. Colonies containing expression construct were inoculated into BRM media, grown to OD=0.600 and induced by adding IPTG to a final concentration of 1 mM. The cells were then grown for a further 3 hours at 37° C.

The induced cells were then centrifuged for 10 minutes at 6000 rpm, supernatant was discarded, and the cells were resuspended in resuspension buffer (100 mM Tris, pH 7.5, 100 mM NaCl). The resuspended cells were sonicated at a setting of 60 (amplitude) for one minute, and then placed on ice for 1 minute. The sonication was repeated in this manner for a total of 5 times. Samples were incubated at 65° C. for 10 minutes and centrifuged at 9000 rpm. The supernatant was recovered and further purified over a Heparin column. Purified polymerase was assayed to measure the dissociation rate constant as described in Example 2.

Heparin DNA Affinity Column

The following results were observed during purification of the modified polymerases on a Heparin column. All mutants exhibited tighter binding to a heparin column. Taq D732R came off the column at a conductivity of 43 mS/cm where the wild type comes off at 39 mS/cm. Klenow D505R came off the column at a conductivity of 47 mS/cm where wild type Klenow comes off at 32 mS/cm.

Template Affinity/Dissociation Assay:

The dissociation rate of each modified and reference polymerase from a DNA template (oligo 221) in the presence of excess competitor DNA (hairpin oligo 173) was measured. Decreasing fluorescence is monitored over time on a spectrophotometer as the polymerase dissociates from the fluorescein-labeled template. The dissociation rate is calculated by fitting the data to a one-phase exponential decay equation.

Figure 8:
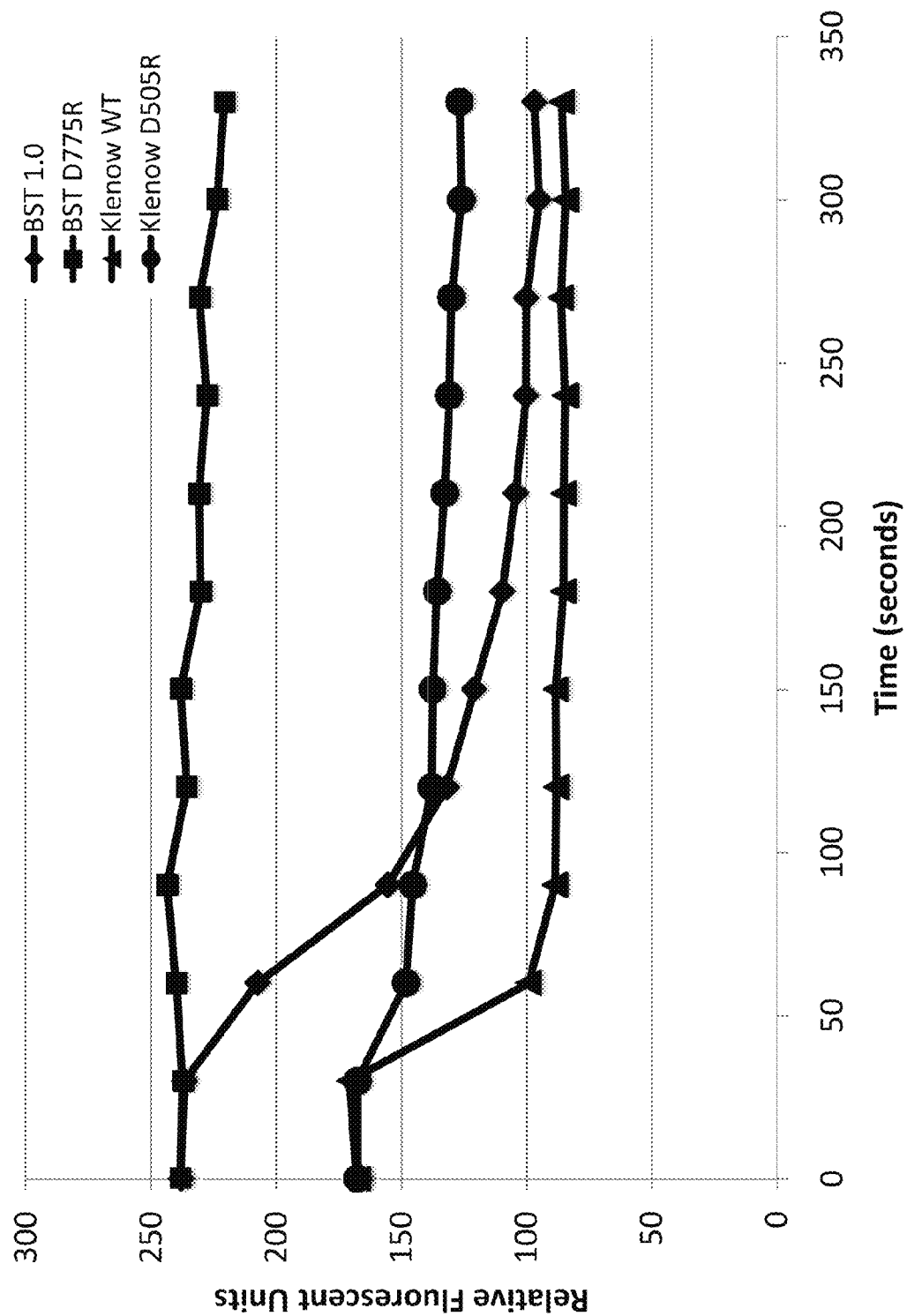
FIG. 8 shows a graph outlining an exemplary dissociation rate curve for exemplary modified polymerases obtained according to the disclosure.

Representative results of an assay where the dissociation rate constant (also referred to as the "dissociation time constant") of various modified polymerases, as well as reference polymerases having the amino acid sequence of SEQ ID NO: 2 or SEQ ID NO: 18, was measured at time intervals (depicted in FIG. 8). The polymerases included in the assay are represented in FIG. 8 as follows: Bst 1.0=Reference polymerase having the amino acid sequence of SEQ ID NO: 2; BST D775R=modified polymerase having the amino acid sequence of SEQ ID NO: 2 and further including the mutation D775R; Klenow WT=reference polymerase having the amino acid sequence of SEQ ID NO: 18; Klenow D505R=modified polymerase having the amino acid sequence of SEQ ID NO: 18 and further including the mutation D505R. As indicated in FIG. 8, the modified polymerases exhibited significantly higher dissociation time constants as compared with the corresponding reference polymerase.

Example 8

Evaluation of DNA Binding Affinities of Bst Polymerase, Klenow Fragment DNA Polymerase and Taq DNA Polymerase Mutants Various exemplary mutations were introduced via site-directed mutagenesis into exemplary reference polymerases to generate modified polymerases. In this example, reference polymerase SEQ ID NO: 2 was modified to contain a further amino acid mutation (D480R). Reference polymerase SEQ ID NO: 15 was also modified to contain a further amino acid mutation (D732R). Additionally, reference polymerase SEQ ID NO: 18 was modified to contain amino acid mutation (D505R). The modified polymerases were sequence verified, and expressed essentially according to the procedure of Example 1. The modified polymerases were then assayed to measure dissociation rate constant essentially according to the procedure of Example 2.

Figure 9:
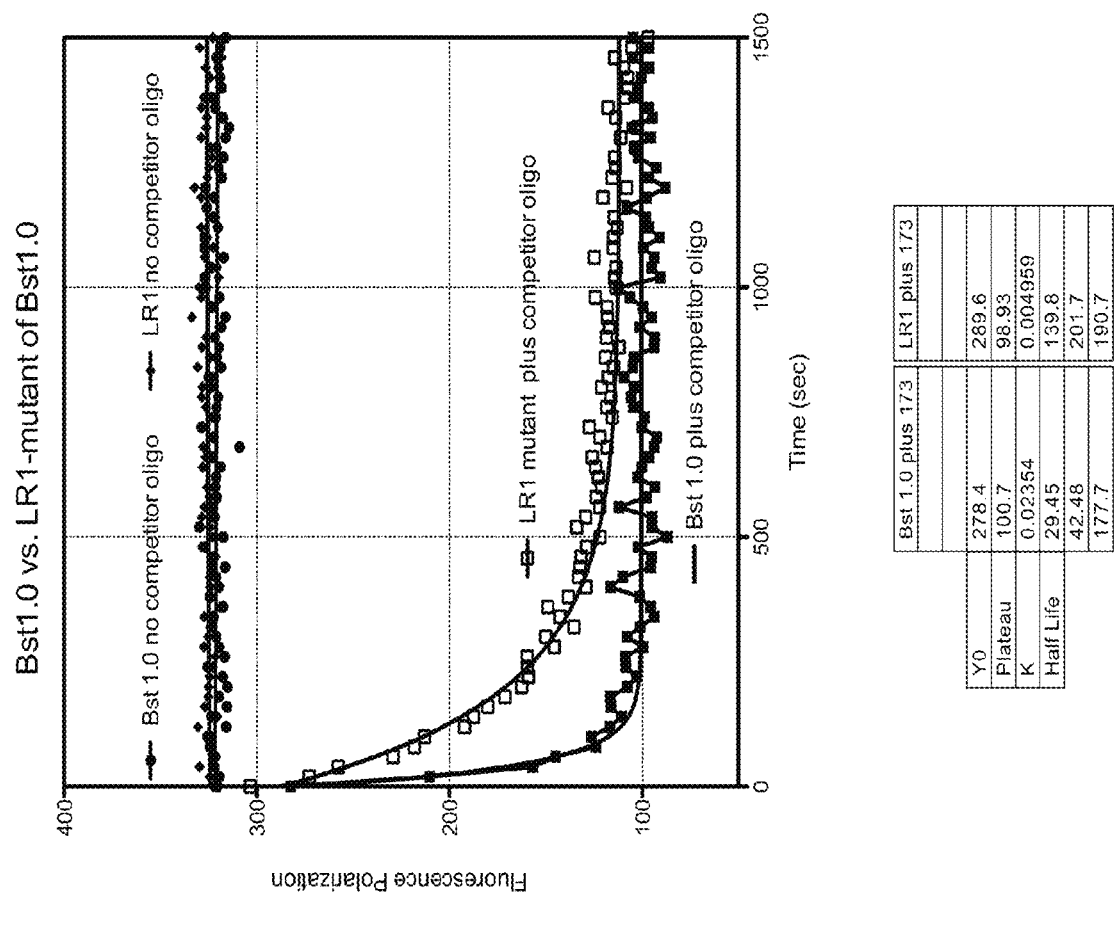
FIG. 9 is a graph showing exemplary binding affinity assay data performed using exemplary modified polymerases obtained according to the disclosure.
Figure 10:
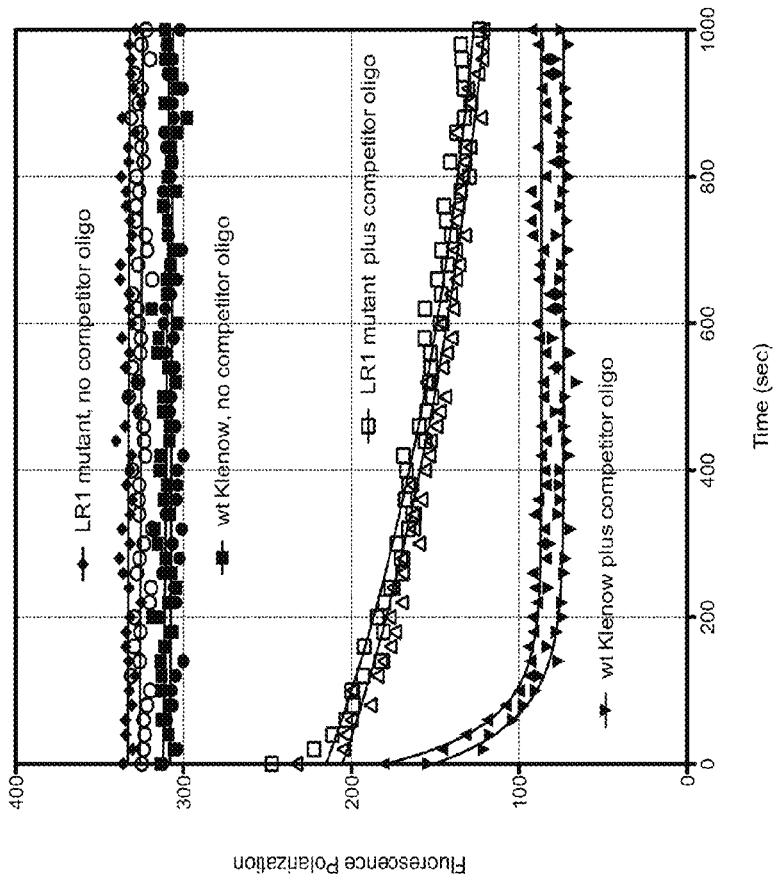
FIG. 10 is a graph showing exemplary binding affinity assay data performed using exemplary modified polymerases obtained according to the disclosure.
Figure 11:
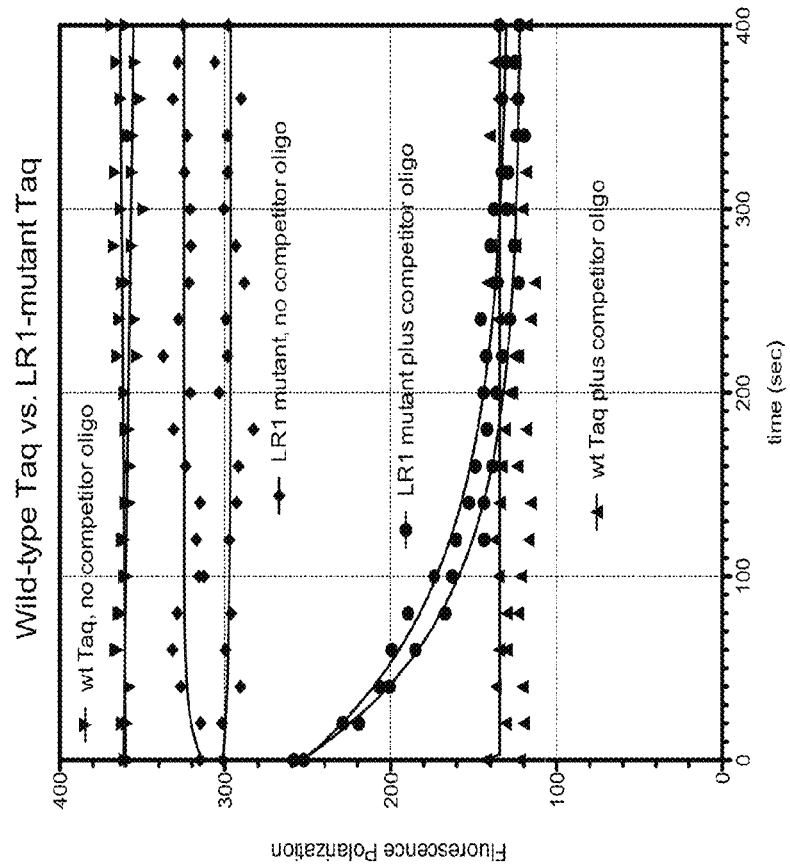
FIG. 11 is a graph showing exemplary binding affinity assay data performed using exemplary modified polymerases obtained according to the disclosure.

Representative results of an assay where the dissociation rate constant (also referred to as the "dissociation time constant") of the modified polymerases, as well as the reference polymerases was measured at specific time intervals (depicted in FIGS. 9-11). The polymerases included in the assay represented in FIG. 9 as follows: Bst 1.0=Reference polymerase having the amino acid sequence of SEQ ID NO: 2; LR1=modified polymerase having the amino acid sequence of SEQ ID NO: 2 and further including the mutation D775R. FIG. 9 also provides the rate constants (K) for each polymerase. The ratio of these values ($K_{Bst1.0}/K_{BstLR1}$) is 4.7, which means that Bst 1.0 polymerase dissociates 4.7 fold faster than the LR1 mutant. Thus, the LR1 mutant decreases dissociation from a nucleic acid template by a factor of about 4.7.

The polymerases included in the assay represented in FIG. 10 are as follows: WT=reference polymerase having the amino acid sequence of SEQ ID NO: 18 (Klenow); LR1=modified polymerase having the amino acid sequence of SEQ ID NO: 18 and further including the mutation D505R. FIG. 10 also provides the rate constants (K) for each polymerase. The ratio of these values ($K_{WT}/K_{LR1}$) is 13, which means that the Klenow polymerase dissociates 13 fold faster than the LR1 mutant. Thus, the LR1 mutant decreases dissociation from a nucleic acid template by a factor of about 13.

The polymerases included in the assay represented in FIG. 11 are as follows: WT=reference polymerase having the amino acid sequence of SEQ ID NO: 15 (wild-type Taq DNA polymerase); LR1=modified polymerase having the amino acid sequence of SEQ ID NO: 18 and further including the mutation D505R. FIG. 11 also provides the rate constants (K) for each polymerase. In this instance, wild-type Taq DNA polymerase dissociated at a fast rate from the template in the experiment, that rate constants were unable to be recorded. However, as noted in FIG. 11, the LR1-Taq DNA polymerase mutant was detected using the same experimental conditions and can therefore be concluded to dissociate at a much slower rate from the nucleic acid template than the corresponding wild-type Taq DNA polymerase.

Example 9

Further Evaluation of DNA Binding Affinities of Taq DNA Polymerase Mutants

Various exemplary mutations were introduced via site-directed mutagenesis into an exemplary reference polymerase (wild-type Taq DNA polymerase SEQ ID NO: 15) to generate a series of modified Taq DNA polymerases. In this example, reference polymerase, SEQ ID NO: 15 was modified to contain a single amino acid mutation selected from D732R, E745Q or E471K. Each modified polymerase was sequence verified, and expressed essentially according to Example 1. The modified polymerases were then assayed to measure dissociation rate constant essentially according to Example 2.

Figure 12:
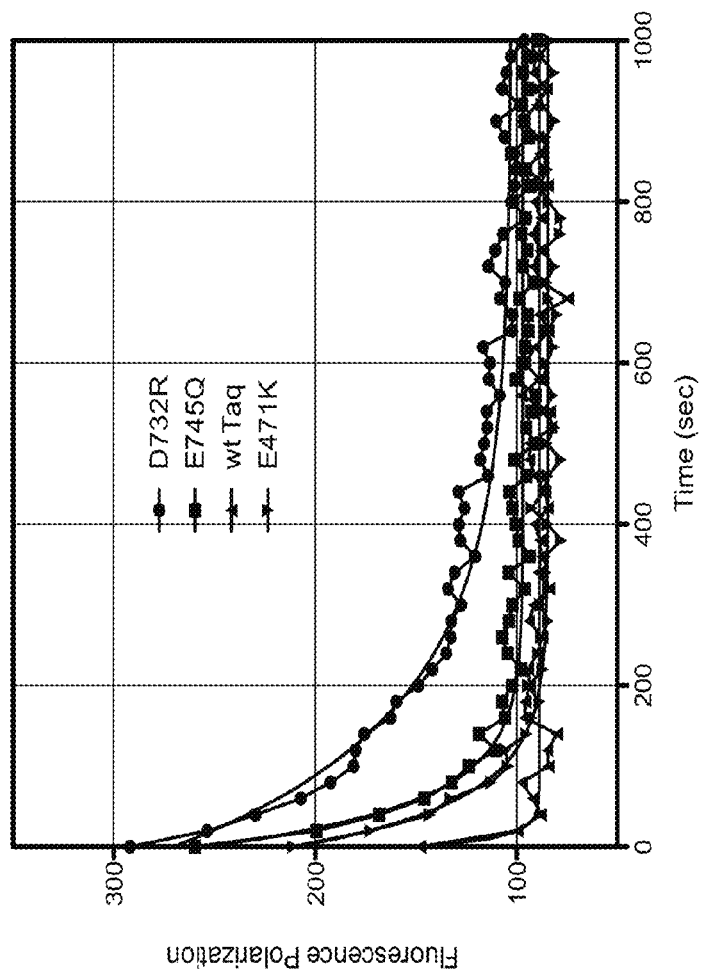
FIG. 12 is a graph showing exemplary binding affinity assay data performed using exemplary modified polymerases obtained according to the disclosure.

Representative results of an assay where the dissociation rate constant (also referred to as the "dissociation time constant") of the modified polymerases, as well as the reference polymerase was measured at specific time intervals (depicted in FIG. 12). The polymerases included in the assay represented in FIG. 12 are as follows wt Taq=Reference polymerase having the amino acid sequence of SEQ ID NO: 15; D732R=modified polymerase having the amino acid sequence of SEQ ID NO: 15 and further including the mutation D732R; E745Q=modified polymerase having the amino acid sequence of SEQ ID NO: 15 and further including the mutation E745Q; E471K=modified polymerase having the amino acid sequence of SEQ ID NO: 15 and further including the mutation E471K.

FIG. 12 also provides the rate constants (K) for each polymerase. The ratio of wild-type Taq to the D732R mutant ($K_{wt\,taq}/K_{D732R}$) is 14.1, which means that the wild-type Taq DNA polymerase dissociates 14 fold faster than the Taq DNA polymerase mutant. Thus, the Taq mutant decreases dissociation from the nucleic acid template by a factor of about 14.

The ratio of wild-type Taq to the E745Q mutant ($K_{wt\,taq}/K_{E745Q}$) is 4.7, which means that the wild-type Taq DNA polymerase dissociates 4.7 fold faster than the Taq DNA polymerase mutant. Thus, the Taq mutant decreases dissociation from the nucleic acid template by a factor of about 4.7.

The ratio of wild-type Taq to the E471K mutant ($K_{wt\,taq}/K_{E471K}$) is 5, which means that the wild-type Taq polymerase dissociates 5 fold faster than the Taq mutant. Thus, the Taq mutant decreases dissociation from the nucleic acid template by a factor of about 5.

All three exemplary modified Taq DNA polymerases, as prepared in this example, demonstrated decreased dissociation from a nucleic acid template as compared to the reference polymerase (wild-type Taq DNA polymerase (SEQ ID NO:15)).

Example 10

Evaluating Modified Polymerase Performance in Nucleic Acid Sequencing

A modified polymerase comprising a mutant Bst polymerase having the amino acid sequence of SEQ ID NO: 2 and further including two amino acid substitutions D264K and E493Q (wherein the numbering is relative to the amino acid sequence of SEQ ID NO: 2) was purified essentially as described in Example 1. The modified polymerase was then evaluated for performance in an ion-based sequencing reaction using the Ion Torrent PGM™ sequencing system (Ion Torrent Systems, Part No. 4462917). Briefly, genomic DNA was purified, adapter-ligated and size selected as described in User Guide for the Ion Fragment Library Kit (Ion Torrent Systems, Part No. 4466464; Publication Part No. 4467320 Rev B). The DNA fragments were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463). The amplified DNA was then loaded into a PGM™ 318 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit c2.0 (Ion Torrent Systems/Life Technologies, Part No. 4466456) and the Ion Chip Kit (Ion Torrent Systems/Life Technologies, Part No. 4462923).

The resulting sets of sequencing reads using the modified polymerase were analyzed to measure the number of AQ17 bases, AQ 20 bases, AQ17 mean, AQ20 mean, number of library reads, and AQ7 alignments. Using the standard software supplied with the PGM™ sequencing system, the total number of AQ17 or AQ20 reads obtained in the sequencing reactions using the modified polymerase were measured and compared. The data for four independent sequencing runs performed as outlined in this example, is shown in FIG. 13. As can be seen, each of the four sequencing runs generated over 1 Gb (gigabyte) of data at AQ17 (average=1.091 Gb).

Example 11

Evaluating Modified Polymerase Performance in Nucleic Acid Sequencing

Two batches of modified polymerase comprising a mutant Bst polymerase having the amino acid sequence of SEQ ID NO: 2 and further including two amino acid substitutions D264K and E493Q (wherein the numbering is relative to the amino acid sequence of SEQ ID NO: 2) were purified essentially as described in Example 1. Each batch (Old LR2 or New LR2) of modified polymerase was then evaluated for performance in an ion-based sequencing reaction using the Ion Torrent PGM™ sequencing system (Ion Torrent Systems, Part No. 4462917). Briefly, genomic DNA was purified, adapter-ligated and size selected as described in User Guide for the Ion Fragment Library Kit (Ion Torrent Systems, Part No. 4466464; Publication Part No. 4467320 Rev B). The DNA fragments were then amplified onto Ion Sphere™ particles (Ion Torrent Systems, Part No. 602-1075-01) essentially according to the protocols provided in the User Guide for the Ion Xpress™ Template Kit v 2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463). The amplified DNA was then loaded into a PGM™ 318 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923).

The resulting sets of sequencing reads using either the old LR2 batch or new LR2 batch of modified polymerase were analyzed to measure the number of AQ17 bases, AQ 20 bases, AQ17 mean, and AQ20 mean. Using the standard software supplied with the PGM™ sequencing system, the total number of AQ17 or AQ20 reads obtained in the sequencing reactions using the modified polymerase were measured and compared. The data for seven independent sequencing runs performed as outlined in this example, is shown in FIG. 14. As can be seen, each of the seven sequencing runs generated over 1 Gb (gigabyte) of data at AQ17; while five of the sequencing runs generated over 1 Gb of data at AQ20.

Example 12

Evaluating Modified Polymerase Performance in Nucleic Acid Sequencing

A modified polymerase comprising a mutant Bst polymerase having the amino acid sequence of SEQ ID NO: 20 was purified essentially as described in Example 1. The modified polymerase was then evaluated for performance in an ion-based sequencing reaction using the Ion Torrent PGM™ sequencing system (Ion Torrent Systems, Part No. 4462917). Briefly, genomic DNA was purified, adapter-ligated and size selected as described in User Guide for the Ion Fragment Library Kit (Ion Torrent Systems, Part No. 4466464; Publication Part No. 4467320 Rev B). The DNA fragments were then amplified onto Ion Sphere™ particles (Ion Torrent Systems, Part No. 602-1075-01) essentially according to the protocols provided in the User Guide for the Ion Xpress™ Template Kit v2.0 (Ion Torrent Systems, Part No. 4469004A) and using the reagents provided in the Ion Template Preparation Kit (Ion Torrent Systems/Life Technologies, Part No. 4466461), the Ion Template Reagents Kit (Ion Torrent Systems/Life Technologies, Part No. 4466462) and the Ion Template Solutions Kit (Ion Torrent Systems/Life Technologies, Part No. 4466463). The amplified DNA was then loaded into a PGM™ 316 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923).

The resulting sequencing read using the modified polymerase were analyzed to measure the number of mapped Q17 bases, the number of mapped Q20 bases, mean coverage depth at Q17, mean coverage depth at Q20, longest Q17 and Q20 alignments, and Q17 and Q20 alignments. The data for the sequencing run performed as outlined in this example is shown in FIG. 15. As can be seen, the sequencing run generated over 1 Gb (gigabyte) of data at Q17 (1.02 Gb); a Q17 accuracy rate of 482 base pairs and a Q20 accuracy rate of 471 base pairs.

Example 13

Evaluating Modified Polymerase Performance in Emulsion PCR

A modified polymerase comprising a mutant Taq DNA polymerase having the amino acid sequence of SEQ ID NO: 15 and further including amino acid mutation D732R was purified essentially as described in Example 1 (SEQ ID NO: 24). This modified polymerase had previously shown a 14-fold decrease in the rate of template dissociation as compared to wild-type Taq DNA polymerase (see Example 9). The modified Taq DNA polymerase was then evaluated for performance in an emulsion PCR reaction to generate nucleic acid libraries. The nucleic acid libraries were prepared using a 400 bp insert and higher salt conditions (125 mM) than previously evaluated. The libraries obtained using the modified Taq DNA polymerase from the emulsion PCR (emPCR) were applied downstream in an ion-based sequencing reaction using the Ion Torrent PGM™ sequencing system (Ion Torrent Systems, Part No. 4462917).

Briefly, genomic DNA was purified, adapter-ligated and size selected as described in User Guide for the Ion Fragment Library Kit (Ion Torrent Systems, Part No. 4466464; Publication Part No. 4467320 Rev B). In this example, DNA fragments of about 400 bp were used as the nucleic acid template for generating nucleic acid libraries. The DNA fragments were then amplified onto Ion Sphere™ particles (Ion Torrent Systems, Part No. 602-1075-01) essentially according to the protocols provided in the User Guide for the Ion Xpress™ Template Kit v2.0 (Ion Torrent Systems, Part No. 4469004A), except for substituting the kit DNA polymerase with the modified Taq DNA polymerase and performing the emPCR process at an elevated salt concentration (150 mM KCl). The amplified DNA was then loaded into a PGM™ 316 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923).

The resulting sequencing read using the modified Taq DNA polymerase during emPCR was analyzed to measure the number of AQ17 bases, AQ 20 bases, AQ17 mean, AQ20 mean, number of library reads, and AQ7 alignments. The data for the sequencing run performed as outlined in this example is shown in FIG. 16. As can be seen, the sequencing run generated over 1 Gb (gigabyte) of data at Q17 (1.025 Gb); a Q17 accuracy rate of 443 base pairs and a Q20 accuracy rate of 443 base pairs. The modified DNA polymerase was capable of generating significant sequencing data, as a result of having created substantial numbers of nucleic acid libraries during the emPCR process.

Example 14

Evaluating Modified Polymerase Performance in Emulsion PCR

A modified polymerase comprising a mutant Taq DNA polymerase having the amino acid sequence of SEQ ID NO: 24 was compared to Wild Type Taq DNA (SEQ ID NO: 15) polymerase for performance in emulsion PCR reactions that generate nucleic acid libraries. The nucleic acid libraries produced using the mutant Taq DNA polymerase were prepared using a 400 bp insert and higher salt conditions than were used for Wild Type Taq DNA polymerase. The libraries obtained using the modified or Wild Type Taq DNA polymerase from the emulsion PCR (emPCR) were applied downstream in an ion-based sequencing reaction using the Ion Torrent PGM™ sequencing system (Ion Torrent Systems, Part No. 4462917).

Briefly, genomic DNA was purified, adapter-ligated and size selected as described in User Guide for the Ion Fragment Library Kit (Ion Torrent Systems, Part No. 4466464; Publication Part No. 4467320 Rev B). In this example, DNA fragments of about 400 bp were used as the nucleic acid template for generating nucleic acid libraries. The DNA fragments were then amplified onto Ion Sphere™ particles (Ion Torrent Systems, Part No. 602-1075-01) essentially according to the protocols provided in the User Guide for the Ion Xpress™ Template Kit v2.0 (Ion Torrent Systems, Part No. 4469004A), except for emulsions which substitute the kit DNA polymerase with the modified Taq DNA polymerase and performing the emPCR process at an elevated salt concentration (150 mM KCl). The amplified DNA was then loaded into a PGM™ 316 sequencing chip. The chip was loaded into an Ion Torrent PGM™ Sequencing system (Ion Torrent Systems/Life Technologies, Part No. 4462917) and sequenced essentially according to the protocols provided in User Guide for the Ion Sequencing Kit v2.0 (Ion Torrent Systems/Life Technologies, Part No. 4469714 Rev A) and using the reagents provided in the Ion Sequencing Kit v2.0 (Ion Torrent Systems/Life Technologies, Part No. 4466456) and the Ion Chip Kit (Ion Torrent Systems/Life Technologies, Part No. 4462923).

The resulting sequencing read using the modified Taq DNA polymerase (SEQ ID NO: 24—LR1Taq) or the Wild Type Taq DNA polymerase (Taq—SEQ ID NO: 15) during emPCR were analyzed to measure the number of AQ17 bases, AQ 20 bases, AQ17 mean, Key Signal, Signal to Noise, and number of library reads. The data for the sequencing run performed as outlined in this example is shown in FIG. 17. As can be seen, the sequencing runs using emulsion made with the modified Taq DNA polymerase (LR1Taq) averaged 0.87 Gigabases of data at Q17 (0.874 Gb) compared to an average of 0.26 Gigabases of data at Q17 (0.263 Gb) for Wild Type Taq DNA polymerase. The modified DNA polymerase was capable of generating significant sequencing data, as a result of having created substantial numbers of nucleic acid libraries during the emPCR process.

Example 15

Construction of Exemplary Modified Polymerases

Various exemplary mutations were introduced via site-directed mutagenesis into an exemplary reference polymerase having the amino acid sequence of SEQ ID NO: 16. It will be readily apparent to the skilled artisan, This example outlines an exemplary high-throughput method to generate a library of modified polymerases or biological active fragments. The examples below also outline methods to assess such modified polymerases or biologically active fragments for polymerase activity.

In this example, a mutagenized library of constructs was prepared based on the amino acid sequence of SEQ ID NO: 16; where every amino acid in the polymerase was individually mutated. Additionally in this exemplary example, select amino acid residues within SEQ ID NO. 16 were mutated with every possible combination of amino acids at the selected amino acid residues. The resulting library of mutant constructs was then applied to a number of 96-well plates where the mutant constructs were grown in BRM media overnight at 30° C. Media containing the mutant constructs were inoculated into deep 96-well plates and grown for 3 hours at 37° C. and induced by adding IPTG to a final concentration of 1 mM. The cells were then grown for a further 3 hours at 37° C. The induced cells were centrifuged for 10 minutes at 3700 rpm, supernatant was discarded, and the cells were resuspended in 100 µl resuspension buffer (10 mM Tris, pH 7.5, 100 mM NaCl). The resuspended cells were sonicated at a setting of 60 (amplitude) for one minute, and then placed at 80° C. overnight.

The above samples were incubated at 65° C. for 10 minutes. The samples were then centrifuged at 3700 rpm for 12 minutes. The supernatant was recovered and further purified with Affinity resin and myOne beads using a biotinylated capture olignucleotide. The purified mutated polymerases or biologically active fragments were eluted in high NaCl and buffer exchanged. The purified mutant polymerases or biologically active fragments were then assayed to measure various polymerase activities such as signal-to-noise ratio, systematic error, read length, raw accuracy, strand bias and total sequencing throughput as outlined in the examples below.

Example 16

Assessing Systematic Error

In this example, the method was catered to assess systematic error generally associated with premature attenuation in one or both strands, extreme strand bias, systematic strand error and high GC content. It will be readily apparent to the skilled artisan that the method disclosed herein can be modified to assess other metrics associated with systematic error, or can be modified to measure one or more other metrics associated with polymerase activity such as template dissociation constant.

Purified polymerases or biologically active fragments thereof were prepared essentially according to Example 15 and used to assess systematic error using a Personal Genome Machine and Ion PGM 318 Chips (Life Technologies Corp, CA).

The library of mutant polymerases or biologically active fragments thereof was prepared according to Example 15 were directly compared to SEQ ID NO: 16 (acting as a control) for performance in emulsion PCR reactions that generate nucleic acid libraries. The nucleic acid libraries were prepared using an E. coli 500 bp insert. The nucleic acid libraries obtained from the emulsion PCR (emPCR) reactions were applied downstream in an ion-based sequencing reaction using the Ion Torrent PGM™ sequencing system (Ion Torrent Systems, Part No. 4462917). Briefly, the template DNA was purified, adapter-ligated and size selected as described in User Guide for the Ion Fragment Library Kit (Ion Torrent Systems, Part No. 4466464; Publication Part No. 4467320 Rev B). The template DNA was amplified onto Ion Sphere™ particles as outlined below. Here, the nucleic acid library used in the 96-well emulsion PCR reactions contained 24 nucleic acid templates having a premature attenuation on one strand, 12 nucleic acid templates that contained a premature attenuation on both strands, 12 nucleic acid templates that contained extreme strand bias, 24 nucleic acid templates that contained systematic strand error, 12 nucleic acid templates that contained high GC content and 12 nucleic acid templates that regularly performed well under the proposed and tested sequencing conditions.

Ion Sphere Particles (ISPs, 20-40 Million) for each of the 96 barcoded emulsions were added separately to individual PCR tubes. The tubes were then filled with Annealing buffer and vortexed. The tubes were spun at max speed (16,500 RPM) for 4 minutes in a table top centrifuge and supernatant was removed. Sequencing primer was added, mixed by pipetting, and annealed to beads by thermocycling. The resuspended primer-annealed ISPs were added to each well of the 96-well plate to yield 400,000 beads per well. Individual mutagenized polymerase's or biologically active fragments thereof were added to each well, with only 1 mutant polymerase or biologically active fragment added per well. The mutant polymerases (or biologically active fragments) and ISPs were incubated at room temperature for 40 min followed by the addition of a mixture of α-thio dGTP/α-thio dTTP to allow for enrichment of the amplified nucleic acid libraries. All 96 wells were combined into a reservoir, transferred to a 2 ml tube, and spun at maximum speed for 3 minutes. The supernatant was removed, the tube vortexed briefly, and then placed tube on a magnetic block. The sample was incubated on the magnetic block for 30 seconds, the supernatant was removed and the entire sample was loaded onto an Ion 318 Chip (Life Technologies, CA, Catalog No. 4484354) using the standard loading protocol provided by the manufacturer. After loading was complete, the chip was washed by pipetting wash solution through the loading port. The wash step was repeated twice, for a total of 3 washes. All liquid was removed from the chip prior to loading on the Ion PGM (Life Technologies, CA, Catalog No. 4462921) and sequenced with the standard Sequencing 400 kit (Life Technologies, CA, Catalog No. 4482002) according to the manufacturers instructions.

The resulting sequencing runs obtained from the library of mutagenized polymerases or biologically active fragments were assessed for systematic error. In particular, metrics such as AQ20 total base count (total sequencing throughput), AQ20 mean, raw read accuracy, strand bias (target bases with no strand bias), and percentage systematic error (measured in this Example as percentage of stochastic errors in sequence motifs containing homopolymers of length 1-6, with systematic deletion occurring on strand with a frequency greater than 15%, when coverage (of the sequencing run) is equal to or greater than 20χ) were measured. Optionally, some of the mutant polymerases were further evaluated using the same metrics against other known polymerases, in addition to direct comparison of the polymerase of SEQ ID NO. 16. The data for exemplary sequencing runs performed as outlined in this example is shown in FIGS. 18-28, discussed in more detail below.

Example 17

Comparing Performance of Modified and Reference Polymerases in Nucleic Acid Sequencing A reference polymerase consisting of amino acid sequence of SEQ ID NO: 16 was used to produce a mutagenic library of polymerases or biologically active fragments thereof essentially as described in Example 15. The library of mutagenic polymerases or biologically active fragments thereof were screened according to Example 16 to assess polymerase activity including signal-to-noise ratio, strand bias, systematic error, read length and/or raw read accuracy for each of the polymerases or biologically active fragments generated in the library. In this example, the reference polymerase having the amino acid sequence of SEQ ID NO. 16 was used to produce a mutagenic library of polymerases having an amino acid substitution at amino acid reside 782, wherein the numbering is relative to the amino acid sequence of SEQ ID NO: 16. In this example, 18 different mutagenic polymerases were constructed, purified and assessed according to Examples 15 and 16, for each of the following polymerase activities: AQ20 total base count (total sequencing throughput), AQ20 mean, raw read accuracy, strand bias (target bases with no strand bias), and percentage systematic error (measured in this example as percentage of stochastic error in sequence motifs containing homopolymers of length 1-6, with systematic deletion occurring on strand with a frequency greater than 15%, when coverage (of the sequencing run) is equal to or greater than 20χ). The data from this Example is presented in FIG. 18.

Example 18

Comparing Performance of Modified and Reference Polymerases in Nucleic Acid Sequencing In this example, the reference polymerase having the amino acid sequence of SEQ ID NO. 16 was used to produce a mutagenic library of polymerases having an amino acid substitution at amino acid reside 780, wherein the numbering is relative to the amino acid sequence of SEQ ID NO: 16. In this example, 18 different mutagenic polymerases were constructed, purified and assessed according to Examples 15 and 16, for each of the following polymerase activities: AQ20 total base count (total sequencing throughput), AQ20 mean, raw read accuracy, strand bias (target bases with no strand bias), and percentage systematic error (measured in this Example as percentage of stochastic errors in sequence motifs containing homopolymers of length 1-6, with systematic deletion occurring on strand with a frequency greater than 15%, when coverage (of the sequencing run) is equal to or greater than 20χ). The data from this Example is presented in FIG. 19.

Example 19

Comparing Performance of Modified and Reference Polymerases in Nucleic Acid Sequencing In this example, the reference polymerase having the amino acid sequence of SEQ ID NO. 16 was used to produce a mutagenic library of polymerases having an amino acid substitution at amino acid reside 788, wherein the numbering is relative to the amino acid sequence of SEQ ID NO: 16. In this example, 16 different mutagenic polymerases were constructed, purified and assessed according to Examples 15 and 16, for each of the following polymerase activities: AQ20 total base count (total sequencing throughput), AQ20 mean, raw read accuracy, strand bias (target bases with no strand bias), and percentage systematic error (measured in this Example as percentage of stochastic errors in sequence motifs containing homopolymers of length 1-6, with systematic deletion occurring on strand with a frequency greater than 15%, when coverage (of the sequencing run) is equal to or greater than 20χ). The data from this Example is presented in FIG. 20.

Example 20

Comparing Performance of Modified and Reference Polymerases in Nucleic Acid Sequencing In this example, the reference polymerase having the amino acid sequence of SEQ ID NO. 16 was used to produce a mutagenic library of polymerases having an amino acid substitution at amino acid reside 558, wherein the numbering is relative to the amino acid sequence of SEQ ID NO: 16. In this example, 18 different mutagenic polymerases were constructed, purified and assessed according to Examples 15 and 16, for each of the following polymerase activities: AQ20 total base count (total sequencing throughput), AQ20 mean, raw read accuracy, strand bias (target bases with no strand bias), and percentage systematic error (measured in this Example as percentage of stochastic errors in sequence motifs containing homopolymers of length 1-6, with systematic deletion occurring on strand with a frequency greater than 15%, when coverage (of the sequencing run) is equal to or greater than 20χ). The data from this Example is presented in FIG. 21.

Example 21

Comparing Performance of Modified and Reference Polymerases in Nucleic Acid Sequencing In this example, the reference polymerase having the amino acid sequence of SEQ ID NO. 16 was used to produce a mutagenic library of polymerases having an amino acid substitution at amino acid reside 559, wherein the numbering is relative to the amino acid sequence of SEQ ID NO: 16. In this example, 18 different mutagenic polymerases were constructed, purified and assessed according to Examples 15 and 16, for each of the following polymerase activities: AQ20 total base count (total sequencing throughput), AQ20 mean, raw read accuracy, strand bias (target bases with no strand bias), and percentage systematic error (measured in this Example as percentage of stochastic errors in sequence motifs containing homopolymers of length 1-6, with systematic deletion occurring on strand with a frequency greater than 15%, when coverage (of the sequencing run) is equal to or greater than 20χ). The data from this Example is presented in FIG. 22.

Example 22

Comparing Performance of Modified and Reference Polymerases in Nucleic Acid Sequencing In this example, the reference polymerase having the amino acid sequence of SEQ ID NO. 16 was used to produce a mutagenic library of polymerases having an amino acid substitution at amino acid reside 559, wherein the numbering is relative to the amino acid sequence of SEQ ID NO: 16. In this example, 2 different mutagenic polymerases with substitutions at 559 (559A and 559R) were constructed, purified and assessed according to Examples 15 and 16, and directly compared for the following polymerase activities AQ20 total base count (total sequencing throughput), AQ20 mean, raw read accuracy, and percentage systematic error (measured in this Example as percentage of stochastic errors in sequence motifs containing homopolymers of length 1-6, with systematic deletion occurring on strand with a frequency greater than 15%, when coverage (of the sequencing run) is equal to or greater than 20$\chi$). The data from this Example is presented in FIG. 23.

Example 23

Comparing Performance of Modified and Reference Polymerases in Nucleic Acid Sequencing In this example, the reference polymerase having the amino acid sequence of SEQ ID NO. 16 was used to produce a mutagenic library of polymerases having an amino acid substitution at amino acid reside 823, wherein the numbering is relative to the amino acid sequence of SEQ ID NO: 16. In this example, 14 different mutagenic polymerases with substitutions at 823 were constructed, purified and assessed according to Examples 15 and 16, for each of the following polymerase activities: AQ20 total base count (total sequencing throughput), AQ20 mean, raw read accuracy, and percentage systematic error (measured in this Example as percentage of stochastic errors in sequence motifs containing homopolymers of length 1-6, with systematic deletion occurring on strand with a frequency greater than 15%, when coverage (of the sequencing run) is equal to or greater than 20$\chi$). The data from this Example is presented in FIG. 24.

Example 24

Comparing Performance of Modified and Reference Polymerases in Nucleic Acid Sequencing In this example, the reference polymerase having the amino acid sequence of SEQ ID NO. 16 was used to produce a mutagenic library of polymerases having an amino acid substitution at amino acid reside 568, wherein the numbering is relative to the amino acid sequence of SEQ ID NO: 16. In this example, 18 different mutagenic polymerases were constructed, purified and assessed according to Examples 15 and 16, for each of the following polymerase activities: AQ20 total base count (total sequencing throughput), AQ20 mean, raw read accuracy, strand bias (target bases with no strand bias), and percentage systematic error (measured in this Example as percentage of stochastic errors in sequence motifs containing homopolymers of length 1-6, with systematic deletion occurring on strand with a frequency greater than 15%, when coverage (of the sequencing run) is equal to or greater than 20$\chi$). The data from this Example is presented in FIG. 25.

Example 25

Comparing Performance of Modified and Reference Polymerases in Nucleic Acid Sequencing In this example, four polymerases prepared according to Example 15, having one or more amino acid mutations with respect to the amino acid sequence of SEQ ID NO. 16 were assessed for various polymerase activities. The first polymerase contained a single amino acid substitution, 782R, as compared to SEQ ID NO.16. The second polymerase contained two amino acid substitutions as compared to SEQ ID NO.16 (782R and 718K). The third polymerase contained one amino acid substitution as compared to SEQ ID NO.16 (718K). The fourth polymerase contained three amino acid substitutions as compared to SEQ ID NO.16 (E515K, N529R and D718K). For each polymerase, the following polymerase activities were assessed AQ17 bases, SNR, raw read accuracy, and systematic error (measured in this Example as percentage of stochastic errors in sequence motifs containing homopolymers of length 1-6, with systematic deletion occurring on strand with a frequency greater than 15%, when coverage (of the sequencing run) is equal to or greater than 20×), among others. The data from this Example is presented in FIG. 26.

Example 26

Comparing Performance of Modified and Reference Polymerases in Nucleic Acid Sequencing In this example, two polymerases prepared according to Example 15, having one or more amino acid mutations with respect to the amino acid sequence of SEQ ID NO. 16 were assessed for various polymerase activities. The first polymerase contained three amino acid substitutions as compared to SEQ ID NO: 16 (782R, 718K and 568N). The second polymerase contained a single amino acid substitution as compared to SEQ ID NO.16 (718K). For each polymerase, the following polymerase activities were assessed AQ20 bases, SNR, raw read accuracy, and systematic error (measured in this Example as percentage of stochastic errors in sequence motifs containing homopolymers of length 1-6, with systematic deletion occurring on strand with a frequency greater than 15%, when coverage (of the sequencing run) is equal to or greater than 20×), among others. The data from this Example is presented in FIG. 27.

Example 27

Comparing Performance of Modified and Reference Polymerases in Nucleic Acid Sequencing In this example, two polymerases prepared according to Example 15, having one or more amino acid mutations with respect to the amino acid sequence of SEQ ID NO: 16 was assessed for various polymerase activities. The first polymerase contained two amino acid substitutions as compared to SEQ ID NO: 16 (782R and 576M). The second polymerase contained a single amino acid substitution as compared to SEQ ID NO:16 (718K). For each polymerase, the following polymerase activities were assessed AQ20 bases, SNR and raw read accuracy, among others. The data from this Example is presented in FIG. 28.

Example 28

Comparing Performance of Modified Polymerases for Systematic Error

In this example, two modified polymerases were prepared according to Example 1. The two modified polymerases were SEQ ID NO: 34 and SEQ ID NO: 35.

SEQ ID NO: 34 contain five amino acid substitutions as compared to SEQ ID NO: 2, namely N487R, H281M, D264A, H273N and E493R.

SEQ ID NO: 35 contain three amino acid substitutions as compared to SEQ ID NO: 2, namely N487R, H281M and D423K.

In this example, the method was catered to assess systematic error. It will be readily apparent to the skilled artisan that the method disclosed herein can be modified to assess other metrics associated with systematic error, or the method can be modified to measure one or more other metrics associated with polymerase activity such as template dissociation constant.

The modified polymerases were prepared essentially according to Example 1 and used to assess systematic error using a Personal Genome Machine (PGM™) and Ion PGM 314 or Ion PGM 318 Chips (Life Technologies Corp, CA).

A first set of nucleic acid libraries were prepared using an E. coli 270 bp insert (short insert). A second set of nucleic libraries were prepared using an E. coli 510 bp insert (long insert). The nucleic acid libraries obtained via emulsion PCR (emPCR) reaction were applied downstream to an ion-based sequencing reaction using the Ion Torrent PGM™ sequencing system (Ion Torrent Systems, Part No. 4462917).

Briefly, template nucleic acids were purified, adapter-ligated and size selected as described in User Guide for the Ion Fragment Library Kit (Ion Torrent Systems, Part No. 4466464; Publication Part No. 4467320 Rev B). The template nucleic acids were amplified onto Ion Sphere™ particles as outlined below.

Here, each nucleic acid library undergoing emulsion PCR contained 24 nucleic acid templates having a premature attenuation on one strand, 12 nucleic acid templates that contained a premature attenuation on both strands, 12 nucleic acid templates that contained extreme strand bias, 24 nucleic acid templates that contained systematic strand error, 12 nucleic acid templates that contained high GC content and 12 nucleic acid templates that regularly performed well under the proposed sequencing conditions.

Ion Sphere Particles (ISPs, 20-40 Million) for each of the barcoded emulsions were added separately to individual PCR tubes. The tubes were then filled with Annealing buffer and vortexed. The tubes were spun at max speed (16,500 RPM) for 4 minutes in a table top centrifuge and supernatant was removed. Sequencing primer was added, mixed by pipetting, and annealed to beads by thermocycling. The resuspended primer-annealed ISPs were added to each well of a plate to yield 400,000 beads per well. SEQ ID NO: 34 or SEQ ID NO: 35 modified polymerases was added to an aliquot of each nucleic acid library (long and short E. coli inserts). The modified polymerases and ISPs were incubated at room temperature for 40 min followed by the addition of a mixture of α-thio dGTP/α-thio dTTP to allow for enrichment of the amplified nucleic acid libraries. All wells (per modified polymerase) were combined into a reservoir, transferred to a 2 ml tube, and spun at maximum speed for 3 minutes. The supernatant was removed, the tube vortexed briefly, and then placed tube on a magnetic block. The sample was incubated on the magnetic block for 30 seconds, the supernatant was removed and the entire sample was loaded onto an Ion 314 or an Ion 318 Chip (Life Technologies, CA) using the standard loading protocol provided by the manufacturer. After loading was complete, the 314 or 318 Ion chip was washed by pipetting wash solution through the loading port. The wash step was repeated twice, for a total of 3 washes. All liquid was removed from the chip prior to loading on the Ion PGM (Life Technologies, CA, Catalog No. 4462921) and sequenced with the standard Sequencing kit (Life Technologies, CA) according to the manufacturers instructions.

The resulting sequencing runs obtained were assessed for systematic error. In particular, metrics such as AQ47 bases (total sequencing throughput), AQ47 mean, raw read accuracy, SNR (signal to noise ratio) and systematic error (SSE)(measured as a percentage of stochastic errors in sequence motifs containing homopolymers of length 1-6, with a systematic deletion occurring on strand with a frequency greater than 15%, when coverage (of the sequencing run) is equal to or greater than $20\chi$) were measured.

Figure 29:
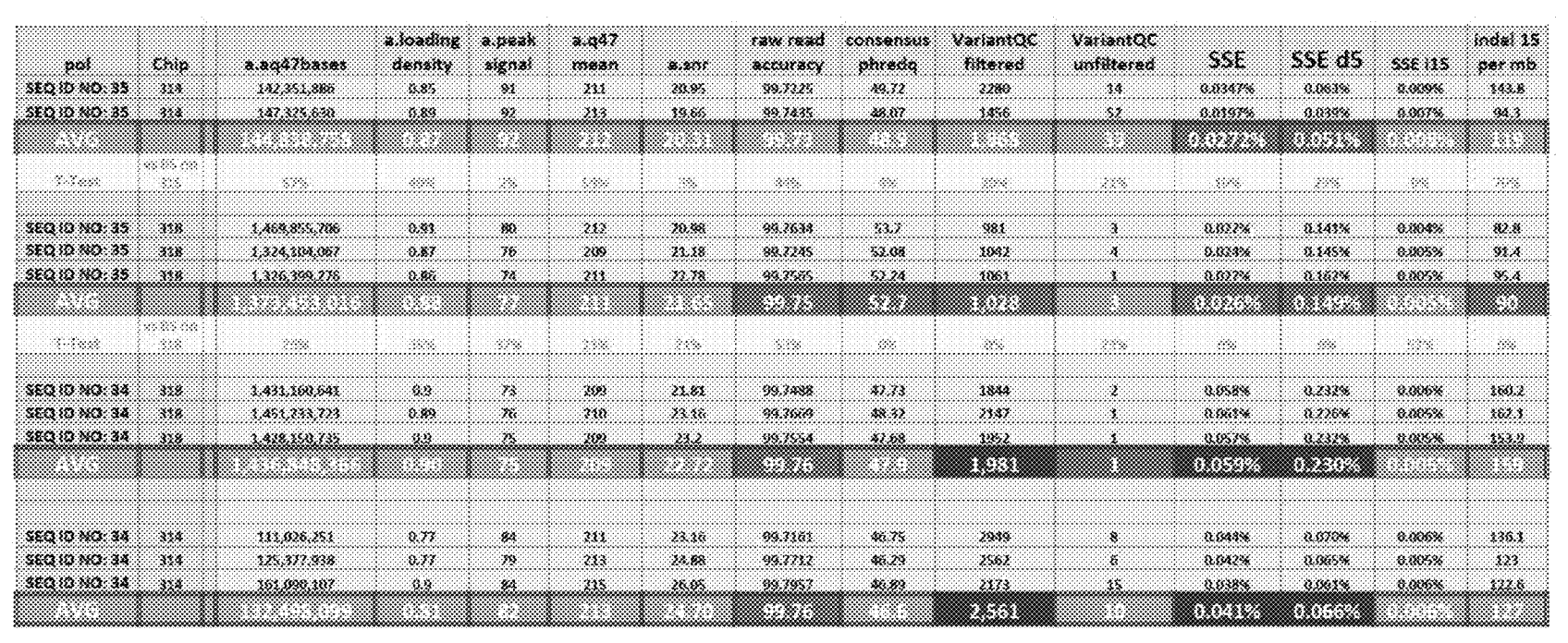
Figure 30:
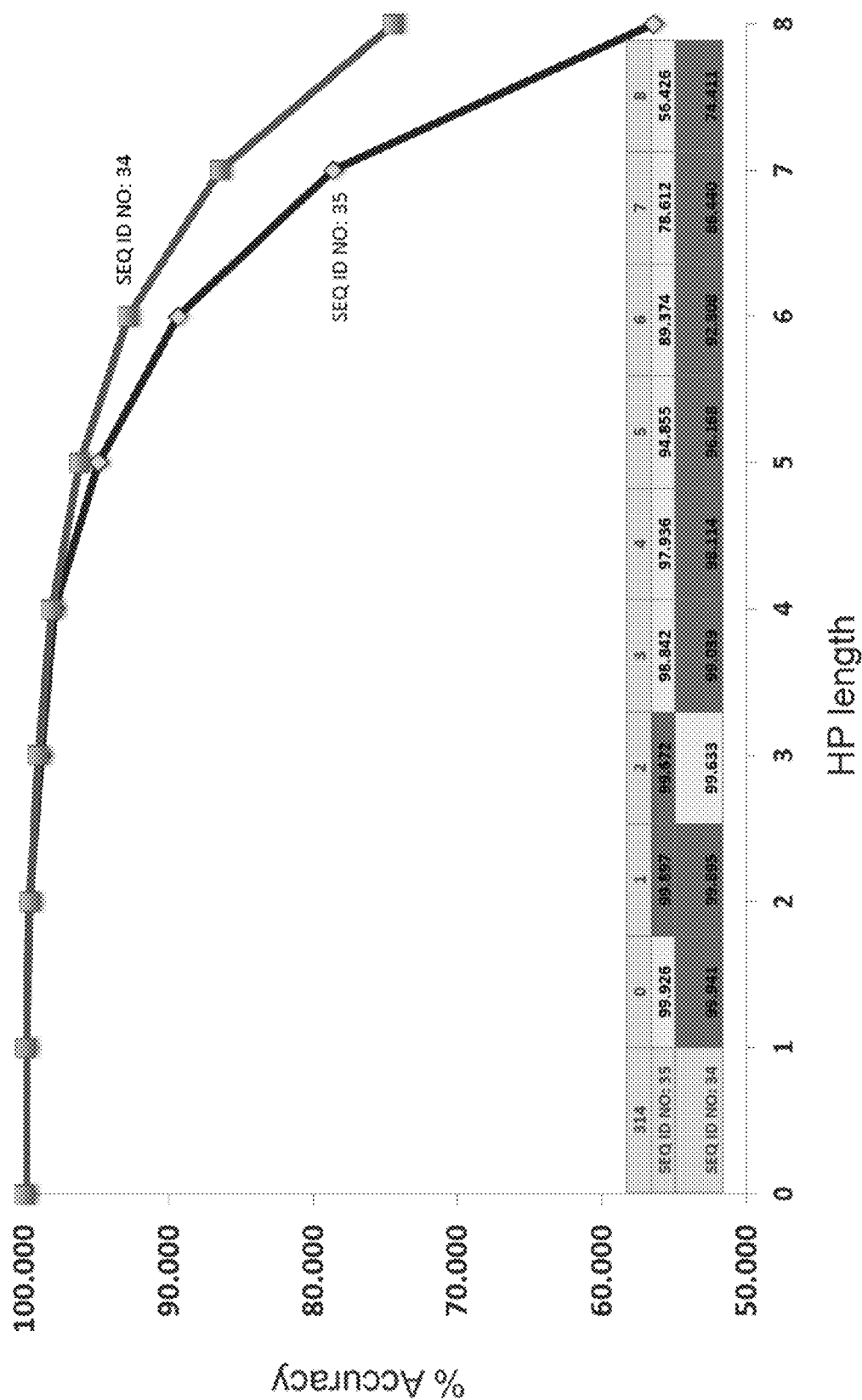
FIG. 30 is a graph and table showing exemplary homopolymer data performed using exemplary modified polymerases obtained according to the disclosure.
Figure 31:
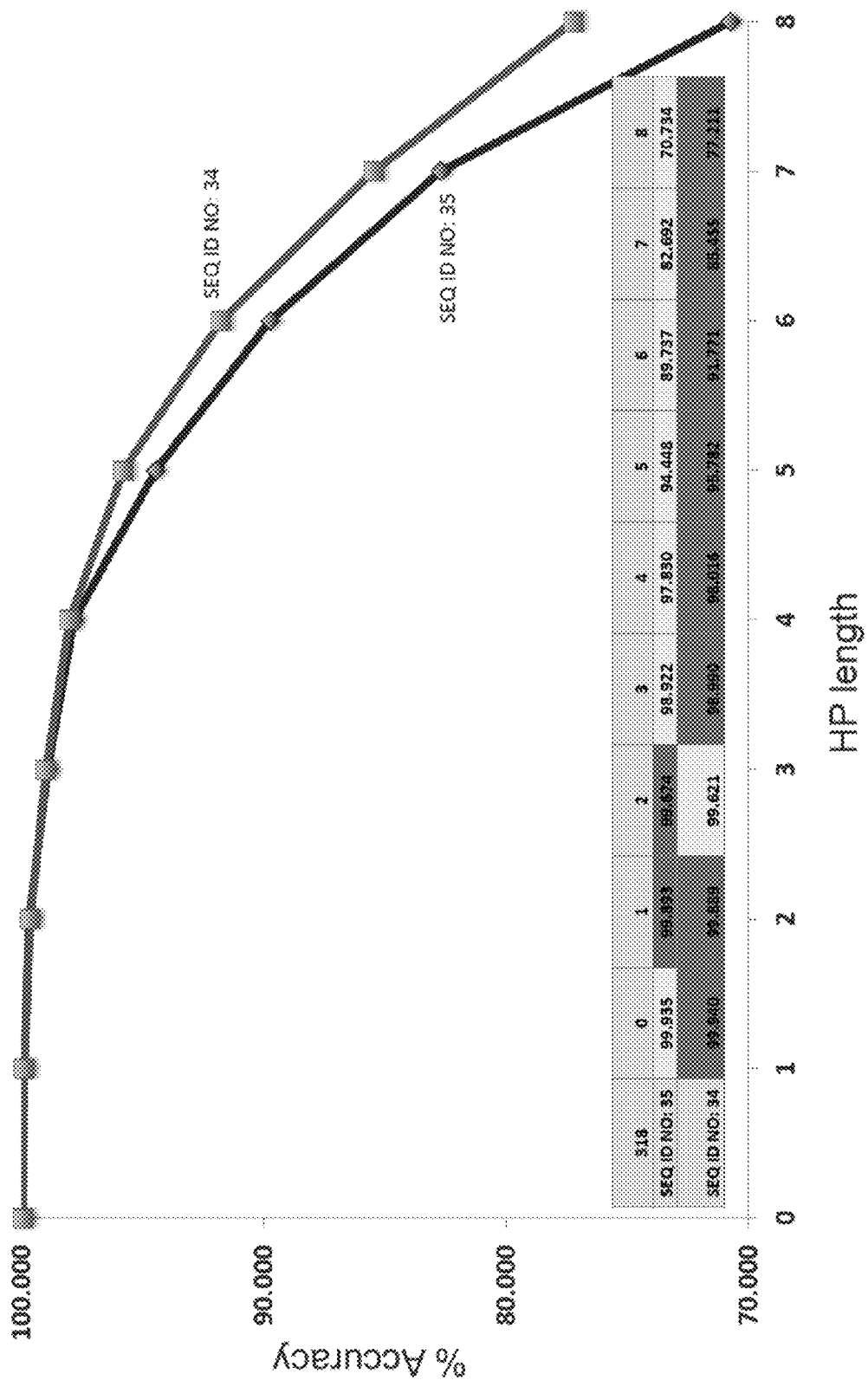
FIG. 31 is a graph and table showing exemplary homopolymer data performed using exemplary modified polymerases obtained according to the disclosure.

Data for an exemplary sequencing run using SEQ ID NO: 34 or SEQ ID NO: 35 in combination with the short insert E. coli library on an Ion 314 chip or Ion 318 chip is shown in FIG. 29. A graph showing exemplary homopolymer data performed using the short insert E. coli library on an Ion 314 chip is shown in FIG. 30. A graph showing exemplary homopolymer data performed using the short insert E. coli library on an Ion 318 chip is shown in FIG. 31.

Figure 32:
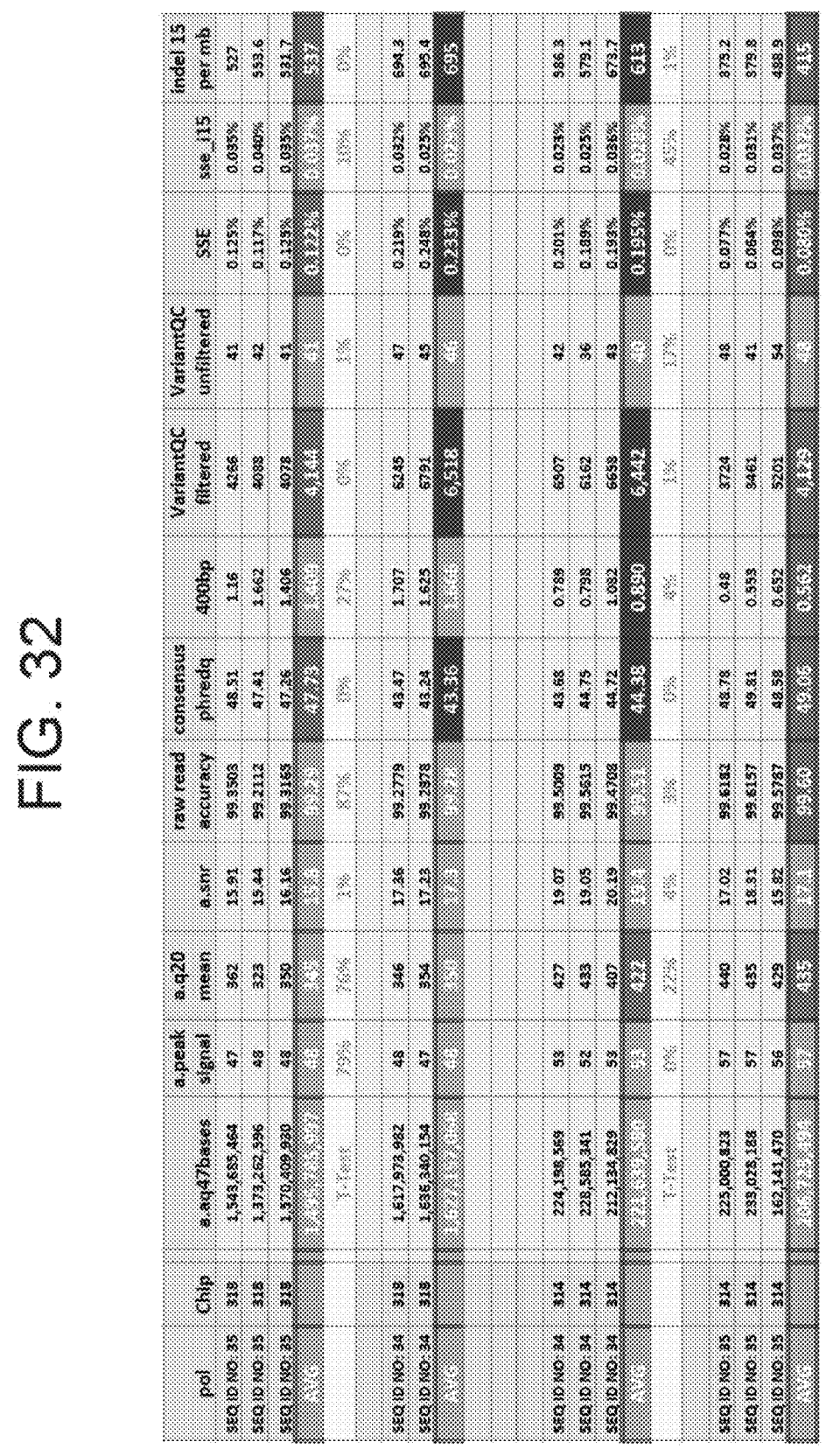
Figure 33:
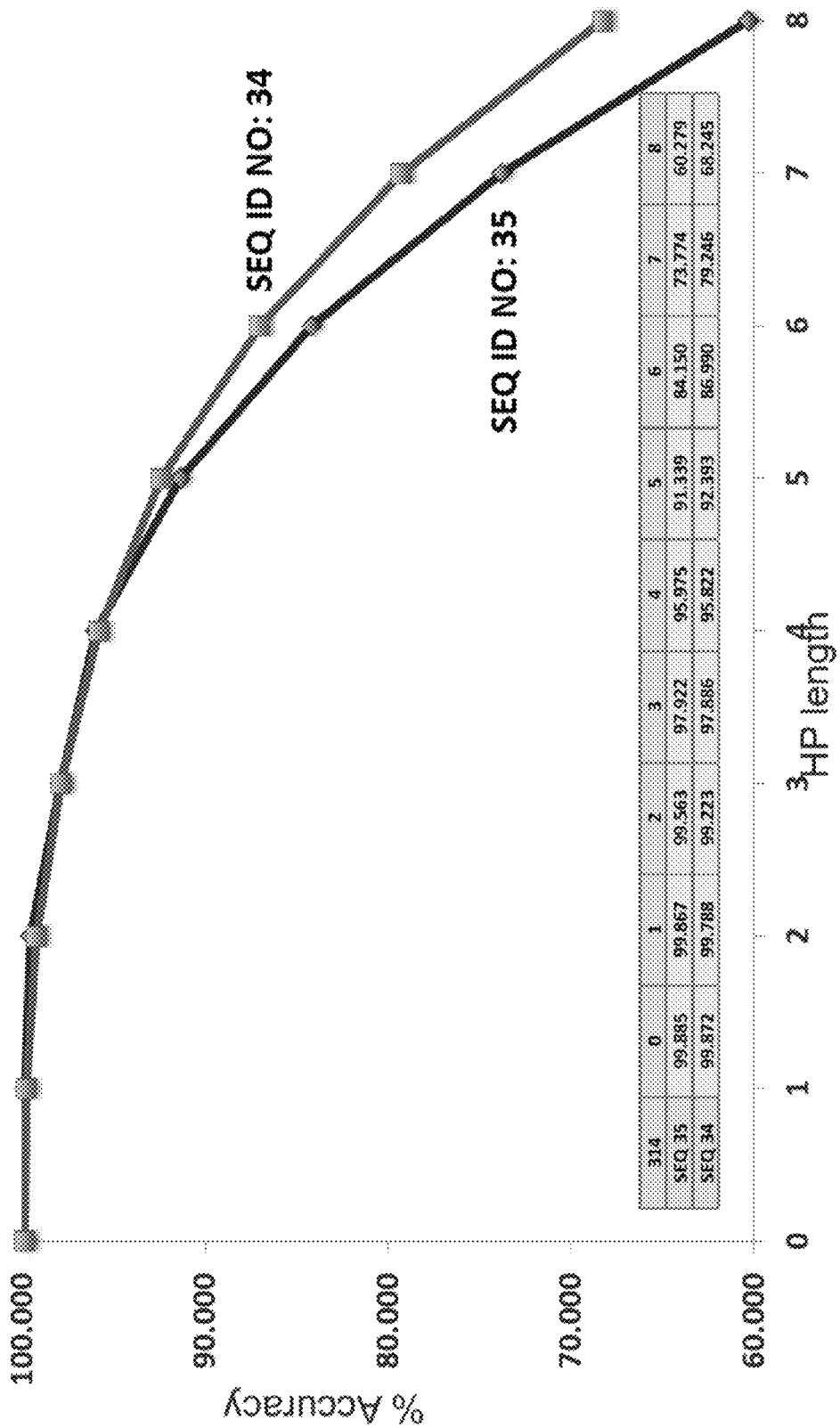
FIG. 33 is a graph and table showing exemplary homopolymer data performed using exemplary modified polymerases obtained according to the disclosure.
Figure 34:
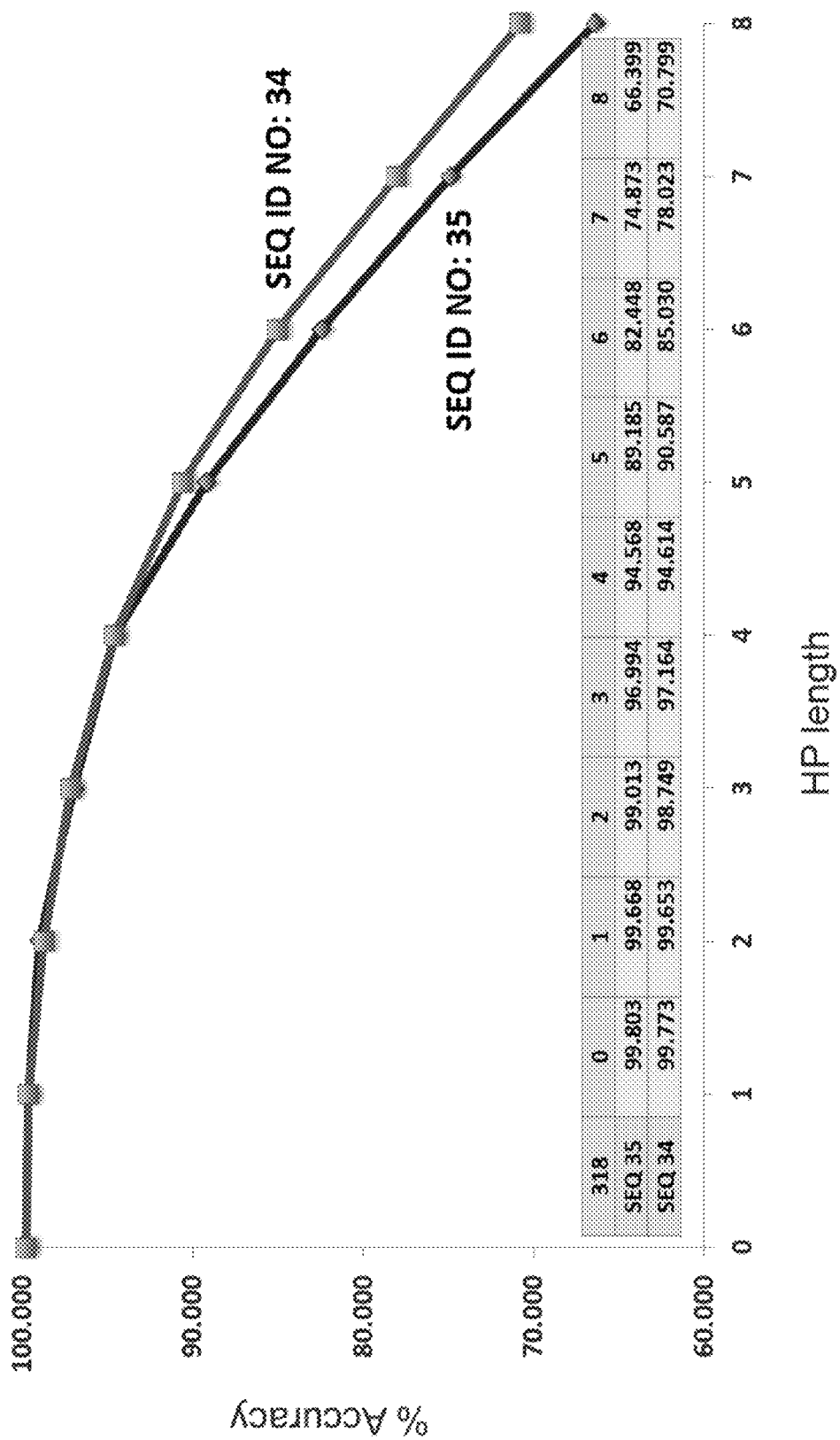
FIG. 34 is a graph and table showing exemplary homopolymer data performed using exemplary modified polymerases obtained according to the disclosure.

Additional data for an exemplary sequencing run using SEQ ID NO: 34 or SEQ ID NO: 35 in combination with the long insert E. coli library on an Ion 314 chip or Ion 318 chip is shown in FIG. 32. A graph showing exemplary homopolymer data performed using the long insert E. coli library on an Ion 314 chip is shown in FIG. 33. A graph showing exemplary homopolymer data performed using the long insert E. coli library on an Ion 318 chip is shown in FIG. 34.

Example 29

Comparing Performance of Modified Polymerases for Systematic Error

In this example, two modified polymerases were prepared according to Example 1. The two modified polymerases were LR2 and SEQ ID NO: 35.

LR2 contains two amino acid substitutions as compared to SEQ ID NO: 2 namely D264K and E493Q.

SEQ ID NO: 35 contain three amino acid substitutions as compared to SEQ ID NO: 2, namely N487R, H281M and D423K.

In this example, the method was catered to assess systematic error. It will be readily apparent to the skilled artisan that the method disclosed herein can be modified to assess other metrics associated with systematic error, or the method can be modified to measure one or more other metrics associated with polymerase activity such as template dissociation constant.

The modified polymerases were prepared essentially according to Example 1 and used to assess systematic error using a Personal Genome Machine (PGM™) and Ion PGM 314 and Ion PGM 318 Chips (Life Technologies Corp, CA).

Nucleic acid libraries were prepared using an E. coli 270 bp insert (short insert). The nucleic acid libraries obtained via emulsion PCR (emPCR) reaction were applied downstream to an ion-based sequencing reaction using the Ion Torrent PGM™ sequencing system (Ion Torrent Systems, Part No. 4462917).

Briefly, template nucleic acids were purified, adapter-ligated and size selected as described in User Guide for the Ion Fragment Library Kit (Ion Torrent Systems, Part No. 4466464; Publication Part No. 4467320 Rev B). The template nucleic acids were amplified onto Ion Sphere™ particles as outlined below.

Here, the nucleic acid libraries undergoing emulsion PCR contained 24 nucleic acid templates having a premature attenuation on one strand, 12 nucleic acid templates that contained a premature attenuation on both strands, 12 nucleic acid templates that contained extreme strand bias, 24 nucleic acid templates that contained systematic strand error, 12 nucleic acid templates that contained high GC content and 12 nucleic acid templates that regularly performed well under the proposed sequencing conditions.

Ion Sphere Particles (ISPs, 20-40 Million) for each of the barcoded emulsions were added separately to individual PCR tubes. The tubes were then filled with Annealing buffer and vortexed. The tubes were spun at max speed (16,500 RPM) for 4 minutes in a table top centrifuge and supernatant was removed. Sequencing primer was added, mixed by pipetting, and annealed to beads by thermocycling. The resuspended primer-annealed ISPs were added to each well of a plate to yield 400,000 beads per well. LR2 or SEQ ID NO: 35 modified polymerases were added to an aliquot of the nucleic acid library (short E. coli insert). The modified polymerases and ISPs were incubated at room temperature for 40 min followed by the addition of a mixture of α-thio dGTP/α-thio dTTP to allow for enrichment of the amplified nucleic acid libraries. All wells (per modified polymerase) were combined into a reservoir, transferred to a 2 ml tube, and spun at maximum speed for 3 minutes. The supernatant was removed, the tube vortexed briefly, and then placed tube on a magnetic block. The sample was incubated on the magnetic block for 30 seconds, the supernatant was removed and the entire sample was loaded onto an Ion 314 or an Ion 318 Chip (Life Technologies, CA) using the standard loading protocol provided by the manufacturer. After loading was complete, the 314 or 318 Ion chip was washed by pipetting wash solution through the loading port. The wash step was repeated twice, for a total of 3 washes. All liquid was removed from the chip prior to loading on the Ion PGM (Life Technologies, CA, Catalog No. 4462921) and sequenced with the standard Sequencing kit (Life Technologies, CA) according to the manufacturers instructions.

The resulting sequencing runs obtained were assessed for systematic error. In particular, metrics such as AQ47 bases (total sequencing throughput), AQ20 mean, raw read accuracy, and systematic error (SSE) were measured.

Data for an exemplary sequencing run using modified polymerases LR2 or SEQ ID NO: 35 in combination with the short insert E. coli library on an Ion 314 chip or Ion 318 chip is shown in FIG. 35. In this example, SEQ ID NO: 35 showed a 10-fold improvement for filtered variants and SSE as compared to LR2 under the same conditions.

The invention claimed is:

1. A composition comprising an isolated recombinant polypeptide comprising a polymerase polypeptide having an amino acid sequence at least 90% identical to SEQ ID NO: 35 and maintaining substitutions H46R, E446Q, H572R, N487R, D423K, and H281M, wherein the isolated recombinant polypeptide has DNA polymerase activity.

2. The composition of claim 1, wherein the isolated recombinant polypeptide has the amino acid sequence of SEQ ID NO: 35.

3. The composition of claim 1, wherein the polymerase polypeptide has the amino acid sequence of SEQ ID NO: 35.

4. The composition of claim 1, wherein the polymerase polypeptide has an amino acid sequence having at least 95% identity to SEQ ID NO: 35.

5. The composition of claim 1, wherein the polymerase polypeptide has an amino acid sequence having at least 98% identity to SEQ ID NO: 35.

6. The composition of claim 1, wherein the polymerase polypeptide has an amino acid sequence having at least 99% identity to SEQ ID NO: 35.

7. The composition of claim 1, wherein the isolated recombinant polypeptide exhibits a decreased systematic error in a sequencing system that uses an ion-based DNA sequencing reaction as compared to LR2 which is DNA polymerase having the amino acid sequence of SEQ ID NO: 2 further comprising mutations D264K and E493Q.

8. A method for performing DNA polymerization comprising:
   (a) providing a reaction mixture comprising the composition of claim 1, and a nucleic acid hybridized to a primer; and
   (b) contacting the nucleic acid with at least one type of nucleotide, wherein the contacting includes incorporating at least one nucleotide onto the primer thereby generating an extended primer product.

9. The method of claim 8, wherein the polymerase polypeptide in the composition of claim 1 further includes one or more amino acid substitutions selected from the group consisting of N485K, E493R, A263K, D264A, D264R, H528S, H528F, H273N, and D480R.

10. A method for obtaining DNA sequence information from a nucleic acid template, comprising:
   (a) providing a reaction mixture comprising the composition of claim 1, and a template nucleic acid hybridized to a sequencing primer;
   (b) contacting the template nucleic acid with at least one type of nucleotide, wherein the contacting includes incorporating one or more nucleotides from the at least one type of nucleotide onto the 3' end of the sequencing primer and generating an extended primer product;
   (c) detecting the presence of the extended primer product in the reaction mixture, thereby determining whether nucleotide incorporation has occurred; and
   (d) identifying at least one of the one or more nucleotides incorporated from the at least one type of nucleotide.

11. The method of claim 10, wherein the polymerase polypeptide in the composition of claim 1 further includes one or more amino acid substitutions selected from the group consisting of N485K, E493R, A263K, D264A, D264R, H528S, H528F, H273N, and D480R.

* * * * *

SEQUENCE LISTING

<160> NUMBER OF SEQ ID NOS: 37

<210> SEQ ID NO 1
<211> LENGTH: 581
<212> TYPE: PRT
<213> ORGANISM: Artificial Sequence
<220> FEATURE:
<223> OTHER INFORMATION: Synthetic: large fragment of Bst DNA polymerase

<400> SEQUENCE: 1

```
Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu His Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190
```

Met Glu Phe Ala Gly Val Lys Val Asp Thr Lys Arg Leu Glu Gln Met
            195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Glu Ser Phe
        435                 440                 445

Pro Gly Val Lys Arg Tyr Met Glu Asn Ile Val Gln Glu Ala Lys Gln
450                 455                 460

Lys Gly Tyr Val Thr Thr Leu Leu His Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr His Tyr Gly Ser Thr
                565                 570                 575

Trp Tyr Asp Ala Lys
            580

<210> SEQ ID NO 2
<211> LENGTH: 581
<212> TYPE: PRT

<213> ORGANISM: Artificial Sequence
<220> FEATURE:
<223> OTHER INFORMATION: Synthetic: large fragment Bst DNA polymerase

<400> SEQUENCE: 2

```
Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
```

```
                385                 390                 395                 400
Glu Val Thr Pro Asn Met Arg Arg Gln Ala Lys Ala Val Asn Phe Gly
                    405                 410                 415
Ile Val Tyr Gly Ile Ser Asp Tyr Gly Leu Ala Gln Asn Leu Asn Ile
                420                 425                 430
Ser Arg Lys Glu Ala Ala Glu Phe Ile Glu Arg Tyr Phe Gln Ser Phe
            435                 440                 445
Pro Gly Val Lys Arg Tyr Met Glu Asn Ile Val Gln Glu Ala Lys Gln
        450                 455                 460
Lys Gly Tyr Val Thr Thr Leu Leu His Arg Arg Tyr Leu Pro Asp
465                 470                 475                 480
Ile Thr Ser Arg Asn Phe Asn Val Arg Ser Phe Ala Glu Arg Met Ala
                    485                 490                 495
Met Asn Thr Pro Ile Gln Gly Ser Ala Ala Asp Ile Ile Lys Lys Ala
                500                 505                 510
Met Ile Asp Leu Asn Ala Arg Leu Lys Glu Glu Arg Leu Gln Ala His
            515                 520                 525
Leu Leu Leu Gln Val His Asp Glu Leu Ile Leu Glu Ala Pro Lys Glu
        530                 535                 540
Glu Met Glu Arg Leu Cys Arg Leu Val Pro Glu Val Met Glu Gln Ala
545                 550                 555                 560
Val Thr Leu Arg Val Pro Leu Lys Val Asp Tyr Arg Tyr Gly Ser Thr
                    565                 570                 575
Trp Tyr Asp Ala Lys
                580

<210> SEQ ID NO 3
<211> LENGTH: 581
<212> TYPE: PRT
<213> ORGANISM: Artificial Sequence
<220> FEATURE:
<223> OTHER INFORMATION: Synthetic:

<400> SEQUENCE: 3

Met Ala Lys Met Ala Phe Thr Leu Ala Asp Arg Val Thr Glu Glu Met
1               5                   10                  15
Leu Ala Asp Lys Ala Ala Leu Val Val Glu Val Val Glu Glu Asn Tyr
                20                  25                  30
His Asp Ala Pro Ile Val Gly Ile Ala Val Val Asn Glu Arg Gly Arg
            35                  40                  45
Phe Phe Leu Arg Pro Glu Thr Ala Leu Ala Asp Pro Gln Phe Val Ala
        50                  55                  60
Trp Leu Gly Asp Glu Thr Lys Lys Lys Ser Met Phe Asp Ser Lys Arg
65                  70                  75                  80
Ala Ala Val Ala Leu Lys Trp Lys Gly Ile Glu Leu Cys Gly Val Ser
                85                  90                  95
Phe Asp Leu Leu Leu Ala Ala Tyr Leu Leu Asp Pro Ala Gln Gly Val
                100                 105                 110
Asp Asp Val Ala Ala Ala Ala Lys Met Lys Gln Tyr Glu Ala Val Arg
            115                 120                 125
Pro Asp Glu Ala Val Tyr Gly Lys Gly Ala Lys Arg Ala Val Pro Asp
        130                 135                 140
Glu Pro Val Leu Ala Glu His Leu Val Arg Lys Ala Ala Ala Ile Trp
145                 150                 155                 160
Glu Leu Glu Arg Pro Phe Leu Asp Glu Leu Arg Arg Asn Glu Gln Asp
```

```
                165                 170                 175
Arg Leu Leu Val Glu Leu Glu Gln Pro Leu Ser Ser Ile Leu Ala Glu
                    180                 185                 190

Met Glu Phe Ala Gly Val Lys Val Asp Thr Lys Arg Leu Glu Gln Met
                195                 200                 205

Gly Lys Glu Leu Ala Glu Gln Leu Gly Thr Val Glu Gln Arg Ile Tyr
            210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
                260                 265                 270

His Glu Ile Val Glu Asn Ile Leu His Tyr Arg Gln Leu Gly Lys Leu
            275                 280                 285

Gln Ser Thr Tyr Ile Glu Gly Leu Leu Lys Val Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
                355                 360                 365

His Ile Ala Glu Asp Asp Asn Leu Met Glu Ala Phe Arg Arg Asp Leu
            370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
                435                 440                 445

Pro Gly Val Lys Arg Tyr Met Glu Asn Ile Val Gln Glu Ala Lys Gln
            450                 455                 460

Lys Gly Tyr Val Thr Thr Leu Leu Arg Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
            515                 520                 525

Leu Leu Leu Gln Val His Asp Glu Leu Ile Leu Glu Ala Pro Lys Glu
        530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580
```

```
<210> SEQ ID NO 4
<211> LENGTH: 581
<212> TYPE: PRT
<213> ORGANISM: Artificial Sequence
<220> FEATURE:
<223> OTHER INFORMATION: Synthetic:

<400> SEQUENCE: 4

Met Ala Lys Met Ala Phe Thr Leu Ala Asp Arg Val Thr Glu Met
1               5                   10                  15

Leu Ala Asp Lys Ala Ala Leu Val Val Glu Val Val Glu Glu Asn Tyr
                20                  25                  30

His Asp Ala Pro Ile Val Gly Ile Ala Val Val Asn Glu Arg Gly Arg
                35                  40                  45

Phe Phe Leu Arg Pro Glu Thr Ala Leu Ala Asp Pro Gln Phe Val Ala
50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
                100                 105                 110

Asp Asp Val Ala Ala Ala Lys Met Lys Gln Tyr Glu Ala Val Arg
                115                 120                 125

Pro Asp Glu Ala Val Tyr Gly Lys Gly Ala Lys Arg Ala Val Pro Asp
                130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
                180                 185                 190

Met Glu Phe Ala Gly Val Lys Val Asp Thr Lys Arg Leu Glu Gln Met
                195                 200                 205

Gly Lys Glu Leu Ala Glu Gln Leu Gly Thr Val Glu Gln Arg Ile Tyr
                210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
                260                 265                 270

Arg Glu Ile Val Glu Asn Ile Leu Ala Tyr Arg Gln Leu Gly Lys Leu
                275                 280                 285

Gln Ser Thr Tyr Ile Glu Gly Leu Leu Lys Val Val Arg Pro Asp Thr
                290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
                340                 345                 350

Leu Ile Phe Ala Ala Asp Tyr Ser Gln Ile Glu Leu Arg Val Leu Ala
                355                 360                 365
```

```
His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
    450                 455                 460

Lys Gly Tyr Val Thr Thr Leu Leu Arg Arg Arg Phe Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
        515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 5
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 5

Asp Xaa Ser Xaa Xaa Glu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(7)
<223> OTHER INFORMATION: Xaa can be any naturally occurring amino acid

<400> SEQUENCE: 6

Lys Xaa Xaa Xaa Xaa Xaa Xaa Tyr Gly
```

```
<210> SEQ ID NO 7
<211> LENGTH: 4
<212> TYPE: PRT
<213> ORGANISM: Artificial Sequence
<220> FEATURE:
<223> OTHER INFORMATION: Synthetic

<400> SEQUENCE: 7

Val His Asp Glu
1

<210> SEQ ID NO 8
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid

<400> SEQUENCE: 8

Asp Xaa Xaa Ser Leu Tyr Pro Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 9

Lys Xaa Xaa Xaa Asn Ser Xaa Tyr Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Tyr Gly Asp Thr Asp Ser
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
```

```
<222> LOCATION: (6)..(6)
<223> OTHER INFORMATION: Xaa is Phe or Tyr

<400> SEQUENCE: 11

Asp Xaa Xaa Xaa Xaa Xaa
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa is Ser or Ala

<400> SEQUENCE: 12

Phe Xaa Gly Xaa Xaa Xaa Xaa
1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 13

Tyr Xaa Asp Asp
1

<210> SEQ ID NO 14
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(8)
<223> OTHER INFORMATION: Xaa can be any naturally occurring amino acid

<400> SEQUENCE: 14

Gly Xaa Xaa Xaa Xaa Xaa Xaa Xaa Lys
1               5

<210> SEQ ID NO 15
<211> LENGTH: 832
<212> TYPE: PRT
<213> ORGANISM: Artificial Sequence
<220> FEATURE:
<223> OTHER INFORMATION: Synthetic:

<400> SEQUENCE: 15

Met Arg Gly Met Leu Pro Leu Phe Glu Pro Lys Gly Arg Val Leu Leu
1               5                   10                  15
```

```
Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
 50                  55                  60

Val Phe Asp Ala Lys Ala Pro Ser Phe Arg His Glu Ala Tyr Gly Gly
 65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430
```

```
Val Glu Arg Pro Leu Ser Ala Val Leu Ala His Met Glu Ala Thr Gly
            435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
        675                 680                 685

Ala Gln Ala Phe Ile Glu Arg Tyr Phe Gln Ser Phe Pro Lys Val Arg
    690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
        755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 16
<211> LENGTH: 876
<212> TYPE: PRT
```

<213> ORGANISM: Artificial Sequence
<220> FEATURE:
<223> OTHER INFORMATION: Synthetic:

<400> SEQUENCE: 16

```
Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Glu Pro Thr His Met Leu Val Ala Phe Asp Ala Gly Lys Thr Thr
    50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                85                  90                  95

Ala Tyr Arg Ile Pro Ala Tyr Glu Leu Glu Asn Tyr Glu Ala Asp Asp
            100                 105                 110

Ile Ile Gly Thr Leu Ala Ala Arg Ala Glu Gln Glu Gly Phe Glu Val
        115                 120                 125

Lys Val Ile Ser Gly Asp Arg Asp Leu Thr Gln Leu Ala Ser Pro His
130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Arg Gln Phe
        195                 200                 205

Gly Thr Val Glu Asn Val Leu Ala Ser Ile Asp Glu Ile Lys Gly Glu
    210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Glu Lys Val Val Ala Leu
            260                 265                 270

Phe Lys Glu Leu Gly Phe Gln Ser Phe Leu Glu Lys Met Glu Ser Pro
        275                 280                 285

Ser Ser Glu Glu Glu Lys Pro Leu Ala Lys Met Ala Phe Thr Leu Ala
    290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
        355                 360                 365

Ser Met Phe Asp Ser Lys Arg Ala Ala Val Ala Leu Lys Trp Lys Gly
    370                 375                 380

Ile Glu Leu Cys Gly Val Ser Phe Asp Leu Leu Leu Ala Ala Tyr Leu
```

```
385                 390                 395                 400
Leu Asp Pro Ala Gln Gly Val Asp Val Ala Ala Ala Lys Met
            405                 410                 415

Lys Gln Tyr Glu Ala Val Arg Pro Asp Glu Ala Val Tyr Gly Lys Gly
            420                 425                 430

Ala Lys Arg Ala Val Pro Asp Glu Pro Val Leu Ala Glu His Leu Val
            435                 440                 445

Arg Lys Ala Ala Ala Ile Trp Glu Leu Glu Arg Pro Phe Leu Asp Glu
            450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
            485                 490                 495

Thr Lys Arg Leu Glu Gln Met Gly Lys Glu Leu Ala Glu Gln Leu Gly
            500                 505                 510

Thr Val Glu Gln Arg Ile Tyr Glu Leu Ala Gly Gln Glu Phe Asn Ile
            515                 520                 525

Asn Ser Pro Lys Gln Leu Gly Val Ile Leu Phe Glu Lys Leu Gln Leu
            530                 535                 540

Pro Val Leu Lys Lys Thr Lys Thr Gly Tyr Ser Thr Ser Ala Asp Val
545                 550                 555                 560

Leu Glu Lys Leu Ala Pro Tyr His Glu Ile Val Glu Asn Ile Leu His
            565                 570                 575

Tyr Arg Gln Leu Gly Lys Leu Gln Ser Thr Tyr Ile Glu Gly Leu Leu
            580                 585                 590

Lys Val Val Arg Pro Asp Thr Lys Lys Val His Thr Ile Phe Asn Gln
            595                 600                 605

Ala Leu Thr Gln Thr Gly Arg Leu Ser Ser Thr Glu Pro Asn Leu Gln
            610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
            645                 650                 655

Ile Glu Leu Arg Val Leu Ala His Ile Ala Glu Asp Asp Asn Leu Met
            660                 665                 670

Glu Ala Phe Arg Arg Asp Leu Asp Ile His Thr Lys Thr Ala Met Asp
            675                 680                 685

Ile Phe Gln Val Ser Glu Asp Glu Val Thr Pro Asn Met Arg Arg Gln
            690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Ser Arg Lys Glu Ala Ala Glu Phe Ile
            725                 730                 735

Glu Arg Tyr Phe Glu Ser Phe Pro Gly Val Lys Arg Tyr Met Glu Asn
            740                 745                 750

Ile Val Gln Glu Ala Lys Gln Lys Gly Tyr Val Thr Thr Leu Leu His
            755                 760                 765

Arg Arg Arg Tyr Leu Pro Asp Ile Thr Ser Arg Asn Phe Asn Val Arg
            770                 775                 780

Ser Phe Ala Glu Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
            805                 810                 815
```

```
Glu Arg Leu Gln Ala His Leu Leu Leu Gln Val His Asp Glu Leu
        820                 825                 830
Ile Leu Glu Ala Pro Lys Glu Met Glu Arg Leu Cys Arg Leu Val
        835                 840                 845
Pro Glu Val Met Glu Gln Ala Val Thr Leu Arg Val Pro Leu Lys Val
        850                 855                 860
Asp Tyr His Tyr Gly Ser Thr Trp Tyr Asp Ala Lys
865                 870                 875
```

<210> SEQ ID NO 17
<211> LENGTH: 1746
<212> TYPE: DNA
<213> ORGANISM: Artificial Sequence
<220> FEATURE:
<223> OTHER INFORMATION: Synthetic:

<400> SEQUENCE: 17

| | | |
|---|---|---|
| atggcaaaaa tggcatttac cctggcagat cgtgttaccg aagaaatgct ggcagataaa | 60 |
| gcagcactgg ttgttgaagt tgtggaagaa aactatcatg atgcaccgat tgttggtatt | 120 |
| gccgttgtta atgaacgcgg tcgttttttt ctgcgtccgg aaaccgcact ggcagatccg | 180 |
| cagtttgttg catggctggg tgatgaaacc aaaaagaaaa gcatgttcga cagcaaacgt | 240 |
| gcagcagttg cactgaaatg gaaggtatt gaactgtgcg gtgtgtcatt tgatctgctg | 300 |
| ctggcagcat atctgctgga tccggcacag ggtgttgatg atgttgcagc agcagcaaaa | 360 |
| atgaaacagt atgaagcagt tcgtccggat gaagcagttt atggtaaagg tgcaaaacgt | 420 |
| gcagttccgg atgaaccggt tctggcagaa catctggttc gtaaagcagc agcaatttgg | 480 |
| gaactggaac gtccgtttct ggatgaactg cgtcgtaatg aacaggatcg tctgctggtt | 540 |
| gaactggaac agccgctgag cagcattctg gcagaaatgg aatttgccgg tgttaaagtt | 600 |
| gataccaaac gtctggaaca atgggtaaa gaactggccg aacaactggg caccgttgaa | 660 |
| cagcgtattt atgaactggc aggccaagaa tttaacatta tagcccgaa acagctgggc | 720 |
| gttatcctgt ttgaaaaaact gcagctgccg gttctgaaaa aaaccaaaac cggttatagc | 780 |
| accagcgcag atgttctgga aaaactggca ccgtatcatg aaattgtgga aaacattctg | 840 |
| cactatcgtc agctgggtaa actgcagagc acctatattg aaggtctgct gaaagttgtg | 900 |
| cgtccggata ccaaaaagt gcataccatt tttaaccagg cactgaccca gaccggtcgt | 960 |
| ctgagcagca ccgaaccgaa tctgcagaat attccgattc gtctggaaga aggtcgtaaa | 1020 |
| attcgtcagg catttgttcc gagcgaaagc gattggctga ttttgcagc agattatagc | 1080 |
| cagattgaac tgcgtgttct ggcacatatt gccgaagatg ataatctgat ggaagcattt | 1140 |
| cgtcgcgatc tggatattca taccaaaacc gccatggata ttttcaggt tagcgaagat | 1200 |
| gaagtgaccc cgaatatgcg tcgtcaggca aaagcagtta ttttggtat tgtgtatggc | 1260 |
| atcagcgatt atggtctggc acagaatctg aatattagcc gtaaagaagc agccgaattt | 1320 |
| atcgaacgtt actttcagag ctttccgggt gttaaacgct atatggaaaa cattgtccaa | 1380 |
| gaagccaaac agaaaggtta tgttaccacc ctgctgcatc gtcgtcgtta tctgccgcgt | 1440 |
| attaccagcc gtaactttaa tgttcgtagc tttcagaac gcatggcaat gaataccccg | 1500 |
| attcagggta gcgcagcaga tattatcaaa aaagccatga tcgatctgaa cgcacgtctg | 1560 |
| aaagaagaac gtctgcaggc acatttactg ctgcaggttc atgatgaact gattctggaa | 1620 |
| gcaccgaaag aagaaatgga acgtctttgt cgtctggttc cggaagttat ggaacaggca | 1680 |

```
gttaccctgc gtgttccgct gaaagttgat tatcgttatg gtagcacctg gtatgatgcc    1740
aaataa                                                                1746

<210> SEQ ID NO 18
<211> LENGTH: 606
<212> TYPE: PRT
<213> ORGANISM: Artificial Sequence
<220> FEATURE:
<223> OTHER INFORMATION: Synthetic:

<400> SEQUENCE: 18

Met Val Ile Ser Tyr Asp Asn Tyr Val Thr Ile Leu Asp Glu Glu Thr
1               5                   10                  15

Leu Lys Ala Trp Ile Ala Lys Leu Glu Lys Ala Pro Val Phe Ala Phe
            20                  25                  30

Asp Thr Glu Thr Asp Ser Leu Asp Asn Ile Ser Ala Asn Leu Val Gly
        35                  40                  45

Leu Ser Phe Ala Ile Glu Pro Gly Val Ala Ala Tyr Ile Pro Val Ala
    50                  55                  60

His Asp Tyr Leu Asp Ala Pro Asp Gln Ile Ser Arg Glu Arg Ala Leu
65                  70                  75                  80

Glu Leu Leu Lys Pro Leu Leu Glu Asp Glu Lys Ala Leu Lys Val Gly
                85                  90                  95

Gln Asn Leu Lys Tyr Asp Arg Gly Ile Leu Ala Asn Tyr Gly Ile Glu
            100                 105                 110

Leu Arg Gly Ile Ala Phe Asp Thr Met Leu Glu Ser Tyr Ile Leu Asn
        115                 120                 125

Ser Val Ala Gly Arg His Asp Met Asp Ser Leu Ala Glu Arg Trp Leu
    130                 135                 140

Lys His Lys Thr Ile Thr Phe Glu Glu Ile Ala Gly Lys Gly Lys Asn
145                 150                 155                 160

Gln Leu Thr Phe Asn Gln Ile Ala Leu Glu Glu Ala Gly Arg Tyr Ala
                165                 170                 175

Ala Glu Asp Ala Asp Val Thr Leu Gln Leu His Leu Lys Met Trp Pro
            180                 185                 190

Asp Leu Gln Lys His Lys Gly Pro Leu Asn Val Phe Glu Asn Ile Glu
        195                 200                 205

Met Pro Leu Val Pro Val Leu Ser Arg Ile Glu Arg Asn Gly Val Lys
    210                 215                 220

Ile Asp Pro Lys Val Leu His Asn His Ser Glu Glu Leu Thr Leu Arg
225                 230                 235                 240

Leu Ala Glu Leu Glu Lys Lys Ala His Glu Ile Ala Gly Glu Glu Phe
                245                 250                 255

Asn Leu Ser Ser Thr Lys Gln Leu Gln Thr Ile Leu Phe Glu Lys Gln
            260                 265                 270

Gly Ile Lys Pro Leu Lys Lys Thr Pro Gly Gly Ala Pro Ser Thr Ser
        275                 280                 285

Glu Glu Val Leu Glu Glu Leu Ala Leu Asp Tyr Pro Leu Pro Lys Val
    290                 295                 300

Ile Leu Glu Tyr Arg Gly Leu Ala Lys Leu Lys Ser Thr Tyr Thr Asp
305                 310                 315                 320

Lys Leu Pro Leu Met Ile Asn Pro Lys Thr Gly Arg Val His Thr Ser
                325                 330                 335

Tyr His Gln Ala Val Thr Ala Thr Gly Arg Leu Ser Ser Thr Asp Pro
            340                 345                 350
```

Asn Leu Gln Asn Ile Pro Val Arg Asn Glu Glu Gly Arg Arg Ile Arg
            355                 360                 365

Gln Ala Phe Ile Ala Pro Glu Asp Tyr Val Ile Val Ser Ala Asp Tyr
        370                 375                 380

Ser Gln Ile Glu Leu Arg Ile Met Ala His Leu Ser Arg Asp Lys Gly
385                 390                 395                 400

Leu Leu Thr Ala Phe Ala Glu Gly Lys Asp Ile His Arg Ala Thr Ala
                405                 410                 415

Ala Glu Val Phe Gly Leu Pro Leu Glu Thr Val Thr Ser Glu Gln Arg
            420                 425                 430

Arg Ser Ala Lys Ala Ile Asn Phe Gly Leu Ile Tyr Gly Met Ser Ala
            435                 440                 445

Phe Gly Leu Ala Arg Gln Leu Asn Ile Pro Arg Lys Glu Ala Gln Lys
        450                 455                 460

Tyr Met Asp Leu Tyr Phe Glu Arg Tyr Pro Gly Val Leu Glu Tyr Met
465                 470                 475                 480

Glu Arg Thr Arg Ala Gln Ala Lys Glu Gln Gly Tyr Val Glu Thr Leu
                485                 490                 495

Asp Gly Arg Arg Leu Tyr Leu Pro Asp Ile Lys Ser Ser Asn Gly Ala
            500                 505                 510

Arg Arg Ala Ala Ala Glu Arg Ala Ala Ile Asn Ala Pro Met Gln Gly
        515                 520                 525

Thr Ala Ala Asp Ile Ile Lys Arg Ala Met Ile Ala Val Asp Ala Trp
    530                 535                 540

Leu Gln Ala Glu Gln Pro Arg Val Arg Met Ile Met Gln Val His Asp
545                 550                 555                 560

Glu Leu Val Phe Glu Val His Lys Asp Val Asp Ala Val Ala Lys
                565                 570                 575

Gln Ile His Gln Leu Met Glu Asn Cys Thr Arg Leu Asp Val Pro Leu
        580                 585                 590

Leu Val Glu Val Gly Ser Gly Glu Asn Trp Asp Gln Ala His
            595                 600                 605

<210> SEQ ID NO 19
<211> LENGTH: 581
<212> TYPE: PRT
<213> ORGANISM: Artificial Sequence
<220> FEATURE:
<223> OTHER INFORMATION: Synthetic:

<400> SEQUENCE: 19

Met Ala Lys Met Ala Phe Thr Leu Ala Asp Arg Val Thr Glu Glu Met
1               5                   10                  15

Leu Ala Asp Lys Ala Ala Leu Val Glu Val Val Glu Glu Asn Tyr
                20                  25                  30

His Asp Ala Pro Ile Val Gly Ile Ala Val Asn Glu Arg Gly Arg
            35                  40                  45

Phe Phe Leu Arg Pro Glu Thr Ala Leu Ala Asp Pro Gln Phe Val Ala
        50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

```
Asp Asp Val Ala Ala Ala Lys Met Lys Gln Tyr Glu Ala Val Arg
        115                 120                 125
Pro Asp Glu Ala Val Tyr Gly Lys Gly Ala Lys Arg Ala Val Pro Asp
130                 135                 140
Glu Pro Val Leu Ala Glu His Leu Val Arg Lys Ala Ala Ile Trp
145                 150                 155                 160
Glu Leu Glu Arg Pro Phe Leu Asp Glu Leu Arg Arg Asn Glu Gln Asp
                    165                 170                 175
Arg Leu Leu Val Glu Leu Glu Gln Pro Leu Ser Ser Ile Leu Ala Glu
                180                 185                 190
Met Glu Phe Ala Gly Val Lys Val Asp Thr Lys Arg Leu Glu Gln Met
            195                 200                 205
Gly Lys Glu Leu Ala Glu Gln Leu Gly Thr Val Lys Gln Arg Ile Tyr
        210                 215                 220
Glu Leu Ala Gly Gln Glu Phe Asn Ile Arg Ser Pro Lys Gln Leu Gly
225                 230                 235                 240
Val Ile Leu Phe Glu Lys Leu Gln Leu Pro Val Leu Lys Lys Thr Lys
                    245                 250                 255
Thr Gly Tyr Ser Thr Ser Ala Asp Val Leu Glu Lys Leu Ala Pro Tyr
                260                 265                 270
His Glu Ile Val Glu Asn Ile Leu His Tyr Arg Gln Leu Gly Lys Leu
            275                 280                 285
Gln Ser Thr Tyr Ile Glu Gly Leu Leu Lys Val Val Arg Pro Asp Thr
        290                 295                 300
Lys Lys Val His Thr Ile Phe Asn Gln Ala Leu Thr Gln Thr Gly Arg
305                 310                 315                 320
Leu Ser Ser Thr Glu Pro Asn Leu Gln Asn Ile Pro Ile Arg Leu Glu
                    325                 330                 335
Glu Gly Arg Lys Ile Arg Gln Ala Phe Val Pro Ser Glu Ser Asp Trp
                340                 345                 350
Leu Ile Phe Ala Ala Asp Tyr Ser Gln Ile Glu Leu Arg Val Leu Ala
            355                 360                 365
His Ile Ala Glu Asp Asp Asn Leu Met Glu Ala Phe Arg Arg Asp Leu
        370                 375                 380
Asp Ile His Thr Lys Thr Ala Met Asp Ile Phe Gln Val Ser Glu Asp
385                 390                 395                 400
Glu Val Thr Pro Asn Met Arg Arg Gln Ala Lys Ala Val Asn Phe Gly
                    405                 410                 415
Ile Val Tyr Gly Ile Ser Lys Tyr Gly Leu Ala Gln Asn Leu Asn Ile
                420                 425                 430
Ser Arg Lys Glu Ala Ala Glu Phe Ile Glu Arg Tyr Phe Gln Ser Phe
        435                 440                 445
Pro Gly Val Lys Arg Tyr Met Glu Asn Ile Val Gln Glu Ala Lys Gln
    450                 455                 460
Lys Gly Tyr Val Thr Thr Leu Leu His Arg Arg Arg Tyr Leu Pro Asp
465                 470                 475                 480
Ile Thr Ser Arg Asn Phe Asn Val Arg Ser Phe Ala Glu Arg Met Ala
                    485                 490                 495
Met Asn Thr Pro Ile Gln Gly Ser Ala Ala Asp Ile Ile Lys Lys Ala
                500                 505                 510
Met Ile Asp Leu Asn Ala Arg Leu Lys Glu Glu Arg Leu Gln Ala His
        515                 520                 525
```

```
Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
                580

<210> SEQ ID NO 20
<211> LENGTH: 581
<212> TYPE: PRT
<213> ORGANISM: Artificial Sequence
<220> FEATURE:
<223> OTHER INFORMATION: Synthetic:

<400> SEQUENCE: 20

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Lys Gln Arg Ile Tyr
    210                 215                 220

Glu Leu Ala Gly Gln Glu Phe Asn Ile Arg Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Val Arg Pro Asp Thr
    290                 295                 300
```

```
Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
            325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
            405                 410                 415

Ile Val Tyr Gly Ile Ser Lys Tyr Gly Leu Ala Gln Asn Leu Asn Ile
            420                 425                 430

Ser Arg Lys Glu Ala Ala Glu Phe Ile Glu Arg Tyr Phe Gln Ser Phe
            435                 440                 445

Pro Gly Val Lys Arg Tyr Met Glu Asn Ile Val Gln Glu Ala Lys Gln
            450                 455                 460

Lys Gly Tyr Val Thr Thr Leu Leu Arg Arg Arg Arg Tyr Leu Pro Asp
465                 470                 475                 480

Ile Thr Ser Arg Asn Phe Asn Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala Ala
            515                 520                 525

Leu Leu Leu Gln Val His Asp Glu Leu Ile Leu Glu Ala Pro Lys Glu
530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
            565                 570                 575

Trp Tyr Asp Ala Lys
            580

<210> SEQ ID NO 21
<211> LENGTH: 36
<212> TYPE: DNA
<213> ORGANISM: Artificial Sequence
<220> FEATURE:
<223> OTHER INFORMATION: Synthetic: Oligo 221
<220> FEATURE:
<221> NAME/KEY: misc_feature
<222> LOCATION: (34)..(34)
<223> OTHER INFORMATION: n is flourescein-dT

<400> SEQUENCE: 21
tttttttgca ggtgacaggt ttttcctgtc accngc                        36

<210> SEQ ID NO 22
<211> LENGTH: 44
<212> TYPE: DNA
<213> ORGANISM: Artificial Sequence
<220> FEATURE:
<223> OTHER INFORMATION: Synthetic: Hairpin oligo

<400> SEQUENCE: 22
```
tttttttccc tttcctttcg ggtgacaggt ttttcctgtc accc                      44

<210> SEQ ID NO 23
<211> LENGTH: 1740
<212> TYPE: DNA
<213> ORGANISM: Artificial Sequence
<220> FEATURE:
<223> OTHER INFORMATION: Synthetic:

<400> SEQUENCE: 23

| | |
|---|---|
| atggctaaaa tggcttttac tcttgctgat cgtgttactg aagaaatgct tgctgataaa | 60 |
| gctgctcttg ttgttgaagt tgttgaagaa aattatcatg atgctcctat tgttggtatt | 120 |
| gctgttgtta atgaacgtgg tcgtttttt cttcgtcctg aaactgctct tgctgatcct | 180 |
| caatttgttg cttggcttgg tgatgaaact aaaaaaaaat ctatgtttga ttctaaacgt | 240 |
| gctgctgttg ctcttaaatg gaaaggtatt gaactttgtg tgtttctttt tgatcttctt | 300 |
| cttgctgctt atcttcttga tcctgctcaa ggtgttgatg atgttgctgc tgctgctaaa | 360 |
| atgaaacaat atgaagctgt tcgtcctgat gaagctgttt atggtaaagg tgctaaacgt | 420 |
| gctgttcctg atgaacctgt tcttgctgaa catcttgttc gtaaagctgc tgctatttgg | 480 |
| gaacttgaac gtccttttct tgatgaactt cgtcgtaatg aacaagatcg tcttcttgtt | 540 |
| gaacttgaac aacctctttc ttctattctt gctgaaatgg aatttgctgg tgttaaagtt | 600 |
| gatactaaac gtcttgaaca atgggtaaa gaacttgctg aacaacttgg tactgttaaa | 660 |
| caacgtattt atgaacttgc tggtcaagaa tttaatattc gttctcctaa acaacttggt | 720 |
| gttattcttt ttgaaaaact tcaacttcct gttcttaaaa aaactaaaac tggttattct | 780 |
| acttctgctg atgttcttga aaaacttgct ccttatcatg aaattgttga aaatattctt | 840 |
| cattatcgtc aacttggtaa acttcaatct acttatattg aaggtcttct taaagttgtt | 900 |
| cgtcctgata ctaaaaaagt tcatactatt tttaatcaag ctcttactca aactggtcgt | 960 |
| ctttcttcta ctgaacctaa tcttcaaaat attcctattc gtcttgaaga aggtcgtaaa | 1020 |
| attcgtcaag cttttgttcc ttctgaatct gattggctta tttttgctgc tgattattct | 1080 |
| caaattgaac ttcgtgttct tgctcatatt gctgaagata taatcttat ggaagctttt | 1140 |
| cgtcgtgatc ttgatattca tactaaaaact gctatggata ttttcaagt ttctgaagat | 1200 |
| gaagttactc ctaatatgcg tcgtcaagct aaagctgtta attttggtat tgtttatggt | 1260 |
| atttctaaat atggtcttgc tcaaaatctt aatatttctc gtaaagaagc tgctgaattt | 1320 |
| attgaacgtt attttcaatc ttttcctggt gttaaacgtt atatggaaaa tattgttcaa | 1380 |
| gaagctaaac aaaaaggtta tgttactact cttcttcatc gtcgtcgtta tcttcctgat | 1440 |
| attacttctc gtaattttaa tgttcgttct tttgctgaac gtatggctat gaatactcct | 1500 |
| attcaaggtt ctgctgctga tattattaaa aaagctatga ttgatcttaa tgctcgtctt | 1560 |
| aaagaagaac gtcttcaagc tcatcttctt cttcaagttc atgatgaact tattcttgaa | 1620 |
| gctcctaaag aagaaatgga acgtctttgt cgtcttgttc ctgaagttat ggaacaagct | 1680 |
| gttactcttc gtgttcctct taaagttgat tatcgttatg gttctacttg gtatgatgct | 1740 |

<210> SEQ ID NO 24
<211> LENGTH: 832
<212> TYPE: PRT
<213> ORGANISM: Artificial Sequence
<220> FEATURE:
<223> OTHER INFORMATION: Synthetic:

```
<400> SEQUENCE: 24

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415
```

```
Trp Gly Arg Leu Glu Gly Glu Arg Leu Leu Trp Leu Tyr Arg Glu
            420             425             430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Glu Lys Thr Gly Lys Arg
                500                 505                 510

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
            610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
                660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Arg Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
            770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
                820                 825                 830
```

-continued

<210> SEQ ID NO 25
<211> LENGTH: 876
<212> TYPE: PRT
<213> ORGANISM: Artificial Sequence
<220> FEATURE:
<223> OTHER INFORMATION: Synthetic:

<400> SEQUENCE: 25

```
Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Glu Pro Thr His Met Leu Val Ala Phe Asp Ala Gly Lys Thr Thr
    50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                85                  90                  95

Ala Tyr Arg Ile Pro Ala Tyr Glu Leu Glu Asn Tyr Glu Ala Asp Asp
            100                 105                 110

Ile Ile Gly Thr Leu Ala Ala Arg Ala Glu Gln Glu Gly Phe Glu Val
        115                 120                 125

Lys Val Ile Ser Gly Asp Arg Asp Leu Thr Gln Leu Ala Ser Pro His
130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Arg Gln Phe
        195                 200                 205

Gly Thr Val Glu Asn Val Leu Ala Ser Ile Asp Glu Ile Lys Gly Glu
    210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Glu Lys Val Val Ala Leu
            260                 265                 270

Phe Lys Glu Leu Gly Phe Gln Ser Phe Leu Glu Lys Met Glu Ser Pro
        275                 280                 285

Ser Ser Glu Glu Glu Lys Pro Leu Ala Lys Met Ala Phe Thr Leu Ala
    290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
        355                 360                 365
```

```
Ser Met Phe Asp Ser Lys Arg Ala Ala Val Ala Leu Lys Trp Lys Gly
    370                 375                 380

Ile Glu Leu Cys Gly Val Ser Phe Asp Leu Leu Leu Ala Ala Tyr Leu
385                 390                 395                 400

Leu Asp Pro Ala Gln Gly Val Asp Val Ala Ala Ala Lys Met
                    405                 410             415

Lys Gln Tyr Glu Ala Val Arg Pro Asp Glu Ala Val Tyr Gly Lys Gly
                420                 425                 430

Ala Lys Arg Ala Val Pro Asp Glu Pro Val Leu Ala Glu His Leu Val
            435                 440                 445

Arg Lys Ala Ala Ala Ile Trp Glu Leu Glu Arg Pro Phe Leu Asp Glu
        450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
                485                 490                 495

Thr Lys Arg Leu Glu Gln Met Gly Lys Glu Leu Ala Glu Gln Leu Gly
                500                 505                 510

Thr Val Glu Gln Arg Ile Tyr Glu Leu Ala Gly Gln Glu Phe Asn Ile
            515                 520                 525

Asn Ser Pro Lys Gln Leu Gly Val Ile Leu Phe Glu Lys Leu Gln Leu
530                 535                 540

Pro Val Leu Lys Lys Thr Lys Thr Gly Tyr Ser Thr Ser Ala Asp Val
545                 550                 555                 560

Leu Glu Lys Leu Ala Pro Tyr His Glu Ile Val Glu Asn Ile Leu His
                565                 570                 575

Tyr Arg Gln Leu Gly Lys Leu Gln Ser Thr Tyr Ile Glu Gly Leu Leu
            580                 585                 590

Lys Val Val Arg Pro Asp Thr Lys Lys Val His Thr Ile Phe Asn Gln
        595                 600                 605

Ala Leu Thr Gln Thr Gly Arg Leu Ser Ser Thr Glu Pro Asn Leu Gln
    610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
                645                 650                 655

Ile Glu Leu Arg Val Leu Ala His Ile Ala Glu Asp Asp Asn Leu Met
            660                 665                 670

Glu Ala Phe Arg Arg Asp Leu Asp Ile His Thr Lys Thr Ala Met Asp
        675                 680                 685

Ile Phe Gln Val Ser Glu Asp Glu Val Thr Pro Asn Met Arg Arg Gln
    690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Ser Arg Lys Glu Ala Ala Glu Phe Ile
                725                 730                 735

Glu Arg Tyr Phe Glu Ser Phe Pro Gly Val Lys Arg Tyr Met Glu Asn
            740                 745                 750

Ile Val Gln Glu Ala Lys Gln Lys Gly Tyr Val Thr Thr Leu Leu His
        755                 760                 765

Arg Arg Arg Tyr Leu Pro Asp Ile Thr Ser Arg Asn Phe Arg Val Arg
    770                 775                 780

Ser Phe Ala Glu Arg Met Ala Met Asn Thr Pro Ile Gln Gly Ser Ala
```

```
                785                 790                 795                 800
Ala Asp Ile Ile Lys Lys Ala Met Ile Asp Leu Asn Ala Arg Leu Lys
                    805                 810                 815

Glu Glu Arg Leu Gln Ala His Leu Leu Leu Gln Val His Asp Glu Leu
                    820                 825                 830

Ile Leu Glu Ala Pro Lys Glu Met Glu Arg Leu Cys Arg Leu Val
                    835                 840                 845

Pro Glu Val Met Glu Gln Ala Val Thr Leu Arg Val Pro Leu Lys Val
                    850                 855                 860

Asp Tyr His Tyr Gly Ser Thr Trp Tyr Asp Ala Lys
865                 870                 875

<210> SEQ ID NO 26
<211> LENGTH: 876
<212> TYPE: PRT
<213> ORGANISM: Artificial Sequence
<220> FEATURE:
<223> OTHER INFORMATION: Synthetic:

<400> SEQUENCE: 26

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
                    20                  25                  30

Asn Ala Val Tyr Gly Phe Thr Met Met Leu Asn Lys Ile Leu Ala Glu
                    35                  40                  45

Glu Glu Pro Thr His Met Leu Val Ala Phe Asp Ala Gly Lys Thr Thr
                    50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                    85                  90                  95

Ala Tyr Arg Ile Pro Ala Tyr Glu Leu Glu Asn Tyr Glu Ala Asp Asp
                    100                 105                 110

Ile Ile Gly Thr Leu Ala Ala Arg Ala Glu Gln Glu Gly Phe Glu Val
                    115                 120                 125

Lys Val Ile Ser Gly Asp Arg Asp Leu Thr Gln Leu Ala Ser Pro His
                    130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                    165                 170                 175

Val Asp Leu Lys Gly Leu Met Gly Asp Lys Ser Asp Asn Ile Pro Gly
                    180                 185                 190

Val Pro Gly Ile Gly Glu Lys Thr Ala Val Lys Leu Leu Arg Gln Phe
                    195                 200                 205

Gly Thr Val Glu Asn Val Leu Ala Ser Ile Asp Glu Ile Lys Gly Glu
                    210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                    245                 250                 255

Asp Asp Ile Ala Tyr Gln Gly Glu Asp Arg Glu Lys Val Val Ala Leu
                    260                 265                 270

Phe Lys Glu Leu Gly Phe Gln Ser Phe Leu Glu Lys Met Glu Ser Pro
```

-continued

```
                275                 280                 285
Ser Ser Glu Glu Glu Lys Pro Leu Ala Lys Met Ala Phe Thr Leu Ala
290                 295                 300
Asp Arg Val Thr Glu Glu Met Leu Ala Asp Lys Ala Ala Leu Val Val
305                 310                 315                 320
Glu Val Val Glu Glu Asn Tyr His Asp Ala Pro Ile Val Gly Ile Ala
                325                 330                 335
Val Val Asn Glu His Gly Arg Phe Phe Leu Arg Pro Glu Thr Ala Leu
            340                 345                 350
Ala Asp Pro Gln Phe Val Ala Trp Leu Gly Asp Glu Thr Lys Lys Lys
            355                 360                 365
Ser Met Phe Asp Ser Lys Arg Ala Ala Val Ala Leu Lys Trp Lys Gly
        370                 375                 380
Ile Glu Leu Cys Gly Val Ser Phe Asp Leu Leu Leu Ala Ala Tyr Leu
385                 390                 395                 400
Leu Asp Pro Ala Gln Gly Val Asp Asp Val Ala Ala Ala Lys Met
            405                 410                 415
Lys Gln Tyr Glu Ala Val Arg Pro Asp Glu Ala Val Tyr Gly Lys Gly
            420                 425                 430
Ala Lys Arg Ala Val Pro Asp Glu Pro Val Leu Ala Glu His Leu Val
        435                 440                 445
Arg Lys Ala Ala Ala Ile Trp Glu Leu Glu Arg Pro Phe Leu Asp Glu
450                 455                 460
Leu Arg Arg Asn Glu Gln Asp Arg Leu Leu Val Glu Leu Glu Gln Pro
465                 470                 475                 480
Leu Ser Ser Ile Leu Ala Glu Met Glu Phe Ala Gly Val Lys Val Asp
            485                 490                 495
Thr Lys Arg Leu Glu Gln Met Gly Lys Glu Leu Ala Glu Gln Leu Gly
            500                 505                 510
Thr Val Glu Gln Arg Ile Tyr Glu Leu Ala Gly Gln Glu Phe Asn Ile
        515                 520                 525
Asn Ser Pro Lys Gln Leu Gly Val Ile Leu Phe Glu Lys Leu Gln Leu
530                 535                 540
Pro Val Leu Lys Lys Thr Lys Thr Gly Tyr Ser Thr Ser Ala Asp Val
545                 550                 555                 560
Leu Glu Lys Leu Ala Pro Tyr His Glu Ile Val Glu Asn Ile Leu His
            565                 570                 575
Tyr Arg Gln Leu Gly Lys Leu Gln Ser Thr Tyr Ile Glu Gly Leu Leu
            580                 585                 590
Lys Val Val Arg Pro Asp Thr Lys Lys Val His Thr Ile Phe Asn Gln
        595                 600                 605
Ala Leu Thr Gln Thr Gly Arg Leu Ser Ser Thr Glu Pro Asn Leu Gln
        610                 615                 620
Asn Ile Pro Ile Arg Leu Glu Glu Gly Arg Lys Ile Arg Gln Ala Phe
625                 630                 635                 640
Val Pro Ser Glu Ser Asp Trp Leu Ile Phe Ala Ala Asp Tyr Ser Gln
            645                 650                 655
Ile Glu Leu Arg Val Leu Ala His Ile Ala Glu Asp Asp Asn Leu Met
            660                 665                 670
Glu Ala Phe Arg Arg Asp Leu Asp Ile His Thr Lys Thr Ala Met Asp
        675                 680                 685
Ile Phe Gln Val Ser Glu Asp Glu Val Thr Pro Asn Met Arg Arg Gln
        690                 695                 700
```

Ala Lys Ala Val Asn Phe Gly Ile Val Tyr Gly Ile Ser Lys Tyr Gly
705                 710                 715                 720

Leu Ala Gln Asn Leu Asn Ile Ser Arg Lys Glu Ala Ala Glu Phe Ile
            725                 730                 735

Glu Arg Tyr Phe Glu Ser Phe Pro Gly Val Lys Arg Tyr Met Glu Asn
        740                 745                 750

Ile Val Gln Glu Ala Lys Gln Lys Gly Tyr Val Thr Thr Leu Leu His
            755                 760                 765

Arg Arg Arg Tyr Leu Pro Asp Ile Thr Ser Arg Asn Phe Arg Val Arg
770                 775                 780

Ser Phe Ala Glu Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
                805                 810                 815

Glu Glu Arg Leu Gln Ala His Leu Leu Leu Gln Val His Asp Glu Leu
            820                 825                 830

Ile Leu Glu Ala Pro Lys Glu Met Glu Arg Leu Cys Arg Leu Val
            835                 840                 845

Pro Glu Val Met Glu Gln Ala Val Thr Leu Arg Val Pro Leu Lys Val
        850                 855                 860

Asp Tyr His Tyr Gly Ser Thr Trp Tyr Asp Ala Lys
865                 870                 875

<210> SEQ ID NO 27
<211> LENGTH: 876
<212> TYPE: PRT
<213> ORGANISM: Artificial Sequence
<220> FEATURE:
<223> OTHER INFORMATION: Synthetic:

<400> SEQUENCE: 27

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Glu Pro Thr His Met Leu Val Ala Phe Asp Ala Gly Lys Thr Thr
    50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                85                  90                  95

Ala Tyr Arg Ile Pro Ala Tyr Glu Leu Glu Asn Tyr Glu Ala Asp Asp
            100                 105                 110

Ile Ile Gly Thr Leu Ala Ala Arg Ala Glu Gln Glu Gly Phe Glu Val
        115                 120                 125

Lys Val Ile Ser Gly Asp Arg Asp Leu Thr Gln Leu Ala Ser Pro His
    130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

-continued

```
Val Pro Gly Ile Gly Glu Lys Thr Ala Val Lys Leu Leu Arg Gln Phe
        195                 200                 205
Gly Thr Val Glu Asn Val Leu Ala Ser Ile Asp Glu Ile Lys Gly Glu
    210                 215                 220
Lys Leu Lys Glu Thr Leu Arg Gln His Arg Glu Met Ala Leu Leu Ser
225                 230                 235                 240
Lys Lys Leu Ala Ala Ile Arg Arg Asp Ala Pro Val Glu Leu Ser Leu
                245                 250                 255
Asp Asp Ile Ala Tyr Gln Gly Glu Asp Arg Glu Lys Val Val Ala Leu
                260                 265                 270
Phe Lys Glu Leu Gly Phe Gln Ser Phe Leu Glu Lys Met Glu Ser Pro
            275                 280                 285
Ser Ser Glu Glu Glu Lys Pro Leu Ala Lys Met Ala Phe Thr Leu Ala
    290                 295                 300
Asp Arg Val Thr Glu Glu Met Leu Ala Asp Lys Ala Ala Leu Val Val
305                 310                 315                 320
Glu Val Val Glu Glu Asn Tyr His Asp Ala Pro Ile Val Gly Ile Ala
                325                 330                 335
Val Val Asn Glu His Gly Arg Phe Phe Leu Arg Pro Gly Thr Ala Leu
            340                 345                 350
Ala Asp Pro Gln Phe Val Ala Trp Leu Gly Asp Glu Thr Lys Lys Lys
        355                 360                 365
Ser Met Phe Asp Ser Lys Arg Ala Ala Val Ala Leu Lys Trp Lys Gly
    370                 375                 380
Ile Glu Leu Cys Gly Val Ser Phe Asp Leu Leu Ala Ala Tyr Leu
385                 390                 395                 400
Leu Asp Pro Ala Gln Gly Val Asp Asp Val Ala Ala Ala Lys Met
                405                 410                 415
Lys Gln Tyr Glu Ala Val Arg Pro Asp Glu Ala Val Tyr Gly Lys Gly
            420                 425                 430
Ala Lys Arg Ala Val Pro Asp Glu Pro Val Leu Ala Glu His Leu Val
        435                 440                 445
Arg Lys Ala Ala Ala Ile Trp Glu Leu Glu Arg Pro Phe Leu Asp Glu
        450                 455                 460
Leu Arg Arg Asn Glu Gln Asp Arg Leu Leu Val Glu Leu Glu Gln Pro
465                 470                 475                 480
Leu Ser Ser Ile Leu Ala Glu Met Glu Phe Ala Gly Val Lys Val Asp
                485                 490                 495
Thr Lys Arg Leu Glu Gln Met Gly Lys Glu Leu Ala Glu Gln Leu Gly
            500                 505                 510
Thr Val Glu Gln Arg Ile Tyr Glu Leu Ala Gly Gln Glu Phe Asn Ile
        515                 520                 525
Asn Ser Pro Lys Gln Leu Gly Val Ile Leu Phe Glu Lys Leu Gln Leu
530                 535                 540
Pro Val Leu Lys Lys Thr Lys Thr Gly Tyr Ser Thr Ser Ala Asp Val
545                 550                 555                 560
Leu Glu Lys Leu Ala Pro Tyr Asn Glu Ile Val Glu Asn Ile Leu His
                565                 570                 575
Tyr Arg Gln Leu Gly Lys Leu Gln Ser Thr Tyr Ile Glu Gly Leu Leu
            580                 585                 590
Lys Val Val Arg Pro Asp Thr Lys Lys Val His Thr Ile Phe Asn Gln
        595                 600                 605
```

Ala Leu Thr Gln Thr Gly Arg Leu Ser Ser Thr Glu Pro Asn Leu Gln
610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
            645                 650                 655

Ile Glu Leu Arg Val Leu Ala His Ile Ala Glu Asp Asn Leu Met
        660                 665                 670

Glu Ala Phe Arg Arg Asp Leu Asp Ile His Thr Lys Thr Ala Met Asp
        675                 680                 685

Ile Phe Gln Val Ser Glu Asp Glu Val Thr Pro Asn Met Arg Arg Gln
        690                 695                 700

Ala Lys Ala Val Asn Phe Gly Ile Val Tyr Gly Ile Ser Lys Tyr Gly
705                 710                 715                 720

Leu Ala Gln Asn Leu Asn Ile Ser Arg Lys Glu Ala Ala Glu Phe Ile
                725                 730                 735

Glu Arg Tyr Phe Glu Ser Phe Pro Gly Val Lys Arg Tyr Met Glu Asn
            740                 745                 750

Ile Val Gln Glu Ala Lys Gln Lys Gly Tyr Val Thr Thr Leu Leu His
        755                 760                 765

Arg Arg Arg Tyr Leu Pro Asp Ile Thr Ser Arg Asn Phe Arg Val Arg
770                 775                 780

Ser Phe Ala Glu Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
                805                 810                 815

Glu Glu Arg Leu Gln Ala His Leu Leu Leu Gln Val His Asp Glu Leu
            820                 825                 830

Ile Leu Glu Ala Pro Lys Glu Glu Met Glu Arg Leu Cys Arg Leu Val
        835                 840                 845

Pro Glu Val Met Glu Gln Ala Val Thr Leu Arg Val Pro Leu Lys Val
        850                 855                 860

Asp Tyr His Tyr Gly Ser Thr Trp Tyr Asp Ala Lys
865                 870                 875

<210> SEQ ID NO 28
<211> LENGTH: 876
<212> TYPE: PRT
<213> ORGANISM: Artificial Sequence
<220> FEATURE:
<223> OTHER INFORMATION: Synthetic:

<400> SEQUENCE: 28

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
        35                  40                  45

Glu Glu Pro Thr His Met Leu Val Ala Phe Asp Ala Gly Lys Thr Thr
50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                85                  90                  95

```
Ala Tyr Arg Ile Pro Ala Tyr Glu Leu Glu Asn Tyr Glu Ala Asp Asp
            100                 105                 110

Ile Ile Gly Thr Leu Ala Arg Ala Glu Gln Glu Gly Phe Glu Val
        115                 120                 125

Lys Val Ile Ser Gly Asp Arg Asp Leu Thr Gln Leu Ala Ser Pro His
    130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Arg Gln Phe
        195                 200                 205

Gly Thr Val Glu Asn Val Leu Ala Ser Ile Asp Glu Ile Lys Gly Glu
    210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Glu Lys Val Val Ala Leu
            260                 265                 270

Phe Lys Glu Leu Gly Phe Gln Ser Phe Leu Glu Lys Met Glu Ser Pro
        275                 280                 285

Ser Ser Glu Glu Glu Lys Pro Leu Ala Lys Met Ala Phe Thr Leu Ala
    290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
        355                 360                 365

Ser Met Phe Asp Ser Lys Arg Ala Ala Val Ala Leu Lys Trp Lys Gly
    370                 375                 380

Ile Glu Leu Cys Gly Val Ser Phe Asp Leu Leu Leu Ala Ala Tyr Leu
385                 390                 395                 400

Leu Asp Pro Ala Gln Gly Val Asp Asp Val Ala Ala Ala Lys Met
                405                 410                 415

Lys Gln Tyr Glu Ala Val Arg Pro Asp Glu Ala Val Tyr Gly Lys Gly
            420                 425                 430

Ala Lys Arg Ala Val Pro Asp Glu Pro Val Leu Ala Glu His Leu Val
        435                 440                 445

Arg Lys Ala Ala Ile Trp Glu Leu Glu Arg Pro Phe Leu Asp Glu
    450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
                485                 490                 495

Thr Lys Arg Leu Glu Gln Met Gly Lys Glu Leu Ala Glu Gln Leu Gly
            500                 505                 510

Thr Val Glu Gln Arg Ile Tyr Glu Leu Ala Gly Gln Glu Phe Asn Ile
```

```
            515                 520                 525
Asn Ser Pro Lys Gln Leu Gly Val Ile Leu Phe Glu Lys Leu Gln Leu
        530                 535                 540
Pro Val Leu Lys Lys Thr Lys Thr Gly Tyr Ser Thr Ser Ala Asp Val
545                 550                 555                 560
Leu Glu Lys Leu Ala Pro Tyr His Glu Ile Val Glu Asn Ile Leu Met
                565                 570                 575
Tyr Arg Gln Leu Gly Lys Leu Ser Thr Tyr Ile Glu Gly Leu Leu
            580                 585                 590
Lys Val Val Arg Pro Asp Thr Lys Val His Thr Ile Phe Asn Gln
        595                 600                 605
Ala Leu Thr Gln Thr Gly Arg Leu Ser Ser Thr Glu Pro Asn Leu Gln
        610                 615                 620
Asn Ile Pro Ile Arg Leu Glu Glu Gly Arg Lys Ile Arg Gln Ala Phe
625                 630                 635                 640
Val Pro Ser Glu Ser Asp Trp Leu Ile Phe Ala Ala Asp Tyr Ser Gln
                645                 650                 655
Ile Glu Leu Arg Val Leu Ala His Ile Ala Glu Asp Asp Asn Leu Met
                660                 665                 670
Glu Ala Phe Arg Arg Asp Leu Asp Ile His Thr Lys Thr Ala Met Asp
            675                 680                 685
Ile Phe Gln Val Ser Glu Asp Glu Val Thr Pro Asn Met Arg Arg Gln
        690                 695                 700
Ala Lys Ala Val Asn Phe Gly Ile Val Tyr Gly Ile Ser Asp Tyr Gly
705                 710                 715                 720
Leu Ala Gln Asn Leu Asn Ile Ser Arg Lys Glu Ala Ala Glu Phe Ile
                725                 730                 735
Glu Arg Tyr Phe Glu Ser Phe Pro Gly Val Lys Arg Tyr Met Glu Asn
            740                 745                 750
Ile Val Gln Glu Ala Lys Gln Lys Gly Tyr Val Thr Thr Leu Leu His
        755                 760                 765
Arg Arg Arg Tyr Leu Pro Asp Ile Thr Ser Arg Asn Phe Asn Val Arg
        770                 775                 780
Ser Phe Ala Glu Arg Met Ala Met Asn Thr Pro Ile Gln Gly Ser Ala
785                 790                 795                 800
Ala Asp Ile Ile Lys Lys Ala Met Ile Asp Leu Asn Ala Arg Leu Lys
                805                 810                 815
Glu Glu Arg Leu Gln Ala His Leu Leu Leu Gln Val His Asp Glu Leu
            820                 825                 830
Ile Leu Glu Ala Pro Lys Glu Glu Met Glu Arg Leu Cys Arg Leu Val
            835                 840                 845
Pro Glu Val Met Glu Gln Ala Val Thr Leu Arg Val Pro Leu Lys Val
        850                 855                 860
Asp Tyr His Tyr Gly Ser Thr Trp Tyr Asp Ala Lys
865                 870                 875

<210> SEQ ID NO 29
<211> LENGTH: 876
<212> TYPE: PRT
<213> ORGANISM: Artificial Sequence
<220> FEATURE:
<223> OTHER INFORMATION: Synthetic:

<400> SEQUENCE: 29

Met Lys Lys Lys Leu Val Leu Ile Asp Gly Ser Ser Val Ala Tyr Arg
```

-continued

```
1               5                   10                  15
Ala Phe Phe Ala Leu Pro Leu Leu His Asn Asp Lys Gly Ile His Thr
            20                  25                  30
Asn Ala Val Tyr Gly Phe Thr Met Met Leu Asn Lys Ile Leu Ala Glu
            35                  40                  45
Glu Glu Pro Thr His Met Leu Val Ala Phe Asp Ala Gly Lys Thr Thr
            50                  55                  60
Phe Arg His Glu Ala Phe Gln Glu Tyr Lys Gly Gly Arg Gln Gln Thr
65                  70                  75                  80
Pro Pro Glu Leu Ser Glu Gln Phe Pro Leu Leu Arg Glu Leu Leu Arg
                85                  90                  95
Ala Tyr Arg Ile Pro Ala Tyr Glu Leu Glu Asn Tyr Glu Ala Asp Asp
                100                 105                 110
Ile Ile Gly Thr Leu Ala Ala Arg Ala Glu Gln Glu Gly Phe Glu Val
                115                 120                 125
Lys Val Ile Ser Gly Asp Arg Asp Leu Thr Gln Leu Ala Ser Pro His
                130                 135                 140
Val Thr Val Asp Ile Thr Lys Lys Gly Ile Thr Asp Ile Glu Pro Tyr
145                 150                 155                 160
Thr Pro Glu Thr Val Arg Glu Lys Tyr Gly Leu Thr Pro Glu Gln Ile
                165                 170                 175
Val Asp Leu Lys Gly Leu Met Gly Asp Lys Ser Asp Asn Ile Pro Gly
                180                 185                 190
Val Pro Gly Ile Gly Glu Lys Thr Ala Val Lys Leu Leu Arg Gln Phe
                195                 200                 205
Gly Thr Val Glu Asn Val Leu Ala Ser Ile Asp Glu Ile Lys Gly Glu
                210                 215                 220
Lys Leu Lys Glu Thr Leu Arg Gln His Arg Glu Met Ala Leu Leu Ser
225                 230                 235                 240
Lys Lys Leu Ala Ala Ile Arg Arg Asp Ala Pro Val Glu Leu Ser Leu
                245                 250                 255
Asp Asp Ile Ala Tyr Gln Gly Glu Asp Arg Glu Lys Val Val Ala Leu
                260                 265                 270
Phe Lys Glu Leu Gly Phe Gln Ser Phe Leu Glu Lys Met Glu Ser Pro
                275                 280                 285
Ser Ser Glu Glu Glu Lys Pro Leu Ala Lys Met Ala Phe Thr Leu Ala
                290                 295                 300
Asp Arg Val Thr Glu Glu Met Leu Ala Asp Lys Ala Ala Leu Val Val
305                 310                 315                 320
Glu Val Val Glu Glu Asn Tyr His Asp Ala Pro Ile Val Gly Ile Ala
                325                 330                 335
Val Val Asn Glu His Gly Arg Phe Phe Leu Arg Pro Glu Thr Ala Leu
                340                 345                 350
Ala Asp Pro Gln Phe Val Ala Trp Leu Gly Asp Glu Thr Lys Lys Lys
                355                 360                 365
Ser Met Phe Asp Ser Lys Arg Ala Ala Val Ala Leu Lys Trp Lys Gly
                370                 375                 380
Ile Glu Leu Cys Gly Val Ser Phe Asp Leu Leu Leu Ala Ala Tyr Leu
385                 390                 395                 400
Leu Asp Pro Ala Gln Gly Val Asp Val Ala Ala Ala Lys Met
                405                 410                 415
Lys Gln Tyr Glu Ala Val Arg Pro Asp Glu Ala Val Tyr Gly Lys Gly
                420                 425                 430
```

```
Ala Lys Arg Ala Val Pro Asp Glu Pro Val Leu Ala Glu His Leu Val
        435                 440                 445
Arg Lys Ala Ala Ala Ile Trp Glu Leu Glu Arg Pro Phe Leu Asp Glu
        450                 455                 460
Leu Arg Arg Asn Glu Gln Asp Arg Leu Leu Val Glu Leu Glu Gln Pro
465                 470                 475                 480
Leu Ser Ser Ile Leu Ala Glu Met Glu Phe Ala Gly Val Lys Val Asp
                485                 490                 495
Thr Lys Arg Leu Glu Gln Met Gly Lys Glu Leu Ala Glu Gln Leu Gly
        500                 505                 510
Thr Val Glu Gln Arg Ile Tyr Glu Leu Ala Gly Gln Glu Phe Asn Ile
        515                 520                 525
Asn Ser Pro Lys Gln Leu Gly Val Ile Leu Phe Glu Lys Leu Gln Leu
        530                 535                 540
Pro Val Leu Lys Lys Thr Lys Thr Gly Tyr Ser Thr Ser Ala Asp Val
545                 550                 555                 560
Leu Glu Lys Leu Ala Pro Tyr His Glu Ile Val Glu Asn Ile Leu His
                565                 570                 575
Tyr Arg Gln Leu Gly Lys Leu Gln Ser Thr Tyr Ile Glu Gly Leu Leu
        580                 585                 590
Lys Val Val Arg Pro Asp Thr Lys Lys Val His Thr Ile Phe Asn Gln
        595                 600                 605
Ala Leu Thr Gln Thr Gly Arg Leu Ser Ser Thr Glu Pro Asn Leu Gln
        610                 615                 620
Asn Ile Pro Ile Arg Leu Glu Glu Gly Arg Lys Ile Arg Gln Ala Phe
625                 630                 635                 640
Val Pro Ser Glu Ser Asp Trp Leu Ile Phe Ala Ala Asp Tyr Ser Gln
                645                 650                 655
Ile Glu Leu Arg Val Leu Ala His Ile Ala Glu Asp Asp Asn Leu Met
                660                 665                 670
Glu Ala Phe Arg Arg Asp Leu Asp Ile His Thr Lys Thr Ala Met Asp
        675                 680                 685
Ile Phe Gln Val Ser Glu Asp Glu Val Thr Pro Asn Met Arg Arg Gln
        690                 695                 700
Ala Lys Ala Val Asn Phe Gly Ile Val Tyr Gly Ile Ser Asp Tyr Gly
705                 710                 715                 720
Leu Ala Gln Asn Leu Asn Ile Ser Arg Lys Glu Ala Ala Glu Phe Ile
                725                 730                 735
Glu Arg Tyr Phe Glu Ser Phe Pro Gly Val Lys Arg Tyr Met Glu Asn
        740                 745                 750
Ile Val Gln Glu Ala Lys Gln Lys Gly Tyr Val Thr Thr Leu Leu His
        755                 760                 765
Arg Arg Arg Tyr Leu Pro Asp Ile Thr Ser Arg Asn Phe Arg Val Arg
        770                 775                 780
Ser Phe Ala Glu Arg Met Ala Met Asn Thr Pro Ile Gln Gly Ser Ala
785                 790                 795                 800
Ala Asp Ile Ile Lys Lys Ala Met Ile Asp Leu Asn Ala Arg Leu Lys
                805                 810                 815
Glu Glu Arg Leu Gln Ala Ser Leu Leu Leu Gln Val His Asp Glu Leu
        820                 825                 830
Ile Leu Glu Ala Pro Lys Glu Glu Met Glu Arg Leu Cys Arg Leu Val
        835                 840                 845
```

```
Pro Glu Val Met Glu Gln Ala Val Thr Leu Arg Val Pro Leu Lys Val
        850                 855                 860

Asp Tyr His Tyr Gly Ser Thr Trp Tyr Asp Ala Lys
865                 870                 875

<210> SEQ ID NO 30
<211> LENGTH: 876
<212> TYPE: PRT
<213> ORGANISM: Artificial Sequence
<220> FEATURE:
<223> OTHER INFORMATION: Synthetic:

<400> SEQUENCE: 30

Met Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
                20                  25                  30

Asn Ala Val Tyr Gly Phe Thr Met Met Leu Asn Lys Ile Leu Ala Glu
                35                  40                  45

Glu Glu Pro Thr His Met Leu Val Ala Phe Asp Ala Gly Lys Thr Thr
        50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                85                  90                  95

Ala Tyr Arg Ile Pro Ala Tyr Glu Leu Glu Asn Tyr Glu Ala Asp Asp
                100                 105                 110

Ile Ile Gly Thr Leu Ala Ala Arg Ala Glu Gln Glu Gly Phe Glu Val
                115                 120                 125

Lys Val Ile Ser Gly Asp Arg Asp Leu Thr Gln Leu Ala Ser Pro His
        130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
                180                 185                 190

Val Pro Gly Ile Gly Glu Lys Thr Ala Val Lys Leu Leu Arg Gln Phe
                195                 200                 205

Gly Thr Val Glu Asn Val Leu Ala Ser Ile Asp Glu Ile Lys Gly Glu
        210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Glu Lys Val Val Ala Leu
                260                 265                 270

Phe Lys Glu Leu Gly Phe Gln Ser Phe Leu Glu Lys Met Glu Ser Pro
                275                 280                 285

Ser Ser Glu Glu Glu Lys Pro Leu Ala Lys Met Ala Phe Thr Leu Ala
        290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                325                 330                 335
```

-continued

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
        355                 360                 365

Ser Met Phe Asp Ser Lys Arg Ala Ala Val Ala Leu Lys Trp Lys Gly
    370                 375                 380

Ile Glu Leu Cys Gly Val Ser Phe Asp Leu Leu Leu Ala Ala Tyr Leu
385                 390                 395                 400

Leu Asp Pro Ala Gln Gly Val Asp Asp Val Ala Ala Ala Lys Met
                405                 410                 415

Lys Gln Tyr Glu Ala Val Arg Pro Asp Glu Ala Val Tyr Gly Lys Gly
            420                 425                 430

Ala Lys Arg Ala Val Pro Asp Glu Pro Val Leu Ala Glu His Leu Val
        435                 440                 445

Arg Lys Ala Ala Ala Ile Trp Glu Leu Glu Arg Pro Phe Leu Asp Glu
        450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
                485                 490                 495

Thr Lys Arg Leu Glu Gln Met Gly Lys Glu Leu Ala Glu Gln Leu Gly
            500                 505                 510

Thr Val Glu Gln Arg Ile Tyr Glu Leu Ala Gly Gln Glu Phe Asn Ile
        515                 520                 525

Asn Ser Pro Lys Gln Leu Gly Val Ile Leu Phe Glu Lys Leu Gln Leu
530                 535                 540

Pro Val Leu Lys Lys Thr Lys Thr Gly Tyr Ser Thr Ser Ala Asp Val
545                 550                 555                 560

Leu Glu Lys Leu Ala Pro Tyr His Glu Ile Val Glu Asn Ile Leu His
                565                 570                 575

Tyr Arg Gln Leu Gly Lys Leu Gln Ser Thr Tyr Ile Glu Gly Leu Leu
            580                 585                 590

Lys Val Val Arg Pro Asp Thr Lys Lys Val His Thr Ile Phe Asn Gln
        595                 600                 605

Ala Leu Thr Gln Thr Gly Arg Leu Ser Ser Thr Glu Pro Asn Leu Gln
        610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
                645                 650                 655

Ile Glu Leu Arg Val Leu Ala His Ile Ala Glu Asp Asp Asn Leu Met
            660                 665                 670

Glu Ala Phe Arg Arg Asp Leu Asp Ile His Thr Lys Thr Ala Met Asp
        675                 680                 685

Ile Phe Gln Val Ser Glu Asp Glu Val Thr Pro Asn Met Arg Arg Gln
        690                 695                 700

Ala Lys Ala Val Asn Phe Gly Ile Val Tyr Gly Ile Ser Lys Tyr Gly
705                 710                 715                 720

Leu Ala Gln Asn Leu Asn Ile Ser Arg Lys Glu Ala Ala Glu Phe Ile
                725                 730                 735

Glu Arg Tyr Phe Glu Ser Phe Pro Gly Val Lys Arg Tyr Met Glu Asn
            740                 745                 750

Ile Val Gln Glu Ala Lys Gln Lys Gly Tyr Val Thr Thr Leu Leu His

```
                755                 760                 765
Arg Arg Arg Tyr Leu Pro Asp Ile Thr Ser Arg Asn Phe Asn Val Arg
770                 775                 780

Ser Phe Ala Glu Arg Met Ala Met Asn Thr Pro Ile Gln Gly Ser Ala
785                 790                 795                 800

Ala Asp Ile Ile Lys Ala Met Ile Asp Leu Asn Ala Arg Leu Lys
                805                 810                 815

Glu Glu Arg Leu Gln Ala His Leu Leu Leu Gln Val His Asp Glu Leu
                820                 825                 830

Ile Leu Glu Ala Pro Lys Glu Glu Met Glu Arg Leu Cys Arg Leu Val
                835                 840                 845

Pro Glu Val Met Glu Gln Ala Val Thr Leu Arg Val Pro Leu Lys Val
                850                 855                 860

Asp Tyr His Tyr Gly Ser Thr Trp Tyr Asp Ala Lys
865                 870                 875

<210> SEQ ID NO 31
<211> LENGTH: 876
<212> TYPE: PRT
<213> ORGANISM: Artificial Sequence
<220> FEATURE:
<223> OTHER INFORMATION: Synthetic:

<400> SEQUENCE: 31

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
                20                  25                  30

Asn Ala Val Tyr Gly Phe Thr Met Met Leu Asn Lys Ile Leu Ala Glu
                35                  40                  45

Glu Glu Pro Thr His Met Leu Val Ala Phe Asp Ala Gly Lys Thr Thr
                50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
                85                  90                  95

Ala Tyr Arg Ile Pro Ala Tyr Glu Leu Glu Asn Tyr Glu Ala Asp Asp
                100                 105                 110

Ile Ile Gly Thr Leu Ala Ala Arg Ala Glu Gln Glu Gly Phe Glu Val
                115                 120                 125

Lys Val Ile Ser Gly Asp Arg Asp Leu Thr Gln Leu Ala Ser Pro His
130                 135                 140

Val Thr Val Asp Ile Thr Lys Lys Gly Ile Thr Asp Ile Glu Pro Tyr
145                 150                 155                 160

Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
                180                 185                 190

Val Pro Gly Ile Gly Glu Lys Thr Ala Val Lys Leu Leu Arg Gln Phe
                195                 200                 205

Gly Thr Val Glu Asn Val Leu Ala Ser Ile Asp Glu Ile Lys Gly Glu
                210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
```

-continued

```
                245                 250                 255
Asp Asp Ile Ala Tyr Gln Gly Glu Asp Arg Glu Lys Val Val Ala Leu
            260                 265                 270
Phe Lys Glu Leu Gly Phe Gln Ser Phe Leu Glu Lys Met Glu Ser Pro
        275                 280                 285
Ser Ser Glu Glu Glu Lys Pro Leu Ala Lys Met Ala Phe Thr Leu Ala
    290                 295                 300
Asp Arg Val Thr Glu Glu Met Leu Ala Asp Lys Ala Ala Leu Val Val
305                 310                 315                 320
Glu Val Val Glu Glu Asn Tyr His Asp Ala Pro Ile Val Gly Ile Ala
                325                 330                 335
Val Val Asn Glu His Gly Arg Phe Phe Leu Arg Pro Glu Thr Ala Leu
            340                 345                 350
Ala Asp Pro Gln Phe Val Ala Trp Leu Gly Asp Glu Thr Lys Lys Lys
        355                 360                 365
Ser Met Phe Asp Ser Lys Arg Ala Ala Val Ala Leu Lys Trp Lys Gly
    370                 375                 380
Ile Glu Leu Cys Gly Val Ser Phe Asp Leu Leu Ala Ala Tyr Leu
385                 390                 395                 400
Leu Asp Pro Ala Gln Gly Val Asp Val Ala Ala Ala Lys Met
                405                 410                 415
Lys Gln Tyr Glu Ala Val Arg Pro Asp Glu Ala Val Tyr Gly Lys Gly
            420                 425                 430
Ala Lys Arg Ala Val Pro Asp Glu Pro Val Leu Ala Glu His Leu Val
        435                 440                 445
Arg Lys Ala Ala Ala Ile Trp Glu Leu Glu Arg Pro Phe Leu Asp Glu
    450                 455                 460
Leu Arg Arg Asn Glu Gln Asp Arg Leu Leu Val Glu Leu Glu Gln Pro
465                 470                 475                 480
Leu Ser Ser Ile Leu Ala Glu Met Glu Phe Ala Gly Val Lys Val Asp
                485                 490                 495
Thr Lys Arg Leu Glu Gln Met Gly Lys Glu Leu Ala Glu Gln Leu Gly
            500                 505                 510
Thr Val Glu Gln Arg Ile Tyr Glu Leu Ala Gly Gln Glu Phe Asn Ile
        515                 520                 525
Asn Ser Pro Lys Gln Leu Gly Val Ile Leu Phe Glu Lys Leu Gln Leu
    530                 535                 540
Pro Val Leu Lys Lys Thr Lys Thr Gly Tyr Ser Thr Ser Ala Asp Val
545                 550                 555                 560
Leu Glu Lys Leu Ala Pro Tyr His Glu Ile Val Glu Asn Ile Leu Met
                565                 570                 575
Tyr Arg Gln Leu Gly Lys Leu Gln Ser Thr Tyr Ile Glu Gly Leu Leu
            580                 585                 590
Lys Val Val Arg Pro Asp Thr Lys Lys Val His Thr Ile Phe Asn Gln
        595                 600                 605
Ala Leu Thr Gln Thr Gly Arg Leu Ser Ser Thr Glu Pro Asn Leu Gln
    610                 615                 620
Asn Ile Pro Ile Arg Leu Glu Glu Gly Arg Lys Ile Arg Gln Ala Phe
625                 630                 635                 640
Val Pro Ser Glu Ser Asp Trp Leu Ile Phe Ala Ala Asp Tyr Ser Gln
                645                 650                 655
Ile Glu Leu Arg Val Leu Ala His Ile Ala Glu Asp Asp Asn Leu Met
            660                 665                 670
```

```
Glu Ala Phe Arg Arg Asp Leu Asp Ile His Thr Lys Thr Ala Met Asp
            675                 680                 685

Ile Phe Gln Val Ser Glu Asp Glu Val Thr Pro Asn Met Arg Arg Gln
690                 695                 700

Ala Lys Ala Val Asn Phe Gly Ile Val Tyr Gly Ile Ser Lys Tyr Gly
705                 710                 715                 720

Leu Ala Gln Asn Leu Asn Ile Ser Arg Lys Glu Ala Ala Glu Phe Ile
            725                 730                 735

Glu Arg Tyr Phe Glu Ser Phe Pro Gly Val Lys Arg Tyr Met Glu Asn
            740                 745                 750

Ile Val Gln Glu Ala Lys Gln Lys Gly Tyr Val Thr Thr Leu Leu His
            755                 760                 765

Arg Arg Arg Tyr Leu Pro Asp Ile Thr Ser Arg Asn Phe Arg Val Arg
770                 775                 780

Ser Phe Ala Glu Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
            805                 810                 815

Glu Glu Arg Leu Gln Ala His Leu Leu Leu Gln Val His Asp Glu Leu
            820                 825                 830

Ile Leu Glu Ala Pro Lys Glu Glu Met Glu Arg Leu Cys Arg Leu Val
            835                 840                 845

Pro Glu Val Met Glu Gln Ala Val Thr Leu Arg Val Pro Leu Lys Val
            850                 855                 860

Asp Tyr His Tyr Gly Ser Thr Trp Tyr Asp Ala Lys
865                 870                 875

<210> SEQ ID NO 32
<211> LENGTH: 876
<212> TYPE: PRT
<213> ORGANISM: Artificial Sequence
<220> FEATURE:
<223> OTHER INFORMATION: Synthetic:

<400> SEQUENCE: 32

Met Lys Lys Lys Leu Val Leu Ile Asp Gly Ser Ser Val Ala Tyr Arg
1               5                   10                  15

Ala Phe Phe Ala Leu Pro Leu Leu His Asn Asp Lys Gly Ile His Thr
            20                  25                  30

Asn Ala Val Tyr Gly Phe Thr Met Met Leu Asn Lys Ile Leu Ala Glu
            35                  40                  45

Glu Glu Pro Thr His Met Leu Val Ala Phe Asp Ala Gly Lys Thr Thr
50                  55                  60

Phe Arg His Glu Ala Phe Gln Glu Tyr Lys Gly Gly Arg Gln Gln Thr
65                  70                  75                  80

Pro Pro Glu Leu Ser Glu Gln Phe Pro Leu Leu Arg Glu Leu Leu Arg
            85                  90                  95

Ala Tyr Arg Ile Pro Ala Tyr Glu Leu Glu Asn Tyr Glu Ala Asp Asp
            100                 105                 110

Ile Ile Gly Thr Leu Ala Ala Arg Ala Glu Gln Glu Gly Phe Glu Val
            115                 120                 125

Lys Val Ile Ser Gly Asp Arg Asp Leu Thr Gln Leu Ala Ser Pro His
            130                 135                 140

Val Thr Val Asp Ile Thr Lys Lys Gly Ile Thr Asp Ile Glu Pro Tyr
145                 150                 155                 160
```

-continued

```
Thr Pro Glu Thr Val Arg Glu Lys Tyr Gly Leu Thr Pro Glu Gln Ile
                165                 170                 175

Val Asp Leu Lys Gly Leu Met Gly Asp Lys Ser Asp Asn Ile Pro Gly
            180                 185                 190

Val Pro Gly Ile Gly Glu Lys Thr Ala Val Lys Leu Leu Arg Gln Phe
        195                 200                 205

Gly Thr Val Glu Asn Val Leu Ala Ser Ile Asp Glu Ile Lys Gly Glu
    210                 215                 220

Lys Leu Lys Glu Thr Leu Arg Gln His Arg Glu Met Ala Leu Leu Ser
225                 230                 235                 240

Lys Lys Leu Ala Ala Ile Arg Arg Asp Ala Pro Val Glu Leu Ser Leu
                245                 250                 255

Asp Asp Ile Ala Tyr Gln Gly Glu Asp Arg Glu Lys Val Val Ala Leu
            260                 265                 270

Phe Lys Glu Leu Gly Phe Gln Ser Phe Leu Glu Lys Met Glu Ser Pro
        275                 280                 285

Ser Ser Glu Glu Glu Lys Pro Leu Ala Lys Met Ala Phe Thr Leu Ala
    290                 295                 300

Asp Arg Val Thr Glu Glu Met Leu Ala Asp Lys Ala Ala Leu Val Val
305                 310                 315                 320

Glu Val Val Glu Glu Asn Tyr His Asp Ala Pro Ile Val Gly Ile Ala
                325                 330                 335

Val Val Asn Glu His Gly Arg Phe Phe Leu Arg Pro Glu Thr Ala Leu
            340                 345                 350

Ala Asp Pro Gln Phe Val Ala Trp Leu Gly Asp Glu Thr Lys Lys Lys
        355                 360                 365

Ser Met Phe Asp Ser Lys Arg Ala Ala Val Ala Leu Lys Trp Lys Gly
    370                 375                 380

Ile Glu Leu Cys Gly Val Ser Phe Asp Leu Leu Leu Ala Ala Tyr Leu
385                 390                 395                 400

Leu Asp Pro Ala Gln Gly Val Asp Asp Val Ala Ala Ala Ala Lys Met
                405                 410                 415

Lys Gln Tyr Glu Ala Val Arg Pro Asp Glu Ala Val Tyr Gly Lys Gly
            420                 425                 430

Ala Lys Arg Ala Val Pro Asp Glu Pro Val Leu Ala Glu His Leu Val
        435                 440                 445

Arg Lys Ala Ala Ala Ile Trp Glu Leu Glu Arg Pro Phe Leu Asp Glu
    450                 455                 460

Leu Arg Arg Asn Glu Gln Asp Arg Leu Leu Val Glu Leu Glu Gln Pro
465                 470                 475                 480

Leu Ser Ser Ile Leu Ala Glu Met Glu Phe Ala Gly Val Lys Val Asp
                485                 490                 495

Thr Lys Arg Leu Glu Gln Met Gly Lys Glu Leu Ala Glu Gln Leu Gly
            500                 505                 510

Thr Val Glu Gln Arg Ile Tyr Glu Leu Ala Gly Gln Glu Phe Asn Ile
        515                 520                 525

Asn Ser Pro Lys Gln Leu Gly Val Ile Leu Phe Glu Lys Leu Gln Leu
    530                 535                 540

Pro Val Leu Lys Lys Thr Lys Thr Gly Tyr Ser Thr Ser Ala Ala Val
545                 550                 555                 560

Leu Glu Lys Leu Ala Pro Tyr Asn Glu Ile Val Glu Asn Ile Leu Met
                565                 570                 575
```

Tyr Arg Gln Leu Gly Lys Leu Gln Ser Thr Tyr Ile Glu Gly Leu Leu
            580                 585                 590

Lys Val Val Arg Pro Asp Thr Lys Val His Thr Ile Phe Asn Gln
        595                 600                 605

Ala Leu Thr Gln Thr Gly Arg Leu Ser Ser Thr Glu Pro Asn Leu Gln
    610                 615                 620

Asn Ile Pro Ile Arg Leu Glu Glu Gly Arg Lys Ile Arg Gln Ala Phe
625                 630                 635                 640

Val Pro Ser Glu Ser Asp Trp Leu Ile Phe Ala Ala Asp Tyr Ser Gln
            645                 650                 655

Ile Glu Leu Arg Val Leu Ala His Ile Ala Glu Asp Asn Leu Met
        660                 665                 670

Glu Ala Phe Arg Arg Asp Leu Asp Ile His Thr Lys Thr Ala Met Asp
    675                 680                 685

Ile Phe Gln Val Ser Glu Asp Glu Val Thr Pro Asn Met Arg Arg Gln
690                 695                 700

Ala Lys Ala Val Asn Phe Gly Ile Val Tyr Gly Ile Ser Asp Tyr Gly
705                 710                 715                 720

Leu Ala Gln Asn Leu Asn Ile Ser Arg Lys Glu Ala Ala Glu Phe Ile
            725                 730                 735

Glu Arg Tyr Phe Glu Ser Phe Pro Gly Val Lys Arg Tyr Met Glu Asn
        740                 745                 750

Ile Val Gln Glu Ala Lys Gln Lys Gly Tyr Val Thr Thr Leu Leu His
    755                 760                 765

Arg Arg Arg Tyr Leu Pro Asp Ile Thr Ser Arg Asn Phe Arg Val Arg
770                 775                 780

Ser Phe Ala Arg Arg Met Ala Met Asn Thr Pro Ile Gln Gly Ser Ala
785                 790                 795                 800

Ala Asp Ile Ile Lys Lys Ala Met Ile Asp Leu Asn Ala Arg Leu Lys
            805                 810                 815

Glu Glu Arg Leu Gln Ala His Leu Leu Leu Gln Val His Asp Glu Leu
        820                 825                 830

Ile Leu Glu Ala Pro Lys Glu Glu Met Glu Arg Leu Cys Arg Leu Val
    835                 840                 845

Pro Glu Val Met Glu Gln Ala Val Thr Leu Arg Val Pro Leu Lys Val
850                 855                 860

Asp Tyr His Tyr Gly Ser Thr Trp Tyr Asp Ala Lys
865                 870                 875

<210> SEQ ID NO 33
<211> LENGTH: 581
<212> TYPE: PRT
<213> ORGANISM: Artificial Sequence
<220> FEATURE:
<223> OTHER INFORMATION: Synthetic:

<400> SEQUENCE: 33

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

```
Trp Leu Gly Asp Glu Thr Lys Lys Lys Ser Met Phe Asp Ser Lys Arg
 65                  70                  75                  80

Ala Ala Val Ala Leu Lys Trp Lys Gly Ile Glu Leu Cys Gly Val Ser
                 85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
    195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
            275                 280                 285

Gln Ser Thr Tyr Ile Glu Gly Leu Leu Lys Val Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Lys Tyr Gly Leu Ala Gln Asn Leu Asn Ile
            420                 425                 430

Ser Arg Lys Glu Ala Ala Glu Phe Ile Glu Arg Tyr Phe Gln Ser Phe
    435                 440                 445

Pro Gly Val Lys Arg Tyr Met Glu Asn Ile Val Gln Glu Ala Lys Gln
    450                 455                 460

Lys Gly Tyr Val Thr Thr Leu Leu His Arg Arg Arg Tyr Leu Pro Asp
465                 470                 475                 480

Ile Thr Ser Arg Asn Phe Asn Val Arg Ser Phe Ala Glu Arg Met Ala
```

-continued

```
                485                 490                 495
Met Asn Thr Pro Ile Gln Gly Ser Ala Ala Asp Ile Ile Lys Lys Ala
                500                 505                 510

Met Ile Asp Leu Asn Ala Arg Leu Lys Glu Arg Leu Gln Ala His
            515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
                580

<210> SEQ ID NO 34
<211> LENGTH: 581
<212> TYPE: PRT
<213> ORGANISM: Artificial Sequence
<220> FEATURE:
<223> OTHER INFORMATION: Synthetic:

<400> SEQUENCE: 34

Met Ala Lys Met Ala Phe Thr Leu Ala Asp Arg Val Thr Glu Glu Met
1               5                   10                  15

Leu Ala Asp Lys Ala Ala Leu Val Glu Val Val Glu Glu Asn Tyr
            20                  25                  30

His Asp Ala Pro Ile Val Gly Ile Ala Val Val Asn Glu Arg Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
                245                 250                 255

Thr Gly Tyr Ser Thr Ser Ala Ala Val Leu Glu Lys Leu Ala Pro Tyr
```

```
            260                 265                 270
Asn Glu Ile Val Glu Asn Ile Leu Met Tyr Arg Gln Leu Gly Lys Leu
            275                 280                 285

Gln Ser Thr Tyr Ile Glu Gly Leu Leu Lys Val Val Arg Pro Asp Thr
        290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
        370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Asp Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
    450                 455                 460

Lys Gly Tyr Val Thr Thr Leu Leu His Arg Arg Arg Tyr Leu Pro Asp
465                 470                 475                 480

Ile Thr Ser Arg Asn Phe Arg Val Arg Ser Phe Ala Arg Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 35
<211> LENGTH: 581
<212> TYPE: PRT
<213> ORGANISM: Artificial Sequence
<220> FEATURE:
<223> OTHER INFORMATION: Synthetic:

<400> SEQUENCE: 35

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
```

```
                35                  40                  45
Phe Phe Leu Arg Pro Glu Thr Ala Leu Ala Asp Pro Gln Phe Val Ala
 50                  55                  60
Trp Leu Gly Asp Glu Thr Lys Lys Lys Ser Met Phe Asp Ser Lys Arg
 65                  70                  75                  80
Ala Ala Val Ala Leu Lys Trp Lys Gly Ile Glu Leu Cys Gly Val Ser
                 85                  90                  95
Phe Asp Leu Leu Leu Ala Ala Tyr Leu Leu Asp Pro Ala Gln Gly Val
                100                 105                 110
Asp Asp Val Ala Ala Ala Lys Met Lys Gln Tyr Glu Ala Val Arg
                115                 120                 125
Pro Asp Glu Ala Val Tyr Gly Lys Gly Ala Lys Arg Ala Val Pro Asp
                130                 135                 140
Glu Pro Val Leu Ala Glu His Leu Val Arg Lys Ala Ala Ala Ile Trp
145                 150                 155                 160
Glu Leu Glu Arg Pro Phe Leu Asp Glu Leu Arg Arg Asn Glu Gln Asp
                165                 170                 175
Arg Leu Leu Val Glu Leu Glu Gln Pro Leu Ser Ser Ile Leu Ala Glu
                180                 185                 190
Met Glu Phe Ala Gly Val Lys Val Asp Thr Lys Arg Leu Glu Gln Met
                195                 200                 205
Gly Lys Glu Leu Ala Glu Gln Leu Gly Thr Val Glu Gln Arg Ile Tyr
210                 215                 220
Glu Leu Ala Gly Gln Glu Phe Asn Ile Asn Ser Pro Lys Gln Leu Gly
225                 230                 235                 240
Val Ile Leu Phe Glu Lys Leu Gln Leu Pro Val Leu Lys Lys Thr Lys
                245                 250                 255
Thr Gly Tyr Ser Thr Ser Ala Asp Val Leu Glu Lys Leu Ala Pro Tyr
                260                 265                 270
His Glu Ile Val Glu Asn Ile Leu Met Tyr Arg Gln Leu Gly Lys Leu
                275                 280                 285
Gln Ser Thr Tyr Ile Glu Gly Leu Leu Lys Val Val Arg Pro Asp Thr
                290                 295                 300
Lys Lys Val His Thr Ile Phe Asn Gln Ala Leu Thr Gln Thr Gly Arg
305                 310                 315                 320
Leu Ser Ser Thr Glu Pro Asn Leu Gln Asn Ile Pro Ile Arg Leu Glu
                325                 330                 335
Glu Gly Arg Lys Ile Arg Gln Ala Phe Val Pro Ser Glu Ser Asp Trp
                340                 345                 350
Leu Ile Phe Ala Ala Asp Tyr Ser Gln Ile Glu Leu Arg Val Leu Ala
                355                 360                 365
His Ile Ala Glu Asp Asp Asn Leu Met Glu Ala Phe Arg Arg Asp Leu
                370                 375                 380
Asp Ile His Thr Lys Thr Ala Met Asp Ile Phe Gln Val Ser Glu Asp
385                 390                 395                 400
Glu Val Thr Pro Asn Met Arg Arg Gln Ala Lys Ala Val Asn Phe Gly
                405                 410                 415
Ile Val Tyr Gly Ile Ser Lys Tyr Gly Leu Ala Gln Asn Leu Asn Ile
                420                 425                 430
Ser Arg Lys Glu Ala Ala Glu Phe Ile Glu Arg Tyr Phe Gln Ser Phe
                435                 440                 445
Pro Gly Val Lys Arg Tyr Met Glu Asn Ile Val Gln Glu Ala Lys Gln
450                 455                 460
```

```
Lys Gly Tyr Val Thr Thr Leu Leu His Arg Arg Tyr Leu Pro Asp
465                 470                 475                 480

Ile Thr Ser Arg Asn Phe Arg Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 36
<211> LENGTH: 581
<212> TYPE: PRT
<213> ORGANISM: Artificial Sequence
<220> FEATURE:
<223> OTHER INFORMATION: Synthetic:

<400> SEQUENCE: 36

Met Ala Lys Met Ala Phe Thr Leu Ala Asp Arg Val Thr Glu Glu Met
1               5                   10                  15

Leu Ala Asp Lys Ala Ala Leu Val Val Glu Val Val Glu Glu Asn Tyr
            20                  25                  30

His Asp Ala Pro Ile Val Gly Ile Ala Val Val Asn Glu His Gly Arg
        35                  40                  45

Phe Phe Leu Arg Pro Glu Thr Ala Leu Ala Asp Pro Gln Phe Val Ala
    50                  55                  60

Trp Leu Gly Asp Glu Thr Lys Lys Ser Met Phe Asp Ser Lys Arg
65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
        115                 120                 125

Pro Asp Glu Ala Val Tyr Gly Lys Gly Ala Lys Arg Ala Val Pro Asp
    130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
                165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
        195                 200                 205

Gly Lys Glu Leu Ala Glu Gln Leu Gly Thr Val Glu Gln Arg Ile Tyr
    210                 215                 220

Glu Leu Ala Gly Gln Glu Phe Asn Ile Asn Ser Pro Lys Gln Leu Gly
225                 230                 235                 240
```

Val Ile Leu Phe Glu Lys Leu Gln Leu Pro Val Leu Lys Lys Thr Lys
                245                 250                 255

Thr Gly Tyr Ser Thr Ser Ala Asp Val Leu Glu Lys Leu Ala Pro Tyr
            260                 265                 270

His Glu Ile Val Glu Asn Ile Leu His Tyr Arg Gln Leu Gly Lys Leu
        275                 280                 285

Gln Ser Thr Tyr Ile Glu Gly Leu Leu Lys Val Arg Pro Asp Thr
    290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
                325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
        355                 360                 365

His Ile Ala Glu Asp Asp Asn Leu Met Glu Ala Phe Arg Arg Asp Leu
    370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                405                 410                 415

Ile Val Tyr Gly Ile Ser Lys Tyr Gly Leu Ala Gln Asn Leu Asn Ile
            420                 425                 430

Ser Arg Lys Glu Ala Ala Glu Phe Ile Glu Arg Tyr Phe Gln Ser Phe
        435                 440                 445

Pro Gly Val Lys Arg Tyr Met Glu Asn Ile Val Gln Glu Ala Lys Gln
    450                 455                 460

Lys Gly Tyr Val Thr Thr Leu Leu His Arg Arg Arg Tyr Leu Pro Asp
465                 470                 475                 480

Ile Thr Ser Arg Asn Phe Arg Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
    530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580

<210> SEQ ID NO 37
<211> LENGTH: 581
<212> TYPE: PRT
<213> ORGANISM: Artificial Sequence
<220> FEATURE:
<223> OTHER INFORMATION: Synthetic:

<400> SEQUENCE: 37

Met Ala Lys Met Ala Phe Thr Leu Ala Asp Arg Val Thr Glu Glu Met
1               5                   10                  15

-continued

```
Leu Ala Asp Lys Ala Ala Leu Val Val Glu Val Val Glu Glu Asn Tyr
            20                  25                  30

His Asp Ala Pro Ile Val Gly Ile Ala Val Val Asn Glu Arg Gly Arg
            35                  40                  45

Phe Phe Leu Arg Pro Glu Thr Ala Leu Ala Asp Pro Gln Phe Val Ala
 50                  55                  60

Trp Leu Gly Asp Glu Thr Lys Lys Ser Met Phe Asp Ser Lys Arg
 65                  70                  75                  80

Ala Ala Val Ala Leu Lys Trp Lys Gly Ile Glu Leu Cys Gly Val Ser
                85                  90                  95

Phe Asp Leu Leu Leu Ala Ala Tyr Leu Leu Asp Pro Ala Gln Gly Val
            100                 105                 110

Asp Asp Val Ala Ala Ala Lys Met Lys Gln Tyr Glu Ala Val Arg
            115                 120                 125

Pro Asp Glu Ala Val Tyr Gly Lys Gly Ala Lys Arg Ala Val Pro Asp
130                 135                 140

Glu Pro Val Leu Ala Glu His Leu Val Arg Lys Ala Ala Ala Ile Trp
145                 150                 155                 160

Glu Leu Glu Arg Pro Phe Leu Asp Glu Leu Arg Arg Asn Glu Gln Asp
            165                 170                 175

Arg Leu Leu Val Glu Leu Glu Gln Pro Leu Ser Ser Ile Leu Ala Glu
            180                 185                 190

Met Glu Phe Ala Gly Val Lys Val Asp Thr Lys Arg Leu Glu Gln Met
            195                 200                 205

Gly Lys Glu Leu Ala Glu Gln Leu Gly Thr Val Glu Gln Arg Ile Tyr
210                 215                 220

Glu Leu Ala Gly Gln Glu Phe Asn Ile Asn Ser Pro Lys Gln Leu Gly
225                 230                 235                 240

Val Ile Leu Phe Glu Lys Leu Gln Leu Pro Val Leu Lys Lys Thr Lys
            245                 250                 255

Thr Gly Tyr Ser Thr Ser Ala Asp Val Leu Glu Lys Leu Ala Pro Tyr
            260                 265                 270

His Glu Ile Val Glu Asn Ile Leu Met Tyr Arg Gln Leu Gly Lys Leu
            275                 280                 285

Gln Ser Thr Tyr Ile Glu Gly Leu Leu Lys Val Val Arg Pro Asp Thr
290                 295                 300

Lys Lys Val His Thr Ile Phe Asn Gln Ala Leu Thr Gln Thr Gly Arg
305                 310                 315                 320

Leu Ser Ser Thr Glu Pro Asn Leu Gln Asn Ile Pro Ile Arg Leu Glu
            325                 330                 335

Glu Gly Arg Lys Ile Arg Gln Ala Phe Val Pro Ser Glu Ser Asp Trp
            340                 345                 350

Leu Ile Phe Ala Ala Asp Tyr Ser Gln Ile Glu Leu Arg Val Leu Ala
            355                 360                 365

His Ile Ala Glu Asp Asp Asn Leu Met Glu Ala Phe Arg Arg Asp Leu
            370                 375                 380

Asp Ile His Thr Lys Thr Ala Met Asp Ile Phe Gln Val Ser Glu Asp
385                 390                 395                 400

Glu Val Thr Pro Asn Met Arg Arg Gln Ala Lys Ala Val Asn Phe Gly
                    405                 410                 415

Ile Val Tyr Gly Ile Ser Asp Tyr Gly Leu Ala Gln Asn Leu Asn Ile
            420                 425                 430
```

-continued

```
Ser Arg Lys Glu Ala Ala Glu Phe Ile Glu Arg Tyr Phe Gln Ser Phe
    435                 440                 445

Pro Gly Val Lys Arg Tyr Met Glu Asn Ile Val Gln Glu Ala Lys Gln
    450                 455                 460

Lys Gly Tyr Val Thr Thr Leu Leu His Arg Arg Arg Tyr Leu Pro Asp
465                 470                 475                 480

Ile Thr Ser Arg Asn Phe Arg Val Arg Ser Phe Ala Glu Arg Met Ala
                485                 490                 495

Met Asn Thr Pro Ile Gln Gly Ser Ala Ala Asp Ile Ile Lys Lys Ala
            500                 505                 510

Met Ile Asp Leu Asn Ala Arg Leu Lys Glu Glu Arg Leu Gln Ala His
        515                 520                 525

Leu Leu Leu Gln Val His Asp Glu Leu Ile Leu Glu Ala Pro Lys Glu
        530                 535                 540

Glu Met Glu Arg Leu Cys Arg Leu Val Pro Glu Val Met Glu Gln Ala
545                 550                 555                 560

Val Thr Leu Arg Val Pro Leu Lys Val Asp Tyr Arg Tyr Gly Ser Thr
                565                 570                 575

Trp Tyr Asp Ala Lys
            580
```